(12) United States Patent
Weigel et al.

(10) Patent No.: US 7,094,581 B2
(45) Date of Patent: Aug. 22, 2006

(54) HYALURONAN SYNTHASES AND METHODS OF MAKING AND USING SAME

(75) Inventors: Paul H. Weigel, Edmond, OK (US); Kshama Kumari, Edmond, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 265 days.

(21) Appl. No.: 10/309,560

(22) Filed: Dec. 3, 2002

(65) Prior Publication Data

US 2003/0235893 A1 Dec. 25, 2003

Related U.S. Application Data

(63) Continuation-in-part of application No. 10/011,771, filed on Dec. 11, 2001, which is a continuation of application No. 09/469,200, filed on Dec. 21, 1999, now Pat. No. 6,833,264, which is a continuation of application No. 09/178,851, filed on Oct. 26, 1998, now abandoned.

(60) Provisional application No. 60/336,105, filed on Dec. 3, 2001.

(51) Int. Cl.
C12N 9/10 (2006.01)
C12P 19/04 (2006.01)
C12P 19/26 (2006.01)

(52) U.S. Cl. ................ 435/84; 435/101; 435/193
(58) Field of Classification Search .......... None
See application file for complete search history.

(56) References Cited

U.S. PATENT DOCUMENTS

| | | | |
|---|---|---|---|
| 4,224,179 A | 9/1980 | Schneider | |
| 4,235,871 A | 11/1980 | Papahadjopoulos et al. | |
| 4,511,478 A | 4/1985 | Nowinski et al. | |
| 4,517,295 A | 5/1985 | Bracke et al. | |
| 4,615,697 A | 10/1986 | Robinson | |
| 4,708,861 A | 11/1987 | Popescu et al. | |
| 4,780,414 A | 10/1988 | Nimrod et al. | |
| 4,782,046 A | 11/1988 | Brown et al. | |
| 4,784,990 A | 11/1988 | Nimrod et al. | |
| 4,801,539 A | 1/1989 | Akasaka et al. | |
| 4,822,867 A | 4/1989 | Erhan | |
| 4,983,392 A | 1/1991 | Robinson | |
| 5,015,577 A | 5/1991 | Weigel et al. | |
| 5,023,175 A | 6/1991 | Hosoya et al. | |
| 5,071,751 A | 12/1991 | Morita et al. | |
| 5,171,689 A | 12/1992 | Kawaguri et al. | |
| 5,217,743 A | 6/1993 | Farah | |
| 5,337,747 A | 8/1994 | Neftel | |
| 5,472,704 A | 12/1995 | Santus et al. | |
| 5,473,034 A | 12/1995 | Yasui et al. | |
| 5,607,694 A | 3/1997 | Marx | |
| 5,610,241 A | 3/1997 | Lee et al. | |
| 5,622,850 A | 4/1997 | Sloma et al. | |
| 5,631,019 A | 5/1997 | Marx | |
| 5,651,982 A | 7/1997 | Marx | |
| 5,948,900 A | 9/1999 | Yother et al. | |
| RE37,336 E | 8/2001 | Weigel et al. | |
| 6,423,514 B1 | 7/2002 | Briskin | |
| 6,455,304 B1 | 9/2002 | Weigel et al. | |
| 6,492,150 B1 | 12/2002 | McDonald | |

FOREIGN PATENT DOCUMENTS

| | | |
|---|---|---|
| EP | 0195303 | 11/1989 |
| EP | 0144019 | 6/1990 |
| EP | 0266578 | 7/1993 |
| EP | 0244757 | 11/1994 |
| EP | 0036776 | 5/1998 |
| GB | 2249315 | 5/1992 |
| JP | 61-257169 | 11/1986 |
| JP | 62032893 | 2/1987 |
| JP | 63094988 | 4/1988 |
| JP | 4-80202 | 3/1992 |
| JP | 4-124854 | 4/1992 |
| JP | 4-134854 | 5/1992 |
| JP | 4-158796 | 6/1992 |
| JP | 8-38336 | 2/1996 |
| WO | 91/03559 | 3/1991 |
| WO | 94/00463 | 1/1994 |
| WO | 95/24497 | 9/1995 |
| WO | 95/33067 | 12/1995 |
| WO | 97/20061 | 6/1997 |

OTHER PUBLICATIONS

"The Combinations of Haemoglobin with Oxygen and with Carbon Monoxide.", Hill, J. Biochem., 7:471-480 (1913).
"The Role of the Mucoid Polysaccharide (Hyaluronic Acid) in the Virulence of Group A Hemalytic Streptococci", Kass et al., J. Of Exp. Med., 79:319-330 (1944).
"The Production of Capsules, Hyaluronic Acid and Hyaluronidase by Group A and Group C Streptocooci", MacLennan, J. Gen. Microbiol., 14:134-142 (1956).

(Continued)

*Primary Examiner*—Robert A. Wax
(74) *Attorney, Agent, or Firm*—Dunlap, Codding & Rogers, P.C.

(57) ABSTRACT

A functionally active hyaluronan synthase having at least one modified amino acid residue therein as compared to a corresponding functionally active native hyaluronan synthase such that the functionally active hyaluronan synthase has an altered enzymatic activity as compared to the corresponding functionally active native hyaluronan synthase is disclosed. Methods of producing hyaluronic acid utilizing a recombinant host cell having an expression construct encoding the functionally active hyaluronan synthase with altered enzymatic activity are also disclosed.

49 Claims, 22 Drawing Sheets

OTHER PUBLICATIONS

"The Isolation and Characterization of a Hyaluronidase Produced by a Capsulated Strain of Group C *Streptococcus*", MacLennan, J. Gen. Microbiol., 14:143-152 (1956).

"The Biosynthesis of Hyaluronic Acid by Group A *Streptococcus*", Markovitz et al., J. Biol. Chem., 234 (9):2343-2350 (1959).

"The Biosynthesis of Hyaluronic Acid by *Streptococcus*," Stoolmiller, et al., Journal of Biological Chemistry, vol. 244, No. 2, pp. 236-246 (1969).

"Cleavage of Structural Proteins During the Assembly of the Head of Bacteriophage T4", Laemmli, Nature, 227:680-685 (1970).

"A Rapid and Sensitive Method for the Quantitation of Microgram Quantities of Protein Utilizing the Principle of Protein-Dye Binding", Bradford, Analytical Biochemistry, 72:248-254 (1976).

"Synthesis and Assembly of the Membrane Proteins in *E. coli*", Ito et al., Cell, 11:551-559 (1977).

"Electrophoretic Transfer of Proteins From Polyacrylamide Gels to Nitrocellulose Sheets: Procedure and Some Applications", Biochemistry, 76: 4350-4354 (1979).

"Biosynthesis of Hyaluronic Acid by *Streptococcus*", Sugahara et al., J. Biol. Chem., 254:6252-6261 (1979).

"Modern Genetics", Ayala, et al., Benjamin/Cummings Publishing Col., Menlo Park CA, p. 45 (1980).

"Hyaluronate Capsule Prevents Attachment of Group A *Streptococci* to Mouse Peritoneal Macrophages", Whitnack et al., Infection and Immunity, 31(3):985-991 (1981).

"Strains of *Escherichia coli* Carrying the Structural Gene for Histidyl-tRNA Synthetase on a High Copy-Number Plasmid", Eisenbeis, et al., Mol. Gen. Genet. 183:115-122 (1981).

"Synthesis of Hyaluronate in Differentiated Teratocaccinoma Cells," Prehm, et al., J. Biochem, vol. 211, pp. 181-189 (1983).

"Streptococcal Hyaluronic Acid: Proposed Mechanisms of Degradation and Loss of Synthesis During Stationary Phase", Van de Rijn, J. Bacteriol., 156(3):1059-1065 (1983).

"Hyaluronate is Synthesized at Plasma Membranes", Prehm, Biochem. J., 220:597-600 (1984).

"Subcellular Locations of Hyaluronate Synthase in Oligodendroglioma Cells", Philipson et al., J. Biol. Chem., 259(8):5017-5023 (1984).

"Solubilization of Hyaluronic Acid Synthetic Activity From Streptococci and its Activation With Phospholipids", Triscott et al., J. Biol. Chem., 261(13):6004-6009 (1986).

"Isolation of Streptococcal Hyaluronate Synthase", Prehm et al., Biochem. J., 235:887-889 (1986).

"Isolation, Structure and Expression of Mammalian Genes for Histidyl-tRNA Synthetase," Tsui, et al., Nucleic Acids Research, vol. 15, No. 8, pp. 3349-3367, (1987).

"Role of Cysteine in Glutathione Synthase From *Escherichia coli* B", Kato et al., J. Biol. Chem., 263(24):11646-11651 (1988).

"The Biology of Hyaluronan", Evered and Whelan Eds., CIBA Foundation Symposium 143 (1989).

"The Role of Bacterial Polysaccharide Capsules as Virulence Factors", Moxon et al., Current Topics in Microbiology and Immunology, 150:65-85 (1990).

"Hyaluronic Acid Capsule is a Virulence Factor for Mucoid Group A *Streptococci*", Wessels et al., Microbiology, 88:8317-8321 (1991).

"Shuttle Vectors Containing a Multiple Cloning Site and a Lacza Gena for Conjugal Transfer of DNA From *Escherichia coli* to Gram-Positive Bacteria," Trieu-Cout, et al., Gene, vol. 102, pp. 99-104, (1991).

"Analysis of the *Streptococcal* Hyaluronic Acid Synthase Complex Using the Photoaffinity Probe 5-Azido-UDP-Glucuronic Acid," Van de Rijn, et al., J. Biol., Chem., vol. 267, No. 34, pp. 24302-24306, (1992).

"Molecular Characterization of a Locus Required for Hyaluronic Acid Capsule Production in Group A *Streptococci*," Dougherty, et al., J. Exp. Med., vol. 175, pp. 1291-1299, (1992).

"Hyaluronan," Laurent, et al., FASEB Journal, vol. 6, pp. 2397-2404, (1992).

"Role of Cysteins 640, 656, and 661 in Steroid Binding to Rat Glucocorticoid Receptors", Chakraborti et al., J. Biol. Chem., 267(16):11366-11373 (1992).

"Localization of Hyaluronan in Mouse Embryos During Implantation, Gastrulation and Organogenesis", Fenderson et al., Differentiation, 54:85-98 (1993).

"Hyaluronan-Binding Proteins in Development, Tissue Homeostasis, and Disease", Knudson et al., FASEB, 7:1233-1241 (1993).

"Molecular Cloning, Identification, and Sequence of the Hyaluronan Synthase Gene From Group A *Streptococcus pyogenes*", DeAngelis et al., J. Biol. Chem., 268(26):19181-19184 (1993).

"Isolation of a *Streptococcus pyogenes* Gene Locus That Directs Hyaluronan Biosynthesis in Acapsular Mutants and in Heterologous Bacteria," DeAngelis, et al., J. Biol. Chem., vol. 268, No. 20, pp. 14568-14571, (1993).

"Hyaluronate Synthase: Cloning and Sequencing of the Gene From *Streptococcus* sp.," Lansing, et al., J. Biochem., vol. 289, pp. 179-184, (1993).

"Molecular Characterization of HASB From an Operon Required for Hyaluronic Acid Synthesis in Group A *Streptococci*," Dougherty, et al., J. Biol. Chem., vol. 268, No. 10, pp. 7118-7124, (1993).

"Effects on Virulence of Mutations in a Locus Essential for Hyaluronic Acid Capsule Expression in Group A *Streptococci*", Wessels et al., Infection and Immunity, 62(2):433-441 (1994).

"A Hyaluronidase Activity of the Sperm Plasma Membrane Protein PH-20 Enables Sperm to Penetrate the Cumulus Cell Layer Surrounding the Egg", Lin et al., The Journal of Cell Biology, 125(5): 1157-1163 (1994).

"Dynamics of Lactose Permease of *Escherichia coli* Determined by Site-Directed Fluorescense Labeling", Jung et al., Biochemistry, 33:3980-3985 (1994).

"Cysteine 148 in the Lactose Permease of *Escherichia coli* is a Component of a Substrate Binding Site", Wu et al., Biochemistry, 33:12166-12171 (1994).

"Molecular Characterization of HASA From an Operon Required for Hyaluronic Acid Synthesis in Group A *Streptococci*," Dougherty, et al., J. Biol. Chem., vol. 269, No. 1, pp. 169-175, (1994).

"The *Streptococcus pyogenes* Hyaluronan Sytnhase: Sequence Comparison and Conservation Among Various Group A Strains," DeAngelis, et al., Biochem. and Biophy. Res. Comm., vol. 199, No. 1, pp. 1-10, (1994).

"Molecular Fingerprinting of *Pasteurella multocida* Associated With Progressive *Atrophic rhinitis* in Swine Herds". Gardner et al. Database Medline on Diaolog, US Nat'l. Library of Medicine (Bethesda, MD, USA) No. 95161494, Abstract, J. Vet. Diagn. Invest. Oct. 1994. vol. 6, No. 4 pp. 442-447, see entire abstract.

The Elucidation of Novel Capsular Genotypes of *Haemophilus influenzae* Type B With the Polymerase Chain Reaction. Leaves et al. J. Medical Microbiology. 1995, vol. 43, pp. 120-124, entire document.

"Homologs of the Xenopus Developmental Gene DG42 are Present in Zebrafish and Mouse and are Involved in the Synthesis of NOD-like Chitin Oligosaccharides During Early Embryogenesis", Semino et al., Proc. Natl Acad. Sci. USA, 93:4548-4553 (1996).

"Enzymological Characterization of the Pasteurella Multocida Hyaluronic Acid Synthase", DeAngelis, Biochemistry, 35 (30): 9768-9771 (1996).

"Construction and Characterization of a Potential Live Oral Carrier-Based Vaccine Against *Vibrio chlorerae*". Favre et al. Infection and Immunity. Sep. 1996. vol. 64, No. 9 pp. 3565-3570, entire document.

"Functional Cloning of the cDNA for a Human Hyaluronan Synthase", Shyjan et al., J. Biol. Chem., 271(38):23395-23399 (1996).

"Coating the Surface: A Model for Expression of Capsular Polysialic Acid in *Escherchia coli* K1", Bliss et al., Molecular Microbiology, 21(2):221-231 (1996).

"Expression Cloning and Molecular Characterization of HAS Protein, a Eukaryotic Hyaluronan Synthase", Itano et al., J. Biol. Chem., 271(17):9875-9878 (1996).

"Molecular Identification of a Putative Human Hyaluronan Synthase", Wantanabe et al., J. Biol. Chem., 271(38):22945-22948 (1996).

"Molecular Cloning of a Human Hyaluronan Synthase", Itano et al., Biochemical and Biophysical Research Communications, 222:816-820 (1996).

"Hyaluronan Synthases", Weigel et al., J. Biol. Chem., 272 (22): 13997-14000 (1997).

"Identification of Sulfhydryl-Modified Cysteine Residues in the Ligand Binding Pocket of Retinoic Acid Receptors β", Wolfgang et al., J. Biol. Chem., 272(2):746-753 (1997).

"Hyaluronan in Morphogenesis", B.P. Toole, Journal of Internal Medicine, 242:35-40 (1997).

"Hyaluronan Synthases", Weigel et al., J. Biol. Chem., 272(22):13997-14000 (1997).

"Hyaluronan Synthase of Chlorella Virus PBCV-1", DeAngelis et al, Science, 278:1800-1803 (1997).

"Molecular Cloning, Expression, and Characterization of the Authentic Hyaluronan Synthase From Group C *Streptococcus equisimilis*", Kumari and Weigel, J. Biol. Chem., 272(51):32539-32546 (1997).

"Site-Directed Spin Labeling of Transmembrane Domain VII and the 4B1 Antibody Epitope in the Lactose Permease of *Escherichia coli*", Voss et al., Biochemistry, 36:15055-15061 (1997).

"Reactive Cysteines of the Yeast Plasma-Membrane H -ATPase (PMA1)", Petrov et al., J. Biol. Chem., 272(3):1688-1693 (1997).

"Identification and Molecular Cloning of a Unique Hyaluronan Synthase From *Pasteurella multocida*", DeAngelis et al., J. Biol. Chem., 273(14): 8454-8458 (1998).

The Capsule Biosynthetic Locus of *Pasteurella multocida* A:1. Chung, et al. FEMS Microbiol. Lett. Sep. 15, 1998, vol. 166, No. 2, pp. 289-296, entire document.

"CYS-Scanning Mutagenesis: A Novel Approach to Structure-Function Relationships in Polytopic Membrane Proteins", Frillingos et al., FASEB, 12:1281-1299 (Oct. 1998).

"Characterization and Molecular Evolution of a Vertabrate Hyaluronan Synthase Gene Family", Spicer et al., J. Biol. Chem., 273(4):1923-1932 (1998).

"Eukaryotic Hyaluronan Synthases", Spicer and McDonald, Glycoforum, Sep. 15, 1998.

"The Active Streptococcal Hyaluronan Synthases (HASs) Contain a Single has Monomer and Multiple Cardiolipin Molecules", Tlapak-Simmons et al., J. Biol. Chem., 273(40):26100-26109 (1998).

"Hyaluronan Synthase Expression in Bovine Eyes", Usui et al., Investigative Opythamology & Visual Science, 40(3):563-567 (Mar. 1999).

"Three Isoforms of Mammalian Hyaluronan Synthases Have Distinct Enzymatic Properties", Itano et al., J. Biol. Chem., 274(35):25085-25092 (1999).

"Hyaluronan Synthases: Fascinating Glycosyltransferases From Vertebrates, Bacterial Pathogens and Algal Viruses", P.L. DeAngelis, CMLS, 56:670-682 (1999).

"Membrane Protein Folding and Stability: Physical Principles", White and Wimley, Annu. Rev. Biophys. Biomol. Struc., 28:319-365 (1999).

"Location of Helix III in the Lactose Permease of *Escherichia coli* as Determined by Site-Directed Thiol Cross-Linking", Wang and Kaback, Biochemistry, 38:16777-16782 (1999).

"Kinetic Characterization of the Recombinant Hyaluronan Synthases From *Streptococcus pyogenes* and *Streptococcus equisimilis*", Tlapak-Simmons, J. Biol. Chem., 274(7):4246-4253 (1999).

"Purification and Lipid Dependence of the Recombinant Hyaluronan Synthases From *Streptococcus pyogenes* and *Streptococcus equisimilis*", Tlapak-Simmons, J. Biol. Chem., 274(7):4246-4253 (1999).

"Structure/Function Studies of Glycoslytransferases", Breton and Imberty, Current Opinion in Structural Biology, 9:563-571 (1999).

"New Frontiers in Medical Sciences: Redefining Hyaluronan", Abatangelo and Weigel Eds., (2000).

"In Vitro Synthesis of Hyaluronan by a Single Protein Derived From Mouse HAS1 Gene and Characterization of Amino Acid Residues Essential for the Activity", Yoshida et al., J. Biol. Chem., 275(1):497-506 (2000).

"Regulation of Plasminogen Activator Inhibitor-1 and Urokinase by Hyaluronan Fragments in Mouse Macrophages", Horton et al., Am. J. Physiol. Lung Cell Mol. Physiol., 279:L707-L715 (2000).

"Complete Cysteine-Scanning Mutagenesis and Site Directed Chemical Modification of the Tn10-Encoded Metal-Tetracycline/H Antiporter", Tamura et al., J. Biol. Chem., 276(23):20330-20339 (2001).

"Identification and Disruption of Two Discrete Loci Encoding Hyaluronic Acid Capsule Biosynthesis Genes hasA, hasB, and hasC in *Streptococcus uberis*", Ward et al., Infection and Immunity, 69(1):392-399 (2001).

"Topological Organization of the Hyaluronan Synthase From *Streptococcus pyogenes*", Heldermon et al., J. Biol. Chem., 276(3):2037-2046 (2001).

"Site-Directed Mutation of Conserved Cysteine Residues Does not Inactivate the *Streptococcus pyogenes* Hyaluronan Synthase", Heldermon et al., Glycobiology, 11(12):1017-1024 (2001).

"Molecular Cloning of Rabbit Hyaluronic Acid Synthases and Their Expression Patterns in Synovial Membrane and Articular Cartilage", Ohno et al., Biochimica et Biophysics Acta, 1520 (71-78) (2001).

"The Streptococcal Hyaluronan Synthases are Inhibited by Sulfhydryl-Modifiying Reagents, but Conserved Cysteine Residues are not Essential for Enzyme Function", Kumari et al., J. Biol. Chem., 277(16):13943-13952 (2002).

"Die Kinetik der Invertinwirkung", Michaelis and Menten, Biochem. Z., 49: 333-338 (1913) (No translation available).

"The Isolation and Characterization of Hyaluronic Acid From Pasteurella Multocida", Cifonelli, et al., Carbohydrate Research, 14, 272-276, (1970).

"Hyaluronidase Production by Type B Pasteurella Multocida From Cases of Hemorrhagic Septicemia", Carter, et al., Journal of Clinical Microbiology, p. 94-96, (1980).

"Hyaluronic Acid and A (1-4)-B-D-XYLAN, Extracellular Polysaccharides of Pasteurella Multocida (Carter Type A) Strain 880", Rosner, et al., Carbohydrate Research, 223, 329-333 (1992).

"Capsular Hyaluronic Acid in Pasteurella Multocida Type A and its Counterpart in Type D", Pandit, Research in Veterinary Science 54, 20-24 (1993).

"Hyaluronidase and Chondroitinase Activity of Pasteurella Multocida Serotype B:2 Involved in Haemorrhagic Septicaemia", Rimier, et al., Veterinary Record 134, 67-68 (1994).

"Capsular Hyaluronic Acid-Mediated Adhesion of Pasteurella Multocida to Turkey Air SAC Macrophages", Pruimboom, et al., Avian Diseases 40:887-893, (1996).

"Transposon Tn916 Insertional Mutagenesis of Pasteurella Multocida and Direct Sequencing of Disruption Site", Paul L. DeAngelis, Microbial Pathogenesis, 24: 203-209 (1998).

FIGURE 1

```
                         C226                                • C262
seHAS  205 RYDNAFGVERAAQSVTGNILVCSGPLSVYRREVVVPNIDRYINQTFLGIPVSIGDDRCLT
suHAS  204 RYDNAFGVERAAQSVTGNILVCSGPLSIYRRSVGIPNLERYTSQTFLGVPVSIGDDRCLT
spHAS  204 RYDNAFGVERAAQSLTGNILVCSGPLSIYRREVIIPNLERYKNQTFLGLPVSIGDDRCLT
ggHAS2 259 RYWMAFNIERACQSYFGCVQCISGPLGMYRNSLLHEFVEDWYNQEFMGSQCSFGDDRHLT
mmHAS1 289 RYWVAFNVERACQSYFHCVSCISGPLGLYRNNLLQQFLEAWYNQKFLGTHCTFGDDRHLT
mmHAs2 259 RYWMAFNIERACQSYFGCVQCISGPLGMYRNSLLHEFVEDWYNQEFMGNQCSFGDDRHLT
mmHAS3 263 RYWMAFNVERACQSYFGCVQCISGPLGMYRNSLLQQFLEDWYHQKFLGSKCSFGDDRHLT
hsHAS1 284 RYWVAFNVERACQSYFHCVSCISGPLGLYRNNLLQQFLEAWYNQKFLGTHCTFGDDRHLT
hsHAS2 259 RYWMAFNIERACQSYFGCVQCISGPLGMYRNSLLHEFVEDWYNQEFMGNQCSFGDDRHLT
hsHAS3 262 RYWMAFNVERACQSYFGCVQCISGPLGMYRNSLLQQFLEDWYHQKFLGSKCSFGDDRHLT
ocHAS2 259 RYWMAFNIERACQSYFGCVQCISGPLGMYRNSLLHEFVEDWYNQEFMGNQCSFGDDRHLT
ocHAS3 261 RYWMAFNVERACQSYFGCVQCISGPLGMYRNSLLQQFLEDWYHQKFLGSKCSFGDDRHLT
btHAS2 259 RYWMAFNIERACQSYFGCVQCISGPLGMYRNSLLHEFVEDWYNQEFMGSQCSFGDDRHLT
rnHAS2 259 RYWMAFNIERACQSYFGCVQCISGPLGMYRNSLLHEFVEDWYNQEFMGNQCSFGDDRHLT
cvHAS2 254 RYYSAFCVERSAQSFFRTVQCVGGPLGAYKIDIIKEIKDPWISQRFLGQKCTYGDDRRLT
xlHAS1 287 RYWMAFNVERACQSYFDCVSCISGPLGMYRNNILQVFLEAWYRQKFLGTYCTLGDDRHLT

C281           •  ••
seHAS  265 NYATDLG-KTVYQSTAKCITDVPDKMSTYLKQQNRWNKSFFRESIISVKKIMNNPFVALW
suHAS  264 NYATDLG-KTVYQSTARCDTDVPDKFKVFIKQQNRWNKSFFRESIISVKKLLATPSVAVW
spHAS  264 NYAIDLG-RTVYQSTARCDTDVPFQLKSYLKQQNRWNKSFFRESIISVKKILSNPIVALW
ggHAS2 319 NRVLSLGYATKYTARSKCLTETPIEYLRWLNQQTRWSKSYFREWLYNAMWFHKHHLWMTY
mmHAS1 349 NRMLSMGYATKYTSRSRCYSETPSSFLRWLSQQTRWSKSYFREWLYNALWWHRHHAWMTY
mmHAs2 319 NRVLSLGYATKYTARSKCLTETPIEYLRWLNQQTRWSKSYFREWLYNAMWFHKHHLWMTY
mmHAS3 323 NRVLSLGYRTKYTARSKCLTETPTRYLRWLNQQTRWSKSYFREWLYNSLWFHKHHLWMTY
hsHAS1 344 NRMLSMGYATKYTSRSRCYSETPSSFLRWLSQQTRWSKSYFREWLYNALWWHRHHAWMTY
hsHAS2 319 NRVLSLGYATKYTARSKCLTETPIEYLRWLNQQTRWSKSYFREWLYNAMWFHKHHLWMTY
hsHAS3 322 NRVLSLGYRTKYTARSKCLTETPTKYLRWLNQQTRWSKSYFREWLYNSLWFHKHHLWMTY
ocHAS2 319 NRVLSLGYATKYTARSKCLTETPIEYLRWLNQQTRWSKSYFREWLYNAMWFHKHHLWMTY
ocHAS3 321 NRVLSLGYRTKYTARSKCLTETPTKYLRWLNQQTRWSKSYFREWLYNSLWFHKHHLWMTY
btHAS2 319 NRVLSLGYATKYTARSKCLTETPIEYLRWLNQQTRWSKSYFREWLYNAMWFHKHHLWMTY
rnHAS2 319 NRVLSLGYATKYTARSKCLTETPIEYLRWLNQQTRWSKSYFREWLYNAMWFHKHHLWMTY
cvHAS2 314 NEILMRGKKVVFTPFAVGWSDSPTNVFRYIVQQTRWSKSWCREIWYTLFAAWKHGLSGIW
xlHAS1 347 NRVLSMGYRTKYTHKSRAFSETPSLYLRWLNQQTRWTKSYFREWLYNAQWWHKHHIWMTY

C367
seHAS  324 TILEVSMFMMLVYSVVDFFVGNVREFDWL-RVLAFLVIIFIVALCRNIHYMLKHPLSFLL
suHAS  323 TITEVSMFIMLVYSIFSLLIGEAQEFNLI-KLVAFLVIIFIVALCRNVHYMVKHPFAFLL
spHAS  323 TIFEVVMFMMLIVAIGNLLFNQAIQLDLI-KLFAFLSIIFIVALCRNVHYMVKHPASFLL
ggHAS2 379 EAVITGFFPFFLIATVIQLFYRGKIWNI---LLFLLTVQLVGLIKSSFASFLRGNIVMVF
mmHAS1 409 EAVVSGLFPFFVAATVLRLFYAGRPWAL---LWVLLCVQGVALAKAAFAAWLRGCVRMVL
mmHAs2 379 EAVITGFFPFFLIATVIQLFYRGKIWNI---LLFLLTVQLVGLIKSSFASCLRGNIVMVF
mmHAS3 383 ESVVTGFFPFFLIATVIQLFYRGKIWNI---LLFLLTVQLVGIIKATYACFLRGNAEMIF
hsHAS1 404 EAVVSGLFPFFVAATVLRLFYAGRPWAL---LWVLLCVQGVALAKAAFAAWLRGCLRMVL
hsHAS2 379 EAIITGFFPFFLIATVIQLFYRGKIWNI---LLFLLTVQLVGLIKSSFASCLRGNIVMVF
hsHAS3 382 ESVVTGFFPFFLIATVIQLFYRGKIWNI---LLFLLTVQLVGIIKATYACFLRGNAEMIF
ocHAS2 379 EAVITGFFPFFLIATVIQLFYRGKIWNI---LLFLLTVQLVGLIKSSFASCLRGNIVMVF
ocHAS3 381 ESVVTGFFPFFLIATVIQLFYRGKIWNI---LLFLLTVQLVGIIKATYACFLRGNAEMIF
btHAS2 379 EAVITGFFPFFLIATVIQLFYRGKIWNT---LLFLLTVQLVGLIKSSFASFLRGNIVMVF
rnHAS2 379 EAVITGFFPFFLIATVIQLFYRGKIWNI---LLFLLTVQLVGLIKSSFASCLRGNIVMVF
cvHAS2 374 LAFECLYQITYFFLVIYLFSRLAVEADPRAQTATVIVSTTVALIKCGYFSFRAKDIRAFY
xlHAS1 407 ESVVSFIFPFFITATVIRLIYAGTIWNV---VWLLLCIQIMSLFKSIYACWLRGNFIMLL
```

FIGURE 2
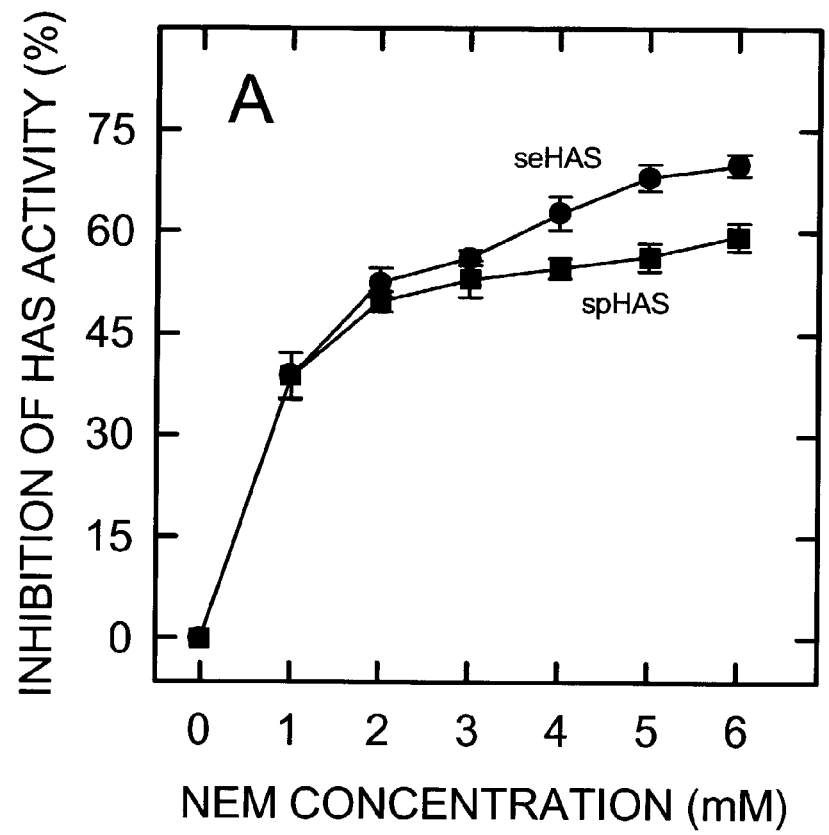
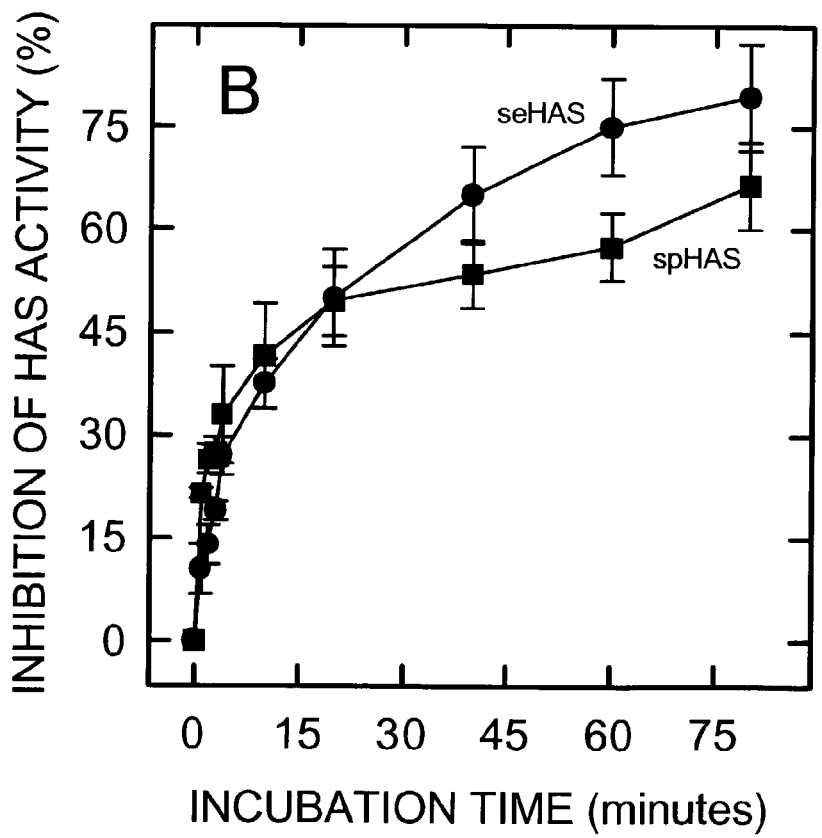

```
                    MD-1                         MD-2 ♦
seHAS   1 MRTLKNLITVVAFSIFWVLLIYVNVYLFGAKGSLSIYGFLLIAYLLVKMSLSFFYKPPKGRAGQYKVAAIIPSYNEDAESLLETLKSVQQQTYPL
suHAS   1 MEKLKNLITFMTFIFLWLIIIGLNVFVFGTKGSLTVYGIILLTYLSIKMGLSFFYRPYKGSVGQYKVAAIIPSYNEDGVGLLETLKSVQKQTYPI
spHAS   1 VPIFKKTLIVLSFIFLISILIYLNMYLFGTS-TVGIYGVILITYLVIKLGLSFLYEPFKGNPHDYKVAAVIPSYNEDAESLLETLKSVLAQTYPL
           *       *    * *    **      **  *  ** *   ++ *** * * *+    *+*** *******  *****+** *****
                                                              motif #1
seHAS  96 AEIYVVDDCSADETGIKRIEDYVRDTGDLSSNVIVHRSEKNQGKRHAQAWAFERSDADVFLTVDSDTYIYPDALEELLKTFNDPTVFAATGHLNV
suHAS  96 AEIFVIDDGSVDKTGIKLVEDYVKLNG-FGDQVIVHQMPENVGKRHAQAWAFERSDADVFLTVDSDTYIYPDALEELLKTFNDPEVYAATGHLNA
spHAS  95 SEIYIVDDGSSNTDAIQLIEEYVNREVDICRNVIVHRSLVNKGKRHAQAWAFERSDADVFLTVDSDTYIYPNALEELLKSFNDETVYAATGHLNA
           **  ****   *  *  * **     *    **** *   ******************* ******+ ***   * *******
                      MD-3                                                              motif #2
seHAS 192 RNRQTNLLTRLTDIRYDNAFGVERAAQSVTGNILVCSGPLSVYRREVVVPNIDRYINQTFLGIPVSIGDDRCLTNYATDLGKTVYQSTARCITDV
suHAS 191 RNRQTNLLTRLTDIRYDNAFGVERAAQSVTGNILVCSGPLSIYRRSVGIPNLERYTSQTFLGVPVSIGDDRCLTNYATDLGKTVYQSTARCDTDV
spHAS 191 RNRQTNLLTRLTDIRYDNAFGVERAAQSLTGNILVCSGPLSIYRREVIIPNLERYKNQTFLGLPVSIGDDRCLTNYAIDLGRTVYQSTARCDTDV
          +*+******+****+*********+**** ************* *++  ** +*  ***** ******** ***+*********+* ***
                   motif #3                    ♦  MD-4                       MD-5
seHAS 286 PDKMSTYLKQQNRWNKSFFRESIISVKKIMNNPFVALWTILEVSMFMMLVYSVVDFFVGNVREFDWLRVLAFLVIIFIVALCRNIHYMLKHPLSF
suHAS 285 PDKFKVFIKQQNRWNKSFFRESIISVKKLLATPSVAVWTITEVSMFIMLVYSIFSLLIGEAQEFNLIKLVAFLVIIFIVALCRNVHYMVKHPFAF
spHAS 285 PFQLKSYLKQQNRWNKSFFRESIISVKKILSNPIVALWTIFEVVMFMMLIVAIGNLLFNQAIQLDLIRLFAFLSIIFIVALCRNVHYMVKHPASF
           *    +****+**+***+******+++  * ****** ** **  ** *        +  *** ******** *** +** *
                MD-6         motif #4 motif #5
seHAS 381 LLSPFYGVLHLFVLQPLKLYSLFTIRNADWGTRKKLL   (417 amino acids -- AAB87874)
suHAS 380 LLSPFYGLIHLFVLQPLKIYSLFTIRNATWGTRKKTSK  (417 amino acids -- CAB46918)
spHAS 380 LLSPLYGILHLFVLQPLKLYSLCTIKNTEWGTRKKVTIFK (419 amino acids -- AAA17981)
          **** ** ********+ *** **+*    ***+++
```

FIGURE 14A

The Size Distributions of HA made by K48 and E327 Mutants of seHAS are Different from Wild-type

HYALURONAN SYNTHASES AND METHODS OF MAKING AND USING SAME

CROSS-REFERENCE TO RELATED APPLICATIONS

This application claims benefit under 35 U.S.C. 119(e) of U.S. Ser. No. 60/336,105, filed Dec. 3, 2001, entitled "NOVEL KINETIC PROPERTIES OF HYALURONIC SYNTHASES", the contents of which are hereby expressly incorporated herein by reference.

This application is also a continuation-in-part of U.S. Ser. No. 10/011,771, filed Dec. 11, 2001, entitled "HYALURONAN SYNTHASE GENE AND USES THEREOF"; which is a continuation of U.S. Ser. No. 09/469,200, filed Dec. 21, 1999, entitled "HYALURONAN SYNTHASE GENE AND USES THEREOF", now U.S. Pat. No. 6,833,264, issued Dec. 21, 2004; which is a continuation of U.S. Ser. No. 09/178,851, filed Oct. 26, 1998 now abandoned, entitled "HYALURONAN SYNTHASE GENE AND USES THEREOF," now abandoned; the contents of each of which are hereby expressly incorporated herein by reference.

STATEMENT REGARDING FEDERALLY SPONSORED RESEARCH OR DEVELOPMENT

This application was supported in part by a grant from the National Institutes of Health (GM35978). The United States Government may have rights in and to this application by virtue of this funding.

BACKGROUND OF THE INVENTION

1. Field of the Invention

The present invention relates to nucleic acid segments having coding regions encoding enzymatically active hyaluronate synthase (HAS), and to the use of these nucleic acid segments in the preparation of recombinant cells which produce hyaluronate synthase and its hyaluronic acid product. Hyaluronate is also known as hyaluronic acid or hyaluronan. More particularly, but not by way of limitation, the nucleic acid segments disclosed and claimed herein have at least one mutation as compared to the native nucleic acid segements such that the at least one mutation results in kinetic or enzymatic changes/modifications to the resulting enzyme.

2. Brief Description of the Related Art

The incidence of streptococcal infections is a major health and economic problem worldwide, particularly in developing countries. One reason for this is due to the ability of Streptococcal bacteria to grow undetected by the body's phagocytic cells, i.e., macrophages and polymorphonuclear cells (PMNs). These cells are responsible for recognizing and engulfing foreign microorganisms. One effective way the bacteria evades surveillance is by coating themselves with polysaccharide capsules, such as a hyaluronic acid (HA) capsule. The structure of HA is identical in both prokaryotes and eukaryotes.

Since HA is generally nonimmunogenic, the encapsulated bacteria do not elicit an immune response and are therefore not targeted for destruction. Moreover, the capsule exerts an antiphagocytic effect on PMNs in vitro and prevents attachment of Streptococcus to macrophages. Precisely because of this, in Group A and Group C Streptococci, the HA capsules are major virulence factors in natural and experimental infections. Group A Streptococcus are responsible for numerous human diseases including pharyngitis, impetigo, deep tissue infections, rheumatic fever and a toxic shock-like syndrome. The Group C Streptococcus equisimilis is responsible for osteomyelitis, pharyngitis, brain abscesses, and pneumonia.

Structurally, HA is a high molecular weight linear polysaccharide of repeating disaccharide units consisting of N-acetylglucosamine (GlcNAc) and glucuronic acid (GlcUA). The number of repeating disaccharides in an HA molecule can exceed 30,000, a $M_r > 10^7$. HA is the only glycosaminogylcan synthesized by both mammalian and bacterial cells, particularly Groups A and C Streptococci and Type A Pasteurella multocida. These strains make HA which is secreted into the medium as well as HA capsules. The mechanism by which these bacteria synthesize HA is of broad interest medicinally since the production of the HA capsule is a very efficient and clever method that bacteria use to evade surveillance by the immune system. Additionally, organic or inorganic molecules coated with HA have properties allowing them to escape detection and destruction by a host's immune system.

HA is synthesized by mammalian and bacterial cells by the enzyme hyaluronate synthase which has been localized to the plasma membrane. It is believed that the synthesis of HA in these organisms is a multi-step process. Initiation involves binding of an initial precursor, UDP-GlcNAc or UDP-GlcUA. This is followed by elongation which involves alternate addition of the two sugars to the growing oligosaccharide chain. The growing polymer is extruded across the plasma membrane region of the cell and into the extracellular space.

HA has been identified in virtually every tissue in vertebrates and has achieved widespread use in various clinical applications, most notably and appropriately as an intraarticular matrix supplement and in eye surgery. The scientific literature has also shown a transition from the original perception that HA is primarily a passive structural component in the matrix of a few connective tissues and in the capsule of certain strains of bacteria to a recognition that this ubiquitous macromolecule is dynamically involved in many biological processes: from modulating cell migration and differentiation during embryogenesis to regulation of extracellular matrix organization and metabolism to important roles in the complex processes of metastasis, wound healing, and inflammation. Further, it is becoming clear that HA is highly metabolically active and that cells focus much attention on the processes of its synthesis and catabolism. For example, the half-life of HA in tissues ranges from 1 to 3 weeks in cartilage to <1 day in epidermis. HA is also used in numerous technical applications (e.g., lubricating compounds), cosmetics and neutraceuticals.

It is now clear that a single protein utilizes both sugar substrates to synthesize HA, i.e., that HA synthases are single enzymes that have dual catalytic properties. The abbreviation HAS, for HA synthase, has gained widespread support for designating this class of enzymes. Markovitz et al. (1959) successfully characterized the HAS activity from Streptococcus pyogenes and discovered the enzymes's membrane localization and its requirements for sugar nucleotide precursors and $Mg^{2+}$. Prehm (1983) found that elongating HA, made by B6 cells, was digested by hyaluronidase added to the medium and proposed that HAS resides at the plasma membrane. Philipson and Schwartz (1984) also showed that HAS activity cofractionated with plasma membrane markers in mouse oligodendroglioma cells.

HAS assembles high $M_r$ HA that is simultaneously extruded through the membrane into the extracellular space (or to make the cell capsule in the case of bacteria) as glycosaminoglycan synthesis proceeds. This mode of biosynthesis is unique among macromolecules since nucleic acids, proteins, and lipids are synthesized in the nucleus, endoplasmic reticulum/Golgi, cytoplasm, or mitochondria. The extrusion of the growing chain into the extracellular space also allows for unconstrained polymer growth, thereby achieving the exceptionally large size of HA, whereas confinement of synthesis within a Golgi or post-Golgi compartment limits the overall amount or length of the polymers formed. High concentrations of HA within a confined lumen may also create a high viscosity environment that might be deleterious for other organelle functions.

Several studies have attempted to solubilize, identify, and purify HAS from strains of *Streptococci* that make a capsular coat of HA as well as from eukaryotic cells. Although the streptococcal and murine oligodendroglioma enzymes were successfully detergent-solubilized and studied, efforts to purify an active HAS for further study or molecular cloning remained unsuccessful for decades. Prehm and Mausolf (1986) used periodate-oxidized UDP-GlcUA or UDP-GlcNAc to affinity label a protein of ~52 kDa in streptococcal membranes that co-purified with HAS. This led to a report claiming that the Group C streptococcal HAS had been cloned, which was unfortunately erroneous. This study failed to demonstrate expression of an active synthase and may have actually cloned a peptide transporter. Triscott and van de Rijn (1986) used digitonin to solubilize HAS from streptococcal membranes in an active form. Van de Rijn and Drake (1992) selectively radiolabeled three streptococcal membrane proteins of 42, 33, and 27 kDa with 5-azido-UDP-GlcUA and suggested that the 33-kDa protein was HAS. As shown later, however, HAS actually turned out to be the 42-kDa protein.

Despite these efforts, progress in understanding the regulation and mechanisms of HA synthesis was essentially stalled, since there were no molecular probes for HAS mRNA or HAS protein. A major breakthrough occurred in 1993 when DeAngelis et al. (1993a and 1993b) reported the molecular cloning and characterization of the Group A streptococcal gene encoding the protein HasA. This gene was known to be part of an operon required for bacterial HA synthesis, although the function of this protein, which is now designated as spHAS (the *S. pyogenes* HAS), was unknown. spHAS was subsequently proven to be responsible for HA elongation (DeAngelis and Weigel, 1994) and was the first glycosaminoglycan synthase identified and cloned and then successfully expressed. The *S. pyogenes* HA synthesis operon encodes two other proteins. HasB is a UDP-glucose dehydrogenase, which is required to convert UDP-glucose to UDP-GlcUA, one of the substrates for HA synthesis. HasC is a UDP-glucose pyrophosphorylase, which is required to convert glucose 1-phosphate and UTP to UDP-glucose. Co-transfection of both hasA and hasB genes into either acapsular *Streptococcus* strains or *Enteroccus faecalis* conferred them with the ability to synthesize HA and form a capsule. This provided the first strong evidence that spHAS (hasA) was an HA synthase. The spHAS was identified and is disclosed in detail in U.S. Ser. No. 09/146,893, filed Sep. 3, 1998, now U.S. Pat. No.6,455,304, the contents of which are expressly incorporated herein in their entirety by reference.

The elusive HA synthase gene was finally cloned by a transposon mutagenesis approach, in which an acapsular mutant Group A strain was created containing a transposon interruption of the HA synthesis operon. Known sequences of the transposon allowed the region of the junction with streptococcal DNA to be identified and then cloned from wild-type cells. The encoded spHAS was 5–10% identical to a family of yeast chitin syntheses and 30% identical to the *Xenopus laevis* protein DG42 whose function was unknown at the time (developmentally expressed during gastrulation), DeAngelis, et al. 1994. DeAngelis and Weigel (1994) expressed the active recombinant spHAS in *Escherichia coli* and showed that this single purified gene product synthesizes high $M_r$ HA when incubated in vitro with UDP-GlcUA and UDP-GlcNAc, thereby showing that both glycosyltransferase activities required for HA synthesis are catalyzed by the same protein, as first proposed in 1959. Utilizing the knowledge that (i) spHAS was a dual action single enzyme and (ii) the areas of sequence homology between the spHAS, chitin synthase, and DG42, the almost simultaneous identification of eukaryotic HAS cDNAs in 1996 by four laboratories, further strengthened the inventor's protein hypothesis that HAS is a multigene family encoding distinct isozymes. Two genes (HAS1 and HAS2) were quickly discovered in mammals, and a third gene HAS3 was later discovered. A second streptococcal seHAS or *Streptococcus equisimilis* hyaluronate synthase, was identified and is disclosed in detail in U.S. Ser. No. 09/469,200, filed Dec. 21, 1999, the contents of which are expressly incorporated herein in their entirety by reference. The seHAS protein has a high level of identity (approximately 70 percent) to the spHAS enzyme. This identity, however, is interesting because the seHAS gene does not cross-hybridize to the spHAS gene.

Membranes prepared from *E. coli* expressing recombinant seHAS synthesize HA when both substrates are provided. The results confirm that the earlier report of Lansing et al. (1993) claiming to have cloned the Group C HAS was wrong. Unfortunately, several studies have employed antibodies to this uncharacterized 52-kDa streptococcal protein to investigate what was believed to be eukaryotic HAS.

Itano and Kimata (1996a) used expression cloning in a mutant mouse mammary carcinoma cell line, unable to synthesize HA, to clone the first putative mammalian HAS cDNA (mmHAS1). Subclones defective in HA synthesis fell into three separate classes that were complementary for HA synthesis in somatic cell fusion experiments, suggesting that at least three proteins are required. Two of these classes maintained some HA synthetic activity, whereas one showed none. The latter cell line was used in transient transfection experiments with cDNA prepared from the parental cells to identify a single protein that restored HA synthetic activity. Sequence analyses revealed a deduced primary structure for a protein of ~65 kDa with a predicted membrane topology similar to that of spHAS. mmHAS1 is 30% identical to spHAS and 55% identical to DG42. The same month this report appeared, three other groups submitted papers describing cDNAs encoding what was initially thought to be the same mouse and human enzyme. However, through an extraordinary circumstance, each of the four laboratories had discovered a separate HAS isozyme in both species.

Using a similar functional cloning approach to that of Itano and Kimata, Shyjan et al. (1996) identified the human homolog of HAS 1. A mesenteric lymph node cDNA library was used to transfect murine mucosal T lymphocytes that were then screened for their ability to adhere in a rosette assay. Adhesion of one transfectant was inhibited by antisera to CD44, a known cell surface HA-binding protein, and was abrogated directly by pretreatment with hyaluronidase. Thus, rosetting by this transfectant required synthesis of HA. Cloning and sequencing of the responsible cDNA identified hsHAS1. Itano and Kimata (1996b) also reported a human HAS1 cDNA isolated from a fetal brain library. The hsHAS1 cDNAs reported by the two groups, however, differ in length; they encode a 578 or a 543 amino acid protein, respectively. HAS activity has only been demonstrated for the longer form.

Based on the molecular identification of spHAS as an authentic HA synthase and regions of near identity among DG42, spHAS, and NodC (a β-GlcNAc transferase nodulation factor in Rhizobium), Spicer et al. (1996) used a degenerate RT-PCR approach to clone a mouse embryo cDNA encoding a second distinct enzyme, which is designated mmHAS2. Transfection of mmHAS2 cDNA into COS cells directed de novo production of an HA cell coat detected by a particle exclusion assay, thereby providing strong evidence that the HAS2 protein can synthesize HA. Using a similar approach, Watanabe and Yamaguchi (1996) screened a human fetal brain cDNA library to identify hsHAS2. Fulop et al. independently used a similar strategy to identify mmHAS2 in RNA isolated from ovarian cumulus cells actively synthesizing HA, a critical process for normal cumulus oophorus expansion in the pre-ovulatory follicle. Cumulus cell-oocyte complexes were isolated from mice immediately after initiating an ovulatory cycle, before HA synthesis begins, and at later times when HA synthesis is just beginning (3 h) or already apparent (4 h). RT-PCR showed that HAS2 mRNA was absent initially but expressed at high levels 3–4 h later suggesting that transcription of HAS2 regulates HA synthesis in this process. Both hsHAS2 are 552 amino acids in length and are 98% identical. mmHAS1 is 583 amino acids long and 95% identical to hsHAS1, which is 578 amino acids long.

Most recently Spicer et al. (1998) used a PCR approach to identify a third HAS gene in mammals. The mmHAS3 protein is 554 amino acids long and 71, 56, and 28% identical, respectively, to mmHAS1, mmHAS2, DG42, and spHAS. Spicer et al. have also localized the three human and mouse genes to three different chromosomes (HAS1 to hsChr 19/mmChr 17; HAS2 to hsChr 8/mmChr 15; HAS3 to hsChr 16/mmChr 8). Localization of the three HAS genes on different chromosomes and the appearance of HA throughout the vertebrate class suggest that this gene family is ancient and that isozymes appeared by duplication early in the evolution of vertebrates. The high identity (~30%) between the bacterial and eukaryotic HASs also suggests that the two had a common ancestral gene. Perhaps primitive bacteria usurped the HAS gene from an early vertebrate ancestor before the eukaryotic gene products became larger and more complex. Alternatively, the bacteria could have obtained a larger vertebrate HAS gene and deleted regulatory sequences nonessential for enzyme activity.

The discovery of X. laevis DG42 by Dawid and co-workers played a significant role in these recent developments, even though this protein was not known to be an HA synthase. Nonetheless, that DG42 and spHAS were 30% identical was critical for designing oligonucleotides that allowed identification of mammalian HAS2. Ironically, definitive evidence that DG42 is a bona fide HA synthase was reported only after the discoveries of the Mammalian isozymes, when DeAngelis and Achyuthan (1996) expressed the recombinant protein in yeast (an organism that cannot synthesize HA) and showed that it synthesizes HA when isolated membranes are provided with the two substrates. Meyer and Kreil (1996) also showed that lysates from cells transfected with cDNA for DG42 synthesize elevated levels of HA. Now that its function is known, DG42 can, therefore, be designated xlHAS.

There are common predicted structural features shared by all the HAS proteins, including a large central domain and clusters of 2–3 transmembrane or membrane-associated domains at both the amino and carboxyl ends of the protein. The central domain, which comprises up to ~88% of the predicted intracellular HAS protein sequences, probably contains the catalytic regions of the enzyme. This predicted central domain is 264 amino acids long in spHAS (63% of the total protein) and 307–328 residues long in the eukaryotic HAS members (54–56% of the total protein). The exact number and orientation of membrane domains and the topological organization of extracellular and intracellular loops has been determined experimentally for spHAS and will be described in detail herein with respect to FIG. 14.

spHAS is a HAS family member that has been purified and partially characterized. Initial studies using spHAS/alkaline phosphatase fusion proteins indicate that the N terminus, C terminus, and the large central domain of spHAS are, in fact, inside the cell. spHAS has 6 cysteines, whereas HAS1, HAS2, and HAS3 have 13, 14 and 14 Cys residues, respectively. Two of the 6 Cys residues in spHAS are conserved and identical in HAS1 and HAS2. Only one conserved Cys residue is found at the same position (Cys-225 in spHAS) in all the HAS family members. This may be an essential Cys whose modification by sulfhydryl poisons partially inhibits enzyme activity. The possible presence of disulfide bonds or the identification of critical Cys residues needed for any of the multiple HAS functions noted below has not yet been elucidated for any members of the HAS family.

In addition to the proposed unique mode of synthesis at the plasma membrane, the HAS enzyme family is highly unusual in the large number of functions required for the overall polymerization of HA. At least six discrete activities are present within the HAS enzyme: binding sites for each of the two different sugar nucleotide precursors (UDP-GlcNAc and UDP-GlcUA), two different glycosyltransferase activities, one or more binding sites that anchor the growing HA polymer to the enzyme (perhaps related to a B—$X_7$—B motif), and a ratchet-like transfer mechanism that moves the growing polymer one or two sugars at a time. This later activity is likely coincident with the stepwise advance of the polymer through the membrane. All of these functions, and perhaps others as yet unknown, are present in a relatively small protein ranging in size from 417 (seHAS) to 588 (xlHAS) amino acids.

Although all the available evidence supports the conclusion that only the spHAS protein is required for HA biosynthesis in bacteria or in vitro, it is possible that the larger eukaryotic HAS family members are part of multicomponent complexes. Since the eukaryotic HAS proteins are ~40% larger than spHAS, their additional protein domains could be involved in more elaborate functions, such as intracellular trafficking and localization, regulation of enzyme activity, and mediating interactions with other cellular components.

The unexpected finding that there are multiple vertebrate HAS genes encoding different synthases strongly supports the emerging consensus that HA is an important regulator of cell behavior and not simply a structural component in tissues. Thus, in less than six months, the field moved from one known, cloned HAS (spHAS) to recognition of a multigene family that promises rapid, numerous, and exciting future advances in our understanding of the synthesis and biology of HA.

For example, disclosed herein are the nucleotide sequences of HAS genes as well as the amino acid sequences encoded therein from *Streptococcus equisimilis* (SEQ ID NOS: 1 and 2, respectively), *Streptococcus pyogenes* (SEQ ID NOS:3 and 4, respectively), *Streptococcus uberis* (SEQ ID NOS:5 and 6, respectively), *Pasteurella multocida* (SEQ ID NOS:7 and 8, respectively), *Xenopus laevis* (SEQ ID NOS:9 and 10, respectively), *Paramecium bursaria* Chlorella virus (PBCV-1; SEQ ID NOS:11 and 12, respectively), and *Sulfolobus solfataricus* (SEQ ID NOS:13 and 14, respectively). The presence of hyaluronan synthase in these systems and the purification and use of the hyaluronan synthase from these different systems indicates an ability to purify and isolate nucleic acid sequences encoding enzymatically active hyaluronan synthase in many different prokaryotic and viral sources, indeed, from microbial sources in general.

Group C *Streptococcus equisimilis* strain D181 synthesizes and secretes hyaluronic acid (HA). Investigators have used this strain and Group A *Streptococcus pyogenes* strains, such as S43 and A111, to study the biosynthesis of HA and to characterize the HA-synthesizing activity in terms of its divalent cation requirement, precursor (UDP-GlcNAc and UDP-GlcUA) utilization, and optimum pH.

Traditionally, HA has been prepared commercially by isolation from either rooster combs or extracellular media from Streptococcal cultures. One method which has been developed for preparing HA is through the use of cultures of HA-producing Streptococcal bacteria. U.S. Pat. No. 4,517,295, the contents of which are herein incorporated by reference in their entirety, describes such a procedure wherein HA-producing *Streptococci* are fermented under anaerobic conditions in a $CO_2$-enriched growth medium. Under these conditions, HA is produced and can be extracted from the broth. It is generally felt that isolation of HA from rooster combs is laborious and difficult, since one starts with HA in a less pure state. The advantage of isolation from rooster combs is that the HA produced is of higher molecular weight. However, preparation of HA by bacterial fermentation is easier, since the HA is of higher purity to start with. Usually, however, the molecular weight of HA produced in this way is smaller than that from rooster combs. Additionally, HA prepared by Streptococcal fermentation oftentimes elicits immune responses as does HA obtained from rooster combs. Therefore, a technique that allows for the production of high molecular weight HA by bacterial fermentation would be a distinct improvement over existing procedures.

As mentioned previously, high molecular weight HA has a wide variety of useful applications—ranging from cosmetics to eye surgery. Due to its potential for high viscosity and its high biocompatibility, HA finds particular application in eye surgery as a replacement for vitreous fluid. HA has also been used to treat racehorses for traumatic arthritis by intra-articular injections of HA, in shaving cream as a lubricant, and in a variety of cosmetic products due to its physiochemical properties of high viscosity and its ability to retain moisture for long periods of time. In fact, in August of 1997 the U.S. Food and Drug Agency approved the use of high molecular weight HA in the treatment of severe arthritis through the injection of such high molecular weight HA directly into the affected joints. In general, the higher the molecular weight of HA that is employed the better. This is because HA solution viscosity increases with the average molecular weight of the individual HA polymer molecules in the solution. Unfortunately, very high molecular weight HA, such as that ranging up to $10^7$, has been difficult to obtain by currently available isolation procedures. The recombinant methods of production disclosed herein, however, allow for the production of HA having an average molecular mass of up to $10^7$ and greater.

To address these or other difficulties, there is a need for new methods and constructs that can be used to produce HA having one or more improved properties such as greater purity, ease of preparation or desired product size. In particular, there is a need to develop methodology for the production of larger amounts of relatively high molecular weight and relatively pure HA than is currently commercially available. There is yet another need to be able to develop methodology for the production of HA having a modified size distribution ($HA_{\Delta size}$) as well as HA having a modified structure ($HA_{\Delta mod}$).

Although the streptococcal HA synthases are relatively small at <49 kDa, they mediate at least six discrete functions: the ability to bind two different sugar nucleotide precursors, to catalyze two distinct glycosyltransferase reactions, to bind the HA acceptor polymer and to translocate the growing HA chain through the enzyme and the cell membrane.

All recombinant HASs, either from vertebrates or prokaryotes, have been shown to synthesize high molecular weight HA in vitro. The class I HAS proteins likely have essentially identical topological organizations in their N-terminal regions, which are highly homologous with spHAS, the only HAS whose membrane topology has been determined experimentally.

There are six Cys residues in spHAS, four of which are conserved perfectly in seHAS and suHAS (FIG. 1); both of these latter enzymes have only four Cys residues (Kumari and Weigel, 1997; Ward et al., 2001). These four Cys residues in turn are generally conserved among the three vertebrate HAS isoenzymes (Weigel et al., 1997, and FIG. 1). However, to date the involvement of one or more of these conserved Cys residues in enzyme activity or disulfide bond formation has not been determined.

The present invention addresses one or more shortcomings in the art. Using recombinant DNA technology, methods of producing enzymatically active HAS having at least one mutation therein (as compared to the native enzyme) is disclosed and claimed in conjunction with the preparation of recombinant cells which produce HAS and its hyaluronic acid product.

BRIEF SUMMARY OF THE INVENTION

The present invention involves the application of recombinant DNA technology to solving one or more problems in the art of hyaluronic acid (HA) preparation. These problems are addressed through the isolation and use of a nucleic acid segment having a coding region encoding an enzymatically active hyaluronate synthase (HAS) gene, a gene responsible for HA chain biosynthesis, such as a HAS gene from Group A or C *Streptococcus, Pasteurella multocida, Sulfolobus solfataricus, Xenopus laevis* and *Ectocarpus siliculosus* virus. The HAS genes disclosed herein were cloned from DNA of an appropriate microbial source and one or more mutations were engineered therein to provide HAS enzymes with novel or modified kinetic or enzymatic activities.

The terms "hyaluronic acid synthase", "hyaluronate synthase", "hyaluronan synthase" and "HA synthase", are used interchangeably herein to describe an enzyme that polymerizes a glycosaminoglycan polysaccharide chain composed of alternating glucuronic acid and N-acetylglucosamine sugars, β1,3 and β1,4 linked. The term "seHAS", for example, describes the HAS enzyme derived from *Streptococcus equisimilis*, wherein expression of the gene encoding the seHAS enzyme correlates with virulence of Streptococcal Group A and Group C strains by providing a means of escaping phagocytosis and immune surveillance.

SUMMARY OF INVENTION

The present invention is directed to a functionally active hyaluronan synthase having at least one modified amino acid residue therein as compared to a corresponding functionally active native hyaluronan synthase. The term "modified amino acid residue" as used herein will be understood to include mutated amino acid residues as well as other modifications to amino acid residues, including but not limited to post-translational modifications of the amino acid residue, such as phosphorylations, glycosylations, methylations, prenylations, and the like. When the amino acid residue is modified by mutation, the mutation may arise by random mutagenesis or targeted or "site directed" mutagenic techniques. For example, it may be desired to target a specific amino acid residue of the hyaluronan synthase to determine if a specific property of enzyme is affected. In particular, it may be desired to target one or more Cysteines of the hyaluronan synthase to determine its involvement in disulfide bond formation or enzymatic activity of the hyaluronan synthase. Alternatively, one may randomly mutagenize the gene encoding hyaluronan synthase and then screen or select for hyaluronan synthase mutants that produce altered amounts of HA as compared with the corresponding wild type HAS (that is, larger or smaller amounts of HA), or for hyaluronan synthase mutants that produce HA having an altered size as compared with HA produced by the corresponding wild type HAS (i.e., larger or smaller HA), without regard for the amino acid(s) that are mutated.

In one embodiment of the present invention, the corresponding functionally active hyaluronan synthase is selected from the group consisting of spHAS, seHAS, suHAS, and pmHAS. The corresponding functionally active hyaluronan synthase may have an amino acid sequence essentially as set forth in at least one of SEQ ID NOs:2, 4, 6, 8, 10, 12 and 14.

In another embodiment of the present invention, at least one of the modified target amino acid residues is a cysteine and thereafter is modified to an alanine or serine residue. In a different embodiment, the functionally active hyaluronan synthase having at least one modified target amino acid residue therein has an amino acid sequence comprising at least one SEQ ID Nos:15–92.

Additionally, the present invention relates to a functionally active hyaluronan synthase having an altered enzymatic activity as compared to a corresponding functionally active native hyaluronan synthase. The term "altered enzymatic activity" as defined herein will be understood to refer to increased or decreased enzymatic activities, or activities that are enzymatically faster or slower than the native enzyme. In addition, the term "altered enzymatic activity" as used herein will also be understood to include enzymes that produce HA products having an altered size, that is, an HA polymer that has a an average molecular mass that is greater or less than the average molecular mass of an HA polymer produced by the native enzyme.

In a different embodiment of the present invention, the functionally active hyaluronan synthase having an altered enzymatic activity is selected from the group consisting of spHAS, seHAS, suHAS and pmHAS and has at least one modified target amino acid residue therein as compared to a corresponding functionally active native hyaluronan synthase. Further, in this embodiment of the invention, at least one of the modified target amino acid residues is a cysteine. The at least one modified target amino acid residue is modified to an alanine or a serine residue. Further, the functionally active hyaluronan synthase having at least one modified target amino acid residue therein has an amino acid sequence essentially as set forth in at least one of SEQ ID NOs:15–92.

Additionally, the present invention relates to a host cell having a functionally active hyaluronan synthase having an altered enzymatic activity as compared to a corresponding functionally active native hyaluronan synthase incorporated therein such that the host cell is capable of producing hyaluronan. In a separate embodiment of the present invention, the functionally active hyaluronan synthase having an altered enzyme activity is selected from the group consisting of spHAS, seHAS, suHAS, and pmHAS. Further, the functionally active hyaluronan synthase has at least one modified target amino acid therein as compared to a corresponding functionally active native hyaluronan synthase. The at least one modified target amino acid residue is a cysteine and thereafter is modified to an alanine or a serine residue. The functionally active hyaluronan synthase has an amino acid sequence essentially as set forth in at least one of SEQ ID NOs:15–92.

Further, the present invention relates to a functionally active hyaluronan synthase having an amino acid sequence comprising SEQ ID NOs:15–92. Also, the present invention relates to a functionally active hyaluronan synthase having an amino acid sequence as essentially set forth in SEQ ID NOs:15–92. Moreover, the present invention is directed to a method of providing a functionally active hyaluronan synthase having an altered enzymatic activity as compared to a corresponding functionally active native hyaluronan synthase. The method includes providing a hyaluronan synthase and modifying at least one target amino acid residue of the hyaluronan synthase to provide a functionally active hyaluronan synthase having an altered enzymatic activity.

In a separate embodiment of the present invention, the hyaluronan synthase is selected from the group consisting of spHAS, seHAS, suHAS, and pmHAS and the at least one modified target amino acid residue is a cysteine. The target amino acid residue may thereafter be modified to an alanine or serine residue or any other desired residue. The functionally active hyaluronan synthase having an altered enzymatic activity has an amino acid sequence essentially as set forth in at least one of SEQ ID NOs:15–92.

In addition, the present invention is related to a method for producing hyaluronic acid. The method includes providing a host cell having at least one expression construct comprising a hyaluronan synthase gene encoding a functionally active hyaluronan synthase incorporated therein such that the host cell is capable of producing hyaluronan, wherein the functionally active hyaluronan synthase has an altered enzymatic activity as compared to a corresponding functionally active native hyaluronan synthase. The host cell is then cultured under conditions appropriate for the production of hyaluronic acid. The method may further include separating the hyaluronic acid from the host cell. The altered enzymatic activity of the functionally active hyaluronan synthase may be an increased or decreased enzymatic activity, or the hyaluronan synthase may produce hyaluronic acid having an average molecular mass that is greater than or less than an average molecular mass of hyaluronic acid produced by a corresponding functionally active native hyaluronan synthase.

The corresponding functionally active native hyaluronan synthase may have an amino acid sequence essentially as set forth in at least one of SEQ ID NOs:2, 4, 6, 8, 10, 12 and 14, while the functionally active hyaluronan synthase having an altered enzymatic activity may have an amino acid sequence essentially as set forth in at least one of SEQ ID NOs:15–92.

The functionally active hyaluronan synthase having an altered enzymatic activity may have at least one modified amino acid residue therein as compared to the corresponding functionally active native hyaluronan synthase, and the at least one modified amino acid residue may be a Cysteine that is modified to a Serine or Alanine.

In another embodiment of the method of producing hyaluronic acid, the expression construct may further include at least one gene encoding an enzyme for synthesis of a hyaluronic acid sugar precursor. Optionally, the gene encoding an enzyme for synthesis of a hyaluronic acid sugar precursor may be present on a separate expression construct or may be chromosomally integrated. The enzyme for synthesis of a hyaluronic acid sugar precursor is selected from the group consisting of a pyrophosphorylase, a transferase, a mutase, a dehydrogenase, or an epimerase, capable of producing UDP-GlcNAc or UDP-GlcUA.

In another embodiment of the method of producing hyaluronic acid, at least one biosynthetic pathway gene of a hyaluronic acid sugar precursor or at least one gene encoding an enzyme for synthesis of a hyaluronic acid sugar precursor may be provided, either in the same or different expression construct or chomosomally integrated into the host cell. In a further alternative embodiment of the method of the present invention, the hyaluronic sugar precursors may be expressed in the host cell by endogenous genes of the host cell.

In another embodiment of the method of producing hyaluronic acid, nutrients utilized for a hyaluronic acid sugar precursor biosynthetic pathway or nutrients supplying the hyaluronic acid sugar precursor biosynthetic pathway are fed or supplied to the host cell.

BRIEF DESCRIPTION OF THE SEVERAL VIEWS OF THE DRAWINGS

FIG. 1. General conservation of four cysteines in seHAS within the Class I HAS protein family. The HAS protein sequences (and their accession numbers) shown are: *Streptococcus equisimilis* (seHAS, AAB87874, SEQ ID NO:2); *Streptococcus uberis* (su HAS, CAB46918, SEQ ID NO:6); *Streptococcus pyogenes* (spHAS, AAA17981, SEQ ID NO:4); chicken (ggHAS2, AF106940_1); mouse (mmHAS1, BAA11654; mmHAS2, AAC53309; mmHAS3, AAC53128); human (hsHAS1, NP_001514; hsHAS2, NP_005319; hsHAS3, AF232772_1); rabbit (ocHAS2, BAB63264; ocHAS3, BAB63265); bovine (btHAS2, CAA06239); rat (rnHAS2, NP_037285); chlorella virus (cvHAS2, AF113757_1) and frog (xlHAS1, AF106940). The sequences were aligned using the DNAsis multiple alignment program (v4.0). Cys residues including the four in seHAS that are conserved in all three streptococcal enzymes, are in boldface. The bars highlight the sequence regions of these four conserved Cys residues within the larger HAS family. Residues that are identical in the three HASs and in some of the other family members are highlighted in dark gray. Residues in seHAS conserved among all other HAS family members are highlighted in light gray. Conserved residues that are within the active sites of all β-glycosyltransferases are indicated by a dot.

FIG. 2. Effect of NEM concentration and incubation time on the activity of seHAS and spHAS. Panel A: *E. coli* membranes containing recombinant seHAS or spHAS were incubated at 4° C. for 1 h with Phosphate Buffered Saline (PBS) alone (minus N-ethylmaleimide (NEM) control) or PBS containing different concentrations of NEM. The unreacted NEM was quenched by addition of dithioerythritol (DTE) to a final concentration of 1–6 mM and the samples were assayed for HAS activity as described hereinafter. Panel B: The effect of incubation time on seHAS and spHAS activity was assessed by incubating the membranes with 5 mM NEM at 4° C. for the indicated times. Aliquots were removed into assay buffer containing 5 mM DTE, and HAS activities were determined. HAS activity in control untreated membranes was stable for 1 h at 4° C. The inhibition of HAS activity is expressed as percent relative to the controls.

FIG. 16 is described hereinafter in detail.

DETAILED DESCRIPTION OF THE INVENTION

Figure 3:
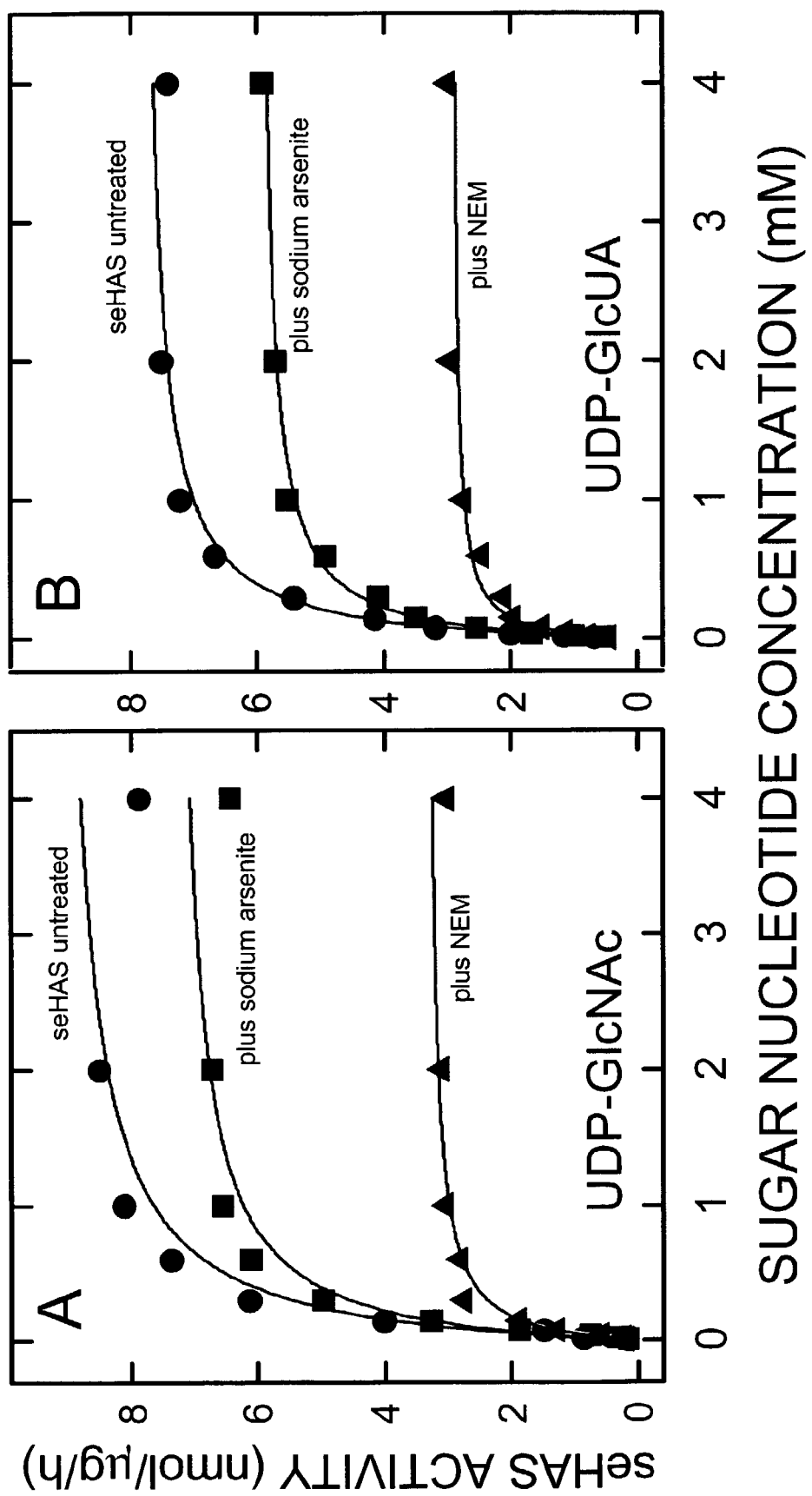
FIG. 3. Effect of NEM or sodium arsenite treatment on the utilization of UDP-GlcUA and UDP-GlcNAc by wild-type seHAS. *E. coli* membranes containing seHAS protein were incubated at 4° C. for 1 h in PBS containing 5 mM NEM or 10 mM Sodium Arsenite (SodArs), and the control membranes were incubated with PBS alone. Michaelis-Menten constants ($K_m$) were calculated from the activities of seHAS at varying concentrations of UDP-GlcUA or UDP-GlcNAc.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

As used herein, the term "nucleic acid segment" and "DNA segment" are used interchangeably and refer to a DNA molecule which has been isolated free of total genomic DNA of a particular species. Therefore, a "purified" DNA or nucleic acid segment as used herein, refers to a DNA segment which contains a Hyaluronate Synthase ("HAS") coding sequence yet is isolated away from, or purified free from, unrelated genomic DNA of the source cell. Included within the term "DNA segment" are DNA segments and smaller fragments of such segments and also recombinant vectors, including, for example, plasmids, cosmids, phage, viruses, and the like.

Similarly, a DNA segment comprising an isolated or purified HAS gene refers to a DNA segment including HAS coding sequences isolated substantially away from other naturally occurring genes or protein encoding sequences. In this respect, the term "gene" is used for simplicity to refer to a functional protein, polypeptide or peptide encoding unit. As will be understood by those in the art, this functional term includes genomic sequences, cDNA sequences or combinations thereof. "Isolated substantially away from other coding sequences" means that the gene of interest, in this case HAS, forms the significant part of the coding region of the DNA segment, and that the DNA segment does not contain large portions of naturally-occurring coding DNA, such as large chromosomal fragments or other functional genes or DNA coding regions. Of course, this refers to the DNA segment as originally isolated, and does not exclude genes or coding regions later added to, or intentionally left in, the segment by the hand of man.

Due to certain advantages associated with the use of prokaryotic sources, one will likely realize the most advantages upon isolation of the HAS gene from prokaryotes. In particular, one may choose to utilize a Class I or Class II HAS, such as a Class I HAS from *S. equisimilis* or *S. pyogenes*, or a Class II HAS from *P. multocida*.

*Streptococcus* is subdivided taxonomically into Lancefield Groups based on different cell wall carbohydrate antigens. There are 18 distinct groups, but the most common pathogens are A, B, C and D. Historically, the most common pathogens are also often given specific species names, but the unified Lancefield testing method is recognized as being a clear method of typing and thus a useful classification scheme. *Streptococcus* species that may be utilized as the source of the HAS gene include Group A *Streptococcus*, such as *S. pyogenes* and *S. haemolyticus*, and Group C *Streptococcus*, such as *S. equi, S. equisimilis, S. zooepidemicus, S. uberis* and *S. dysgalactiae*.

One such advantage of isolating the HAS gene from prokaryotes is that, typically, eukaryotic enzymes may require significant post-translational modifications that can only be achieved in a eukaryotic host. This will tend to limit the applicability of any eukaryotic HA synthase gene that is obtained. Moreover, those of ordinary skill in the art will likely realize additional advantages in terms of time and ease of genetic manipulation where a prokaryotic enzyme gene is sought to be employed. These additional advantages include (a) the ease of isolation of a prokaryotic gene because of the relatively small size of the genome and, therefore, the reduced amount of screening of the corresponding genomic library, and (b) the ease of manipulation because the overall size of the coding region of a prokaryotic gene is significantly smaller due to the absence of introns. Furthermore, if the product of the HAS gene (i.e., the enzyme) requires posttranslational modifications, these would best be achieved in a similar prokaryotic cellular environment (host) from which the gene was derived.

Preferably, DNA sequences in accordance with the present invention will further include genetic control regions which allow the expression of the sequence in a selected recombinant host. Of course, the nature of the control region employed will generally vary depending on the particular use (e.g., cloning host) envisioned.

In particular embodiments, the invention concerns isolated DNA segments and recombinant vectors incorporating DNA sequences which encode a HAS gene, that includes within its amino acid sequence an amino acid sequence in accordance with at least one of SEQ ID NOs:2, 4, 6, 8, 10, 12 and 14–92. Moreover, in other particular embodiments, the invention concerns isolated DNA segments and recombinant vectors incorporating DNA sequences which encode a gene that includes within its amino acid sequence the amino acid sequence of a HAS gene or DNA, and in particular to a HAS gene or cDNA, corresponding to at least one of *Streptococcus equisimilis* HAS, *Streptococcus pyogenes* HAS, *Streptococcus uberis* HAS, *Pasteurella multocida* HAS, *Xenopus laevis* HAS, and *Sulfolobus solfataricus* HAS. For example, where the DNA segment or vector encodes a full length HAS protein, or is intended for use in expressing the HAS protein, preferred sequences are those which are essentially as set forth in at least one of SEQ ID NOs:2, 4, 6, 8, 10, 12 and 14–92.

Nucleic acid segments having HA synthase activity may be isolated by the methods described herein. The term "a sequence essentially as set forth in SEQ ID NO:X" or "a sequence as set forth in SEQ ID NO:X" means that the sequence substantially corresponds to a portion of SEQ ID NO:X and has relatively few amino acids which are not identical to, or a biologically functional equivalent of, the amino acids of SEQ ID NO:X. The term "biologically functional equivalent" is well understood in the art and is further defined in detail herein, as a gene having a sequence essentially as set forth in SEQ ID NO:X or comprising SEQ ID NO:X, and that is associated with the ability of prokaryotes or eukaryotes to produce HA or a hyaluronic acid coat.

For instance, the seHAS and spHAS coding sequences are approximately 70% identical and rich in the bases adenine (A) and thymine (T). SeHAS base content is A-26.71%, C-19.13%, G-20.81%, and T-33.33% (A/T=60%), whereas spHAS is A-31.34%, C-16.42%, G-16.34%, and T-35.8% (A/T=67%). Those of ordinary skill in the art would be surprised that the seHAS coding sequence does not hybridize with the spHAS gene and vice versa, despite their being 70% identical. This unexpected inability to cross-hybridize could be due to short interruptions of mismatched bases throughout the open reading frames. The longest stretch of identical nucleotides common to both the seHAS and the spHAS coding sequences is only 20 nucleotides. In addition, the very A–T rich sequences will form less stable hybridization complexes than G–C rich sequences. Another possible explanation could be that there are several stretches of As or Ts in both sequences that could hybridize in a misaligned and unstable manner. This would put the seHAS and spHAS gene sequences out of frame with respect to each other, thereby decreasing the probability of productive hybridization.

Because of this unique phenomena of two genes encoding proteins which are 70% identical not being capable of cross-hybridizing to one another, it is beneficial to think of the claimed nucleic acid segment in terms of its function; i.e. a nucleic acid segment which encodes enzymatically active hyaluronate synthase. One of ordinary skill in the art would appreciate that a nucleic acid segment encoding enzymatically active hyaluronate synthase may contain conserved or semi-conserved substitutions to the sequences set forth in SEQ ID NOs:2, 4, 6, 8, 10, 12 and 14–92, and yet still be within the scope of the invention.

In particular, the art is replete with examples of practitioners ability to make structural changes to a nucleic acid segment (i.e. encoding conserved or semi-conserved amino acid substitutions) and still preserve its enzymatic or functional activity. See for example: (1) Risler et al. "Amino Acid Substitutions in Structurally Related Proteins. A Pattern Recognition Approach." J. Mol. Biol. 204:1019–1029 (1988); (2) Niefind et al. "Amino Acid Similarity Coefficients for Protein Modeling and Sequence Alignment Derived from Main-Chain Folding Anoles." J. Mol. Biol. 219:481–497 (1991) [similarity parameters allow amino acid substitutions to be designed]; and (3) Overington et al. "Environment-Specific Amino Acid Substitution Tables: Tertiary Templates and Prediction of Protein Folds," Protein Science 1:216–226 (1992) ["Analysis of the pattern of observed substitutions as a function of local environment shows that there are distinct patterns . . . " Compatible changes can be made.], the contents of each being expressly incorporated herein by reference in their entirety.

These references and countless others indicate that one of ordinary skill in the art, given a nucleic acid sequence, could make substitutions and changes to the nucleic acid sequence without changing its functionality. Also, a substituted nucleic acid segment may be highly identical and retain its enzymatic activity with regard to its unadulterated parent, and yet still fail to hybridize thereto.

The invention discloses nucleic acid segments encoding enzymatically active hyaluronate syntheses, such as seHAS, spHAS, suHAS, xlHAS and pmHAS. Although seHAS and spHAS are 70% identical and both encode enzymatically active hyaluronate synthase, they do not cross hybridize. Thus, one of ordinary skill in the art would appreciate that substitutions can be made to the HAS nucleic acid segments listed in SEQ ID NOS: 1, 3, 5, 7, 9, 11 and 13 without deviating outside the scope and claims of the present invention. Standardized and accepted functionally equivalent amino acid substitutions are presented in Table I.

TABLE I

| Amino Acid Group | Conservative and Semi-Conservative Substitutions |
|---|---|
| NonPolar R Groups | Alanine, Valine, Leucine, Isoleucine, Proline, Methionine, Phenylalanine, Tryptophan |
| Polar, but uncharged, R Groups | Glycine, Serine, Threonine, Cysteine, Asparagine, Glutamine |
| Negatively Charged R Groups | Aspartic Acid Glutamic Acid |
| Positively Charged R Groups | Lysine, Arginine, Histidine |

Another preferred embodiment of the present invention is a purified nucleic acid segment that encodes a protein in accordance with SEQ ID NOs:2, 4, 6, 8, 10, 12 and 14–92 further defined as a recombinant vector. As used herein, the term "recombinant vector" refers to a vector that has been modified to contain a nucleic acid segment that encodes an HAS protein, or fragment thereof. The recombinant vector may be further defined as an expression vector comprising a promoter operatively linked to said HAS encoding nucleic acid segment.

A further preferred embodiment of the present invention is a host cell, made recombinant with a recombinant vector comprising an HAS gene. The preferred recombinant host cell may be a prokaryotic cell. In another embodiment, the recombinant host cell is a eukaryotic cell. As used herein, the term "engineered" or "recombinant" cell is intended to refer to a cell into which a recombinant gene, such as a gene encoding HAS, has been introduced. Therefore, engineered cells are distinguishable from naturally occurring cells which do not contain a recombinantly introduced gene. Engineered cells are thus cells having a gene or genes introduced through the hand of man. Recombinantly introduced genes will either be in the form of a cDNA gene, a copy of a genomic gene, or will include genes positioned adjacent to a promoter not naturally associated with the particular introduced gene.

The recombinant host cell may further contain at least one gene encoding an enzyme for synthesis of a HA sugar precursor. The HA sugar precursor may be selected from a pyrophosphorylase, a transferase, a mutase, a dehydrogenase, or an epimerase, capable of producing UDP-GlcNAc or UDP-GlcUA, or combinations thereof. The recombinant host cell may further contain a biosynthetic pathway gene of a HA sugar precursor or an enzyme for synthesis of a HA sugar precursor. These one or more genes may be present on the same expression construct as the HAS gene or on separate expression construct. Optionally, these genes may be chromosomally integrated, as described in more detail hereinbelow.

Where one desires to use a host other than *Streptococcus*, as may be used to produce recombinant HA synthase, it may be advantageous to employ a prokaryotic system such as *E. coli* Bacillus strains, *Lactococcus sp.*, or even eukaryotic systems such as yeast or Chinese hamster ovary, African green monkey kidney cells, VERO cells, or the like. Of course, where this is undertaken it will generally be desirable to bring the HA synthase gene under the control of sequences which are functional in the selected alternative host. The appropriate DNA control sequences, as well as their construction and use, are generally well known in the art as discussed in more detail hereinbelow. For example, in a preferred embodiment, the host cell may be a Bacillus cell, such as a *Bacillus subtilis* or *Bacillus licheniformis* cell, and the vector introduced therein contains a Bacillus-compatible promoter to which the has gene is operably linked.

In a more preferred embodiment, the host cell is a *Bacillus* cell, such as *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus metaterium, Bacillus pumilus, Bacillus stearothermophilus, Bacillus subtilis* and *Bacillus thuringiensis*.

In preferred embodiments, the HA synthase-encoding DNA segments further include DNA sequences, known in the art functionally as origins of replication or "replicons", which allow replication of contiguous sequences by the particular host. Such origins allow the preparation of extrachromosomally localized and replicating chimeric segments or plasmids, to which HA synthase DNA sequences are ligated. In more preferred instances, the employed origin is one capable of replication in bacterial hosts suitable for biotechnology applications. However, for more versatility of cloned DNA segments, it may be desirable to alternatively or even additionally employ origins recognized by other host systems whose use is contemplated (such as in a shuttle vector).

The isolation and use of other replication origins such as the SV40, polyoma or bovine papilloma virus origins, which may be employed for cloning or expression in a number of higher organisms, are well known to those of ordinary skill in the art. In certain embodiments, the invention may thus be defined in terms of a recombinant transformation vector which includes the HA synthase coding gene sequence together with an appropriate replication origin and under the control of selected control regions.

Thus, it will be appreciated by those of skill in the art that other means may be used to obtain the HAS gene or cDNA, in light of the present disclosure. For example, polymerase chain reaction or RT-PCR produced DNA fragments may be obtained which contain full complements of genes or cDNAs from a number of sources, including other strains of *Streptococcus*, or from eukaryotic sources, such as cDNA libraries. Virtually any molecular cloning approach may be employed for the generation of DNA fragments in accordance with the present invention. Thus, the only limitation generally on the particular method employed for DNA isolation is that the isolated nucleic acids should encode a biologically functional equivalent HA synthase.

Once the DNA has been isolated, it is ligated together with a selected vector. Virtually any cloning vector can be employed to realize advantages in accordance with the invention. Typical useful vectors include plasmids and phages for use in prokaryotic organisms and even viral vectors for use in eukaryotic organisms. Examples include pKK223-3, pSA3, recombinant lambda, SV40, polyoma, adenovirus, bovine papilloma virus and retroviruses. However, it is believed that particular advantages will ultimately be realized where vectors capable of replication in both *Lactococcus* or *Bacillus* strains and *E. coli* are employed.

Vectors such as these, exemplified by the pSA3 vector of Dao and Ferretti or the pAT19 vector of Trieu-Cuot, et al., allow one to perform clonal colony selection in an easily manipulated host such as *E. coli*, followed by subsequent transfer back into a food grade *Lactococcus* or *Bacillus* strain for production of HA. These are benign and well studied organisms used in the production of certain foods and biotechnology products. These are advantageous in that one can augment the *Lactococcus* or *Bacillus* strain's ability to synthesize HA through gene dosaging (i.e., providing extra copies of the HA synthase gene by amplification) and/or inclusion of additional genes to increase the availability of HA precursors. The inherent ability of a bacterium to synthesize HA can also be augmented through the formation of extra copies, or amplification, of the plasmid that carries the HA synthase gene. This amplification can account for up to a 10-fold increase in plasmid copy number and therefore the HA synthase gene copy number.

Another procedure that would further augment HA synthase gene copy number is the insertion of multiple copies of the gene into the plasmid. Another technique would include integrating the HAS gene and/or the sugar precursor gene(s) into chromosomal DNA. This extra amplification would be especially feasible, since the bacterial HA synthase gene size is small. In some scenarios, the chromosomal DNA-ligated vector is employed to transfect the host that is selected for clonal screening purposes such as *E. coli*, through the use of a vector that is capable of expressing the inserted DNA in the chosen host.

In another preferred embodiment, the HA synthase gene is introduced into the host cell chromosome via homologous or heterologous recombination. The has gene may be more stable in this configuration, especially without drug selection. Various vectors may be employed to introduce the has gene into *Bacillus*, such as pTLH or pKSV7, or into yeast, such as YIp211, or into animal cells, such as pcDNA/FRT. The DNA is first introduced into the host cell by transformation, transduction or electroporation. The DNA segment with the has gene is then stably integrated into the host chromosome. For example, the spHAS gene was used to repair a mutant *Streptococcus* chromosome by transduction and integration; this operation resulted in HA production (DeAngelis et al, 1993a).

Where a eukaryotic source such as dermal or synovial fibroblasts or rooster comb cells is employed, one will desire to proceed initially by preparing a cDNA library. This is carried out first by isolation of mRNA from the above cells, followed by preparation of double stranded cDNA using an enzyme with reverse transcriptase activity and ligation with the selected vector. Numerous possibilities are available and known in the art for the preparation of the double stranded cDNA, and all such techniques are believed to be applicable. A preferred technique involves reverse transcription. Once a population of double stranded cDNAs is obtained, a cDNA library is prepared in the selected host by accepted techniques, such as by ligation into the appropriate vector and amplification in the appropriate host. Due to the high number of clones that are obtained, and the relative ease of screening large numbers of clones by the techniques set forth herein, one may desire to employ phage expression vectors, such as λgt11, λgt12, λGem11, and/or λZAP for the cloning and expression screening of cDNA clones.

In certain other embodiments, the invention concerns isolated DNA segments and recombinant vectors that include within their sequence a nucleic acid sequence essentially as set forth at least one of in SEQ ID NOS:1, 3, 5, 7, 9, 11, 13 or a variant thereof wherein the variant encodes an amino acid sequence essentially as set forth in at least one of SEQ ID NOs:15–92. The term "essentially as set forth in SEQ ID NO:X" or "as set forth in SEQ ID NO:X", for example, is used in the same sense as described hereinabove and means that the nucleic acid sequence substantially corresponds to a portion of SEQ ID NO:X, and has relatively few codons which are not identical, or functionally equivalent, to the codons of SEQ ID NO:X. The term "functionally equivalent codon" is used herein to refer to codons that encode the same amino acid, such as the six codons for arginine or serine, and also refers to codons that encode biologically equivalent amino acids as set forth in Table I.

It will also be understood that amino acid and nucleic acid sequences may include additional residues, such as additional N- or C-terminal amino acids or additional 5' or 3' nucleic acid sequences, and yet still be essentially as set forth in one of the sequences disclosed herein, so long as the, sequence meets the criteria set forth above, including the maintenance of biological protein activity where protein expression and enzyme activity are concerned. The addition of terminal sequences particularly applies to nucleic acid sequences which may, for example, include various non-coding sequences flanking either of the 5' or 3' portions of the coding region or may include various internal sequences, which are known to occur within genes. In particular, the amino acid sequence of the has gene product in eukaryotes appears to be 40% larger than that found in prokaryotes, yet the prokaryotic and eukaryotic HASs display essentially identical enzymologic abilities to synthesize HA.

Allowing for the degeneracy of the genetic code as well as conserved and semi-conserved substitutions, sequences which have between about 40% and about 80%; or more preferably, between about 80% and about 90%; or even more preferably, between about 90% and about 99%; of nucleotides which are identical to the nucleotides of SEQ ID NOS:1, 3, 5, 7, 9, 11, 13 or a variant thereof wherein the variant encodes an amino acid sequence essentially as set forth in at least one of SEQ ID NOs:15–92 will be sequences which are "essentially as set forth in SEQ ID NO:X" or "comprising SEQ ID NO:X". Sequences which are essentially the same as those set forth in SEQ ID NOS:1, 3, 5, 7, 9, 11, 13 or a variant thereof wherein the variant encodes an amino acid sequence essentially as set forth in at-least one of SEQ ID NOs:15–92 may also be functionally defined as sequences which are capable of hybridizing to a nucleic acid segment containing the complement of SEQ ID NOs:1, 3, 5, 7, 9, 11, 13 or a variant thereof wherein the variant encodes an amino acid sequence essentially as set forth in at least one of SEQ ID NOs:15–92 under "standard stringent hybridization conditions," moderately stringent hybridization conditions," "less stringent hybridization conditions," or "low stringency hybridization conditions." Suitable "standard" or "less stringent" hybridization conditions will be well known to those of skill in the art and are clearly set forth hereinbelow. In a preferred embodiment, standard stringent hybridization conditions or less stringent hybridization conditions are utilized.

The terms "standard stringent hybridization conditions," "moderately stringent conditions," and "less stringent hybridization conditions" or "low stringency hybridization conditions" are used herein, describe those conditions under which substantially complementary nucleic acid segments will form standard Watson-Crick base-pairing and thus "hybridize" to one another. A number of factors are known that determine the specificity of binding or hybridization, such as pH; temperature; salt concentration; the presence of agents, such as formamide and dimethyl sulfoxide; the length of the segments that are hybridizing; and the like. There are various protocols for standard hybridization experiments. Depending on the relative similarity of the target DNA and the probe or query DNA, then the hybridization is performed under stringent, moderate, or under low or less stringent conditions.

The hybridizing portion of the hybridizing nucleic acids is typically at least about 14 nucleotides in length, and preferably between about 14 and about 100 nucleotides in length. The hybridizing portion of the hybridizing nucleic acid is at least about 60%, e.g., at least about 80% or at least about 90%, identical to a portion or all of a nucleic acid sequence encoding a HAS or its complement, such as SEQ ID NO: 2 or 4 or the complement thereof. Hybridization of the oligonucleotide probe to a nucleic acid sample typically is performed under standard or stringent hybridization conditions. Nucleic acid duplex or hybrid stability is expressed as the melting temperature or $T_m$, which is the temperature at which a probe nucleic acid sequence dissociates from a target DNA. This melting temperature is used to define the required stringency conditions. If sequences are to be identified that are related and substantially identical to the probe, rather than identical, then it is useful to first establish the lowest temperature at which only homologous hybridization occurs with a particular concentration of salt (e.g., SSC, SSPE, or HPB). Then, assuming that 1% mismatching results in a 1° C. decrease in the $T_m$, the temperature of the final wash in the hybridization reaction is reduced accordingly (for example, if sequences having >95% identity with the probe are sought, the final wash temperature is decreased by about 5° C.). In practice, the change in $T_m$ can be between about 0.5° C. and about 1.5° C. per 1% mismatch. Examples of standard stringent hybridization conditions include hybridizing at about 68° C. in 5×SSC/5× Denhardt's solution/1.0% SDS, followed with washing in 0.2×SSC/0.1% SDS at room temperature or hybridizing in 1.8×HPB at about 30° C. to about 45° C. followed by washing a 0.2–0.5×HPB at about 45° C. Moderately stringent conditions include hybridizing as described above in 5×SSC 5× Denhardt's solution 1% SDS washing in 3×SSC at 42° C. The parameters of salt concentration and temperature can be varied to achieve the optimal level of identity between the probe and the target nucleic acid. Additional guidance regarding such conditions is readily available in the art, for example, by Sambrook et al., 1989, Molecular Cloning, A Laboratory Manual, (Cold Spring Harbor Press, N.Y.); and Ausubel et al. (eds.), 1995, Current Protocols in Molecular Biology, (John Wiley & Sons, N.Y.). Several examples of low stringency protocols include: (A) hybridizing in 5×SSC, 5× Denhardts reagent, 30% formamide at about 30° C. for about 20 hours followed by washing twice in 2×SSC,0.1% SDS at about 30° C. for about 15 min followed by 0.5×SSC, 0.1% SDS at about 30° C. for about 30 min (FEMS Microbiology Letters, 2000, vol. 193, p. 99–103); (B) hybridizing in 5×SSC at about 45° C. overnight followed by washing with 2×SSC, then by 0.7×SSC at about 55° C. (J. Biological Methods, 1990, vol. 30, p. 141–150); or (C) hybridizing in 1.8×HPB at about 30° C. to about 45° C.; followed by washing in 1×HPB at 23° C.

Naturally, the present invention also encompasses DNA segments which are complementary, or essentially complementary, to the sequence set forth in SEQ ID NOs:1, 3, 5, 7, 9, 11, 13 or a variant thereof wherein the variant encodes an amino acid sequence essentially as set forth in at least one of SEQ ID NOs:15–92. Nucleic acid sequences which are "complementary" are those which are capable of base-pairing according to the standard Watson-Crick complementarity rules. As used herein, the term "complementary sequences" means nucleic acid sequences which are substantially complementary, as may be assessed by the same nucleotide comparison set forth above, or as defined as being capable of hybridizing to the nucleic acid segment of SEQ ID NOS:1, 3, 5, 7, 9, 11, 13 or a variant thereof wherein the variant encodes an amino acid sequence essentially as set forth in at least one of SEQ ID NOs:15–92.

The nucleic acid segments of the present invention, regardless of the length of the coding sequence itself, may be combined with other DNA sequences, such as promoters, polyadenylation signals, additional restriction enzyme sites, multiple cloning sites, epitope tags, poly histidine regions, other coding segments, and the like, such that their overall length may vary considerably. It is therefore contemplated that a nucleic acid fragment of almost any length may be employed, with the total length preferably being limited by the ease of preparation and use in the intended recombinant DNA protocol.

Naturally, it will also be understood that this invention is not limited to the particular nucleic acid and amino acid sequences of SEQ ID NOs:1, 3, 5, 7, 9, 11 or 13 (or a variant thereof wherein the variant encodes an amino acid sequence essentially as set forth in at least one of SEQ ID NOs:15–92) and SEQ ID NOS:15–92, respectively. Recombinant vectors and isolated DNA segments may therefore variously include the HAS coding regions themselves, coding regions bearing selected alterations or modifications in the basic coding region, or they may encode larger polypeptides which nevertheless include HAS-coding regions or may encode biologically functional equivalent proteins or peptides which have variant amino acids sequences.

Sulfhydryl Reagents Inhibit the Activity of seHAS and spHAS.

SeHAS is the smallest HAS protein (417 amino acids) and contains four Cys residues. The four cysteines of seHAS are completely conserved among the three prokaryotic HASs (excluding pmHAS) and are conserved positionally among all the vertebrate HASs (FIG. 1). To explore the possible role of cysteines in the function of HAS, the activities of seHAS and spHAS were assayed in the presence of different sulfhydryl reagents (Table II). Almost identical sensitivities were observed for the two enzymes. For example, seHAS activity was inhibited >93% by methylmethanethiosulfonate (0.05 mM) and ~70% by NEM (5 mM), whereas IAA inhibited only 15%. Sodium arsenite and 5,5'-dithiobis-(2-nitrobenzoic acid) also inhibited each HAS activity. These results indicate that one or more Cys residues are important for the overall HA synthesis activity of the seHAS and spHAS proteins. The inhibition of each HAS by NEM was examined in more detail with respect to time of incubation and NEM concentration (FIG. 2). Both seHAS and spHAS were inhibited in a biphasic manner, with respect to incubation time or NEM concentration. Although the extent of inhibition varied from experiment to experiment, a 60–70% effect was typical. About half of the observed inactivation occurred at ≦1 mM NEM, whereas the remaining inactivation occurred from 1–6 mM (FIG. 2A). Kinetically, there was a fast initial inactivation and then a much slower phase of inhibition; again each of the phases involved about half of the affected activity (FIG. 2B).

A potential complication in the above NEM studies is that the effects of a sulfhydryl modifying reagent may be due to secondary effects caused by modification of other molecules in the membranes being tested. Although this possibility is highly unlikely, since seHAS is the only protein necessary for HA biosynthesis, the effect of sulfhydryl reagents on the seHAS Cys-null mutant in isolated membranes was also examined under the conditions shown in FIG. 3.

TABLE II

Effect of different sulfhydryl reagents on seHAS or spHAS activity.

| Sulfhydryl Reagent | Inhibition of HAS Activity (% relative to control) | |
|---|---|---|
| | seHAS | spHAS |
| N-ethylmaleimide | 70 ± 4.8 | 60 ± 3.5 |
| Iodacetic acid | 15 ± 6.0 | 13 ± 5.4 |
| 5,5'-dithiobis-(2-nitrobenzoic acid) | 52 ± 6.5 | 52 ± 4.9 |
| Methylmethanethiosulfonate | 93 ± 5.4 | 89 ± 5.5 |
| Sodium Arsenite | 40 ± 4.0 | 46 ± 5.1 |

*E. coli* membranes expressing the recombinant seHAS-$H_6$ or spHAS-$H_6$ proteins were incubated at 4° C. for 1 h with PBS containing either 5 mM NEM, 5 mM IAA, 0.5 mM 5,5'-dithiobis-(2-nitrobenzoic acid), 0.05 mM methylmethanethiosulfonate, 10 mM sodium arsenite or no addition (control, which was set as 100%). The remaining seHAS activity was then determined in quadruplicate and expressed as % relative to the control. The mean values and standarddeviations are shown.

and Table III). The $K_m$ values for either UDP-GlcNAc (FIG. 3A) or UDP-GlcUA (FIG. 3B) were not altered significantly by treatment with NEM or sodium arsenite, whereas the maximum enzymatic velocity was reduced by up to ~70%.

Effect of Site-Specific Cys Mutagenesis on the HA Synthase Activity of seHAS.

Figure 4:
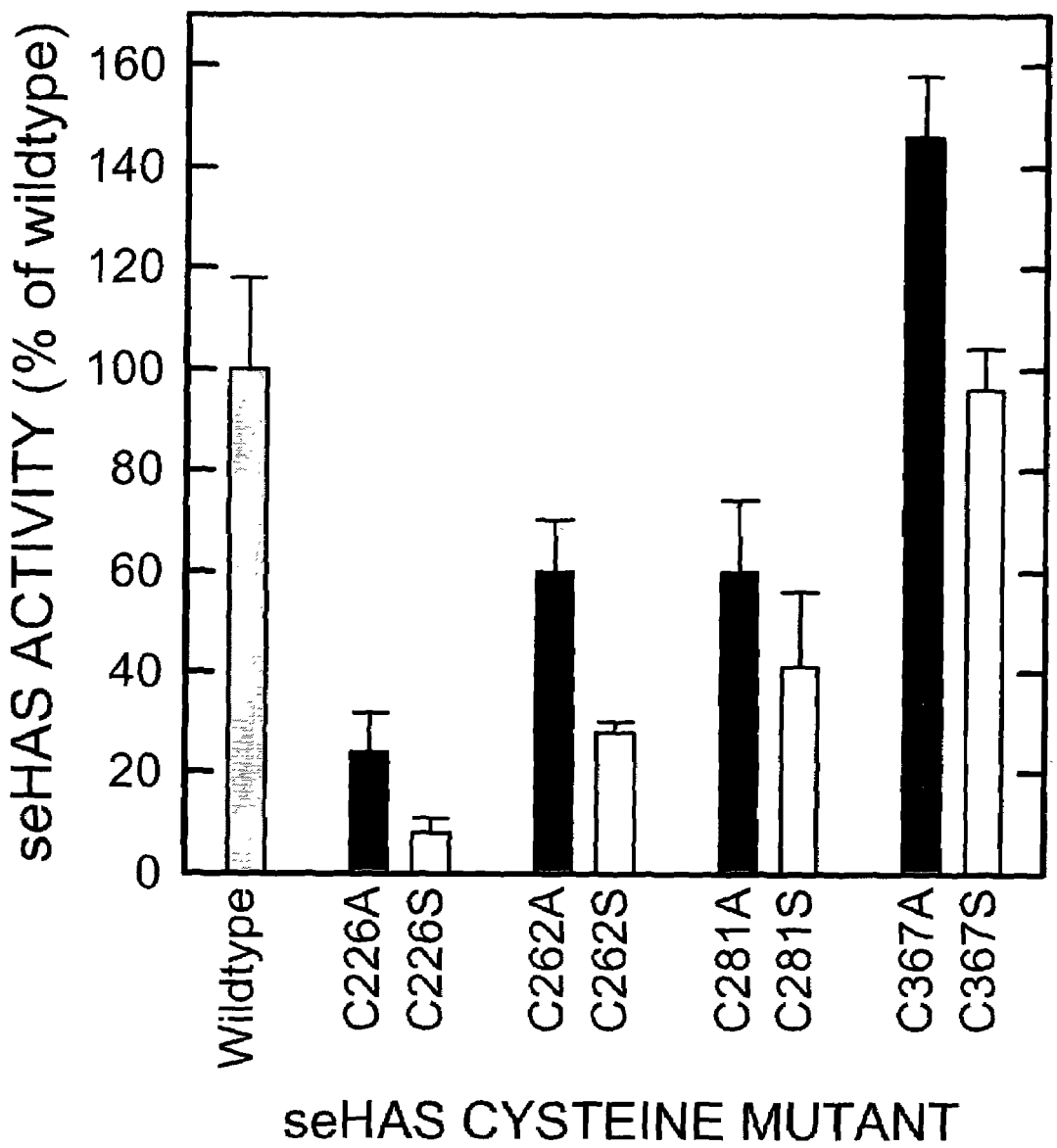
FIG. 4. Relative enzyme activities of the Cys-to-Ala or Cys-to-Ser single Cys-mutants of seHAS. Membranes from *E. coli* (SURE) cells expressing either wild-type seHAS or the indicated single Cys-mutants of seHAS were assayed for HAS activity under linear conditions with respect to time and protein concentration, and the amount of HAS protein expressed in each membrane preparation was determined as described hereinafter. The normalized seHAS specific activities were calculated as nmol of UDP-GlcUA incorporated per pmol of HAS per hour. The specific activities of seHAS mutants are given as a percent relative to wild-type activity as 100%.

Site-specific Cys-to-Ala and Cys-to-Ser mutants of seHAS were made in order to explore the possible functional role of each Cys residue in HAS activity. In all of the following kinetic studies using the wild-type (or native) and mutant seHAS proteins, the data obtained were normalized to the amount of intact seHAS protein as described herein. The single Cys-to-Ala or Cys-to-Ser mutants of seHAS had lower enzyme activities compared to the wild-type enzyme, except for the C367A and C367S variants (FIG. 4 and Table IV). This result indicates that $Cys^{226}$, $Cys^{262}$ and $Cys^{281}$ contribute to the catalytic activity of seHAS. The $K_m$ values for UDP-GlcUA of the C226A and C262A mutants were higher when compared to the corresponding values for the C226S and C262S variants. However, the $K_m$ values for UDP-GlcNAc were not quite as clear-cut. The $K_{UDP-GlcNAc}$ value for the C226S mutant was higher than that of the C226A mutant, whereas the C262A and C281A mutant proteins both had higher $K_{UDP-GlcNAc}$ values compared to the C262S and C281S variants. At the C367 position, similar $K_m$ values for each nucleotide-sugar were obtained for both the Ala and Ser mutants.

From these results it is shown that functional constraints are put on the HAS enzyme by particular alterations of at least one of its Cys residues. Since the C226A and C226S mutants were the least active, $Cys^{226}$ appears to be the most important Cys residue for enzyme activity. The seHAS (C367A) variant was actually more active than wild-type (~145%) and the seHAS(C367S) variant was not significantly altered. In each of the four cases, the Cys-to-Ala change resulted in a variant with greater activity than the

TABLE III

Effect of NEM or sodium arsenite treatment on the utilization of UDP-GlcUA and UDP-GlcNAc by wild-type seHAS

| | UDP-GlcUA | | | UDP-GlcNAc | | |
|---|---|---|---|---|---|---|
| | Control | NEM | Sodium Arsenite | Control | NEM | Sodium Arsenite |
| $K_m$ (μM) | 85 ± 10 | 57 ± 5 | 67 ± 23 | 122 ± 30 | 82 ± 17 | 112 ± 38 |
| $V_{max}$ (nmol/μg/h) | 14.9 ± 3.6 | 7.3 ± 2.2 | 9.5 ± 1.1 | 14.9 ± 3.6 | 7.3 ± 2.2 | 9.5 ± 1.1 |

*E. coli* membranes containing seHAS protein were incubated at 4° C. for 1 h with PBS alone (control) or PBS containing 5 mM NEM or 10 mM sodium arsenite. The activity of seHAS was determined in triplicate with varying concentrations of UDP-GlcUA or UDP-GlcNAc as described in Materials and Methods, and the Michaelis-Menten Constants ($K_m$ and $V_{max}$) ± standard errors were calculated.

The activity of seHAS$^{Cys-null}$ was not affected (≦1%) by treatment with NEM, IAA or sodium arsenite, which eliminates the possibility that modified secondary proteins in the membranes preparations were responsible for the altered HAS activity.

Modification of the protein by NEM could affect any one or several of the six discrete functions that HAS must perform in order to synthesize HA. In order to determine if one of the nucleotide-sugar binding sites was affected by NEM, we examined the UDP-GlcUA and UDP-GlcNAc saturation profiles for treated and untreated seHAS (FIG. 3

Cys-to-Ser change. The least tolerated single Cys change was C226S; this mutant was inhibited >90%.

Figure 5:
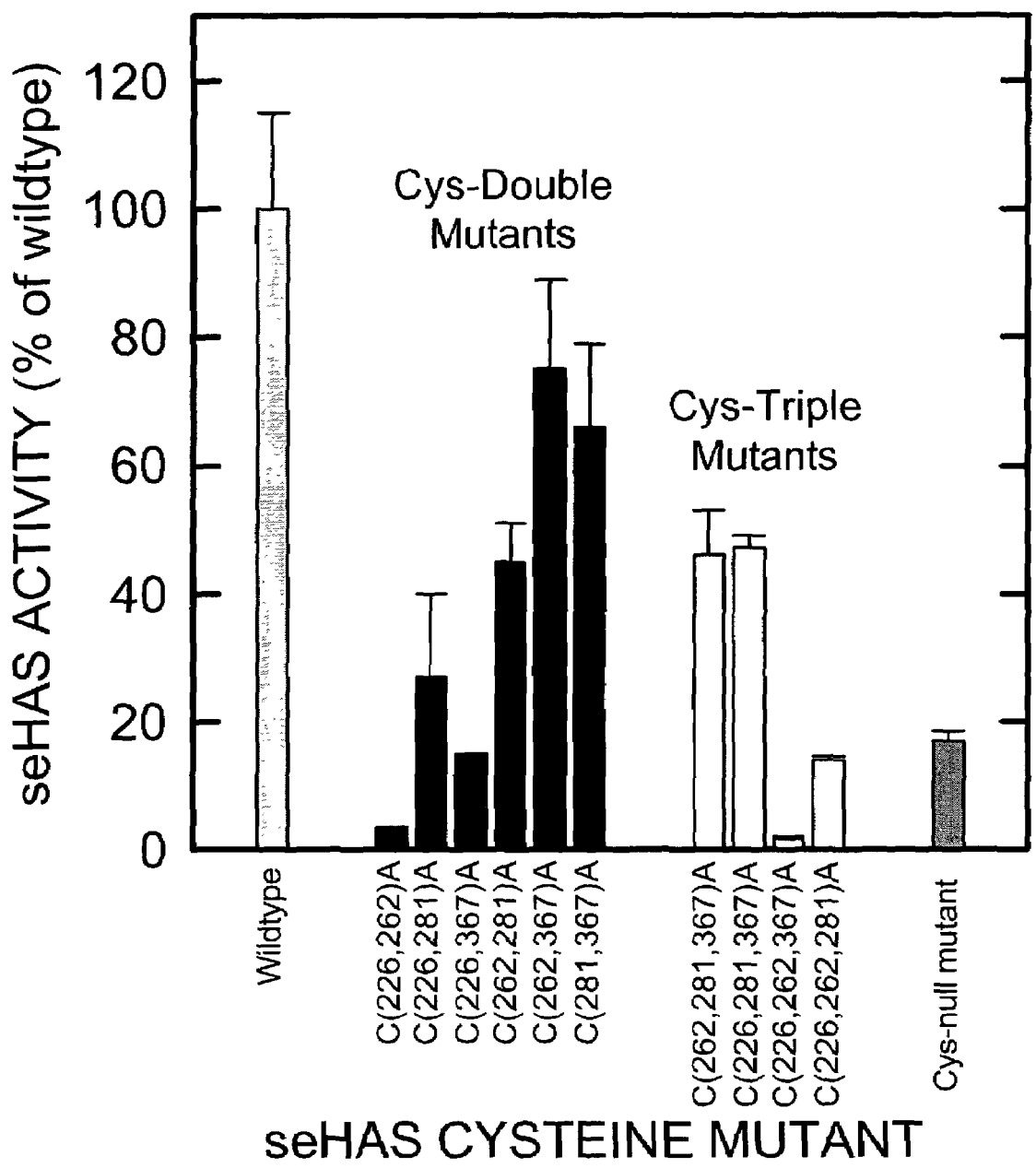
FIG. 5. Relative enzyme activities of the Cys-to-Ala multiple Cys-mutants of seHAS. Membranes expressing wild-type seHAS, the indicated multiple Cys-mutants of seHAS or the seHAS$^{Cys-null}$ were assayed and normalized as described in FIG. 4.

All the possible Cys-to-Ala double mutants (C226,262A; C226,281A; C226,367A; C262,281A; C262,367A; C281, 367A) as well as the triple mutants and the Cys-null mutant were constructed and examined. For simplicity, the triple Cys-mutants are designated by a convention that indicates which of the four Cys residues remains unaltered. For example, the triple mutant containing C(226,281,367)A changes is seHAS(Δ3C)$C^{262}$, which has only one Cys at position 262 as in the wild-type protein. The HA synthase activities of these multiple-Cys seHAS mutants were then determined under saturating conditions for each substrate and normalized to the amount of seHAS protein present in the isolated membranes (FIG. 5). The least active double mutant was C(226,262)A, which had only 2–3% of the specific activity of the wild-type enzyme. All three double mutants, in which $Cys^{226}$ was changed to Ala, had lower activity compared to the other three double mutants. Two of the triple mutants, seHAS($\Delta$3C)$C^{226}$ and seHAS($\Delta$3C)$C^{262}$ were significantly more active (~3–30 fold) than the other two triple mutants seHAS($\Delta$3C)$C^{281}$ and seHAS($\Delta$3C)$C^{367}$.

Surprisingly, the Cys-null seHAS mutant was more active than the two least active triple Cys-mutants and two of the six double Cys-mutants (FIG. 5). The decreased activities of the single and multiple Cys-mutants are consistent with the inhibition of seHAS or spHAS by sulfhydryl reagents described above. Based on the lower specific activities of most of these Cys-mutants, it was concluded that no particular cysteine residue in seHAS is required for a critical step during HA synthesis. Nonetheless, these data also

TABLE IV

Michaelis-Menten Constants for single Cys-Mutants of seHAS

| seHAS MUTANTS | Vmax (nmol/pmol/h)[a] | Km for UDPGlcUA ($\mu$M) | Km for UDPGlcNAc ($\mu$M) |
|---|---|---|---|
| WT | 5.60 ± 0.48 | 77 ± 5 | 74 ± 7 |
| C226A | 1.34 ± 0.21 | 88 ± 17 | 154 ± 23[b] |
| C226S | 0.45 ± 0.08[c] | 44 ± 7[b] | 232 ± 0.2[c] |
| C262A | 3.36 ± 0.26 | 146 ± 41 | 186 ± 26[b] |
| C262S | 1.56 ± 0.05 | 96 ± 10 | 153 ± 0.5[c] |
| C281A | 3.36 ± 0.37 | 40 ± 9[b] | 130 ± 12[b] |
| C281S | 2.29 ± 0.40 | 56 ± 0.6[b] | 98 ± 11 |
| C367A | 8.17 ± 0.32 | 85 ± 12 | 90 ± 10 |
| C367S | 5.37 ± 0.21 | 79 ± 10 | 91 ± 1 |

Kinetic analyses were performed as described herein using membranes prepared from *E. coli* SURE cells expressing the indicated seHAS variants. Hill numbers for the wild-type seHAS and single Cys-mutants of seHAS ranged from 0.9 to 1.2 and none of the mutant vales were significantly different from wild-type.
[a]All values were significantly different than wild-type (p ≤ 0.05) except for C367S.
[b]Significantly different from wild-type (p ≤ 0.05)
[c]Significantly different from wild-type (p ≤ 0.005)

TABLE V

Michaelis-Menton Constants for double Cys-Mutants of seHAS

| seHAS MUTANT | Vmax (nmol/pmol/h)[a] | Km for UDPGlcUA ($\mu$M) | Km for UDPGlcNAc ($\mu$M) | Hill number |
|---|---|---|---|---|
| WT | 5.60 ± 0.48 | 77 ± 5 | 74 ± 7 | 1.1 ± 0.1 |
| (C226,262A) | 0.18 ± 0.01[c] | 134 ± 27[b] | 650 ± 66[c] | 1.8 ± 0.2[c] |
| (C226,281A) | 1.51 ± 0.42 | 53 ± 5 | 108 ± 4[b] | 1.0 ± 0.1 |
| (C226,367A) | 0.84 ± 0.03[c] | 79 ± 19 | 149 ± 13[b] | 1.1 ± 0.1 |
| (C262,281A) | 2.52 ± 0.19 | 113 ± 40 | 298 ± 39[c] | 1.5 ± 0.1[c] |
| (C262,367A) | 4.20 ± 0.44 | 121 ± 3[b] | 172 ± 3[c] | 1.4 ± 0.2[b] |
| (C281,367A) | 3.69 ± 0.42 | 65 ± 24 | 131 ± 1[b] | 1.2 ± 0.2 |

Kinetic analyses were performed as described herein using membranes prepared from *E. coli* SURE cells expressing the indicated seHAS variants.
[a]All values were significantly different than wild-type (p ≤ 0.05)
[b]Significantly different from wild-type (p ≤ 0.05)
[c]Significantly different from wild-type (p ≤ 0.005)

TABLE VI

Michaelis-Menton Constants for triple and quadruple Cys-Mutants of seHAS

| MUTANTS | Vmax (nmol/pmol/h)[a] | Km for UDPGlcUA ($\mu$M) | Km for UDPGlcNAc ($\mu$M) | Hill number |
|---|---|---|---|---|
| WT | 5.60 ± 0.48 | 77 ± 5 | 74 ± 7 | 1.1 ± 0.1 |
| ($\Delta$3C)$C^{226}$ | 2.57 ± 0.22 | 81 ± 11 | 273 ± 21[c] | 1.7 ± 0.3[b] |
| ($\Delta$3C)$C^{262}$ | 2.63 ± 0.06 | 87 ± 15 | 189 ± 34[b] | 1.5 ± 0.2[b] |
| ($\Delta$3C)$C^{281}$ | 0.08 ± 0.02 | 109 ± 7[b] | 453 ± 137[b] | 1.9 ± 0.4[c] |
| ($\Delta$3C)$C^{367}$ | 0.78 ± 0.02 | 120 ± 12[b] | 444 ± 46[c] | 1.8 ± 0.5[b] |
| Cys null | 0.95 ± 0.05 | 210 ± 46[b] | 447 ± 31[c] | 1.6 ± 0.1[c] |

Kinetic analyses were performed as described herein using membranes prepared from *E. coli* SURE cells expressing the indicated seHAS variants.
[a]All values were significantly different than wild-type (p ≤ 0.05)
[b]Significantly different from wild-type (p ≤ 0.05)
[c]All values were significantly different from wild-type (p ≤ 0.005)

support the conclusion that $Cys^{226}$ and $Cys^{262}$ may play a role, or at least influence, one or more of the six sub-activities required for the overall activity of HAS. At least the alteration or modification of these latter two residues hinders the enzyme and results in apparently lower $V_{max}$ values.

Enzymatic Analysis of seHAS Cys-Mutants.

To determine which sub-activities of seHAS might be altered by mutating its Cys residues, kinetic analyses of the wild-type enzyme and all the Cys-mutants were performed and their respective $K_m$ and $V_{max}$ values calculated (Tables IV–VI). A comparison of the $V_{max}$ values for each of the single, double, and triple Cys-to-Ala mutants of seHAS verified that the least active mutants were C(226,262)A and seHAS($\Delta$3C)$C^{281}$, with only ~1–3% of the wild-type activity (as suggested by the results in FIG. 5). The seHAS (C226S) mutant had ~10% of the wild-type activity (Table IV). The C226A, C(226,367)A, seHAS($\Delta$3C)$C^{367}$ and Cys-null mutants had activities between 17–30% of wild-type. The remaining eight seHAS Cys-mutants retained 40% or more of the activity of wild-type seHAS. The only mutant (Table IV) that had a higher activity than wild-type was seHAS(C367A).

The $K_m$ values for UDP-GlcUA for all the Cys-mutants (Tables IV–VI) differed by no more than 2–3 fold from wild-type seHAS. For most of the Cys-mutants, the $K_m$ values for UDP-GlcNAc also did not change dramatically (within 1–3 fold). These relatively modest changes indicate that the altered Cys residues in these seHAS variants play a relatively minor role in how the enzyme binds and uses each nucleotide-sugar. However, some combinations of Cys-mutations had more dramatic effects on nucleotide-sugar utilization. For example, the $K_{UDP\text{-}GlcNAc}$ value for seHAS($\Delta$3C)$^{226}$ was ~4-fold higher (Table VI). The $K_{UDP\text{-}GlcNAc}$ values for the C(226,262)A mutant (Table V) and the seHAS($\Delta$3C)$C^{281}$, seHAS($\Delta$3C)$C^{367}$ and Cys-null mutants (Table VI) were even more affected; they were ~6–9 fold more than wild-type. These latter mutants were clearly less efficient in their utilization of UDP-GlcNAc than the wild-type seHAS. Interestingly, these mutants also had Hill numbers >1.5, compared to a value of 1.0 for the wild-type enzyme, indicating that they had acquired a new level of cooperativity in their utilization of UDP-GlcNAc. All of the above kinetic results indicate a potentially important, though not absolutely essential, role for $Cys^{226}$ and $Cys^{262}$ in seHAS activity.

Cysteine Residues are not Essential for HAS Activity but are in or Near Substrate Binding Sites.

Figure 6:
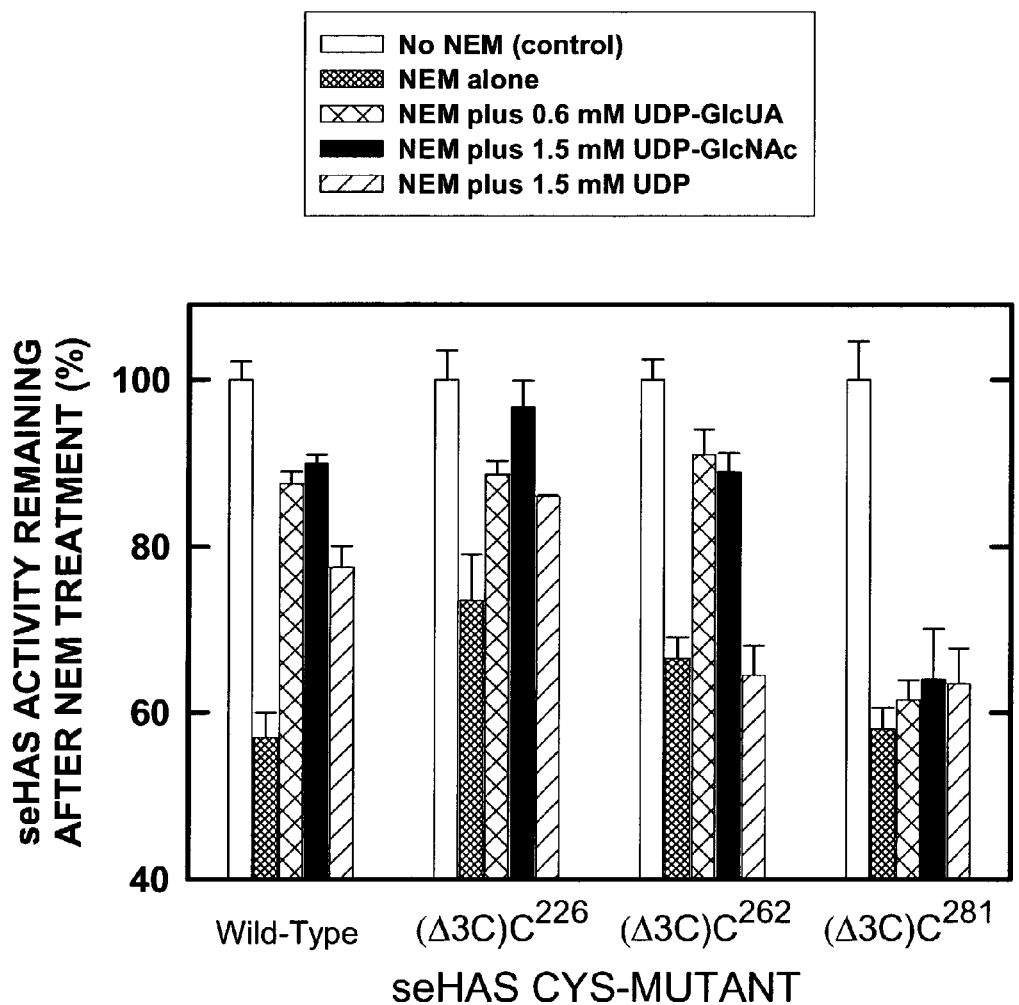
FIG. 6. Substrates protect triple Cys-mutants of seHAS from inactivation by NEM. *E. coli* membranes containing the indicated triple Cys-mutant of seHAS (each with a single remaining Cys residue) were treated at 4° C. for 10 min with no additions (control; 100% values) or with 5 mM NEM alone and in the presence of either UDP, UDP-GlcUA or UDP-GlcNAc. Unreacted Nem was then quenched and HAS activity was determined. Results are not shown for the mutant containing only Cys$^{367}$, since NEM inactivation of this mutant is ~10% and all values were essentially identical.

Although the 4 Cys residues in seHAS (positions 226, 262, 281 and 367) are roughly conserved in all Class I HAS family members, the Cys-null mutants of seHAs and spHAS are active, with minimal changes in their kinetics compared to wild type. It is also shown here that neither HAS contains disulfide bonds. To understand why these four cysteines are, nevertheless, largely conserved within the Class I HASs, NEM sensitivity was examined (i.e., the time- and dose-dependent inhibition) of all possible Cys-to-Ala mutants of seHAS. Chemical modification studies of seHAS showed that Cys226, Cys262 and Cys281 react with NEM, whereas Cys367 is not accessible. Substrate protection studies comparing the wild-type and Cys-mutants indicated that NEM-reactive Cys226 and Cys262 are located in or near a substrate binding site(s), because the presence of UDP-GlcUA or UDP-GlcNAc prevented inactivation by NEM. Cys281 appears not to be within a UDP-sugar binding site, since the triple Cys-mutant seHAS (A3C)C281 was not protected from NEM inhibition by UDP, UDP-GlcUA or UDP-GlcNAc (FIG. 6). Since sodium arsenite, which can crosslink two close Cys residues, similarly inhibited the double Cys-mutant seHAS C(226,367)A and wild type-seHAS, it is believed that Cys281 and Cys262 are very close (essentially vicinal) in the protein.

Relative Size Distributions of HA Synthesized by Various Cys-Mutants of seHAS.

Figure 7:
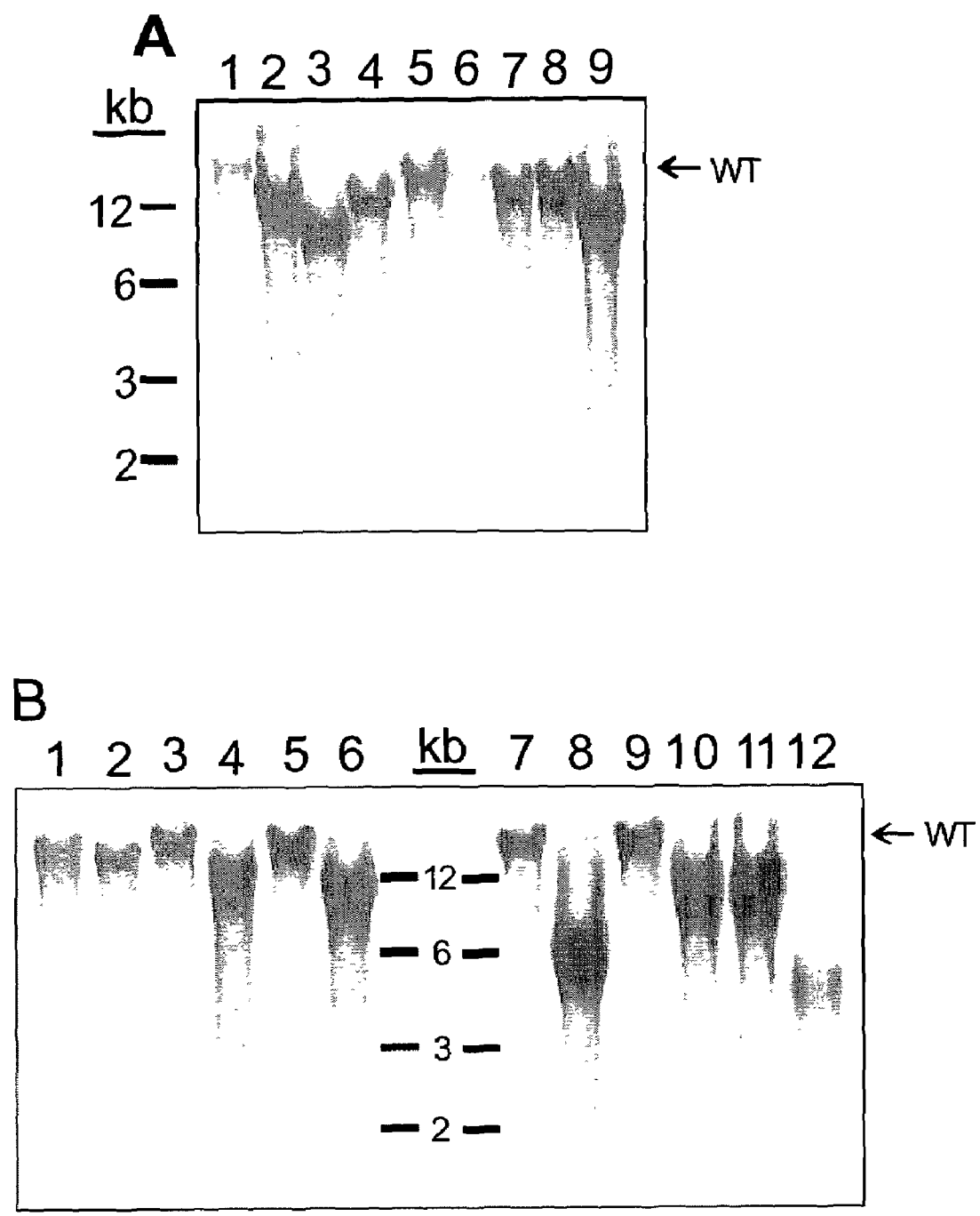
FIG. 7. Relative sizes of HA synthesized by wild-type seHAS and the Cys-mutants of seHAS. *E. coli* membranes containing wild-type or the 19 Cys-mutants of seHAS were incubated with UDP-[$^{14}$C]GlcUA and the other components described hereinafter for the assay of HAS activity. The $^{14}$C-labeled HA products were then recovered and analyzed by agarose gel electrophoresis and autoradiography as described hereinafter. The molecular weight markers used were the indicated DNA fragments of defined length (kb). A 7 kb DNA fragment corresponds to an HA molecular weight of approximately 10$^6$ (32). SeHAS variants shown are as follows. Panel A: Lane 1,C226A; Lane 2, C262A; Lane 3, C281A; Lane 4, C367A; Lane 5, wild-type; lane 6, C226S; Lane 7, C262S; Lane 8, C281S; Lane 9, C367S. Panel B: Lane 1, C(226,262)A; Lane 2, C(226,281)A; Lane 3, C(226,367)A; Lane 4, C(262,281)A; Lane 5, C(262,367)A; Lane 6, C(281,367)A; Lane 7, wild-type; Lane 8, (Δ3C)C$^{262}$; Lane 9, (Δ3C)C$^{281}$; Lane 10, (Δ3C)C$^{367}$; Lane 11, seHAS$^{cys-null}$; Lane 12, (Δ3 C)C$^{226}$.

HASs from different species synthesize HA products with a characteristic, and often different, distribution of sizes. To determine whether any of the Cys-mutants of seHAS synthesize HA having an altered size distribution, compared to wild-type seHAS, agarose gel electrophoresis was used to fractionate the radiolabelled HA products made by each variant enzyme (FIG. 7). The majority of the single (FIG. 7A) and double Cys-mutants (FIG. 7B) synthesized HA of essentially identical size compared to the wild-type enzyme. The C281A and C367S single mutants and the C(262,281)A and C(281,367)A double mutants made smaller products. Three of the four triple mutants (all except seHAS($\Delta$3C)$C^{281}$) and the Cys-null mutant made smaller HA products (FIG. 6B). The smallest relative HA size distribution was made by the triple mutant seHAS($\Delta$3C)$C^{226}$. Interestingly, the HA size distributions of the seHAS mutants C(226)S, C(226,262)A and ($\Delta$3C)$C^{281}$ were similar to that of the wild-type enzyme, even though these mutants had the lowest activity (1.4–8% of wild-type), and therefore the lowest HA elongation rates. Overall, these results clearly show that mutations of various combinations of Cys residues cause seHAS to synthesize shorter HA chains than the wild-type enzyme, indicating that Cys residues can influence the HA size distribution made by seHAS.

Assessment of Disulfide Bond Formation in seHAS.

Figure 8A:
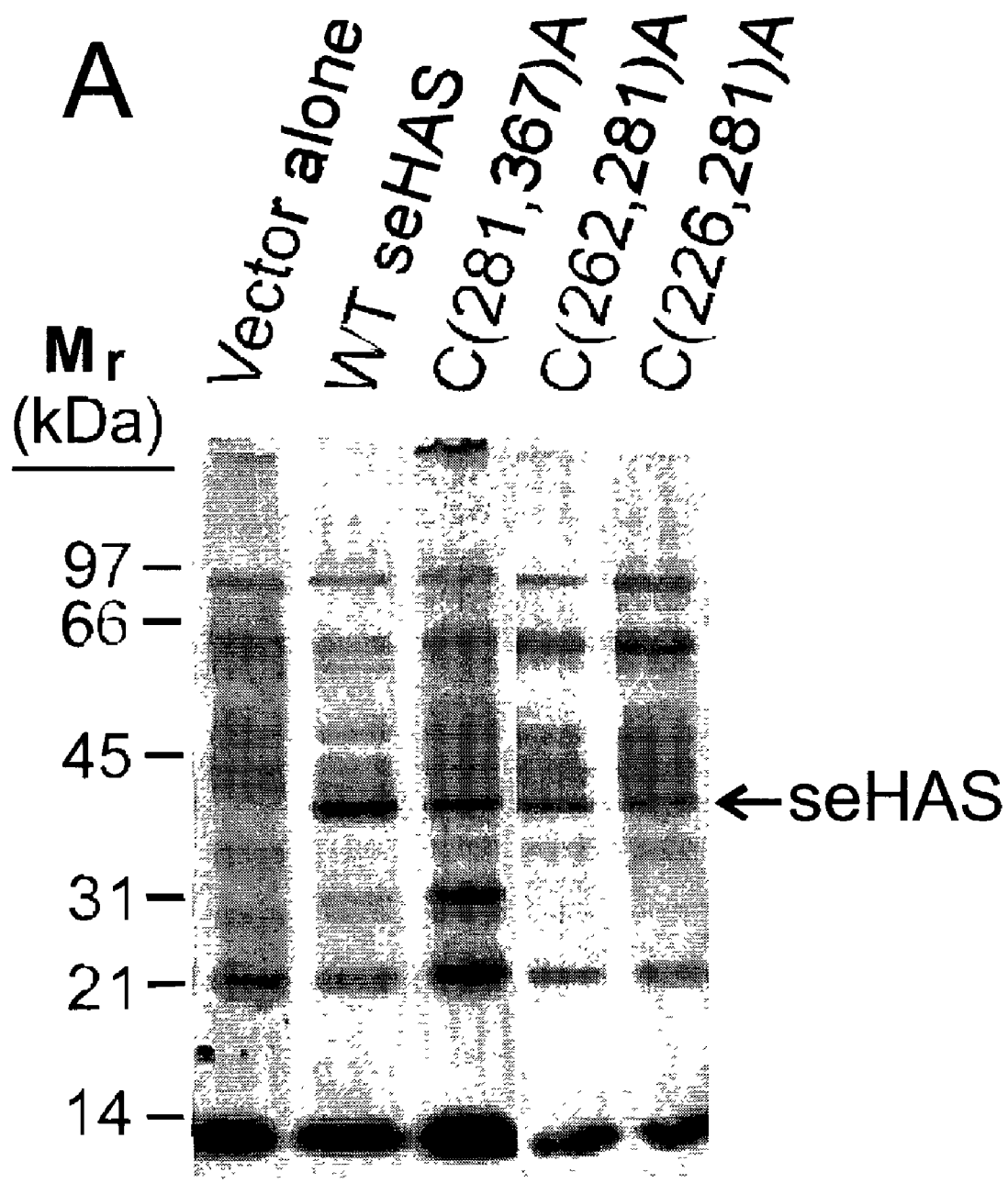
FIG. 8. Reactivity of $^{14}$C-NEM with the Cys-to-Ala double mutants of seHAS. *E. coli* membranes containing wild-type or double Cys-mutants of seHAS were incubated in two separate experiments (panels A and B) with 2.5 mM $^{14}$C-NEM (8×10$^6$ dpm) at 4° C. for 10 min. The excess of $^{14}$C-NEM was quenched by addition of 40 mM DTE and incubation for 5 min at 4° C. Trichloroacetic acid was added to a final concentration of 10%, and the samples were incubated at 4° C. overnight. The membrane pellet was washed by centrifugation 3 times with 5% TCA, suspended in 20 µl of Laemmli sample buffer (33) and neutralized with sodium hydroxide. The samples were heated at 95° C. for 3 minutes and subjected to SDS-PAGE. The gels were processed and analyzed as described hereinafter.
Figure 8B:
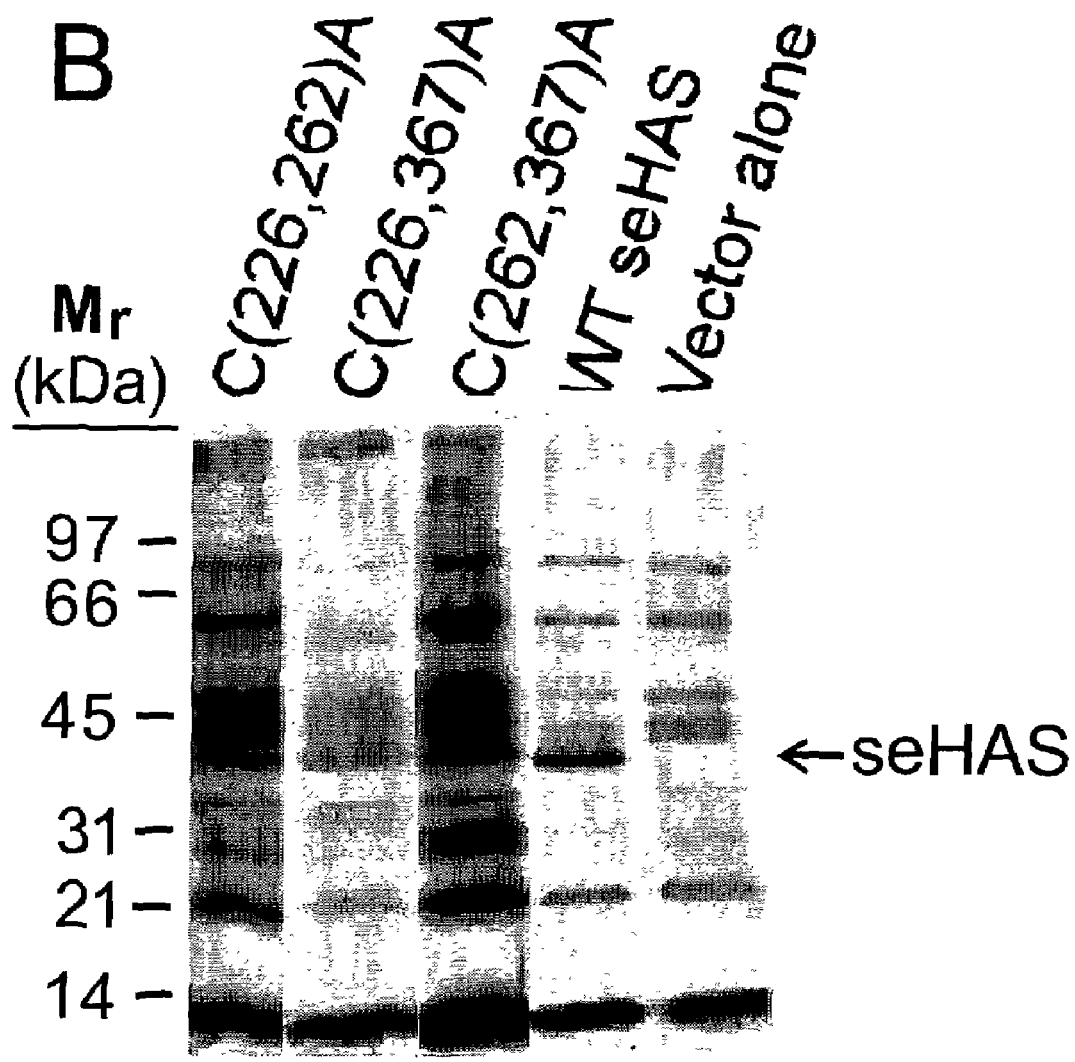

In order to understand the potential role of Cys residues in the function of seHAS, it is necessary to determine if any of its four cysteines are involved in the formation of disulfide bonds. Two approaches were undertaken to answer this question. In the first approach, *E. coli* membranes containing recombinant seHAS were treated with $^{14}$C-NEM to determine whether the wild-type or Cys-mutant seHAS proteins could be radio-labeled and then identified by autoradiography following SDS-PAGE (FIG. 8). This NEM-reactivity was used to indicate the presence of free cysteines, which are not involved in disulfide bond formation. Each of the six Cys-to-Ala double Cys-mutants of seHAS was radiolabeled by $^{14}$C-NEM. The labeling was specific because the vector-alone control and the Cys-null mutant did not show significant labeling. These results indicate that none of the Cys residues in seHAS are involved in disulfide bonds. A 31 kDa band, which was present in the mixture of NEM-labeled proteins from the wild-type and several double-Cys mutants, could be a degradation product of HAS, since it was not present in the vector-alone controls. Such a fragment is expected to be inactive and illustrates the importance of normalizing the kinetic data to the amount of intact HAS protein, as assessed by protein staining of SDS-PAGE gels.

Figure 9A:
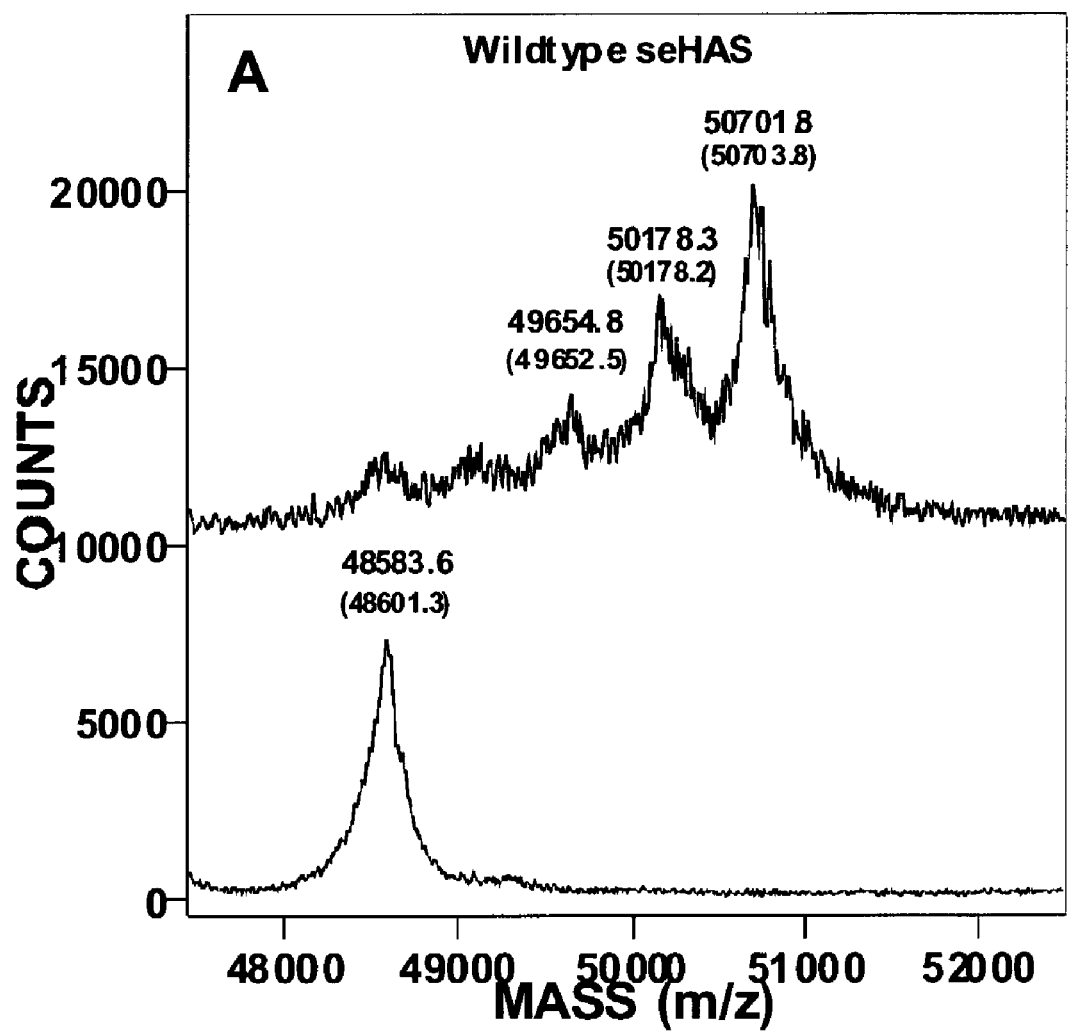
FIG. 9. MALDI-TOF mass spectrographs of seHAS-His$_6$ derivatives covalently modified by a sulfhydryl reagent. Wild-type seHAS-His$_6$ (panel A) or seHAS-His$_6$$^{Cys-null}$ (panel B) were incubated with (the upper traces in each panel) or without (lower traces in each panel) biotin-PEO-maleimide, and the eluted proteins were then prepared for mass analysis as described hereinafter. The predicted mass-to-charge ratios for covalent adducts containing 2, 3 or 4 biotin-PEO-maleimide groups per wild-type enzyme molecule (in parentheses) and the observed centroid mass-to-charge ratios are indicated above the peaks. The predicted m/z ratio for the (MH)$^+$ ion of unmodified seHAS$_{Cys-null}$-His$_6$ (with four Ala residues replacing the four Cys residues) is 48,473.1.
Figure 9B:
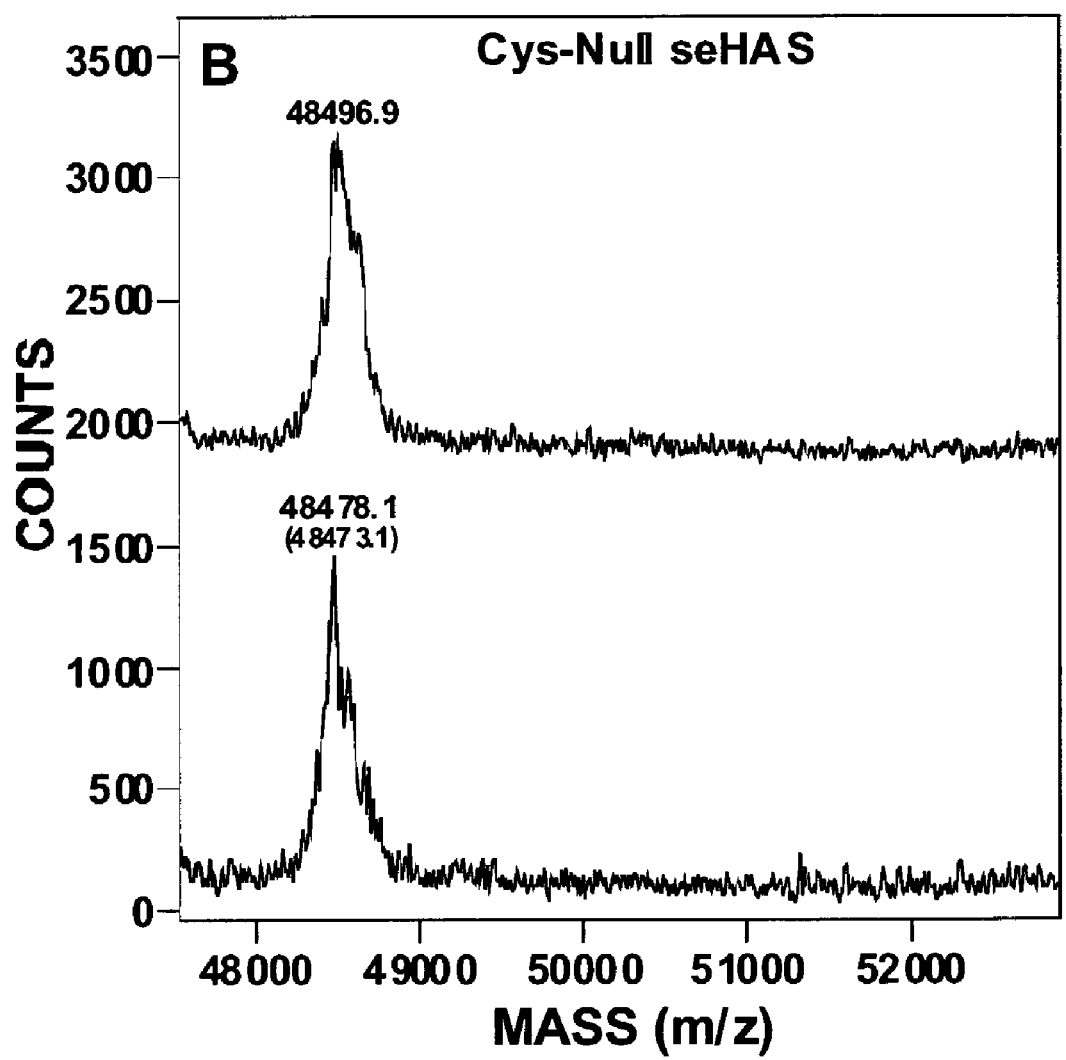

In the second approach to assess the presence of disulfide bonds, the purified enzyme was treated with biotin-PEO-maleimide, and the modified protein products were then analyzed by MALDI-TOF mass spectrometry (FIG. 9). For each biotin-PEO-maleimidyl group added, the mass of the seHAS derivative increased 525.6 Da. The treated wild-type seHAS contained a distribution of derivatized products with increased masses equal to the addition of one-to-four biotin-PEO-maleimide groups per seHAS (FIG. 9A). Most of the proteins were modified by the addition of 3 or 4 groups, demonstrating that the enzyme has no disulfide bonds. The observed mass values for the three largest adducts differed from the predicted values by <0.005%. The degree of modification was only slightly higher when the wild-type seHAS was treated with biotin-PEO-maleimide in the presence of 6 M guanidinium hydrochloride (not shown). This latter result indicates that none of the four Cys residues is substantially buried in the native enzyme; they are all accessible to react with the relatively large modifying reagent. The seHAS$^{Cys-null}$ protein was also treated with biotin-PEO-maleimide, as a control, to verify that no derivitized enzyme products could be formed in the absence of Cys groups (FIG. 9B). The result confirms that the modifying reagent does not react with any other amino acid side chains and is specific for Cys; no covalent adducts were formed with the Cys-null protein.

Mutagenesis of Cys Residues and Expression of spHAS

To explore the possible presence of disulfide bonds and the functional roles of the conserved Cys residues in the enzymatic activity of the *S. pyogenes* HAS, each of the six Cys residues in spHAS was mutated to Ser or Ala. Subsequently, spHAS mutants with combinations of Cys-to-Ala changes were produced by using site directed mutagenesis or restriction enzyme digestion and ligation of HAS fragments from different mutants. Studies with crude membranes, in which the enzyme activity of spHAS mutants were initially normalized to total membrane protein, indicated that alteration of some Cys residues had a dramatic affect on HA production. For example, spHAS(C225A) appeared to be nearly inactive, and spHAS(C261A) and spHAS(C280A) had less than half the activity of wildtype. However, these initial impressions were incorrect due to significant variations in the expression of spHAS protein among the various mutants.

Therefore, in order to normalize for the level of HAS protein expression, a sensitive and quantitative Western blot-based assay was developed (Heldermon, et al. 2001). Since all of the HAS constructs contain a C-terminal His$_6$ tag, which is efficiently recognized by a commercial anti-His$_5$ monoclonal antibody, this antibody was used, after biotinylation, as the primary antibody for analysis of Western blots followed by incubation with $^{125}$I-streptavidin as the secondary reagent. Unlike standard Western analysis, this detection protocol provides greater sensitivity as well as the ability to quantitate HAS protein over a much broader concentration range. The normalizations for HAS protein expression were performed relative to known amounts of purified spHAS-His$_6$ included in each analysis as internal standards. Based on the normalized results, it was clear that spHAS(C225S) was expressed at the lowest level relative to any of the other mutants, ~66% of wildtype (Table VII). The protein expression levels for the majority of single Cys-mutants were not significantly different than wildtype, although the spHAS(C124S) and spHAS(C261A) variants may have been elevated by ~35% (p ~0.05). Interestingly, most of the multiple Cys-mutants as well as the Cys-null mutant were expressed at 3-to-5 fold higher levels than the wildtype enzyme. These above differences in relative expression of these spHAS variants were consistent in multiple experiments, with independent cell growth and enzyme induction, indicating that several of the Cys residues in spHAS, particularly the conserved Cys at position 225, may influence the initial folding and stability of the enzyme.

Enzymatic Analysis of Mutants

Figure 10:
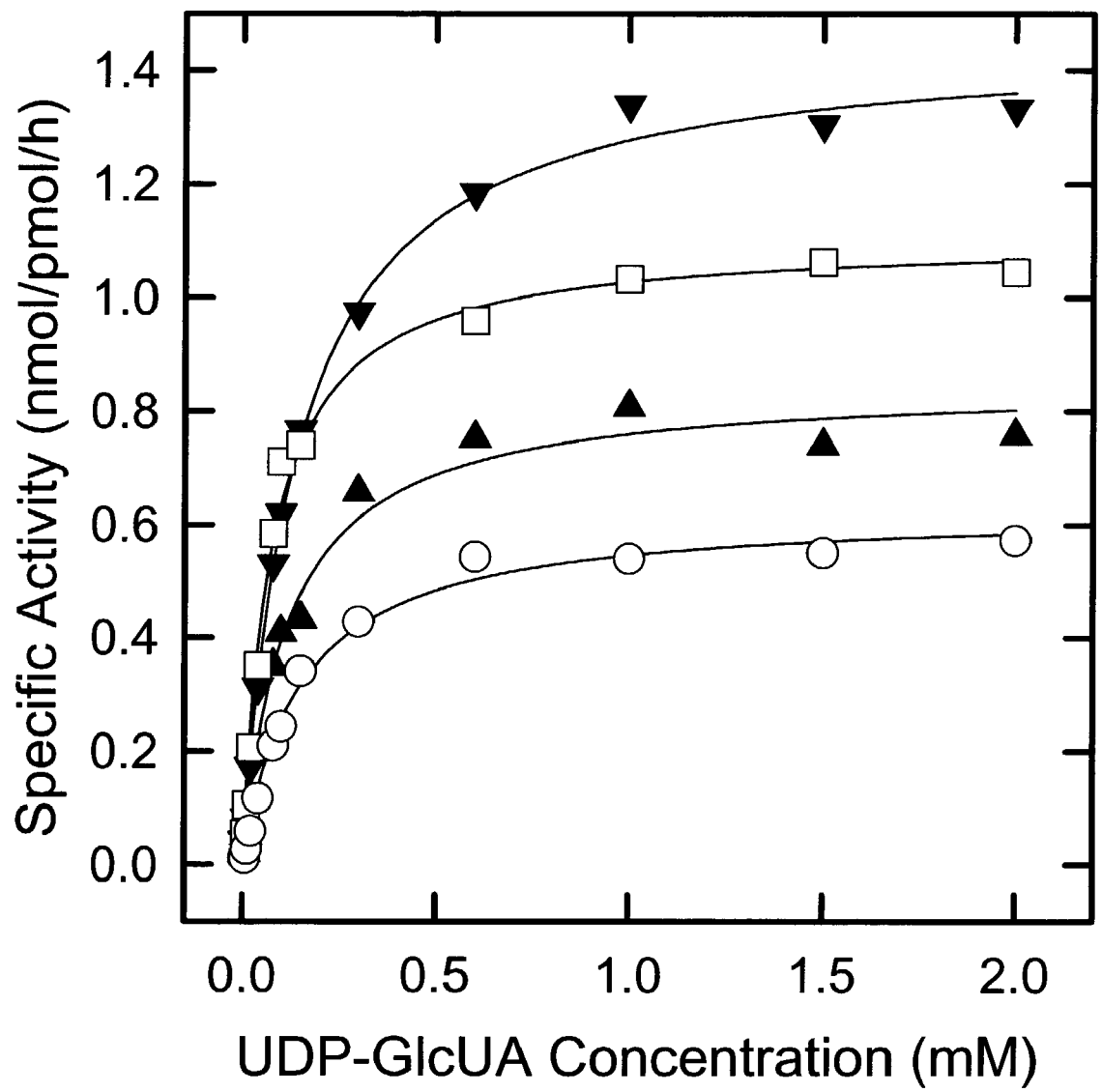
FIG. 10. Kinetic analysis of UDP-GlcUA utilization by Cys-mutants of spHAS. Membranes prepared from cells expressing the indicated spHAS mutant were assayed as described hereinafter to assess the Michaelis-Menton constants for UDP-GlcUA: wildtype (□), C(124,366,402)A (▼), C(124,261,280,366,402)A (▲), and the Cys-null mutant (○).
Figure 11:
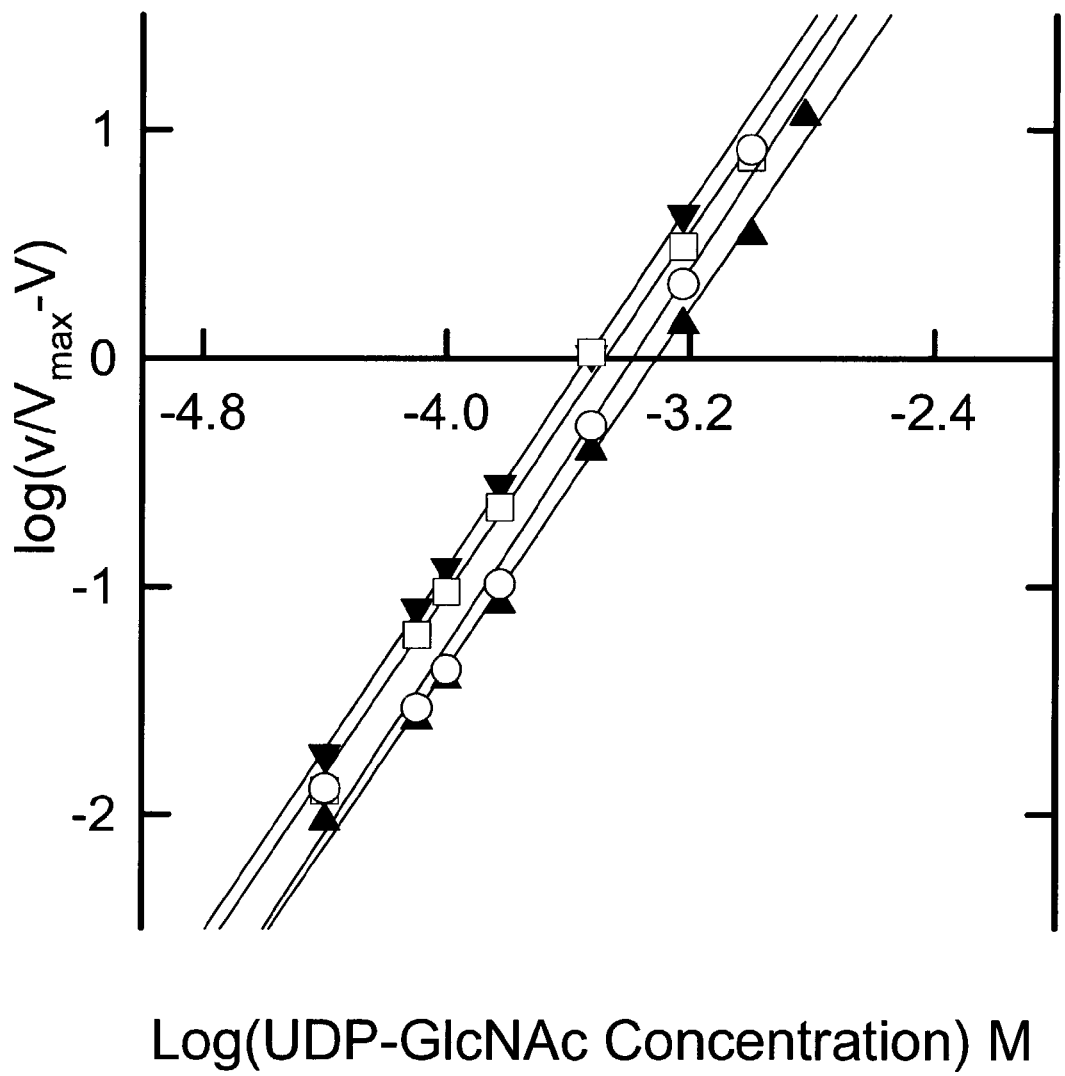
FIG. 11. Hill analysis of UDP-GlcNAc utilization by Cys-mutants of spHAS. Hill plots of data obtained from K$_m$ assays of wildtype and several mutant spHAS proteins, performed as in FIG. 10, demonstrate that the cooperative nature of UDP-GlcNAc utilization is not affected by alteration of Cys residues. The spHAS variants shown are: wildtype (□), C(124,366,402)A (▼), C(124,261,280,366,402)A (▲), and the Cys-null mutant (○).

Kinetic analyses of the single and multiple spHAS Cys-mutants were performed to investigate the possibility that multiple Cys residues are critical in a coordinated way for enzyme activity. The activity of each of the mutants was assayed and normalized by the above method to determine its maximum velocity ($V_{max}$) and Michaelis-Menton ($K_m$) constants for UDP-GlcUA and UDP-GlcNAc (FIGS. 10 and 11; Table VIII). This analysis revealed no dependence of HAS activity on any single Cys residue. These assays also revealed no extreme changes in maximal enzyme activity relative to wildtype spHAS. The spHAS(C225S) and spHAS(C280A) mutants had the most reduced activities with $V_{max}$ values at 30–50% of wildtype. The spHAS(C261,280A) and Cys-null mutant had 50–75% of the wildtype activity. Interestingly, spHAS(C124,366,402A) and spHAS(C366A) had an increased activity that was ~150% of wildtype. The other single mutants, as well as spHAS(C124,402A), and spHAS(C124,261,280,366,402A) demonstrated less than a 25% variation from the wildtype $V_{max}$.

All the mutant spHASs were also within 25% of the wildtype enzyme for their $K_{UDP-GlcNAc}$ values. There were no changes in the sigmoidal behavior for UDP-GlcNAc utilization by any of the mutant enzymes. When these data were analyzed using the method of Hill (1913), the Hill numbers were all ~2 (Table VIII), which indicates a high degree of cooperativity associated with the ability of all the mutant enzymes to bind and use UDP-GlcNAc at a fixed UDP-GlcUA concentration. Thus, the cooperativity observed for the utilization of UDP-GlcNAc by the spHAS enzyme (Tlapak-Simmons et al., 1999b) is not influenced

TABLE VII

Expression levels of various Cys-mutants of spHAS.

| spHAS Construct | Relative Concentration | Standard Deviation | n | t-test (p value) |
|---|---|---|---|---|
| Wildtype | 1.00 | 0.18 | 8 | — |
| C124A | 1.01 | 0.12 | 4 | 0.89 |
| C124S | 1.35 | 0.39 | 4 | 0.06 |
| C225A | 1.24 | 0.52 | 4 | 0.24 |
| C225S | 0.66 | 0.22 | 4 | 0.02 |
| C261A | 1.35 | 0.10 | 3 | 0.01 |
| C261S | 1.16 | 0.14 | 4 | 0.16 |
| C280A | 1.04 | 0.25 | 4 | 0.73 |
| C280S | 1.30 | 0.42 | 4 | 0.10 |
| C366A | 0.97 | 0.30 | 4 | 0.84 |
| C366S | 1.11 | 0.24 | 4 | 0.38 |
| C402A | 1.05 | 0.07 | 2 | 0.75 |
| C402S | 0.86 | 0.14 | 4 | 0.21 |
| C(124,402)A | 0.82 | 0.33 | 6 | 0.21 |
| C(261,280)A | 3.20 | 1.48 | 6 | <0.001 |
| C(124,366,402)A | 3.61 | 1.72 | 6 | <0.001 |
| C(124,261,280,366,402)A | 3.98 | 0.50 | 6 | <0.0001 |
| Cys-Null | 4.94 | 1.08 | 6 | <0.0001 |

Membranes prepared from *E. coli* SURE cells expressing the indicated spHAS variants were fractionated by SDS-PAGE and the proteins were transferred to nitrocellulose. SpHAS protein levels were quantitated as described in Methods and the values were normalized to that of the wildtype. Student t-tests were performed to assess the significance of differences compared to the expression of the wildtype enzyme.

TABLE VIII

Kinetic constants for Cys-to-Ser/Ala mutants of spHAS.

| spHAS Construct | Vmax (μmol/pmol/h) | Km UDP-GlcUA (μM) | Km UDP-GlcNAc (μM) | Hill Number |
|---|---|---|---|---|
| Wildtype | 791 ± 215 | 50.4 ± 10.8 | 398 ± 112 | 1.8 ± 0.1 |
| C124A | 617 ± 132 | 37.3 ± 10.1 | 458 ± 60 | 1.8 ± 0.1 |
| C124S | 584 ± 176* | 32.7 ± 0.6 | 459 ± 8.0 | 1.8 ± 0.1 |
| C225A | 852 ± 306 | 62.2 ± 4.1 | 372 ± 26.5 | 1.8 ± 0.1 |
| C225S | 366 ± 37** | 42.7 ± 4.6 | 464 | 1.7 |
| C261A | 923 ± 173 | 42.6 | 454 ± 6.5 | 2.0 ± 0.1 |
| C261S | 764 ± 103 | 45.6 | 499 ± 7.0 | 1.9 ± 0.1 |
| C280A | 264 ± 147** | 33.8 ± 9.7 | 344 ± 45.5 | 1.7 ± 0.1 |
| C280S | 680 ± 90 | 29.4 ± 1.6* | 325 ± 9.0 | 1.8 ± 0.1 |
| C366A | 1201 ± 154** | 56.8 ± 12.8 | 397 ± 1.5 | 1.8 ± 0.0 |
| C366S | 721 ± 121 | 34.1 ± 2.9 | 472 ± 4.5 | 1.8 ± 0.0 |
| C402A | 969 ± 163 | 43.8 ± 9.2 | 427 ± 20.5 | 1.8 ± 0.0 |
| C402S | 774 ± 98 | 44.4 ± 9.4 | 443 ± 35.5 | 1.8 ± 0.0 |
| C(124,402)A | 894 ± 306 | 39.5 ± 7.0 | 330 ± 38.8 | 1.9 ± 0.1 |
| C(261,280)A | 436 ± 105* | 54.8 ± 36.7 | 389 ± 20.8 | 1.9 ± 0.1 |
| C(124,366,402)A | 1247 ± 127** | 130 ± 21.6** | 285 ± 4.5 | 1.8 ± 0.2 |

TABLE VIII-continued

Kinetic constants for Cys-to-Ser/Ala mutants of spHAS.

| spHAS Construct | Vmax (μmol/pmol/h) | Km UDP-GlcUA (μM) | Km UDP-GlcNAc (μM) | Hill Number |
|---|---|---|---|---|
| C(124,261,280,366,402)A | 702 ± 112 | 101 ± 24.1* | 471 ± 20.8 | 1.9 ± 0.1 |
| Cys-Null | 522 ± 47* | 153 ± 39.3** | 450 ± 40.7 | 1.8 ± 0.1 |

The $V_{max}$ values are in μmol of both substrates incorporated per hour per pmol spHAS. The $K_m$ values for UDP-GlcNAc and UDP-GlcUA were determined at 0.5 mM UDP-GlcUA and 1.5 mM UDP-GlcNAc, respectively. Experiments were performed in duplicate or triplicate for the single or multiple Cys-mutants, respectively. For the wildtype, n = 7. Values that differ significantly, based on the Student t-test, from that of the wildtype enzyme are indicated by*($p < 0.05$) or **($p < 0.001$).

by, or dependent on, any of its six Cys residues. Similarly, none of these Cys residues contribute structurally, or otherwise, to a possible secondary binding site for UDP-GlcNAc, i.e. an allosteric binding site.

The $K_{UDP-GlcUA}$ values for all of the single Cys-mutants and the two double Cys-to-Ala mutants were within 50% of wildtype. The remaining multiple Cys- to-Ala mutants exhibited $K_{UDP-GlcUA}$ values that were 2–3 times that of wildtype. Although these multiple Cys-mutations do alter the activity of the enzyme by decreasing the efficiency of utilizing UDP-GlcUA, they do not do so in a large way. Furthermore, the relatively modest difference in activity between the Cys-null mutant and wildtype spHAS clearly shows that cysteine residues are not absolutely necessary for HA synthesis, either catalytically or structurally.

Inhibition of spHAS Activity by NEM

Figure 12:
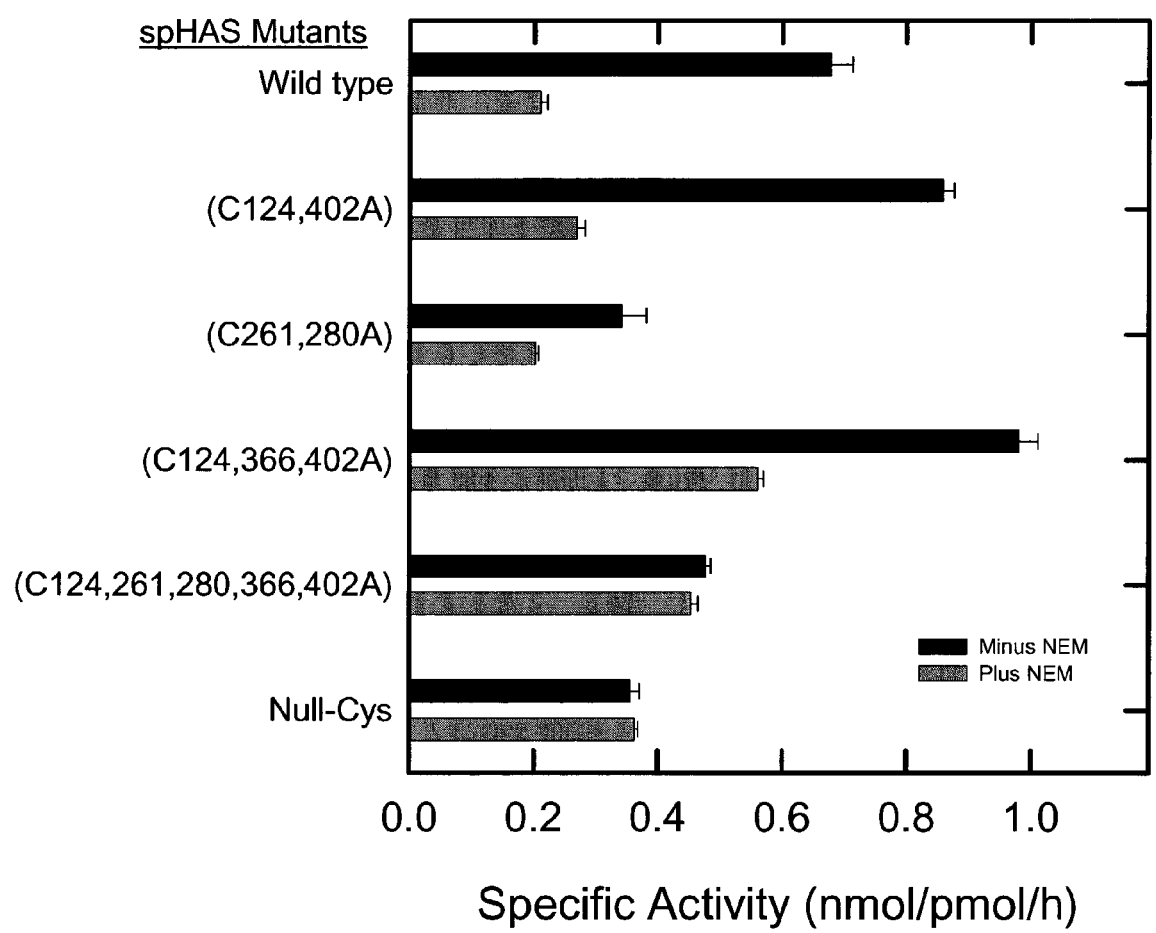
FIG. 12. Inhibition of wildtype and Cys-mutants of spHAS by NEM. The activity of the indicated spHAS enzymes in membranes was assessed after pretreatment with (gray bars) or without (black bars) 20 mM NEM at room temperature for 90 min. Wildtype and many of the Cys-mutant variants of spHAS with multiple Cys residues mutated are still sensitive to NEM inhibition. The mutant containing only one Cys residue at Cys$^{225}$ and the Cys-null mutant were not sensitive to NEM inhibition.

NEM treatment of membranes from a panel of multiple Cys-mutants showed that this inhibition was no longer present in spHAS$^{Cys-null}$ or the mutant with only Cys$^{225}$ intact, whereas NEM sensitivity remained in the other multiple Cys-mutants (FIG. 12). These results indicate that the inhibition of the wildtype enzyme by NEM or other sulfhydryl/reactive agents is most likely due to modification of the Cys residues alone, rather than the loss of the S–H group. The lack of inhibition of the single Cys-containing mutant demonstrates that Cys$^{225}$ is either predominantly inaccessible to modification by NEM due to its position in the enzyme or that this particular cysteine residue is not involved in the inhibition response of the enzyme when modified by NEM.

Assessment of Disulfide Bond Formation

Figure 13A:
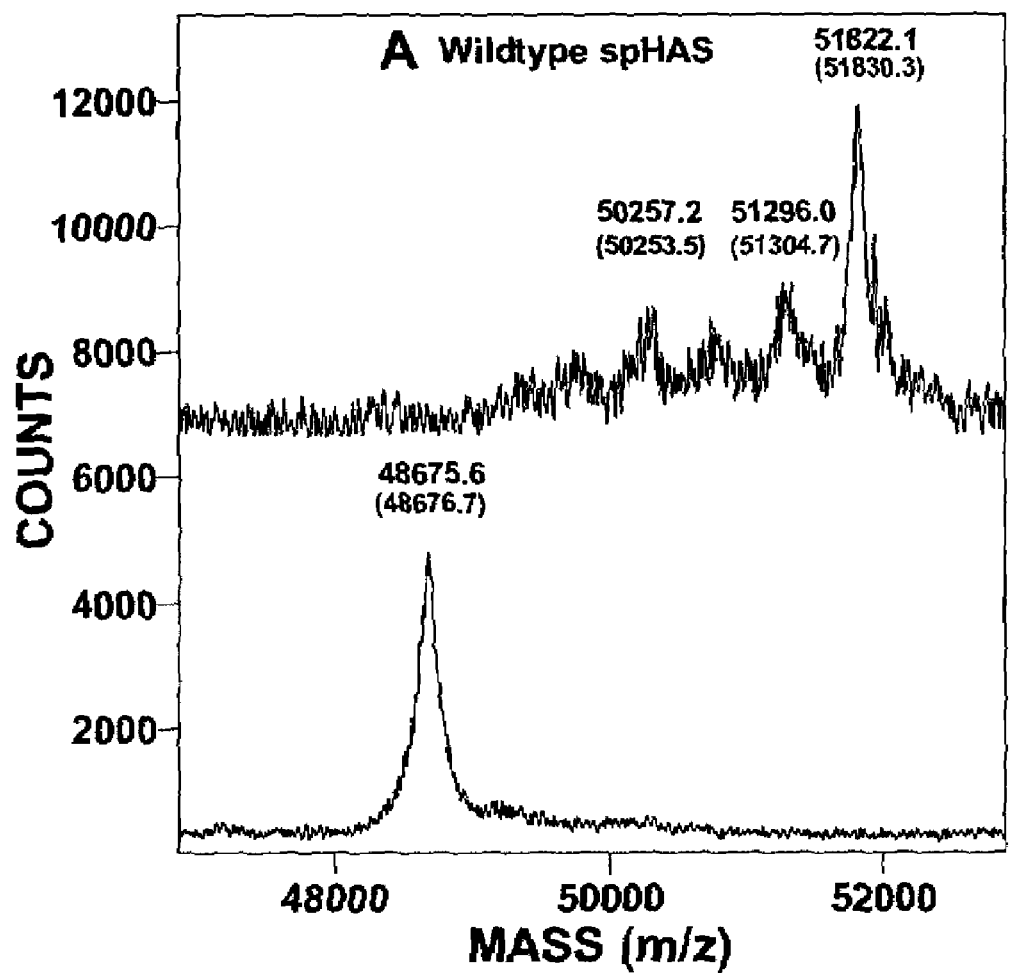
FIG. 13. MALDI-TOF mass spectrographs of spHAS-His$_6$ covalently modified by a sulfhydryl reagent. Wildtype spHAS-His$_6$ (panel A) or the Cys-null mutant of spHAS-His$_6$ (panel B) were bound to Ni$^{+2}$-NTA resin, washed and incubated for 2 h at 4° C. with (the upper traces in each panel) or without (lower traces in each panel) 10 mg/ml biotin-PEO-maleimide. The columns were washed and the proteins were then eluted and prepared for mass analysis as described hereinafter. The centroid mass-to-charge ratios are indicated above the observed peaks and the, predicted mass-to-charge ratios for covalent adducts containing 2, 3, 4, 5 or 6 biotin-PEO-maleimide groups per wildtype enzyme molecule are indicated in parentheses. The predicted m/z ratio for the (MH)$^+$ ion of unmodified spHAS$^{Cys-null}$-HiS$_6$(with six Ala residues replacing the six Cys residues) is 48,484.4.
Figure 13B:
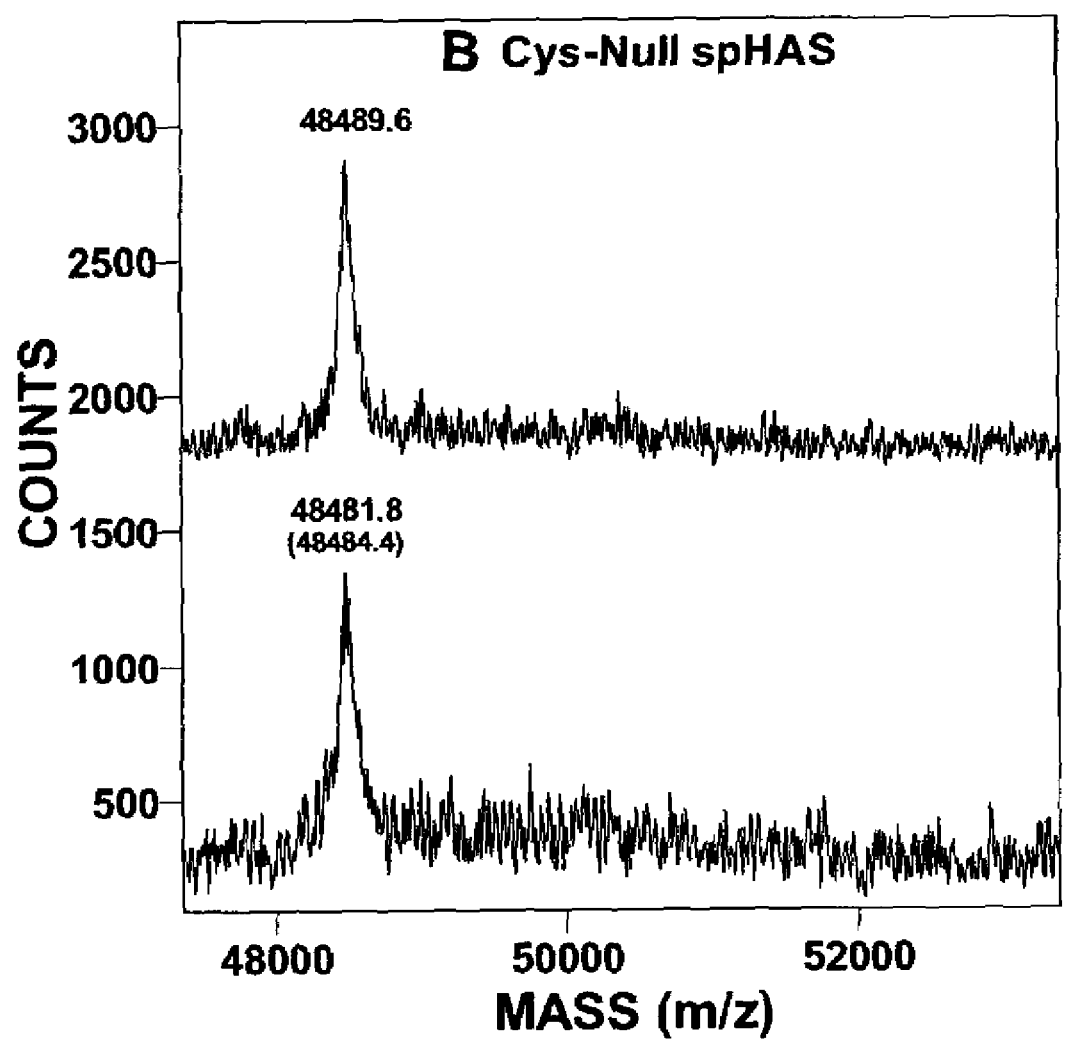

Although Cys residues may not be required for the enzymatic activity of the HAS proteins, they could still be important in the structural integrity and long-term stability of the enzyme as indicated by the reduced expression of the spHAS(C225S) mutant and the increased expression of the spHAS(C124S) and spHAS(C261A) mutants (Table VII). Cys residues may also be important for maintaining the proper enzyme conformation to allow extrusion of the growing HA chain through the membrane. The primary manner in which Cys residues play structural roles in proteins is by forming either inter- or intra-molecular disulfide bonds. To investigate the possibility of disulfide bonds in spHAS, a chemical labeling approach was utilized to determine the number of Cys residues that are free and, therefore, could not be involved in disulfide bonding. Biotin-PEO-maleimide was allowed to react with purified spHAS, while bound to a Ni$^{+2}$-loaded NTA column, and the modified protein products were then analyzed by MALDI-TOF mass spectrometry (FIG. 13). In nondenaturing conditions, treated wildtype spHAS samples revealed a distribution of derivatized products with increased masses equal to the addition of from one-to-six biotin-PEO-maleimide groups per spHAS, with the majority of the protein being modified by the addition of 5 or 6 groups (FIG. 13A). As a control for this chemical modification approach, samples of spHAS$^{Cys-null}$ were treated with biotin-PEO-maleimide in the same way to verify that no derivitized enzyme products would be formed in the absence of Cys groups. The result (FIG. 13B) demonstrates that no covalent adducts form with the Cys-null protein, which confirms that the modifying reagent is specific for Cys and does not react with any other amino acid side chains. Treatment of the wildtype or Cys-null spHAS proteins with biotin-PEO-maleimide in the presence of 6 M guanidinium hydrochloride gave essentially the same results as obtained in the absence of the denaturing agent, although the degree of modification was slightly greater (not shown). This latter result indicates that spHAS contains no weak disulfide bonds that might be susceptible to reversible reduction when the protein is denatured. The overall results demonstrate that there are no disulfide bonds in the wildtype spHAS enzyme, and that there is a mixed degree of exposure of the six Cys residues in this protein to the biotin-PEO-maleimide reagent in solution.

Mutant HAS HA Size Range and Prevalent Size of HA.

Because spHAS mutants in which C280 was substituted with alanine synthesized HA of a lower weight average mass than the spHAS wild type enzyme, other amino acid substitutions were also examined (Table IX). For example, the C280T and C280V mutants made HA with a larger size distribution

TABLE IX

Mutant HAS HA Size Range and Prevalent Size

| Mutant | Peak Size (MDa) | <2 MDa (<3 Kb) | 2–4 MDa (3–6 Kb) | 4–6 MDa (6–9 Kb) | >6 MDa (9–>48.5 Kb) |
|---|---|---|---|---|---|
| WT (spHAS) | 2–3 | 33 ± 5 | 29 ± 8 | 12 ± 2 | 26 ± 8 |
| C280A | ~1 | 65 ± 12 | 15 ± 2 | 5 ± 3 | 15 ± 7 |
| C280G | ~1 | 58 ± 10 | 17 ± 5 | 5 ± 2 | 19 ± 4 |
| C280S | 3–4 | 27 ± 4 | 40 ± 3 | 13 ± 3 | 21 ± 3 |
| C280T | 8–32 | 14 ± 2 | 27 ± 2 | 14 ± 3 | 44 ± 4 |
| C280V | 4–5 | 26 ± 3 | 40 ± 2 | 14 ± 3 | 21 ± 6 |
| C124S | ~2 | 35 | 37 | 13 | 15 |
| C124A | ~2 | 31 | 33 | 17 | 19 |
| C225S | 3–4 | 33 | 45 | 14 | 8 |
| C225A | 5–6 | 16 | 29 | 23 | 32 |
| C261S | 5–6 | 18 | 31 | 22 | 29 |
| C261A | 4–5 | 22 | 35 | 20 | 23 |
| C366S | ~2 | 38 | 36 | 11 | 14 |
| C402S | 2–3 | 25 | 36 | 17 | 22 |

TABLE IX-continued

Mutant HAS HA Size Range and Prevalent Size

| Mutant | Peak Size (MDa) | <2 MDa (<3 Kb) | 2–4 MDa (3–6 Kb) | 4–6 MDa (6–9 Kb) | >6 MDa (9–>48.5 Kb) |
|---|---|---|---|---|---|
| C402A | ~2 | 34 | 37 | 12 | 17 |
| C402A | ~2 | 37 | 35 | 12 | 16 |
| C124, 402A | 1–2 | 38 | 0 | 12 | 20 |
| seHAS | 1–2 | 42 ± 21 | 25 ± 7 | 14 ± 5 | 19 ± 9 |
| C226A | ~5 | 12 ± 1 | 38 ± 2 | 23 ± 0 | 27 ± 1 |
| C262A | 1–2 | 48 ± 0 | 28 ± 1 | 9 ± 0 | 15 ± 1 |
| C281A | 1 | 55 ± 1 | 26 ± 1 | 5 ± 1 | 14 ± 1 |
| C367A | ~3 | 15 ± 1 | 62 ± 0 | 4 ± 1 | 19 ± 2 |

HA produced by mutants of spHAS and seHAS in one hour at saturating substrate concentration were run on 1% agarose gels. Reactions were radiolabeled by including UDP-[$^{14}$C]GlcUA in the reaction mix and HA product distribution was assessed with a Molecular Dynamics Phosphoimager. Size was estimated relative to High Molecular Weight and Kb DNA ladder standards. Distribution of product is reported as the percentage of total counts (IDV) between various size ranges. The prevalent HA size produced ("Peak Size") is reported as the approximate MW in MDa at which the greatest IDV intensity was located. MW ranges are shown as MDa and kbp of DNA in parentheses. C226A, C262A, C281A, and C367A are mutants of seHAS.

than the wild type, whereas the C280G mutant made HA that had a smaller weight average mass than wild type.

Targeted Mutagenesis Within Two Membrane Domains of seHAS and Generation of the "Double Switch" Mutant.

There is a paradox in understanding how HASs polymerize long HA chains. HA chains must be free to move through the enzyme at rapid rates as they are elongated. Thus, one expects that the HA-binding ability of HAS would not be a "high affinity" interaction, since a low off-rate would hinder chain movement (i.e., translocation though the membrane). Yet, HA-binding "affinity" cannot be very low because some chains are held for >10,000 cycles of HA disaccharide assembly and translocation before large HA chains (~4×10$^6$) are released. It is expected that HAS possesses multiple HA-binding regions whose interactions with the growing polymer must be made and broken in a coordinated manner to enable the growing HA chain to translocate within the enzyme without being released prematurely. FIG. 14A illustrates 5 motifs that are putative HA-binding motifs of the type B—X$_7$—B, where B is a basic amino acid (i.e. Arg or Lys) and X is any amino acid, as described by Yang et al., 1994. It is anticipated that HAS utilizes two types of HA-binding regions; one type that holds and orients the donor HA-UDP chain for assembly of the next disaccharide unit and one type that holds the growing HA chain when it is released from the former site(s) and is translocated through the membrane.

Although there is no information about the possible HA-binding regions within HAS, it is intriguing that motifs #2–5 are absolutely conserved in the strepHASs and are generally conserved at these positions in the Class I HAS family (i.e., conserved within the same general region of the primary sequence). In addition, although motif #1 in suHAS contains Gln, rather than Arg/Lys (which could still H-bond with HA), it is still a good candidate motif, because partial or "weaker" HA-binding motifs must be considered for the reasons noted above. An overlapping motif at position #1 is highly conserved in the Class I family. Further, complete conservation of HA-binding regions within the Class I family are not expected because the three human HASs intrinsically make HA of different sizes; this reflects the different abilities of HAS1, HAS2 and HAS3 to retain their HA chains. In particular, motif #4 (with Asn rather than R/K) and motif #5 are conserved in all HASs, except the chlorella enzyme.

Figure 14B:
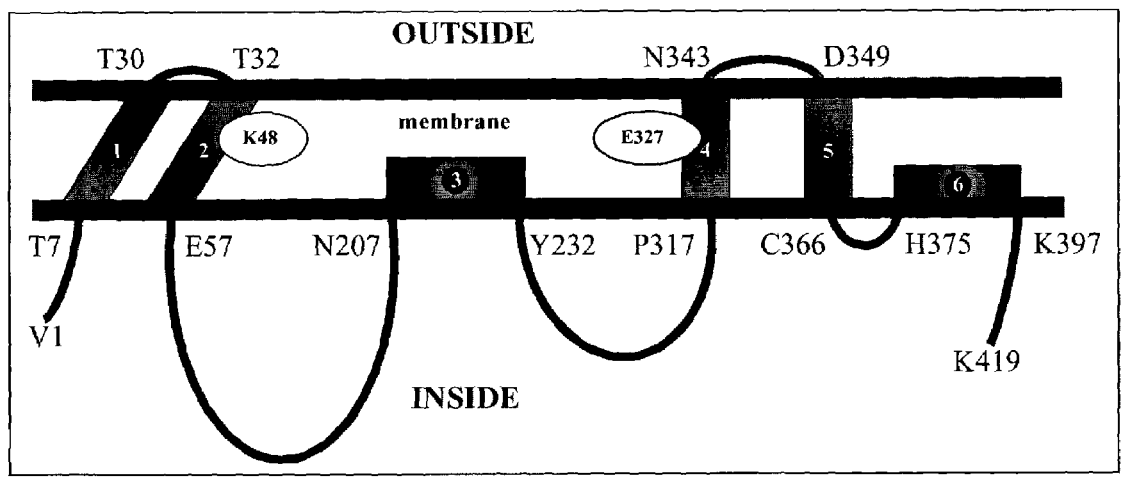
FIG. 14. Alignment of seHAs, spHAS and suHAS sequences (FIG. 14A), and topological organization of spHAS and probably all Class I HASs (FIG. 14B). Membrane domains (MDs) are numbered 1–6 starting from the N-terminus.

The topological organization of spHAS and probably all Class I HASs is shown in FIG. 14B. The experimentally determined topology of spHAS is similar to that initially predicted except for two membrane domains (MD3 and MD6) that are not transmembrane domains (TMDs). The N- and the C-termini and the large central domain are intracellular. The first two TMDs are β-sheets (not α-helices) and create a small extracellular loop that is inaccessible to proteases. MD3 within the large internal central domain is associated with, but does not traverse, the membrane.

There are then two TMDs connected by a second small extracellular loop that is also inaccessible to proteases. MD6, which has amphipathic helices, is within the C-terminal 50 amino acids of spHAS and does not cross the membrane. Numerous Mds may be required for HAS to create a pore-like structure through which a growing HA chain can be extruded to the exterior. Based on their similarities, all Class I HASs should have similar topological organizations of their spHAS-related domains.

Figure 15A:
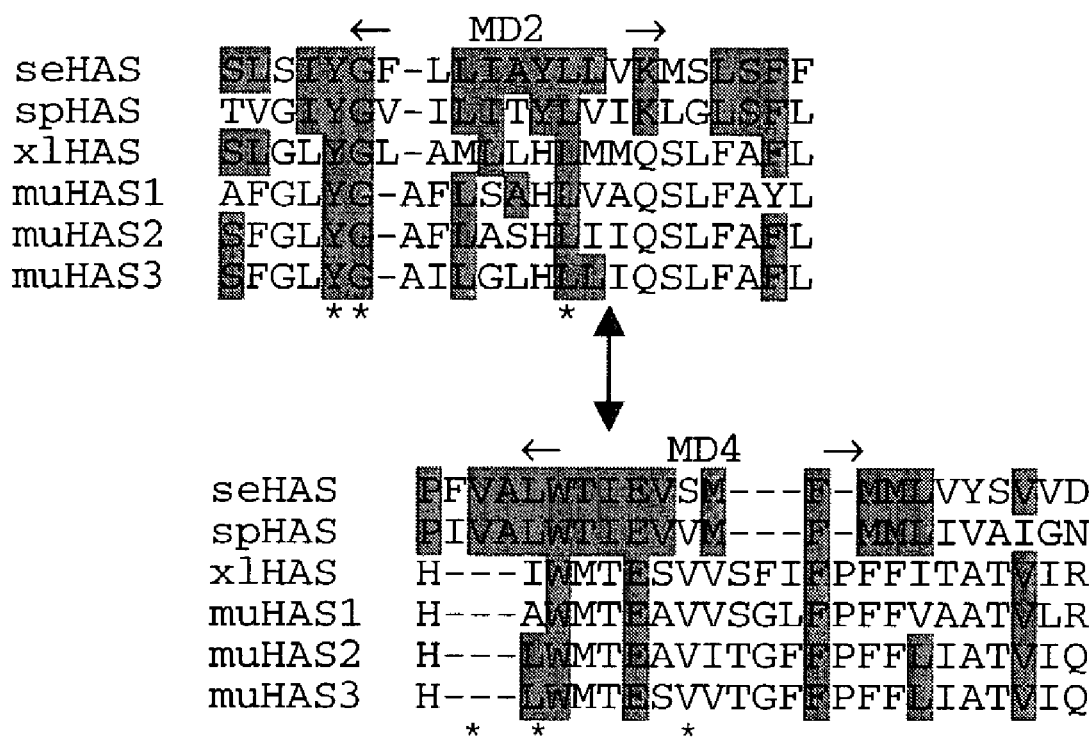
FIG. 15. Activity of seHAS mutants at K48 and E327. Panel A: the sequence alignments show K48 of seHAS within MD2 (using the nomenclature in FIG. 14). Note that seHAS and spHAS contain 417 and 419 amino acids, respectively, and their numbering is not identical. The analogous position in spHAS is also Lys, and in the eukaryotic HASs this is a conserved polar residue: Gln, which could be involved in one or more H-bonds. MD4 contains an absolutely conserved Glu residue in the Class I HAS family, which is E327 in seHAS. Alteration of either K48 or E327 to the opposite charged residue caused substantial loss of HAS activity (FIG. 15B). Activity was normalized for HAS expression as described herein. HAS activity is substantially rescued in the "double-switch" mutant, in which K48E and E327K mutations have exchanged the two charged residues at their respective positions.
Figure 15B:
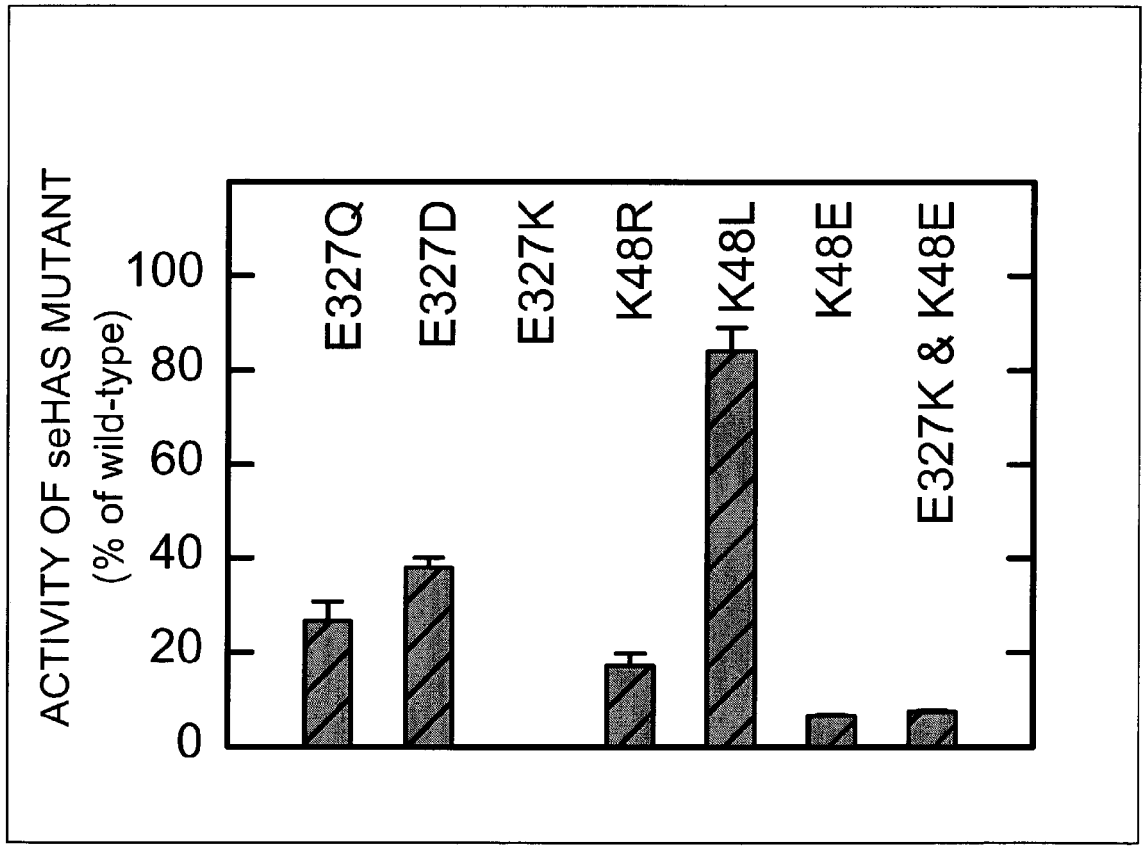

The presence in all Class I HASs of a possible charge/polar-pair between two membrane domains was noted, and in seHAS, these residues are K48 and E327 (indicated by the ovals in FIG. 14B and as seen in FIG. 15A). It is believed that the two charged or polar residues form a salt bridge or strong H-bond link that anchors MD2 (which traverses the membrane from outside to inside) and MD4 (which traverses the membrane from inside to outside). A series of site-directed mutants of seHAS were generated in which one or both of these residues was changed either to destroy this putative interaction or to reverse the position of charged residues. Vmax values for these seHAS mutants varied greatly (FIG. 15B). Since the "double switch" mutation partially rescues the E327K mutant, the results support the idea that the two residues interact with each other. Although most of the above seHAS mutants were expressed, the level was reduced, indicating that the proteins do not fold correctly and are degraded, e.g., seHAS(E327K) had only ~0.2% of wild-type activity. However, creating a "double switch" mutant seHAS(K48E/E327K), in which the charged residues were switched, restored HAS activity to ~8% of wild-type. These results, therefore, support the idea that K48 and E327 interact with each other and that MD2 and MD4 are close enough for these residues to form an ion-pair or H-bonds.

Light scattering is routinely used to obtain important information that complements the kinetic characterization of HAS variants. For example, a current study uses E. coli membranes containing a HAS variant, to examine the HA size produced by all the Cys-mutants of seHAS and spHAS. Analysis of HA size is not as straightforward as one might expect, since it has been discovered that HA size distributions made by HAS can change slightly with time and are surprisingly sensitive to HAS concentration—even under conditions of high concentrations and kinetic linearity with time and protein. Kinetic analyses assess the overall rates of sugar incorporation into HA regardless of size, and do not reflect changes in the size of the HA products being made. We are only aware of this because GPC-MALLS analysis is so sensitive. The time-dependent changes in HA size distribution are not surprising when one considers that the HAS molecules present in a sample may need to go through several rounds of chain synthesis before a steady-state size distribution is reached. Additionally, based on the changing ratio of substrates:HAS, very large chains are made at early times when this ratio is the highest and smaller chains are made latter as this ratio falls. The standard conditions utilized in the method of the present invention for comparing HA size differences by MALLS is that ≦5% of the substrates should be consumed, synthesis must be linear for ≧2 h and the HA size distribution observed should not change significantly over a several-fold range of increasing protein concentration.

Figure 16:
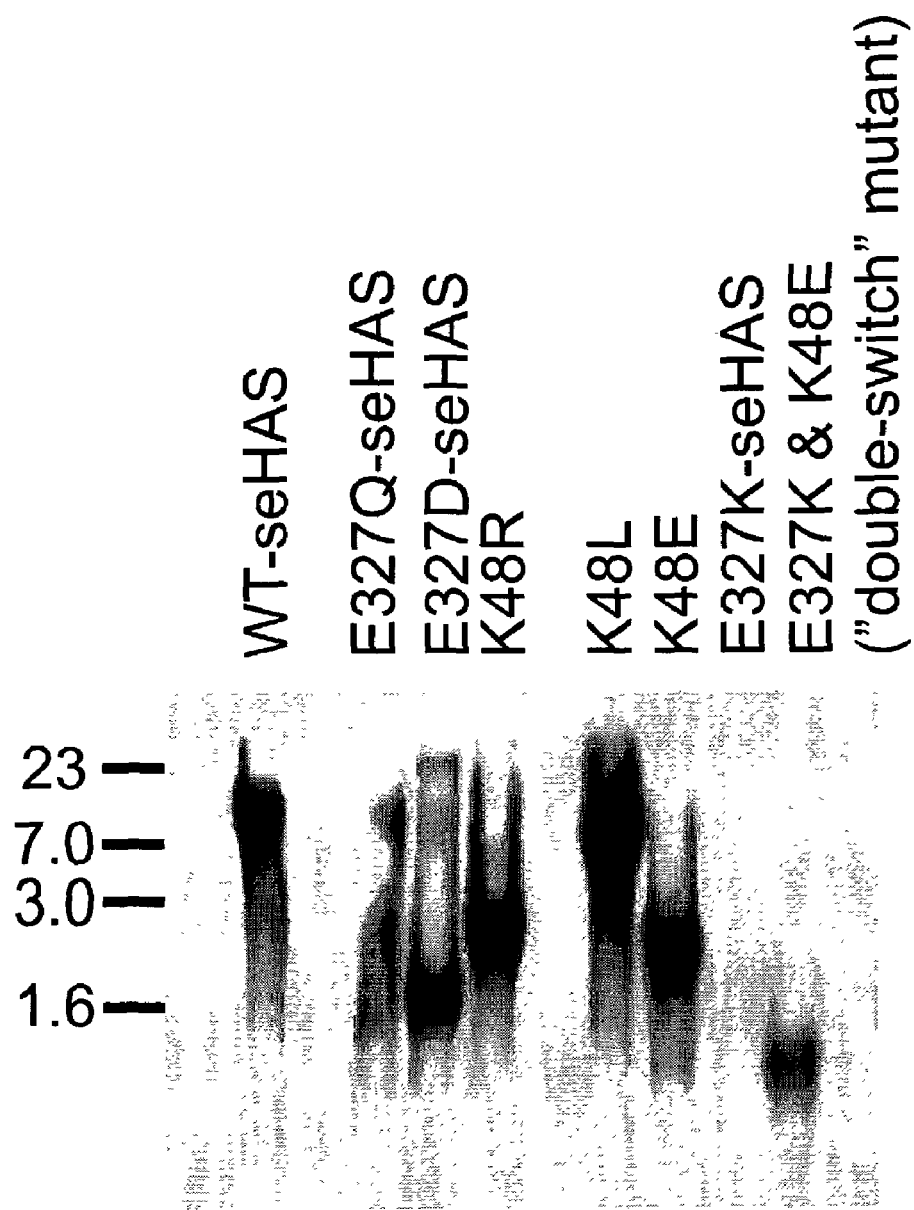
FIG. 16. Size distributions of HA made by K48 and E327 mutants of seHAS are different from wild type. Data supporting

The seHAS(E327K) mutant has only ~0.2% of wild-type activity. However, creating a "double-switch mutant" seHAS(K48E/E327K), in which the charged residues were switched, restored a significant level of HAS activity (~8% of wilt-type). These results, therefore, suggest that Lys48 and Glu327 interact with each other and that MD2 and MD4 are close enough for these residues to form an ion-pair or H-bonds. The interaction of K48 and E327 appears to be very important, perhaps critical, for enzyme activity. Further supporting this conclusion is the very interesting result that the size distribution of HA produced by the double-switch mutant is shifted dramatically to smaller size (FIG. 15 and 16). Based on GPC-MALLS analysis the weight average mass (Mw) for the mutant is 0.26 million compared to 2.8 million for wild-type seHAS.

The HAS enzymes are unique in that they polymerize two sugars, GlcUA and GlcNAc, in an alternate fashion and simultaneously extrude the growing HA chain through the plasma membrane. The streptococcal HASs are the smallest members of the Class I HAS family, and perform all the functions required for HA synthesis and secretion from cells. Unlike the eukaryotic HAS enzymes, with which they share substantial homology and probably an identical topological organization in their common regions, the streptococcal enzymes have been easier to study because they can be readily overexpressed, purified and characterized. To date, only one eukaryotic enzyme, mouse HAS1, has been overexpressed, purified and characterized kinetically.

The importance of Cys residues in seHAS and spHAS was initially focused on for three reasons. First, Cys residues play important structural and functional roles in many proteins (e.g. 35). Second, the four Cys residues in seHAS at positions 226, 262, 281, and 367 are completely conserved in the two other streptococcal enzymes, suHAS and spHAS, and are generally conserved in all the other eukaryotic HASs (FIG. 1). Finally, p-chloro-mercurobenzoate had been reported to inhibit HA biosynthesis by the Group A spHAS in a cell-free system (Sugahara et al., 1979). Although no further studies on the role of sulfhydryls in HAS function had appeared since that report, it was important to investigate the possibility that Cys residues may be required for HAS activity.

The present results demonstrate that a variety of sulfhydryl reagents inhibit both the spHAS and seHAS enzymes. This inhibition could reflect an important role of Cys in the function of these bacterial HAS proteins. However, interpretation of these results is complicated by the fact that Cys-modification creates two changes in the enzyme; the S-H group is eliminated but a new S-R group is also introduced, where R depends on the sulfhydryl reagent used. Because all the R groups are larger than the initial H, modified Cys residues may create new steric constraints for particular enzyme functions such as substrate binding. Alternatively, different degrees of HAS inhibition by different sulfhydryl reagents could indicate their different reactivity towards Cys residues, which would depend upon their size, charge or polarity. The use of site directed mutagenesis to alter the native Cys residues, while subject to the same concerns noted above, provides a complementary approach to determine the importance of Cys residues in HAS function. Both approaches show that although HAS activity is decreased by altering Cys residues, it is not eliminated; the completely modified seHAS and spHAS Cys-null enzymes were still able to perform all of the functions needed for HA synthesis.

The experiments and results detailed herein demonstrate clearly that neither the seHAS enzyme nor the spHAS enzyme contains any disulfide bonds. It is reasonable to conclude, therefore, that the streptococcal HAS proteins do not have disulfide bonds. It may be more difficult to determine if the eukaryotic HAS proteins contain disulfide bonds, since these proteins are difficult to purify in high yield and contain more Cys residues (≧14) than the streptococcal proteins.

All HAS enzymes make a broad size range of HA, rather than a discrete size. This heterogeneity of product size may be important biologically for particular functions of the three vertebrate HAS enzymes. In addition, the HA size distribution made varies among the streptococcal HASs and also among the three mammalian HAS isoforms. These enzymatic differences in the size distribution of HA products, which have only been observed in vitro (e.g. in isolated cells or membrane preparations), could have very significant biological consequences if they also occur in vivo in various eukaryote cells and tissues. Numerous studies during the last decade have demonstrated that HA is not simply a structural component of the extracellular matrices of most vertebrate tissues, but also a cell signaling molecule capable of modifying important aspects of cell behavior, including migration and adhesion. The most interesting and surprising aspect of this new paradigm regarding the biological functions of HA is that many cells respond only if the HA is a specific size. In particular, small oligosaccharides of HA have very different biological activities than large, native-size HA.

Figure 17:
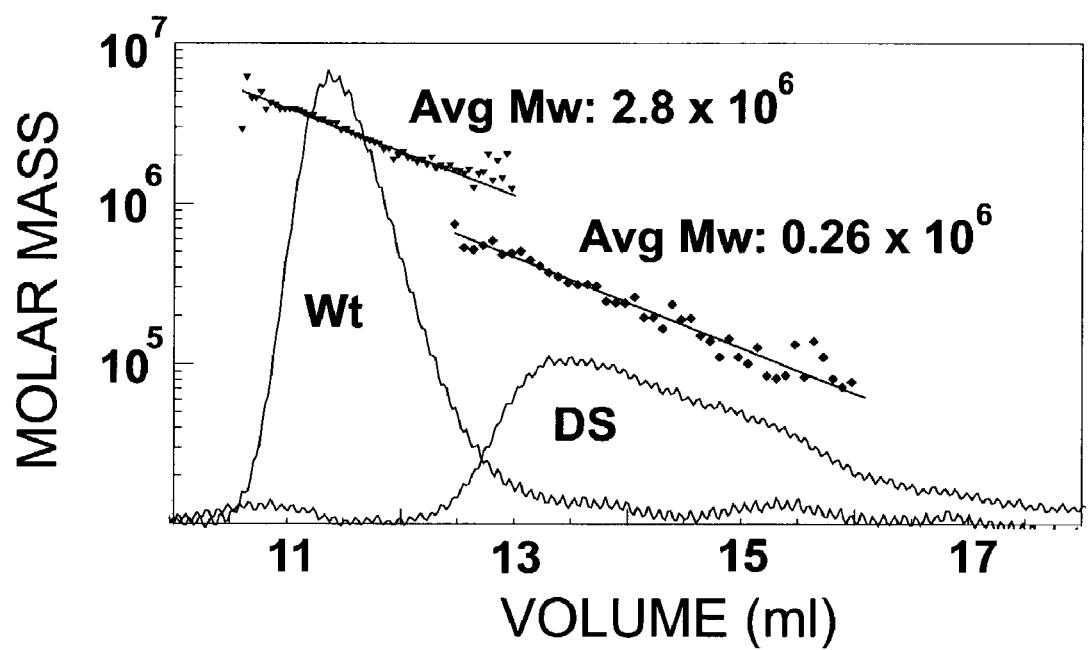
FIG. 17. The HA size distribution made by mutants of seHAS can be altered. Membranes from wild-type seHAS (WT) and the seHAS(E327K/K48E) double-switch (DS) mutant were incubated with 1 mM UDP-GlcNAc and UDP-GlcUA for 1 h at 30° C. as described by Tiapak-Simmons et al (1999). Reactions were terminated by chilling the samples on ice, centrifuging 20,000×g at 4° C. for 20 min and adding EDTA to the supernatant to a final concentration of 40 mM. Prior to GPC-MALLS analysis, samples were heated at 100° C. for 1 min. GPC fractionation was over TSK-GEL G4000PW$_{XL}$ and then TSK-GEL G6000PW$_{XL}$ columns (7.8× 30 cm) from TOSO BIOSEP (Montgomeryville, Pa.). The chromatography buffer was 50 mM Na$_2$HPO$_4$, pH 7.0, 150 mM NaCl and the flow rate was 0.5 ml/min. MALLS is performed using a DAWN DSP Laser Photometer with an Optilab DSP refractometer (WYATT Technology, Santa Barbara, Calif.).

An intriguing finding of the present invention is that some, but not all, combinations of Cys-mutations in seHAS cause the enzyme to synthesize HA products having an altered size. Eight of the 19 Cys-mutants examined synthesized HA with an apparently normal distribution of sizes that were shifted to varying degrees to smaller mass. There was no apparent correlation between changes in HA elongation rate ($V_{max}$ values) and HA size distribution among these Cys-mutants. The least active seHAS variants, nonetheless, made HA products that were similar in size to the HA made by the wild-type enzyme. The agarose gel electrophoresis technique is very suitable for obtaining a qualitative assessment of size differences. However, it is very difficult to assess the reliability of size assessments outside the narrow range in which migration is proportional to size. For example, several Cys-mutants (e.g. one each of the single, double and triple mutants in FIG. 7) may actually synthesize substantially larger HA than wild-type but the migration differences compared to wild-type are very small. For these reasons, a study to characterize the HA size distributions of these seHAS mutants using gel permeation chromatography coupled to dynamic light scattering (MALLS) is shown in FIG. 17. The present invention demonstrates a role of Cys residues in controlling HA chain length. In particular, the single seHAS Cys-mutant C281A makes much smaller HA, whereas the seHAS C281S mutant makes HA products very similar in size, compared to wild-type seHAS. In addition, the spHAS Cys mutant C280A also makes much smaller HA, as seen in co-pending U.S. Ser. No. 10/011,771, the contents of which have been previously incorporated herein by reference in their entirety.

Although NEM treatment of seHAS caused the velocity maximum ($V_{max}$) of the enzyme to decrease, it did not substantially change the $K_m$ values for either nucleotide-sugar compared to untreated seHAS. These results indicate that the ability of the NEM-treated enzyme to bind each substrate is not greatly decreased by modification of its Cys residues, but the overall catalytic rate is slowed. In contrast, some of the site specific Cys-mutants showed greater changes in their kinetic constants.

None of the single Cys-to-Ala or Cys-to-Ser mutants of seHAS or spHAS are inactive, indicating that no single Cys residue plays a critical, necessary role in HA synthesis. The specific HAS activity remaining in the single, double, triple, and Cys-null mutants confirms that Cys is not required at any position within the enzyme for a critical step in HA synthesis. Nonetheless, $Cys^{226}$ and $Cys^{262}$ together appear to play an important role in the activity of seHAS, since the double mutant seHAS(C226,262A) was the least active Cys-mutant with only 2–3% of the wild-type activity. Despite its low activity, this double mutant, nonetheless, synthesized HA of normal size. The triple Cys-mutant seHAS($\Delta 3C$)$C^{281}$ also had very low activity, similar to the double Cys-mutant seHAS(C226,262A), and also synthesized normal size HA. These results indicate that alteration of $Cys^{367}$ does not cause decrease in HAS activity and is consistent with the single Cys-mutant results in Table VIII. In fact, the seHAS C367A and spHAS C366A mutants both exhibited increases in activity over the corresponding wild-type enzymes.

Interestingly, the lower functionality of seHAS(C226, 262A) was substantially relieved by the introduction of a C281A change to create the triple Cys-mutant seHAS($\Delta 3C$)$C^{367}$. Possibly, a structural or functional constraint, perhaps related to HA chain length, brought about by mutating $Cys^{226}$ and $Cys^{262}$ to Ala is substantially relieved by simultaneously mutating $Cys^{281}$. The triple mutant SeHAS($\Delta 3C$)$C^{367}$ and the Cys-null mutant had similar activities and HA product sizes, suggesting a similar degree of compensation for the otherwise deleterious $Cys^{226}$/$Cys^{262}$ double mutation. The Cys-null mutant of seHAS retained approximately 20% of wild-type activity. The results indicate that $Cys^{226}$ and $Cys^{262}$ play an important role in the overall activity and kinetic characteristics of seHAS, but $Cys^{281}$ may play a role in regulating HA size. Based on the recently determined topology of spHAS and its high level of homology with seHAS (72% identical plus 10% similar residues), we know that $Cys^{226}$, $Cys^{262}$, and $Cys^{281}$ are present in the central domain region of seHAS (FIG. 1), which is the region that contains β-glycosyltransferase family motifs. The topological model predicts that $Cys^{367}$ is very close to transmembrane domain 4 and is probably not near the glycosyltransferase motifs.

Based on the NEM-modification and Cys-mutagenesis results, it appears that one or more Cys residues may be located close to the nucleotide-sugar binding sites of the seHAS or spHAS enzymes. This possibility provides a rationale to explain why modification or alteration of these Cys residues interferes with enzyme function and lowers enzyme activity. Preliminary results suggest that either substrate, UDP-GlcUA or UDP-GlcNAc, can protect seHAS from inhibition by NEM (FIG. 6), supporting the premise that at least one Cys residue is located in or near a nucleotide-sugar binding pocket. Substrate binding to this site appears to interfere with the reaction between NEM and the nearby Cys residue(s). Similar conclusions about the proximity of Cys residues to substrate binding sites have been reported for several other proteins, including the lactose permease, glutathione synthetase, glucocorticoid receptor, retinoic acid receptor β, and plasma membrane proton-ATPase. All of these studies found that modification of Cys residues by sulfhydryl reagents decreased the activity of the protein, even though Cys mutagenesis did not inactivate the protein. Another recent study generated 400 Cys-scanning mutants of a tetracycline transporter in order to map the membrane topology and active site of the protein in membrane preparations. The ability of tetracycline to protect only particular Cys residues from reaction with NEM, and subsequent inactivation of the protein, allowed the tetracycline binding site and channel to be mapped.

Another important consideration in evaluating the importance of Cys residues in spHAS, and the other Class I HAS family members in general, may be their involvement in HA translocation. The mechanism by which these enzymes are able to hold onto the growing HA chain, while they continuously extrude the polysaccharide through the bacterial cell or plasma membrane, is still unknown. This extrusion process is referred to as a translocation, since the HA is not completely transferred across the membrane and released as would occur in a typical transport process. The synthesis and extracellular accumulation by some bacteria of polysaccharides, such as polysialic acid, often requires multiple factors and proteins encoded by very complex multi-gene operons (Moxon and Kroll, 1990; Bliss and Silver, 1996). In contrast, all of the genetic and biochemical evidence to date (reviewed in Weigel, 1998) demonstrate that the streptococcal enzymes are able to initiate HA chain formation and then rapid extension of the HA chain in the absence of any primer or other proteins. Other than the two sugar nucleotide substrates and $Mg^{+2}$, the purified spHAS or seHAS enzymes only require a phospholipid (Tlapak-Simmons et al., 1999a) in order to produce high molecular weight HA ($>10^6$ Da). In particular, cardiolipin dramatically stimulates the specific activity of detergent solubilized or purified spHAS and seHAS. The size distribution of HA products is very similar for enzyme in isolated membranes or after solubilization with dodecylmaltoside and affinity purification (data not shown). Therefore, the presence of a natural intact phospholipid bilayer and membrane does not affect the ability of the HAS enzymes to synthesize HA. Presently, a suitable assay to evaluate the ability of the wildtype or Cys-mutant enzymes to translocate HA is not available.

The creation of seHAS$^{Cys-null}$ and/or spHAS$^{Cys-null}$ mutants that retain enzymatic activity enables a more in depth analysis of the tertiary structure of the HAS enzyme and conformational changes that occur during substrate binding, catalysis or HA translocation. To understand these processes, it is necessary to determine the interactions and molecular proximity of various domains within the protein in a more defined way. Cys-scanning mutants of seHAS or spHAS containing a single unique Cys residue at a desired position could enable one to employ electron paramagnetic resonance studies by modifying this Cys residue with a suitable probe. This approach, for example, allowed Voss et al., to determine the proximity of that modified residue to another region of the Lac permease. Similarly, chemical modification of a single unique Cys residue with a fluorescent probe enables a systematic analysis of the localized environment within different regions of the protein. Interacting or proximal domains within seHAS or spHAS may also be determined by assessing the formation of disulfide bonds in specific mutants containing two Cys residues. Such approaches help to elucidate the structure and function of seHAS and increase our understanding of how the HAS family is able to synthesize HA.

MATERIALS AND METHODS

Vectors, Primers, and Reagents pEx-1 was purchased from Promega as part of the Altered Sites Mutagenesis kit. The expression vector pKK223 was from Pharmacis Biotech Inc. *E. coli* SURE cells were from Stratagene. Successful mutagenesis was achieved with the QUICK CHANGE™ Mutagenesis kit from Stratagene. Primers were synthesized by The Great American Gene Company (Ransom Hill Bioscience, Inc., CA), NBI, or Midland Certified Reagent Company. All of the mutagenic oligonucleotides were synthesized by Genosys Biotechnologies, Inc. (Spring, Tex.) and were purified by reverse-phase chromatography. Cy-5 fluorescent sequencing primers were synthesized by the Molecular Biology Resource Facility, Oklahoma University Health Sciences Center. Nonradiolabeled UDP-GlcUA, and 2,4,6-trihydroxyacetophenone were from Fluka. UDP-GlcNAc was from Sigma. UDP-[$^{14}$C] GlcUA (300 mCi/mmol) and $^{14}$C-NEM (40 mCi/mmol) were from New England Nuclear. Agarose was from Bio-Rad. (+)-Biotinyl-3-maleimidopropionamidyl-3,6-dioxaoctanediamine (biotin-PEO-maleimide) was from Pierce Chemical Co. NEM and all other reagents were from Sigma unless otherwise noted. To confirm the entire ORF of HAS mutants, DNA sequencing was performed either using the T7 or PCR sequencing kits from Amersham, or by the micro-sequencing facility operated by the Department of Microbiology & Immunology at the University of Oklahoma Health Sciences Center. Anti-His$_5$ monoclonal antibody and Ni$^{+2}$-NTA resin were from Qiagen.

Site-Directed Mutagenesis

The seHAS gene with a fusion at the 3' end encoding a His$_6$ tail (seHAs-His$_6$) was cloned into pKK233. Mutagenic primers were designed to change the cysteines to either Ala or Ser at positions 226, 262, 281 and 367. Two complementary oligonucleotide primers encoding the desired mutation were used to create the single Cys mutations (Table X). Mutagenesis was carried out using the Quick Change method according to the manufacturer's instructions. The pKK233 plasmid containing the seHAS-His$_6$ gene was grown in SURE cells, purified using a Spin Miniprep Kit (Qiagen) and analyzed by agarose gel electrophoresis to verify the correct size. The purified PDNA was used as the template for the primer extension reaction with a pair of mutagenic primers. The PCR Amplification conditions for PCR, using pfu DNA polymerase, were 16 cycles of the following: 95° C. for 1 min, 58° C. for 1 min, and 68° C. for 18 min. This amplification generated mutated plasmids with staggered nicks, which was then treated with DpnI to digest the methylated and

TABLE X

Synthetic oligonucleotides used to make seHAS mutants
The boldface font indicates the altered codon. All primers shown are in the sense orientation.

| seHAS mutant | Sequence | SEQ ID NO: |
|---|---|---|
| C226A | 5'-GGTAATATCCTTGTTGCCTCAGGTCCGCTTAGC | |
| C226S | 5'-GGTAATATCCTTGTTTCCTCAGGTCCGCTTAGC | |
| C262A | 5'-ATTGGTGATGACAGGGCCTTGACCAACTATGCA | |
| C226S | 5'-ATTGGTGATGACAGGTCCTTGACCAACTATGCA | |
| C281A | 5'-CAATCCACTGCTAAAGCTATTACAGATGTTCCT | |
| C281S | 5'-CAATCCACTGCTAAATCTATTACAGATGTTCCT | |
| C367A | 5'-TTCATTGTTGCCCTGGCTCGGAACATTCATTAC | |
| C367S | 5'-TTCATTGTTGCCCTGTCTCGGAACATTCATTAC | |

TABLE XI

Oligonucleotides for Cys-to-Ser/Ala site directed mutagenesis of spHAS.
Cys residues within spHAS at positions 124, 225, 261, 280, 366 and 402 were converted either to Ser using a single mutagenic oligonucleotide, complementary to the coding strand, and the Altered Sites kit or to Ala using a pair of complementary mutagenic oligonucleotides and the Quick Change Mutagenesis kit (in the latter case only the forward primers complementary to the coding strand are shown). The altered codons are indicated in boldface.

| SpHAS mutation | Mutagenic Oligonucleotide | SEQ ID NO: |
|---|---|---|
| (C124S) | 5'-TAACGTTTCGAGAAATATCCAC | |
| (C225S) | 5'-GGTCCTGAGGAAACTAAAAT | |
| (C261S) | 5'-ATTTGTTAAAGATCGATCATC | |

TABLE XI-continued

Oligonucleotides for Cys-to-Ser/Ala site directed mutagenesis of spHAS.
Cys residues within spHAS at positions 124, 225, 261, 280, 366 and 402 were converted either to Ser using a single mutagenic oligonucleotide, complementary to the coding strand, and the Altered Sites kit or to Ala using a pair of complementary mutagenic oligonucleotides and the Quick Change Mutagenesis kit (in the latter case only the forward primers complementary to the coding strand are shown). The altered codons are indicated in boldface.

| SpHAS mutation | Mutagenic Oligonucleotide | SEQ ID NO: |
|---|---|---|
| (C280S) | 5'-ATCAGTATCAGATCTAGCTGT | |
| (C366S) | 5'-AACATTACGAGATAAAGCAAC | |
| (C402S) | 5'-TTTAATGGTGGATAAAGAATA | |
| (C124A) | 5'-AACGATAACGTTTCGAGCAATATCCACTTCTCT | |
| (C225A) | 5'-CAATGGTCCTGAGGCAACTAAAATATTACC | |
| (C261A) | 5'-AGCATAATTTGTTAAAGCTCGATCATCCCCAAT | |
| (C280A) | 5'-AGGTACATCAGTATCAGCTCTAGCTGTTGATTG | |
| (C366A) | 5'-AACATTACGAGCTAAAGCAAC | |
| (C402A) | 5'-CGTATTTTTAATGGTGGCTAAAGAATAAAGTTT | |

TABLE XII

All Possible Cysteine Mutants of seHAS and spHAS.

| HAS | Cysteine(s) mutated | SEQ ID NO: |
|---|---|---|
| seHAS | 226 | 15 |
| seHAS | 262 | 16 |
| seHAS | 281 | 17 |
| seHAS | 367 | 18 |
| seHAS | 226,262 | 19 |
| seHAS | 226,281 | 20 |
| seHAS | 226,367 | 21 |
| seHAS | 262,281 | 22 |
| seHAS | 262,367 | 23 |
| seHAS | 281,367 | 24 |
| seHAS | 262,281,367 | 25 |
| seHAS | 226,281,367 | 26 |
| seHAS | 226,262,367 | 27 |
| seHAS | 226,262,281 | 28 |
| seHAS | Cys-null (226,262,281,367) | 29 |
| spHAS | 124 | 30 |
| spHAS | 225 | 31 |
| spHAS | 261 | 32 |
| spHAS | 280 | 33 |
| spHAS | 366 | 34 |
| spHAS | 402 | 35 |
| spHAS | 125,225 | 36 |
| spHAS | 124,261 | 37 |
| spHAS | 124,280 | 38 |
| spHAS | 124,366 | 39 |
| spHAS | 124,402 | 40 |
| spHAS | 225,261 | 41 |
| spHAS | 225,280 | 42 |
| spHAS | 225,366 | 43 |
| spHAS | 225,402 | 44 |
| spHAS | 261,280 | 45 |
| spHAS | 261,366 | 46 |
| spHAS | 261,402 | 47 |
| spHAS | 280,366 | 48 |
| spHAS | 280,402 | 49 |
| spHAS | 366,402 | 50 |
| spHAS | 124,225,261 | 51 |
| spHAS | 124,225,280 | 52 |
| spHAS | 124,225,366 | 53 |
| spHAS | 124,225,402 | 54 |
| spHAS | 124,261,280 | 55 |
| spHAS | 124,261,366 | 56 |
| spHAS | 124,261,402 | 57 |
| spHAS | 124,280,366 | 58 |
| spHAS | 124,280,402 | 59 |
| spHAS | 124,366,402 | 60 |
| spHAS | 225,261,280 | 61 |
| spHAS | 225,261,366 | 62 |
| spHAS | 225,261,402 | 63 |
| spHAS | 225,280,366 | 64 |
| spHAS | 225,280,402 | 65 |
| spHAS | 225,366,402 | 66 |
| spHAS | 261,280,366 | 67 |
| spHAS | 261,280,402 | 68 |
| spHAS | 261,366,402 | 69 |
| spHAS | 280,366,402 | 70 |
| spHAS | 124,225,261,280 | 71 |
| spHAS | 124,225,261,366 | 72 |
| spHAS | 124,225,261,402 | 73 |
| spHAS | 124,225,280,366 | 74 |
| spHAS | 124,225,280,402 | 75 |
| spHAS | 124,225,366,402 | 76 |
| spHAS | 124,261,280,366 | 77 |
| spHAS | 124,261,280,402 | 78 |
| spHAS | 124,261,366,402 | 79 |
| spHAS | 124,280,366,402 | 80 |
| spHAS | 225,261,280,366 | 81 |
| spHAS | 225,261,280,402 | 82 |
| spHAS | 225,261,366,402 | 83 |
| spHAS | 225,280,366,402 | 84 |
| spHAS | 261,280,366,402 | 85 |
| spHAS | 124,225,261,280,366 | 86 |
| spHAS | 124,225,261,280,402 | 87 |
| spHAS | 124,225,261,366,402 | 88 |

TABLE XII-continued

All Possible Cysteine Mutants of seHAS and spHAS.

| HAS | Cysteine(s) mutated | SEQ ID NO: |
|---|---|---|
| spHAS | 124,225,280,366,402 | 89 |
| spHAS | 124,261,280,366,402 | 90 |
| spHAS | 225,261,280,366,402 | 91 |
| spHAS | Cys-null (124,225,261,280,366,402) | 92 |

Each of the Cysteines listed may be mutated to Alanine, Serine, or any other amino acid as described herein previously. In addition, when more than one Cysteine is mutated, all the mutations may be the same (i.e., all Cys-Ala mutations), or a mutant containing multiple Cysteine mutations may have a combination of Cys-Ala, Cys-Ser and Cys-Xaa mutations.

hemi-methylated parental DNA. The digested pDNA was transformed into SURE cells and colonies were screened for the desired mutations by sequencing the isolated plasmid DNA using fluorescently labeled terminators (ABI Prism 377 MODEL program, v2.1.1). The complete ORFs of selected mutants were confirmed by sequencing in both directions with Cy-5 labeled vector primers on a Pharmacia ALF Express DNA Sequencer. Data were analyzed using ALF Manager, v3.02. The double, triple and null Cys-mutants of seHAS-His$_6$ were made using the appropriate single, double or triple Cys-mutant plasmid DNA as the template, respectively.

Single mutants of spHAS were generated by the Altered Sites Mutagenesis or Quick Change Mutagenesis protocols using primers (Table XI) designed to change the Cys residues at positions 124, 225, 261, 280, 366, or 402 of spHAS containing His$_6$ at the C-terminus (Tlapak-Simmons, et al., 1999a). After generating and confirming the entire sequence of each spHAS(Cys-to-Ser) mutant produced in the Altered Sites vector, internal restriction sites within the HAS ORF were used to transfer mutated regions to the spHAS insert in pKK223 (this vector carrying HAS is designated pKK3K). Cys-to-Ala mutants of spHAS were generated directly in the pKK3K vector using the Quick Change mutagenesis method. Site directed mutagenesis was used to generate the C124, C402A double mutant, and then C366A was added by restriction fragment exchange to generate a triple mutant. Site directed mutagenesis was also used to create the double mutant spHAS(C261A,C280A). The mutants containing five or six mutated Cys residues were generated by utilizing restriction sites to combine fragments of spHAS containing different mutations. For example, AvrII and MfeI were used to combine the spHAS(C124A,C366A,C402A) triple Cys-mutant and the spHAS(C261A,C280A) double mutant to create spHAS with only Cys$^{225}$ intact. Finally, BglII and AvrII were used to splice spHAS(C225A) into the latter quintuplecys-mutant to generate the Cys-null clone, designated spHAS$^{Cys-null}$. All Cys-to-Ala/Ser mutants were confirmed over the full ORF by automated DNA sequencing.

Effect of Sulfhydryl Reagent Treatments on seHAS and spHAS Activity and Determination of the Kinetic Constants of seHAS Cys Mutants.

E. coli SURE cells transformed with plasmids containing various seHAS mutants were grown in LB medium with vigorous shaking at 32° C. to A$_{600}$ ~0.8 and induced with 1 mM isopropyl-β-thiogalactoside for 3 h. Cells were harvested and membranes were prepared as described previously. The kinetic constants for HAS were determined at 37° C. in 100 μl of 50 mM sodium and potassium phosphate, pH 7.0, with 20 mM MgCl$_2$, 1 mM DTE, 240 μM UDP-GlcUA, 0.7 μM UDP-[$^{14}$C]GlcUA and 0.6–1.0 mM UDP-GlcNAc. in 100 μl of 25 mM sodium and potassium phosphate, pH 7, containing 50 mM NaCl, 20 mM MgCl$_2$, 1 mM dithiothreitol, 1 mM UDP-GlcUA, 0.68 μM UDP-GlcUA and 1 mM UDP-GlcNAc. Some assays also contained 0.1 mM EDTA and 20% glycerol (v/v). To initiate the enzyme reaction, ~0.5–40 μg of membrane protein was added and the mixtures were gently shaken in a MicroMixer X-36 (Tiatec) at 30° C. for 1–2 h. Reactions were terminated by the addition of SDS to a final concentration of 2% (w/v). The incorporation of radioactive [$^{14}$C]GlcUA was determined by descending paper chromatography and the $K_m$ and $V_{max}$ values were determined as described by Tlapak-Simmons et al (1999b). Data were analyzed by the methods of Michaelis-Menton or Hill. Protein content was determined by the method of Bradford using bovine serum albumin as the standard. All Cys-mutant or sulfhydryl-treated seHAS samples were assayed in duplicate or triplicate using two or three independent membrane preparations. Results are presented as the mean±standard errors. All enzyme assays were performed under conditions that were linear with respect to time and protein concentration. None of the seHAS variant enzymes were unstable under the conditions employed.

Determination of HA Size Produced by seHAS Variants.

The relative $M_r$ of the HA synthesized by wild-type seHAS or the Cys-mutants was determined by agarose gel electrophoresis of $^{14}$C-labeled HA products synthesized under the assay conditions described above. The wild-type seHAS synthesizes and releases an HA chain in <5 min under these steady-state conditions, so that each enzyme molecule on average synthesizes >10 HA chains during the incubation. Reactions were terminated by heating at 95° C. for 1 min, the mixtures were then centrifuged at high speed and the HA-containing supernatants were recovered. The samples were concentrated ~10-fold using Microcon YM-3 filters (Amicon Biosearations, Inc.) and treated with DNase and RNase (4 μg/ml each) in the presence of 60 mM MgCl$_2$ for 30 min at 22° C. The samples and a combination of DNA standards were then electrophoresed on a 1.3% (w/v) agarose gel at 80–90 V. The gels were dried without heating and exposed to Biomax-MR film (Kodak) for 1–4 weeks. The autoradiograms were scanned to create digital files using a Fluorchem™ 8000 (Alpha Innotech Corp.) image analysis station. As a control, samples were treated with Streptomyces hyaluronate lyase (80 units) at 37° C. overnight, which resulted in the complete loss of radiolabeled bands.

Determination of HA Chain Length Produced by spHAS Variants (Table IX).

HAS mutant HA size distribution was determined by agarose gel electrophoresis. Membranes containing wild-type or mutant Has were incubated in 0.5 mM UDP-GlcUA and 1.5 mM UDP-GlcNAc in 25 mM sodium/potassium phosphate, pH 7.0, 75 mM NaCl, 1 mM DTT, 15% glycerol, 10 mM MgCl$_2$, with 0.68–8.16 μM UDP-[$^{14}$C]GlcUA for one hour at 30° C., while shaking in a Taitec E-36 micromixer. EDTA was added to 0.1 M to stop the reactions. 1 mg/ml ovine testicular hyaluronidase was added to control tubes and incubated 1 hour at 37° C. to ensure the product formed was HA. 5 mg/ml Pronase was added to digest protein components that may bind HA, and the reactions were incubated >12 hours at 4° C. Reactions were either loaded directly to 1% agarose gels or were ethanol precipitated prior to loading. Components of the reaction were retained in or near the wells after electrophoresis. Ethanol precipitation was done to reduce this contamination. Reactions were centrifuged at 21,000×g for 10 min. One-tenth the volume of 3 M sodium acetate, pH 5.2, and three volumes of ethanol were added to supernatants. The tubes were mixed and incubated at −20° C. for 1 hour. The HA was collected by centrifugation at 21,000×g for 10 min. The pellet was air dried and suspended in either water or PBS. The suspension was loaded to agarose gels along with High Molecular Weigh and KB ladder DNA standards from Gibco BRL. After electrophoresis was stopped, the gel was dried and exposed to a phosphoscreen for 1 hour to >2 weeks. The gel image was obtained from the screen using a Molecular Dynamics Phosphoimager. HA chain size was estimated by migration distance relative to DNA standards. HA product size distribution was estimated by integration over MW ranges of the integrated density value (IDV) curve obtained for each lane. The preferred HA product size (peak size) was designated by the MW range in which the greatest IDV was located.

Determination of seHAS Protein Concentration in Membranes and Normalization of seHAS Activity.

The recombinant seHAS protein in isolated membranes is a major component comprising ~5–8% of the total protein, is well separated from other major proteins by SDS-PAGE and can be readily identified in Coomassie Blue-stained gels. $E.$ $coli$ membranes containing wild-type or mutant seHASs were solubilized and electrophoresed on 10% (w/v) gels following the procedure of Laemmli for SDS-PAGE. The amount of seHAS protein in each membrane preparation was quantitated by image analysis of the stained gel using a Fluorchem™ 8000 (Alpha Innotech Corp). The linearity of Coomassie Blue-stained seHAS bands was verified by loading different amounts of membrane protein. To generate a standard curve, various amounts of affinity purified seHAS-His$_6$ were subjected to identical SDS-PAGE and the Integrated Density Value (IDV) was determined for each band. The IDVs were plotted against pmol of pure seHAS. The IDV values for seHAS bands in membranes containing wild-type or mutant proteins were then compared with the standard to estimate the seHAS protein content per mg membrane protein. These data were then used to normalize the seHAS enzyme activity in the membrane preparations for wild-type and each variant seHAS.

Chemical Modification of HAS in Membranes.

Stock solutions (10–100 mM) of NEM, IAA or other sulfhydryl reagents were made in PBS, pH 7.0. Suspensions of membranes containing seHAS or spHAS were incubated with 0–5 mM of the sulfhydryl reagent at 4° C. and the reactions were stopped by adding DTE to a final concentration of 10 mM. The membranes were then assayed for HAS activity as described above.

Labeling of seHAS with $^{14}$C-NEM.

Isolated membranes from wild-type seHAS and each of the six double Cys-mutants of seHAS were incubated at 4° C. with 2.5 mM $^{14}$C-NEM (~8×10$^6$ dpm) for 5 min. The reactions were terminated by the addition of DTE to a final concentration of 5 mM. Total membrane proteins were precipitated by incubation with 10% trichloroacetic acid overnight at 4° C. and free $^{14}$C-NEM was then removed by two cycles of centrifugation and resuspension with 5% trichloroacetic acid. The precipitated proteins were dissolved in 1× SDS Laemmli sample buffer, neutralized by the addition of 0.1 N NaOH and analyzed by SDS-PAGE using a 10% gel. The Coomassie Blue-stained gel was scanned using a Model PDSIP60 densitometer (Molecular Dynamics), then treated with scintillants and subjected to fluorography using Biomax-MR (Kodak) film and an exposure of approximately one week. $E.$ $Coli$ membranes prepared from cells transformed with vector alone, containing no seHAS, were included as a control.

MALDI-TOF Analysis of seHAS Derivatives.

Wild-type seHAS-His$_6$ was bound to a Ni$^{+2}$-nitrilotriacetic acid chelate resin (Qiagen), washed and treated with biotin-PEO-maleimide (10 mg/ml) for 2 h on ice. After washing the column, the enzyme was eluted with distilled water containing 0.5% (v/v) trifluoroacetic acid and 0.02% (w/v) dodecylmaltoside. The degree of modification of Cys residues in treated seHAS samples was determined using a MALDI-TOF Voyager Elite mass spectrometer (Applied Biosystems, Framingham, Mass.), which was equipped with a N$_2$ laser (337 nm), located in the NSF EPSCOR Oklahoma Laser Mass Spectrometry Facility. The sample (1 µl) was spotted to a sample plate, followed by matrix solution (1 µl) and allowed to air dry. The matrix used was a 20 mg/ml solution of 2,4,6-trihydroxyacetophenone in 50% acetonitrile containing 0.1% trifluoroacetic acid and 0.05% (w/v) dodecylmaltoside. Samples were analyzed in the linear, positive ion mode using (a delayed extraction of 300 ns, a grid voltage of 87.8%, and were subject to a 25 kV accelerating voltage. External and internal calibrations were routinely performed using horse apomyoglobin and bovine serum albumin (16,951 and 66,430 Da, respectively). Spectra were an average of 80–120 scans and were processed using the 19 point Savitsky-Golay smoothing option included in the software provided by the manufacturer.

Determination of Recombinant spHAS-H$_6$ Content in Membranes

Membranes were isolated from $E.$ $coli$ SURE strains expressing mutant or wildtype spHAS, fractionated by SDS-PAGE according to the procedure of Laemmli (1970) and the proteins were electrotransferred to nitrocellulose as described by Towbin et al. (1979) with minor modifications (Tlapak-Simmons, et al., 1998). Western analysis was performed by incubating these blots for 1 h at room temperature with a biotinylated anti-His$_5$ monoclonal antibody, as the primary antibody, then washing and incubating with 3 µg/ml $^{125}$I-streptavidin, prepared as described hereinabove. After 1 h at room temperature, the blots were washed, dried and exposed to a Phosphoscreen for 1 to 72 h. The screens were analyzed using a Molecular Dynamics Phosphoimager and integrated density values were obtained for each spHAS band. Integrated density values were also obtained for increasing amounts of affinity-purified spHAS (Tlapak-Simmons et al., 1999a), which was used as an internal standard in the same blot to generate a standard curve. Dilutions of membrane samples were made as necessary to ensure that all estimates of HAS quantity were in the linear range of the assay. Those membrane samples giving a linear response with increasing protein were then compared to the standard curve to calculate the amount of spHAS present per µl membrane suspension. These values were then used to normalize the kinetic results obtained using membranes from the various spHAS mutants.

Enzymatic Analysis of HAS Mutants $E.$ $coli$ SURE cells, previously transformed with plasmids containing wildtype or mutant spHAS genes, were grown to an A$_{600}$ of ~1.2 and induced with 1 mM isopropyl thio-β-D-galactoside for three h. Cells were harvested and membranes were prepared as described previously (Tlapak-Simmons, et al., 1999a). The activities of mutant spHAS variants were assessed by measuring their V$_{max}$ and K$_m$ values in isolated membranes, normalized as described above for the amount of enzyme expressed. The K$_m$ values were determined using a descending paper chromatography assay (Tlapak-Simmons, et al., 1999b), holding one UDP-sugar substrate constant and varying the other from 0.01 to 4 mM.

Data were analyzed by linear regression using Haynes-Wolf plots for UDP-GlcUA or Hill plots for UDP-GlcNAc.

Inhibition of spHAS Activity by NEM

Membrane preparations from wildtype and various spHAS mutants (i.e. C124,402A, C261,280A, C124,366, 402A, C124,261,280,366,402A, and the Cys-null mutant) were incubated in 50 mM sodium, potassium phosphate, pH 7.0, 75 mM NaCl and 10% (v/v) glycerol with or without 20 mM NEM for 90 min on ice. The ability of the membrane samples to synthesize HA was then assessed by adding the following to the final concentrations indicated: 1 mM UDP-GlcUA, 1 mM UDP-GlcNAc, 0.68 μM UDP-[$^{14}$C]GlcUA in 25 mM sodium/potassium phosphate, pH 7, 75 mM NaCl, 10 mM $MgCl_2$, 1 mM dithiothreitol, 0.1 mM EGTA, 15% glycerol. Reactions were shaken for 1 h at 30° C. in a Taitec E-36 micromixer, stopped by the addition of SDS to 2% (w/v), and spotted onto No. 3MM Whatman paper for descending paper chromatography overnight using 1 mM ammonium acetate pH 5.5/ethanol (7:13). [$^{14}$C]GlcUA incorporation into high molecular weight HA was assessed by liquid scintillation spectroscopy to determine the radioactivity remaining at the origin. Confirmation that the latter material is authentic HA was obtained by showing its complete loss after treatment with streptomyces hyaluronidase.

Assessment of Disulfide Bond Formation in spHAS by MALDI-TOF MS.

Wildtype spHAS-His$_6$ was bound to a $Ni^{+2}$ chelate column (Qiagen) and washed as previously described (Tlapak-Simmons, et al,. 1999a). While still bound to the resin, the enzyme was incubated with biotin-PEO-maleimide (10 mg/ml) in the presence or absence of 6 M guanidinium-HCl for 2 h at 4° C. The column was washed and spHAS-His$_6$ was eluted with distilled water containing 0.5% (v/v) trifluoroacetic acid and 0.02% (w/v) dodecylmaltoside. To assess the degree of modification of Cys residues, samples containing purified spHAS were analyzed by MALDI-TOF mass spectrometry using a Voyager Elite mass spectrometer (Applied Biosystems, Framingham, Mass.), which was equipped with a $N_2$ laser (337 nm), located in the NSF EPSCoR Oklahoma Laser Mass Spectrometry Facility. A 1 μl aliquot of sample was spotted to a sample plate followed by 1 μl of matrix and allowed to air dry. The matrix used was a saturated solution of 2,4,6-trihydroxyacetophenone in 50% acetonitrile containing 0.1% trifluoroacetic acid and 0.005% (w/v) dodecylmaltoside. Samples were analyzed in the linear, positive ion mode using a delayed extraction of 300 ns, a grid voltage of 87.8%, and were subject to a 25 kV accelerating voltage. External calibrations were performed routinely using horse apomyoglobin and bovine serum albumin (16,951 and 66,430 Da, respectively). Data were routinely processed using the 19 point Savitsky-Golay smoothing option included in the software provided by the manufacturer.

Thus it should be apparent that there has been provided in accordance with the present invention a recombinant host cell having a purified nucleic acid segment having a coding region encoding enzymatically active HAS introduced therein, as well as methods of producing hyaluronic acid from the recombinant host cell, that fully satisfies the objectives and advantages set forth above. Although the invention has been described in conjunction with specific embodiments thereof, it is evident that many alternatives, modifications, and variations will be apparent to those skilled in the art. Accordingly, it is intended to embrace all such alternatives, modifications, and variations that fall within the spirit and broad scope of the appended claims.

REFERENCES

The following references, to the extent that they provide exemplary procedural or other details supplementary to those set forth herein, are specifically incorporated herein by reference in their entirety as though set forth herein particular.

Abatangelo, G., and Weigel, P. H. (2000) (editors) *New Frontiers in Medical Sciences: Redefining Hyaluronan.* Elsevier Science B. V., Amsterdam.

Appel, A., Horwitz, A. L., and Dorfman, A. (1979) *J. Biol. Chem.* 254, 12199–12203.

Atkinson, E. M. and Long, S. R. (1992) *Mol. Plant. Microbe. Interact.* 5, 439–442.

Bliss, J. M. and Silver, R. P. (1996) *Mol. Microbiol.* 21, 221–231.

Bradford, M. M. (1976) *Anal. Biochem.* 72, 248–254.

Breton, C., and Imberty, A. (1999) *Curr. Opin. Struct. Biol.* 9, 563–571.

Chakraborti, P. K., Garabedian, M. J., Yamamoto, K. R., and Simons, S. S., Jr. (1992) *J. Biol. Chem.* 267, 11366–73.

DeAngelis, P. L., Papaconstantinou, J. and Weigel, P. H. (1993a) *J. Biol. Chem.* 268, 14568–14571.

DeAngelis, P. L., Papaconstantinou, J. and Weigel, P. H. (1993b) *J. Biol. Chem.* 268, 19181–19184.

DeAngelis, P. L., Yang, N. and Weigel, P. H. (1994) *Biochem. Biophys. Res. Commun.* 199, 1–10.

DeAngelis, P. L and Weigel, P. H. (1994) *Biochem.* 33, 9033–9039.

DeAngelis, P. L. (1996) *Biochem.* 35, 9768–9771.

DeAngelis, P. L. and Achyuthan, A. M. (1996) *J. Biol. Chem.* 271, 23657–23660.

DeAngelis, P. L., Jing, W., Drake, R. R. and Achyuthan, A. M. (1998) *J. Biol. Chem.* 273, 8454–8458.

DeAngelis, P. L., Jing, W., Graves, M. V., Burbank, D. E. and Van Etten, J. L. (1997) *Science,* 278, 1800–1803.

DeAngelis, P. L. (1999) *Cell. Mol. Life Sci.* 56, 670–682.

Determan, H. (1968) *Gel Chromatography,* Springer-Verlag, Inc. New York.

Evered, D., and Whelan, J. (eds.) (1989) The biology of hyaluronan. *Ciba Fnd. Symposium* 143, 1–288.

Fenderson, B. A., Stamenkovic, I., and Aruffo, A. (1993) *Differentiation* 54, 85–98.

Frillingos, S., Sahin-Toh, M., Wu, J. and Kaback, H. R. (1998) *FASEB J.* 12, 1281–1299.

Heldermon, C. D., DeAngelis, P. L. and Weigel P. H. (2001) *J. Biol. Chem.* 276, 2037–2046.

Hill, A. V. (1913) *Biochem. J.* 7, 471–480.

Horton, M. R., Olman, M. A., Bao, C., White, K. E., Choi, A. M., Chin, B. Y., Noble, P. W., and Lowenstein, C. J. (2000) *Am. J. Physiol. Lung Cell. Mol. Physiol.* 279, 707–715.

Itano, N. and Kimata, K. (1996a) *J. Biol. Chem.* 271, 9875–9878.

Itano, N. and Kimata, K. (1996b) *Biochem. Biophys. Res. Commun.* 222, 816–820.

Ishimoto, N., Temin, H. M., and Strominger, J. L. (1966) *J. Biol. Chem.* 241, 2052–2057.

Itano, N., Sawai, T., Yoshida, M., Lenas, P., Yamada, Y., Imagawa, M., Shinomura, T., Hamaguchi, M., Yoshida, Y., Ohnuki, Y., Miyauchi, S., Spicer, A. P., McDonald, J. A., and Kimata, K. (1999) *J. Biol. Chem.* 274, 25085–25092.

Ito, K., Sato, T., and Yura, T. (1977) *Cell,* 11, 551–559.

Jung, K., Jung, H., and Kaback, H. R. (1994) *Biochemistry* 33, 3980–3985.

Kass, E. H. and Seastone, C. V. (1944) *J. Exp. Med.* 79, 319–330.

Kato, H., Tanaka, T., Nishioka, T., Kimura, A., and Oda, J. (1988) *J. Biol. Chem.* 263, 11646–11651.

Knudson, C. B., and Knudson, W. (1993) *FASEB J.* 7, 1233–1241.

Kumari, K. and Weigel, P. H. (1997) *J. Biol. Chem.*, 272, 32539–32546.

Laemmli, U. K. (1970) *Nature* 227, 680–685.

Lansing, M., Lellig, S., Mausolf, A., Martini, I., Crescenzi, F., O'Regan, M., and Prehm, P. (1993) *Biochem. J.* 289, 179–184.

Laurent, T. C., and Fraser, J. R. E. (1992) Hyaluronan. *FASEB J.* 6, 2397–2404.

Lee, H. G. and Cowman, M. K. (1994) *Anal. Biochem.* 219, 278–287.

Lin, Y., Mahan, K., Lathrop, W. F., Myles, D. G., and Primakoff, P. (1994) *J. Cell Biol.* 125, 1157–1163.

Malinowski, N. M., Cysyk, R. L., and August, E. M. (1995) *Biochem. and Molec. Biol. Intl.* 35, 1123–1132.

Markovitz, A., J. A. Cifonelli, and Dorfman A. (1959) *J. Biol. Chem.* 234, 2343–2350.

McDonald, J. and Spicer, A. (1998). In *Science of Hyaluronan Today* (V. C. Hascall and M. Yanagishita, eds) chapter 7, www.GlycoForum.gr.ip.

Meyer, M. F. and Kreil, G. (1996) *Proc. Natl. Acad. Sci. USA* 93, 4543–4547.

Michaelis, L. and Menten, M. L. (1913) *Biochem. Z.* 49, 333–338.

Moxon, E. R. and Kroll, J. S. (1990) *Curr. Top. Microbiol. Immunol.* 6, 65–85.

Ng, K. F. and Schwartz, N. B. (1989) *J. Biol. Chem.* 264, 11776–11783.

Ohno, S., Tanimoto, K., Fujimoto, K., Ijuin, C., Honda, K., Tanaka, N., Doi, T., Nakaharra, M., Tanne, K. (2001) *Biochim Biophys Acta* 1520, 71–78.

Ohya, T. and Kaneko, Y. (1970) *Biochim. Biophys. Acta* 198, 607–609.

Petrov, V. V., Pardo, J. P., and Slayman, C. W. (1997) *J. Biol. Chem.* 272, 1688–1693.

Philipson, L. H., and Schwartz, N. B. (1984) *J. Biol. Chem.* 259, 5017–5023.

Prehm, P. (1983) *Biochem. J.* 211, 181–189.

Prehm, P. (1983) *Biochem. J.* 211, 191–198.

Prehm, P. (1984). *Biochem. J.* 220: 597–600.

Prehm, P. and Mausolf, A. 1986. *Biochem. J.* 235:887–889.

Rosa, F., Sargent, T. D., Rebbert, M. L. Michaels, G. S., Jamrich, M., Grunz, H., Jonas, E., Winkles, J. A. and Dawid, I. B. (1988) *Dev. Biol.* 129, 114–123.

Shyjan, A. M., Heldin, P., Butcher, E. C., Yoshino, T. and Briskin, M. J. (1996) *J. Biol. Chem.* 271, 23395–23399.

Spicer, A. P., Augustine, M. L. and McDonald, J. A. (1996) *J. Biol. Chem.* 271, 23400–23406.

Spicer, A. P. and McDonald, J. A. (1998) *J. Biol. Chem.* 273, 1923–1932.

Sugahara, K., Schwartz, B. N., and Dorfman, A. (1979) *J. Biol. Chem.* 254: 6252–6261.

Tamura, N., Konishi, S., Iwaki, S., Kimura-Someya, T., Nada, S., Yamaguchi, A. (2001) *J. Biol. Chem.* 276, 20330–20339.

Tlapak-Simmons V. L., Baggenstoss, B. A., Clyne, T. and Weigel, P. H. (1999a) *J. Biol. Chem.* 274, 4239–4245.

Tlapak-Simmons V. L., Baggenstoss, B. A., Kumari, K., Heldermon, C., and Weigel, P. H. (1999b) *J. Biol. Chem.* 274, 4246–4253.

Tlapak-Simmons, V. L., Kempner, E. S., Baggenstoss, B. A. and Weigel, P. H. (1998) *J. Biol. Chem.* 273, 26100–26109.

Toole, B. P. (1997) *J. Intern. Med.* 242, 35–40.

Towbin, H., Steahelin, T. and Gordon, J. (1979) *Proc. Natl. Acad. Sci. U.S.A.* 76, 4350–4354.

Triscott, M. X. and van de Rijn, I. (1986) *J. Biol. Chem.* 261, 6004–6009.

Usui, T., Suzuki K., Kaji, Y., Amano, S., Miyata, K., Heldin, P., Yamashita, H. (1999) *Invest. Ophthalmol. Vis. Sci.* 40, 563–7.

van de Rijn, I. and Drake, R. R. (1992) *J. Biol. Chem.* 267, 24302–24306.

Voss, J., Hubbell, W. L., Hernandez-Borrell, J. and Kaback, H. R. (1997) *Biochemistry* 36, 15061–15066.

Wang, Q. and Kaback, H. R. (1999) *Biochemistry* 38, 16777–16782.

Ward, P. N., Field, T. R., Ditcham, W. G. Maguin, E. and Leigh, J. A. (2001) *Infect. Immun.* 69, 392–399.

Watanabe, K. and Yamaguchi, Y. (1996) *J. Biol. Chem.* 271, 22945–22948.

Weigel, P. H., Hascall, V. C. and Tammi, M. (1997) *J. Biol. Chem.* 272, 13997–14000.

Weigel, P. H. (1998). Bacterial hyaluronan synthases. In *Science of Hyaluronan Today* (V. C. Hascall and M. Yanagishita, eds) chapter 6, www.GlycoForum.gr.ip.

Wessels, M. R., Goldberg, J. B., Moses, A. E., and Dicesare, T. J. (1994) *Infect. Immun.* 62, 433–441.

Wessels, M. R., Moses, A. E., Goldberg, J. B., and Dicesare T. J. (1991) *Proc. Natl. Acad. Sci. U.S.A.* 88, 8317–8321.

White, S. H. and Wimley, W. C. (1999) *Annu. Rev. Biophys. Biomol. Struct.* 28, 319–365.

Whitnack, E., Bisno, A. L., and Beachey, E. H. (1981) *Infect. Immun.* 31, 985–991.

Wolfgang, C. L., Zhang, Z-P., Gabriel, J. L., Pieringer, R. A., Soprano, K. J., and Soprano, D. R. (1997) *J. Biol. Chem.* 272, 746–753.

Wu, J., and Kaback, R. H., (1994) *Biochem.* 33, 12166–12171.

Yang, et al., (1994) *EMBO J.* 13:286–960.

Yoshida, M., Itano, N., Yamada, Y. and Kimata, K. (2000) *J. Biol. Chem.* 275, 497–506.

What is claimed is:

1. A functionally active hyaluronan synthase having an amino acid sequence comprising at least one of SEQ ID NOS:15–29.

2. A functionally active hyaluronan synthase having an amino acid sequence as set forth in at least one of SEQ ID NOS:15–29.

3. A method of providing a functionally active hyaluronan synthase having an altered enzymatic activity as compared to a corresponding functionally active native hyaluronan synthase, comprising the steps of:
providing a hyaluronan synthase as set forth in SEQ ID NO:2; and
modifying at least one cysteine residue of the hyaluronan synthase to an alanine or serine residue to provide a functionally active hyaluronan synthase having an altered enzymatic activity.

4. The method of claim 3 wherein, in the step of modifying at least one cysteine residue of the hyaluronan synthase, the functionally active hyaluronan synthase having an altered enzymatic activity has an amino acid sequence as set forth in at least one of SEQ ID NOS:15–29.

5. The method of claim 3 wherein, in the step of modifying at least one cysteine residue of the hyaluronan synthase to provide a functionally active hyaluronan synthase having an altered enzymatic activity, the functionally active hyaluronan synthase has an increased enzymatic activity.

6. The method of claim 3 wherein, in the step of modifying at least one cysteine residue of the hyaluronan synthase to provide a functionally active hyaluronan synthase having an altered enzymatic activity, the functionally active hyaluronan synthase has a decreased enzymatic activity.

7. The method of claim 3 wherein, in the step of modifying at least one cysteine residue of the hyaluronan synthase to provide a functionally active hyaluronan synthase having an altered enzymatic activity, the functionally active hyaluronan synthase produces hyaluronic acid having an average molecular mass that is less than an average molecular mass of hyaluronic acid produced by a corresponding functionally active native hyaluronan synthase.

8. The method of claim 3 wherein, in the step of modifying at least one cysteine residue of the hyaluronan synthase to provide a functionally active hyaluronan synthase having an altered enzymatic activity, the functionally active hyaluronan synthase produces hyaluronic acid having an average molecular mass that is greater than an average molecular mass of hyaluronic acid produced by a corresponding functionally active native hyaluronan synthase.

9. A method for producing hyaluronic acid, comprising the steps of:
provsiding a host cell having at least one expression construct comprising a hyaluronan synthase gene encoding a functionally active hyaluronan synthase incorporated therein such that the host cell is capable of producing hyaluronan, wherein the functionally active hyaluronan synthase has an altered enzymatic activity as compared to a corresponding functionally active native hyaluronan synthase, wherein the corresponding functionally active native hyaluronan synthase is seHAS, and wherein the functionally active hyaluronan synthase has at least one modified amino acid residue therein as compared to a corresponding functionally active native hyaluronan synthase, and wherein the at least one modified amino acid residue is a cysteine modified to an alanine or a serine residue; and
culturing the host cell under conditions appropriate for the production of hyaluronic acid.

10. The method of claim 9 wherein, in the step of providing a host cell, the corresponding functionally active native hyaluronan synthase has an amino acid sequence essentially as set forth in SEQ ID NO:2.

11. The method of claim 9 wherein, in the step of providing a host cell, the functionally active hyaluronan synthase having an altered enzymatic activity has an amino acid sequence as set forth in at least one of SEQ ID NOS:15–29.

12. The method of claim 9, further comprising the step of separating the hyaluronic acid from the host cell.

13. The method of claim 9, wherein the at least one expression construct further comprises at least one gene encoding an enzyme for synthesis of a hyaluronic acid sugar precursor.

14. The method of claim 13, wherein the at least one gene encoding an enzyme for synthesis of a hyaluronic acid sugar precursor is selected from the group consisting of a pyrophosphorylase, a transferase, a mutase, a dehydrogenase, or an epimerase, capable of producing UDP-GlcNAc or UDP-GlcUA.

15. The method of claim 9, wherein the at least one expression construct further comprises at least one biosynthetic pathway gene of a hyaluronic acid sugar precursor.

16. The method of claim 9, wherein the at least one expression construct further includes at least one gene encoding an enzyme for synthesis of a hyaluronic acid sugar precursor.

17. The method of claim 9, further including a second at least one expression construct having at least one gene encoding an enzyme for synthesis of a hyaluronic acid sugar precursor.

18. The method of claim 9, wherein the host cell includes at least one integrated or plasmid-borne gene encoding an enzyme for synthesis of a hyaluronic acid sugar precursor.

19. The method of claim 9, wherein nutrients utilized for a hyaluronic acid sugar precursor biosynthetic pathway are supplied to the host cell.

20. The method of claim 19, wherein the nutrients supplying the hyaluronic acid sugar precursor biosynthetic pathway are fed to the host cell.

21. The method of claim 19, wherein the hyaluronic acid sugar precursors are expressed in the host cell by endogenous genes thereof.

22. The method of claim 19, wherein the hyaluronic acid sugar precursors enzymes are expressed in the host cell by an introduced construct including genes thereof.

23. The method of claim 9 wherein, in the step of providing a host cell, the functionally active hyaluronan synthase has an increased enzymatic activity.

24. The method of claim 9 wherein, in the step of providing a host cell, the functionally active hyaluronan synthase has a decreased enzymatic activity.

25. The method of claim 9 wherein, in the step of providing a host cell, the functionally active hyaluronan synthase produces hyaluronic acid having an average molecular mass that is less than an average molecular mass of hyaluronic acid produced by a corresponding functionally active native hyaluronan synthase.

26. The method of claim 9 wherein, in the step of providing a host cell, the functionally active hyaluronan synthase produces hyaluronic acid having an average molecular mass that is greater than an average molecular mass of hyaluronic acid produced by a corresponding functionally active native hyaluronan synthase.

27. A functionally active hyaluronan synthase having at least one modified amino acid residue therein as compared to a corresponding functionally active native hyaluronan synthase, wherein the corresponding functionally active native hyaluronan synthase is seHAS, and wherein the at least one modified amino acid residue is a cysteine modified to an alanine or a serine residue, and wherein the functionally active hyaluronan synthase has an amino acid residue as set forth in at least one of SEQ ID NOS:15–29.

28. The functionally active hyaluronan synthase of claim 27, wherein the functionally active hyaluronan synthase has an increased enzymatic activity.

29. The functionally active hyaluronan synthase of claim 27, wherein the functionally active hyaluronan synthase has a decreased enzymatic activity.

30. The functionally active hyaluronan synthase of claim 27, wherein the functionally active hyaluronan synthase produces hyaluronic acid having an average molecular mass that is less than an average molecular mass of hyaluronic acid produced by a corresponding functionally active native hyaluronan synthase.

31. The functionally active hyaluronan synthase of claim 27, wherein the functionally active hyaluronan synthase produces hyaluronic acid having an average molecular mass that is greater than an average molecular mass of hyaluronic acid produced by a corresponding functionally active native hyaluronan synthase.

32. A functionally active hyaluronan synthase having an altered enzymatic activity as compared to a corresponding functionally active native hyaluronan synthase, wherein the corresponding functionally active native hyaluronan synthase is seHAS, and wherein the functionally active hyaluronan synthase has at least one modified amino acid residue therein as compared to a corresponding functionally active native hyaluronan synthase, and wherein the at least one modified amino acid residue is a cysteine modified to an alanine or a serine residue.

33. The functionally active hyaluronan synthase of claim 32, wherein the functionally active hyaluronan synthase having at least one modified amino acid residue therein has an amino acid sequence as set forth in at least one of SEQ ID NOS:15–29.

34. The functionally active hyaluronan synthase of claim 32, wherein the functionally active hyaluronan synthase has an increased enzymatic activity.

35. The functionally active hyaluronan synthase of claim 32, wherein the functionally active hyaluronan synthase has a decreased enzymatic activity.

36. The functionally active hyaluronan synthase of claim 32, wherein the functionally active hyaluronan synthase produces hyaluronic acid having an average molecular mass that is less than an average molecular mass of hyaluronic acid produced by a corresponding functionally active native hyaluronan synthase.

37. The functionally active hyaluronan synthase of claim 32, wherein the functionally active hyaluronan synthase produces hyaluronic acid having an average molecular mass that is greater than an average molecular mass of hyaluronic acid produced by a corresponding functionally active native hyaluronan synthase.

38. A functionally active hyaluronan synthase having at least one modified amino acid residue therein as compared to a corresponding functionally active native hyaluronan synthase, wherein the corresponding functionally active native hyaluronan synthase has an amino acid sequence as set forth in SEQ ID NO:2, wherein the at least one modified amino acid residue is a cysteine, and wherein the cysteine is modified to an alanine or a serine residue.

39. The functionally active hyaluronan synthase of claim 38, wherein the functionally active hyaluronan synthase has an amino acid sequence as set forth in at least one of SEQ ID NOS:15–29.

40. The functionally active hyaluronan synthase of claim 38, wherein the functionally active hyaluronan synthase has an increased enzymatic activity.

41. The functionally active hyaluronan synthase of claim 38, wherein the functionally active hyaluronan synthase has a decreased enzymatic activity.

42. The functionally active hyaluronan synthase of claim 38, wherein the functionally active hyaluronan synthase produces hyaluronic acid having an average molecular mass that is less than an average molecular mass of hyaluronic acid produced by a corresponding functionally active native hyaluronan synthase.

43. The functionally active hyaluronan synthase of claim 38, wherein the functionally active hyaluronan synthase produces hyaluronic acid having an average molecular mass that is greater than an average molecular mass of hyaluronic acid produced by a corresponding functionally active native hyaluronan synthase.

44. A functionally active hyaluronan synthase having an altered enzymatic activity as compared to a corresponding functionally active native hyaluronan synthase, wherein the corresponding functionally active native hyaluronan synthase has an amino acid sequence as set forth in SEQ ID NO:2, wherein the functionally active hyaluronan synthase has at least one modified amino acid residue therein as compared to a corresponding functionally active native hyaluronan synthase, and wherein the at least one modified amino acid residue is a cysteine modified to an alanine or a serine residue.

45. The functionally active hyaluronan synthase of claim 44, wherein the functionally active hyaluronan synthase has an amino acid sequence as set forth in at least one of SEQ ID NOS:15–29.

46. The functionally active hyaluronan synthase of claim 44, wherein the functionally active hyaluronan synthase has an increased enzymatic activity.

47. The functionally active hyaluronan synthase of claim 44, wherein the functionally active hyaluronan synthase has a decreased enzymatic activity.

48. The functionally active hyaluronan synthase of claim 44, wherein the functionally active hyaluronan synthase produces hyaluronic acid having an average molecular mass that is less than an average molecular mass of hyaluronic acid produced by a corresponding functionally active native hyaluronan synthase.

49. The functionally active hyaluronan synthase of claim 44, wherein the functionally active hyaluronan synthase produces hyaluronic acid having an average molecular mass that is greater than an average molecular mass of hyaluronic acid produced by a corresponding functionally active native hyaluronan synthase.

* * * * *

UNITED STATES PATENT AND TRADEMARK OFFICE
CERTIFICATE OF CORRECTION

| | |
|---|---|
| PATENT NO. | : 7,094,581 B2 |
| APPLICATION NO. | : 10/309560 |
| DATED | : August 22, 2006 |
| INVENTOR(S) | : Paul H. Weigel and Kshama Kumari |

It is certified that error appears in the above-identified patent and that said Letters Patent is hereby corrected as shown below:

Page 3 of "Other Publications", Column 1, before line 1, a reference is missing:
--"MOLECULAR CLONING AND CHARACTERIZATION OF A PUTATIVE MOUSE HYALURONAN SYNTHASE", Spicer et al., J. Biol. Chem., 271(38):23400-23406 (1996).--

Page 3 of "Other Publications", Column 1, between lines 9 & 10, a reference is missing:
--"MOLECULAR CLONING, EXPRESSION, AND CHARACTERIZATION OF THE AUTHENTIC HYALURONAN SYNTHASE FROM GROUP C STREPTOCOCCUS EQUISIMILIS", Kumari and Weigel, J. Biol. Chem., 272(51): 32539-32546 (1997).--

Page 3 of "Other Publications", Column 1, between lines 46 & 47, a reference is missing:
--"IDENTIFICATION AND MOLECULAR CLONING OF A UNIQUE HYALURONAN SYNTHASE FROM PASTURELLA MULTOCIDA", DeAngelis et al., J. Biol. Chem., 273(14):8454-8458 (1998).--

Column 1,  Line 19: Delete "now abandoned".

Column 1,  Line 44: Delete "segements" and replace with --segments --.

Column 2,  Line 7: Delete "GIcNAc" and replace with --GlcNAc--.
Line 8: Delete "GIcUA" and replace with --GlcUA--.
Line 11: Insert a space between "Streptococci" and "and".
Line 25: Delete "GIcNAc" and replace with --GlcNAc--.
Line 26: Delete "GIcUA" and replace with --GlcUA--.

Column 3,  Line 20: Delete "GIcUA" and replace with --GlcUA--.
Line 21: Delete "GIcNAc" and replace with --GlcNAc--.
Line 31: Delete "GIcUA" and replace with --GlcUA--.
Line 50: Delete "GIcUA" and replace with --GlcUA--.

Column 4,  Line 2: Delete "syntheses" and replace with --synthases--.
Line 8: Delete "GIcUA" and replace with --GlcUA--.
Line 9: Delete "GIcNAc" and replace with --GlcNAc--.

Column 5,  Line 6: Delete "GIcNAc" and replace with --GlcNAc--.
Line 64: Delete "xIHAS" and replace with --xlHAS--.

Column 6,  Line 34: Delete "GIcNAc" and "GIcUA" and replace with --GlcNAc--and --GlcUA--, respectively.
Line 43: Delete "xIHAS" and replace with --xlHAS--.

UNITED STATES PATENT AND TRADEMARK OFFICE
CERTIFICATE OF CORRECTION

PATENT NO.       : 7,094,581 B2
APPLICATION NO.  : 10/309560
DATED            : August 22, 2006
INVENTOR(S)      : Paul H. Weigel and Kshama Kumari It is certified that error appears in the above-identified patent and that said Letters Patent is hereby corrected as shown below:

| | |
|---|---|
| Column 7, | Line 18: Delete "GIcNAc" and replace with --GlcNAc--. |
| | Line 19: Delete "GIcUA" and replace with --GlcUA--. |
| Column 11, | Line 17: Delete "GIcNAc" and "GIcUA" and replace with --GlcNAc-- and --GlcUA--, respectively. |
| | Line 41: Delete "su HAS" and replace with --suHAS--. |
| | Line 49: Delete "xIHAS1" and replace with --xlHAS1--. |
| Column 12, | Line 12: After "utilization of UDP-GlcUA" insert --(FIG. 3B)-- and before "by wild-type" insert --(FIG. 3A)--. |
| Column 12, | Line 12: Delete "GIcUA" and "GIcNAc" and replace with --GlcUA-- and --GlcNAc--, respectively. |
| | Line 18: Delete "GIcUA" and "GIcNAc" and replace with --GlcUA-- and --GlcNAc--, respectively. |
| | Line 27: Delete "GIcUA" and replace with --GlcUA--. |
| | Line 41: Delete "GIcUA" and replace with --GlcUA--. |
| | Line 42: Delete "GIcNAc" and replace with --GlcNAc--. |
| Column 12, | Line 42: Delete "Nem" and replace with --NEM --. |
| Column 12, | Line 56: Delete "(32)". |
| Column 13, | Line 8: Delete "(33)". |
| Column 13, | Line 26: Delete "GIcUA" and replace with --GlcUA--. |
| | Line 30: Delete "GIcUA" and replace with --GlcUA--. |
| | Line 33: Delete "GIcNAc" and replace with --GlcNAc--. |
| | Line 37: Delete "GIcNAc" and replace with --GlcNAc--. |
| Column 14, | Line 26: Delete "GIcNAc" and replace with --GlcNAc--. |
| | Line 27: Delete "GIcUA" and replace with --GlcUA--. |
| | Line 27: Delete "Tiapak" and replace with --Tlapak--. |
| Column 17, | Line 17: Delete "syntheses" and replace with --synthases--. |
| | Line 18: Delete "xIHAS" and replace with --xlHAS--. |
| Column 18, | Line 3: Delete "GIcNAc" and replace with --GlcNAc--. |
| | Line 4: Delete "GIcUA" and replace with --GlcUA--. |
| Column 18, | Line 27: Delete "has" and replace with --*has* --. |

UNITED STATES PATENT AND TRADEMARK OFFICE
CERTIFICATE OF CORRECTION

PATENT NO. : 7,094,581 B2
APPLICATION NO. : 10/309560
DATED : August 22, 2006
INVENTOR(S) : Paul H. Weigel and Kshama Kumari It is certified that error appears in the above-identified patent and that said Letters Patent is hereby corrected as shown below:

Column 19, Line 46: Delete "has" and replace with -- *has* --.
Line 53: Delete "has" and replace with -- *has* --.

Column 20, Line 31: Delete the "comma" after the word "end" at the end of the line.
Line 40: Delete "has" and replace with -- *has* --.

Column 23, Line 36: Delete "standarddeviations" and replace with -- standard deviations -- .

Column 23, Line 66: Delete "GIcUA" and "GIcNAc" and replace with --GlcUA-- and --GlcNAc--, respectively.

Column 24, Line 1: Delete "GIcNAc" and replace with --GlcNAc--.
Line 2: Delete "GIcUA" and replace with --GlcUA--.
Line 18: Delete "GIcUA" and replace with --GlcUA--.
Line 21: Delete "$K_{UDP-GIcNAc}$" and replace with --$K_{UDP-GlcNAc}$--.
Line 24: Delete "$K_{UDP-GIcNAc}$" and replace with --$K_{UDP-GlcNAc}$--.

Column 25, Table V: Delete "Menton" and replace with --Menten--.

Column 26, Table VI: Delete "Menton" and replace with --Menten--.

Column 26, Line 45: Delete "GIcUA" and replace with --GlcUA--.
Line 48: Delete "GIcNAc" and replace with --GlcNAc--.
Line 54: Delete "$K_{UDP-GIcNAc}$" and replace with --$K_{UDP-GlcNAc}$--.
Line 56: Delete "$K_{UDP-GIcNAc}$" and replace with --$K_{UDP-GlcNAc}$--.
Line 60: Delete "GIcNAc" and replace with --GlcNAc--.
Line 64: Delete "GIcNAc" and replace with --GlcNAc--.

Column 27, Line 17: Delete "GIcUA" and replace with --GlcUA--.
Line 18: Delete "GIcNAc" and replace with --GlcNAc--.
Line 21: Delete "GIcUA" and "GIcNAc" and replace with --GlcUA-- and --GlcNAc--, respectively.
Line 42: Delete "(FIG. 6B)" and replace with -- (FIG. 7B)-- .

Column 29, Line 23: Delete "GIcUA" and "GIcNAc" and replace with --GlcUA-- and --GlcNAc--, respectively.
Line 37: Delete "$K_{UDP-GIcNAc}$" and replace with --$K_{UDP-GlcNAc}$--.
Line 38: Delete "GIcNAc" and replace with --GlcNAc--.

UNITED STATES PATENT AND TRADEMARK OFFICE
CERTIFICATE OF CORRECTION

| | |
|---|---|
| PATENT NO. | : 7,094,581 B2 |
| APPLICATION NO. | : 10/309560 |
| DATED | : August 22, 2006 |
| INVENTOR(S) | : Paul H. Weigel and Kshama Kumari |

It is certified that error appears in the above-identified patent and that said Letters Patent is hereby corrected as shown below:

Column 30,     Line 2: Delete "GIcNAc" and replace with --GlcNAc--.
                    Line 3: Delete "GIcUA" and replace with --GlcUA--.
                    Line 4: Delete "GIcNAc" and replace with --GlcNAc--.

Column 31,     Line 19: Delete "GIcNAc" and replace with --GlcNAc--.
                    Line 21: Delete "$K_{UDP\text{-}GIcUA}$" and replace with --$K_{UDP\text{-}GlcUA}$--.
                    Line 24: Delete "$K_{UDP\text{-}GIcUA}$" and replace with --$K_{UDP\text{-}GlcUA}$--.
                    Line 27: Delete "GIcUA" and replace with --GlcUA--.

Column 35,     Line 13: Delete "wilt-type" and replace with -- wild-type --.
                    Line 25: Delete "GIcUA" and "GIcNAc" and replace with
                              --GlcUA-- and --GlcNAc--, respectively.

Column 37,     Line 60: Delete "GIcUA" and "GIcNAc" and replace with
                              --GlcUA-- and --GlcNAc--, respectively.

Column 39,     Line 17: Delete "GIcUA" and replace with --GlcUA--.
                    Line 18: Delete "GIcNAc" and replace with --GlcNAc--.
                    Line 19: Delete "GIcUA" and replace with --GlcUA--.

Column 43,     Line 65: Delete "GIcUA" and replace with --GlcUA--.
                    Line 66: Delete "GIcUA" and replace with --GlcUA--.
                    Line 66: Delete "GIcNAc" and replace with --GlcNAc--.

Column 44,     Line 1: Delete "NaCI" and replace with --NaCl--.
                    Line 2: Delete both occurrences of "GIcUA" and replace with
                              --GlcUA--.
                    Line 3: Delete "GIcNAc" and replace with --GlcNAc--.
                    Line 9: Delete "GIcUA" and replace with --GlcUA--.
                    Line 13: Delete "Menton" and replace with --Menten--.
                    Line 49: Delete "GIcUA" and replace with --GlcUA--.
                    Line 50: Delete "GIcNAc" and replace with --GlcNAc--.
                    Line 52: Delete "GIcUA" and replace with --GlcUA--.

Column 45,     Line 65: Delete "*E. Coli*" and replace with --*E. coli*--.

Column 46,     Line 11: Delete "EPSCOR" and replace with --EPSCoR--.
                    Line 18: After the word "using" delete the "(".

UNITED STATES PATENT AND TRADEMARK OFFICE
CERTIFICATE OF CORRECTION

PATENT NO. : 7,094,581 B2
APPLICATION NO. : 10/309560
DATED : August 22, 2006
INVENTOR(S) : Paul H. Weigel and Kshama Kumari It is certified that error appears in the above-identified patent and that said Letters Patent is hereby corrected as shown below:

Column 47, Line 2: Delete "GIcUA" and "GIcNAc" and replace with --GlcUA-- and --GlcNAc--, respectively.
Line 12: Delete both occurrences of "GIcUA" and replace with --GlcUA--.
Line 12: Delete "GIcNAc" and replace with --GlcNAc--.
Line 19: Delete "GIcUA" and replace with --GlcUA--.

Column 281, Line 39: Delete "GIcNAc" and replace with -- GlcNAc -- .
Line 40: Delete "GIcUA" and replace with -- GlcUA -- .

Signed and Sealed this

Twentieth Day of March, 2007

JON W. DUDAS
*Director of the United States Patent and Trademark Office*

UNITED STATES PATENT AND TRADEMARK OFFICE
CERTIFICATE OF CORRECTION

PATENT NO. : 7,094,581 B2 Page 1 of 1
APPLICATION NO. : 10/309560
DATED : August 22, 2006
INVENTOR(S) : Paul H. Weigel and Kshama Kumari It is certified that error appears in the above-identified patent and that said Letters Patent is hereby corrected as shown below:

Column 1, lines 27-30: Delete entirety of paragraph and replace with -- This invention was made with government support under Contract Number GM035978 awarded by the National Institutes of Health. The government has certain rights in the invention. --

Signed and Sealed this

Seventh Day of September, 2010

David J. Kappos
*Director of the United States Patent and Trademark Office*

SEQUENCE LISTING

<160> NUMBER OF SEQ ID NOS: 92

<210> SEQ ID NO 1
<211> LENGTH: 1254
<212> TYPE: DNA
<213> ORGANISM: Streptococcus equisimilis

```
<400> SEQUENCE: 1
atgagaacat taaaaaacct cataactgtt gtggccttta gtattttttg ggtactgttg      60
atttacgtca atgtttatct ctttggtgct aaaggaagct tgtcaattta tggctttttg     120
ctgatagctt acctattagt caaaatgtcc ttatcctttt tttacaagcc atttaaggga     180
agggctgggc aatataaggt tgcagccatt attccctctt ataacgaaga tgctgagtca     240
ttgctagaga ccttaaaaag tgttcagcag caaacctatc ccctagcaga aatttatgtt     300
gttgacgatg gaagtgctga tgagacaggt attaagcgca ttgaagacta tgtgcgtgac     360
actggtgacc tatcaagcaa tgtcattgtt catcggtcag agaaaaatca aggaaagcgt     420
catgcacagg cctgggcctt tgaaagatca gacgctgatg tcttttttgac cgttgactca     480 gatacttata tctaccctga tgctttagag gagttgttaa aaacctttaa tgacccaact     540 gttttttgctg cgacgggtca ccttaatgtc agaaatagac aaaccaatct cttaacacgc     600
ttgacagata ttcgctatga taatgctttt ggcgttgaac gagctgccca atccgttaca     660
ggtaatatcc ttgtttgctc aggtccgctt agcgtttaca gacgcgaggt ggttgttcct     720
aacatagata gatacatcaa ccagaccttc ctgggtattc ctgtaagtat tggtgatgac     780
aggtgcttga ccaactatgc aactgattta ggaaagactg tttatcaatc cactgctaaa     840
tgtattacag atgttcctga caagatgtct acttacttga agcagcaaaa ccgctggaac     900
aagtccttct ttagagagtc cattatttct gttaagaaaa tcatgaacaa tccttttgta     960
gccctatgga ccatacttga ggtgtctatg tttatgatgc ttgtttattc tgtggtggat    1020
ttctttgtag gcaatgtcag agaatttgat tggctcaggg ttttagcctt tctggtgatt    1080
atcttcattg ttgccctgtg tcggaacatt cattacatgc ttaagcaccc gctgtccttc    1140
ttgttatctc cgttttatgg ggtgctgcat ttgtttgtcc tacagccctt gaaattatat    1200 tctctttta ctattagaaa tgctgactgg ggaacacgta aaaaattatt ataa          1254

<210> SEQ ID NO 2
<211> LENGTH: 417
<212> TYPE: PRT
<213> ORGANISM: Streptococcus equisimilis

<400> SEQUENCE: 2

Met Arg Thr Leu Lys Asn Leu Ile Thr Val Val Ala Phe Ser Ile Phe
1               5                   10                  15

Trp Val Leu Leu Ile Tyr Val Asn Val Tyr Leu Phe Gly Ala Lys Gly
                20                  25                  30

Ser Leu Ser Ile Tyr Gly Phe Leu Leu Ile Ala Tyr Leu Leu Val Lys
        35                  40                  45

Met Ser Leu Ser Phe Phe Tyr Lys Pro Phe Lys Gly Arg Ala Gly Gln
    50                  55                  60

Tyr Lys Val Ala Ala Ile Ile Pro Ser Tyr Asn Glu Asp Ala Glu Ser
65                  70                  75                  80

Leu Leu Glu Thr Leu Lys Ser Val Gln Gln Gln Thr Tyr Pro Leu Ala
                85                  90                  95

Glu Ile Tyr Val Val Asp Asp Gly Ser Ala Asp Glu Thr Gly Ile Lys
                100                 105                 110

Arg Ile Glu Asp Tyr Val Arg Asp Thr Gly Asp Leu Ser Ser Asn Val
            115                 120                 125

Ile Val His Arg Ser Glu Lys Asn Gln Gly Lys Arg His Ala Gln Ala
    130                 135                 140
```

| | | | | | | | | | | | | | | | |
|---|---|---|---|---|---|---|---|---|---|---|---|---|---|---|---|
|Trp|Ala|Phe|Glu|Arg|Ser|Asp|Ala|Asp|Val|Phe|Leu|Thr|Val|Asp|Ser|
|145| | | |150| | | |155| | | |160| | | |

Asp Thr Tyr Ile Tyr Pro Asp Ala Leu Glu Leu Leu Lys Thr Phe
            165                 170                 175

Asn Asp Pro Thr Val Phe Ala Ala Thr Gly His Leu Asn Val Arg Asn
180                 185                 190

Arg Gln Thr Asn Leu Leu Thr Arg Leu Thr Asp Ile Arg Tyr Asp Asn
            195                 200                 205

Ala Phe Gly Val Glu Arg Ala Ala Gln Ser Val Thr Gly Asn Ile Leu
    210                 215                 220

Val Cys Ser Gly Pro Leu Ser Val Tyr Arg Arg Glu Val Val Pro
225                 230                 235                 240

Asn Ile Asp Arg Tyr Ile Asn Gln Thr Phe Leu Gly Ile Pro Val Ser
                245                 250                 255

Ile Gly Asp Asp Arg Cys Leu Thr Asn Tyr Ala Thr Asp Leu Gly Lys
            260                 265                 270

Thr Val Tyr Gln Ser Thr Ala Lys Cys Ile Thr Asp Val Pro Asp Lys
        275                 280                 285

Met Ser Thr Tyr Leu Lys Gln Gln Asn Arg Trp Asn Lys Ser Phe Phe
    290                 295                 300

Arg Glu Ser Ile Ile Ser Val Lys Lys Ile Met Asn Asn Pro Phe Val
305                 310                 315                 320

Ala Leu Trp Thr Ile Leu Glu Val Ser Met Phe Met Met Leu Val Tyr
                325                 330                 335

Ser Val Val Asp Phe Val Gly Asn Val Arg Glu Phe Asp Trp Leu
            340                 345                 350

Arg Val Leu Ala Phe Leu Val Ile Ile Phe Ile Val Ala Leu Cys Arg
        355                 360                 365

Asn Ile His Tyr Met Leu Lys His Pro Leu Ser Phe Leu Leu Ser Pro
    370                 375                 380

Phe Tyr Gly Val Leu His Leu Phe Val Leu Gln Pro Leu Lys Leu Tyr
385                 390                 395                 400

Ser Leu Phe Thr Ile Arg Asn Ala Asp Trp Gly Thr Arg Lys Lys Leu
            405                 410                 415

Leu

<210> SEQ ID NO 3
<211> LENGTH: 1440
<212> TYPE: DNA
<213> ORGANISM: Streptococcus pyogenes

<400> SEQUENCE: 3

```
tttaatggaa acacaatttt attaaaaata tctctatatc tagttgacat tatttcttat      60
ttatattata atattgaggt cctttctttc aaggaaatta aaaagaaag aggtgtaatt     120
gtgcctattt ttaaaaaaac tttaattgtt ttatccttta ttttttttgat atctatcttg    180
atttatctaa atatgtatct atttggaaca tcaactgtag gaatttatgg agtaatatta    240
ataacctatc tagttatcaa acttggatta tctttccttt atgagccatt taaggaaat    300
ccacatgact ataagttgc tgctgtaatt ccttcttata tgaagatgc cgagtcatta    360
ttagaaacac ttaaaagtgt gttagcacag acctatccgt tatcagaaat ttatattgtt    420
gatgatggga gttcaaacac agatgcaata caattaattg aagagtatgt aaatagagaa    480
gtggatattt gtcgaaacgt tatcgttcac cgttcccttg tcaataaagg aaaacgccat    540
```

```
gctcaagcgt gggcatttga aagatctgac gctgacgttt ttttaaccgt agactcagat    600
acttatatct atccaaatgc cttagaagaa ctcctaaaaa gcttcaatga tgagacagtt    660
tatgctgcaa caggacattt gaatgctaga aacagacaaa ctaatctatt aacgcgactt    720
acagatatcc gttacgataa tgcctttggg gtggagcgtg ctgctcaatc attaacaggt    780
aatattttag tttgctcagg accattgagt atttatcgac gtgaagtgat tattcctaac    840
ttagagcgct ataaaaatca acattccta ggtttacctg ttagcattgg ggatgatcga    900
tgtttaacaa attatgctat tgatttagga cgcactgtct accaatcaac agctagatgt    960
gatactgatg taccttttcca attaaaaagt tatttaaagc aacaaaatcg atggaataaa   1020
tcttttttta gagaatctat tatttctgtt aaaaaaattc tttctaatcc catcgttgcc   1080
ttatggacta ttttcgaagt cgttatgttt atgatgttga ttgtcgcaat tgggaatctt   1140
ttgtttaatc aagctattca attagacctt attaaacttt ttgccttttt atccatcatc   1200
tttatcgttg ctttatgtcg taatgttcat tatatggtca aacatcctgc tagttttttg   1260
ttatctcctc tgtatggaat attacacttg tttgtcttac agcccctaaa actttattct   1320
ttatgcacca ttaaaaatac ggaatgggga acacgtaaaa aggtcactat ttttaaataa   1380
tatatgcatc gagtagttag agaaggagta attttatgaa aatagcagtt gctggatcag   1440
```

<210> SEQ ID NO 4
<211> LENGTH: 419
<212> TYPE: PRT
<213> ORGANISM: Streptococcus pyogenes

<400> SEQUENCE: 4

```
Met Pro Ile Phe Lys Lys Thr Leu Ile Val Leu Ser Phe Ile Phe Leu
1               5                   10                  15

Ile Ser Ile Leu Ile Tyr Leu Asn Met Tyr Leu Phe Gly Thr Ser Thr
                20                  25                  30

Val Gly Ile Tyr Gly Val Ile Leu Ile Thr Tyr Leu Val Ile Lys Leu
            35                  40                  45

Gly Leu Ser Phe Leu Tyr Glu Pro Phe Lys Gly Asn Pro His Asp Tyr
        50                  55                  60

Lys Val Ala Ala Val Ile Pro Ser Tyr Asn Glu Asp Ala Glu Ser Leu
65                  70                  75                  80

Leu Glu Thr Leu Lys Ser Val Leu Ala Gln Thr Tyr Pro Leu Ser Glu
                85                  90                  95

Ile Tyr Ile Val Asp Asp Gly Ser Asn Thr Asp Ala Ile Gln Leu
                100                 105                 110

Ile Glu Glu Tyr Val Asn Arg Glu Val Asp Ile Cys Arg Asn Val Ile
            115                 120                 125

Val His Arg Ser Leu Val Asn Lys Gly Lys Arg His Ala Gln Ala Trp
        130                 135                 140

Ala Phe Glu Arg Ser Asp Ala Asp Val Phe Leu Thr Val Asp Ser Asp
145                 150                 155                 160

Thr Tyr Ile Tyr Pro Asn Ala Leu Glu Glu Leu Leu Lys Ser Phe Asn
                165                 170                 175

Asp Glu Thr Val Tyr Ala Ala Thr Gly His Leu Asn Ala Arg Asn Arg
            180                 185                 190

Gln Thr Asn Leu Leu Thr Arg Leu Thr Asp Ile Arg Tyr Asp Asn Ala
        195                 200                 205

Phe Gly Val Glu Arg Ala Ala Gln Ser Leu Thr Gly Asn Ile Leu Val
    210                 215                 220
```

Cys Ser Gly Pro Leu Ser Ile Tyr Arg Arg Glu Val Ile Ile Pro Asn
225                 230                 235                 240

Leu Glu Arg Tyr Lys Asn Gln Thr Phe Leu Gly Leu Pro Val Ser Ile
            245                 250                 255

Gly Asp Asp Arg Cys Leu Thr Asn Tyr Ala Ile Asp Leu Gly Arg Thr
        260                 265                 270

Val Tyr Gln Ser Thr Ala Arg Cys Asp Thr Asp Val Pro Phe Gln Leu
    275                 280                 285

Lys Ser Tyr Leu Lys Gln Gln Asn Arg Trp Asn Lys Ser Phe Phe Arg
290                 295                 300

Glu Ser Ile Ile Ser Val Lys Lys Ile Leu Ser Asn Pro Ile Val Ala
305                 310                 315                 320

Leu Trp Thr Ile Phe Glu Val Val Met Phe Met Met Leu Ile Val Ala
                325                 330                 335

Ile Gly Asn Leu Leu Phe Asn Gln Ala Ile Gln Leu Asp Leu Ile Lys
            340                 345                 350

Leu Phe Ala Phe Leu Ser Ile Ile Phe Ile Val Ala Leu Cys Arg Asn
        355                 360                 365

Val His Tyr Met Val Lys His Pro Ala Ser Phe Leu Leu Ser Pro Leu
    370                 375                 380

Tyr Gly Ile Leu His Leu Phe Val Leu Gln Pro Leu Lys Leu Tyr Ser
385                 390                 395                 400

Leu Cys Thr Ile Lys Asn Thr Glu Trp Gly Thr Arg Lys Lys Val Thr
                405                 410                 415

Ile Phe Lys

<210> SEQ ID NO 5
<211> LENGTH: 3466
<212> TYPE: DNA
<213> ORGANISM: Streptococcus uberis

<400> SEQUENCE: 5
gcaaagtttt aaaggaggaa ttatggaaaa actaaaaaat ctcattacat ttatgacttt      60
tattttcctg tggctcataa ttattgggct taatgttttt gtatttggaa ctaaaggaag     120
tctaacagtg tatgggatta ttctattaac ctatttgtcg ataaaaatgg gattatcttt     180
tttttatcgt ccctataaag gaagtgtagg tcaatataag gtagcagcta ttatcccatc     240
ttataatgag gatggtgtcg gtttactaga aactctaaag agtgttcaaa acaaacata      300
tccaattgca gaaattttcg taattgacga tgggtcagta gataaaacag gtataaaatt     360
ggtcgaagac tatgtgaagt taatggcctt tggagaccaa gttatcgttc atcagatgcc     420
tgaaaatgtt ggtaaaagac atgctcaggc ttgggcattt gaaaggtctg atgctgatgt     480
tttcttaaca gtggattcag atacctacat ctatcctgat gctcttgaag aattattaaa     540
gacatttaat gatccagagg tctacgctgc aactggtcat ttaaatgcaa gaaatagaca     600
aactaatctc ttaactagac tgactgatat tcgttacgat aatgcatttg gtgtagaacg     660
tgctgctcag tctgttacgg gaaatatttt ggtttgttcc ggacctttaa gtatttatag     720
acgttccgtc ggtattccaa atcttgaacg ctatacctca caaacatttc ttggtgtccc     780
tgtaagcata ggggatgacc gttgtttgac aaattatgca actgatttgg gaaaaacggt     840
ttatcagtca actgcaagat gtgatactga cgttccagat aagtttaagg ttttcatcaa     900
acaacaaaat cgttggaata agtcattttt tagggagtct attatctctg ttaagaagtt     960

```
attagccaca ccaagtgttg ctgtttggac tattacagaa gtttccatgt tcatcatgct   1020
agtttattct atctttagct tattgatagg agaggctcaa gaatttaatc tcataaaact   1080
ggttgctttt ttagttatta ttttcatagt agctctttgt agaaatgttc attacatggt   1140
taagcatcca tttgctttt tattgtcacc gttttatgga ttgatacatc tattcgtttt     1200
gcaacctctt aagatatatt cgttatttac tataagaaat gctacatggg gaactcgtaa   1260
aaagacaagt aaataattca attagagaaa ggacaaaata gtgaaaattg cagttgcagg   1320
ttctggctat gttggcctat cattaagtgt attattagca cagaaaaatc ctgttacagt   1380
tgtagatatt attgagaaga aagtaaatct cataaatcaa aaacaatcac caatccagga   1440
tgttgatatt gaaaactatt taaaagaaaa aaagttacaa ttaagagcta ctctagacgc   1500
cgatcaagca tttagggatg cagatatact aattattgct acaccaacca attatgatgt   1560
ggagaagaat ttttttgata ctagtcatgt tgagactgta attgagaaag ctttagcttt   1620
aaatagtcag gctttgttag ttattaaatc aacgatacca cttggttta ttaaaaagat     1680 gcgtcaaaaa tatcagacag accgtattat ttttagtccc gaatttctta gagagtctaa   1740
agctttaaaa gataatcttt atcctagtcg aataattgtt cctttgaag atgatgattc     1800 tatggaagta atagaagcag caaagacttt tgctcaattg ttaaaagatg gttctttgga   1860
taaagatgtt cctgtacttt ttatgggttc agcagaggct gaagcagtaa aattatttgc   1920 caataccta ttagctatgc gtgtctccta ttttaatgag ttagatacat atgctgaaaa    1980
gaatggttta cgtgtggata atattattga gggcgtttgc catgatcgac cataggaat    2040 tcattataat aaccttctt tggctatgg aggatactgc ttacctaaag ataccaaaca     2100
gttgctagca ggctatgatg gtattcctca atcgcttata aaagcaattg ttgattctaa   2160
taaaattcgt aaagagtata tcgcatcaca aattttacaa caattgagtg atattaatgt   2220
agatcctaaa gatgcaacga ttggtattta ccgccttatc atgaaaagta actctgataa   2280
tttcagagag agtgcaataa aagatattat tgatcatatt aagagctatc aaattaatat   2340
agtcttgtat gagccaatga tgaatgaaga ttttgattta ccaatcattg atgatttatc   2400
tgacttcaaa gccatgtcac atattatcgt ttcaaataga tatgatttag ccttagaaga   2460
tgttaaagaa aaagtttaca ccagagatat ttacggtgtg gattaagttt gatttttaac   2520
aaatctccaa aaaatagata aaaaaaacag actctgataa aagagtctgt ttttaaaag    2580 tgtgagcatc ctattgctag gatgctcagg aaatttatga aaagggagat aagagggaac   2640
ttatcttccc caacggtttg ggagaccatt atttaggata gtcttatcat aagctatcaa   2700
ccttaaagat ttcttaactc gttttcgttt gggtcttgtc ttttttaattt tttgatgaga   2760 attaaacttg atggaatgag aatcaggaca ctgcctatcc aggctgctgg attagctgaa   2820
gccacaccaa caaaaccaaa gtataacagg ccaataatgg cgactcctgc tctcatgact   2880
aattccataa tgccagctaa agtaggaaca aaaccgtatc cgagaccttg aatgaaactt   2940
cttagtataa ataggatggc taaaatccaa taagagagc cattaatcag ataatagaga   3000
taggctaaat ggaaaacagc tggatcagcc ttactaatga aaatgccaga gaaaagcgg   3060 tgttggaaaa ttaacagaat agcaaaaaga acagaccaaa taatacagat aatgagtgaa   3120
tctttaagac cctcaaggat tcttttataa gctttagcgc catagttctg agctgtaaag   3180
gttgacaagg ctaagcccag atttaacatc ggtagcatgg ccagttggtc tgttttactg   3240
gcaatagcaa tagctgcgat agcttcggtc cccaacttat taatggttac ctgcagtgta   3300
atggctccaa tggctataat actagcctga aatgccatgg gaaaaccaag gcgagcatga   3360
```

```
tttctgagat ttccctatc aagagtcaaa tcgtctttct tcagtcggaa atgggggatc      3420
tttttgttga tgtaaaggac caaatagagt acggagaaag cttgca                   3466
```

<210> SEQ ID NO 6
<211> LENGTH: 417
<212> TYPE: PRT
<213> ORGANISM: Streptococcus uberis

<400> SEQUENCE: 6

```
Met Glu Lys Leu Lys Asn Leu Ile Thr Phe Met Thr Phe Ile Phe Leu
1               5                   10                  15

Trp Leu Ile Ile Ile Gly Leu Asn Val Phe Val Phe Gly Thr Lys Gly
            20                  25                  30

Ser Leu Thr Val Tyr Gly Ile Ile Leu Leu Thr Tyr Leu Ser Ile Lys
        35                  40                  45

Met Gly Leu Ser Phe Phe Tyr Arg Pro Tyr Lys Gly Ser Val Gly Gln
    50                  55                  60

Tyr Lys Val Ala Ala Ile Ile Pro Ser Tyr Asn Glu Asp Gly Val Gly
65                  70                  75                  80

Leu Leu Glu Thr Leu Lys Ser Val Gln Lys Gln Thr Tyr Pro Ile Ala
                85                  90                  95

Glu Ile Phe Val Ile Asp Asp Gly Ser Val Asp Lys Thr Gly Ile Lys
            100                 105                 110

Leu Val Glu Asp Tyr Val Lys Leu Asn Gly Phe Gly Asp Gln Val Ile
        115                 120                 125

Val His Gln Met Pro Glu Asn Val Gly Lys Arg His Ala Gln Ala Trp
    130                 135                 140

Ala Phe Glu Arg Ser Asp Ala Asp Val Phe Leu Thr Val Asp Ser Asp
145                 150                 155                 160

Thr Tyr Ile Tyr Pro Asp Ala Leu Glu Glu Leu Leu Lys Thr Phe Asn
                165                 170                 175

Asp Pro Glu Val Tyr Ala Ala Thr Gly His Leu Asn Ala Arg Asn Arg
            180                 185                 190

Gln Thr Asn Leu Leu Thr Arg Leu Thr Asp Ile Arg Tyr Asp Asn Ala
        195                 200                 205

Phe Gly Val Glu Arg Ala Ala Gln Ser Val Thr Gly Asn Ile Leu Val
    210                 215                 220

Cys Ser Gly Pro Leu Ser Ile Tyr Arg Arg Ser Val Gly Ile Pro Asn
225                 230                 235                 240

Leu Glu Arg Tyr Thr Ser Gln Thr Phe Leu Gly Val Pro Val Ser Ile
                245                 250                 255

Gly Asp Asp Arg Cys Leu Thr Asn Tyr Ala Thr Asp Leu Gly Lys Thr
            260                 265                 270

Val Tyr Gln Ser Thr Ala Arg Cys Asp Thr Asp Val Pro Asp Lys Phe
        275                 280                 285

Lys Val Phe Ile Lys Gln Gln Asn Arg Trp Asn Lys Ser Phe Phe Arg
    290                 295                 300

Glu Ser Ile Ile Ser Val Lys Lys Leu Leu Ala Thr Pro Ser Val Ala
305                 310                 315                 320

Val Trp Thr Ile Thr Glu Val Ser Met Phe Ile Met Leu Val Tyr Ser
                325                 330                 335

Ile Phe Ser Leu Leu Ile Gly Glu Ala Gln Glu Phe Asn Leu Ile Lys
            340                 345                 350
```

-continued

```
Leu Val Ala Phe Leu Val Ile Ile Phe Ile Val Ala Leu Cys Arg Asn
        355                 360                 365

Val His Tyr Met Val Lys His Pro Phe Ala Phe Leu Leu Ser Pro Phe
    370                 375                 380

Tyr Gly Leu Ile His Leu Phe Val Leu Gln Pro Leu Lys Ile Tyr Ser
385                 390                 395                 400

Leu Phe Thr Ile Arg Asn Ala Thr Trp Gly Thr Arg Lys Lys Thr Ser
                405                 410                 415

Lys

<210> SEQ ID NO 7
<211> LENGTH: 2937
<212> TYPE: DNA
<213> ORGANISM: Pasteurella multocida
<400> SEQUENCE: 7 atttttaag gacagaaaat gaatacatta tcacaagcaa taaaagcata taacagcaat     60
gactatcaat tagcactcaa attatttgaa aagtcggcgg aaatctatgg acggaaaatt    120
gttgaatttc aaattaccaa atgccaagaa aaactctcag cacatccttc tgttaattca    180
gcacatcttt ctgtaaataa agaagaaaaa gtcaatgttt gcgatagtcc gttagatatt    240
gcaacacaac tgttactttc caacgtaaaa aaattagtac tttctgactc ggaaaaaaac    300
acgttaaaaa ataaatggaa attgctcact gagaagaaat ctgaaaatgc ggaggtaaga    360
gcggtcgccc ttgtaccaaa agattttccc aaagatctgg ttttagcgcc tttacctgat    420
catgttaatg attttacatg gtacaaaaag cgaaagaaaa gacttggcat aaaacctgaa    480
catcaacatg ttggtctttc tattatcgtt acaacattca atcgaccagc aattttatcg    540
attacattag cctgtttagt aaaccaaaaa acacattacc cgtttgaagt tatcgtgaca    600
gatgatggta gtcaggaaga tctatcaccg atcattcgcc aatatgaaaa taaattggat    660
attcgctacg tcagacaaaa agataacggt tttcaagcca gtgccgctcg gaatatggga    720
ttacgcttag caaaatatga ctttattggc ttactcgact gtgatatggc gccaaatcca    780
ttatgggttc attcttatgt tgcagagcta ttagaagatg atgatttaac aatcattggt    840
ccaagaaaat acatcgatac acaacatatt gacccaaaag acttcttaaa taacgcgagt    900
ttgcttgaat cattaccaga agtgaaaacc aataatagtg ttgccgcaaa aggggaagga    960
acagtttctc tggattggcg cttagaacaa ttcgaaaaaa cagaaaatct ccgcttatcc   1020
gattcgcctt tccgtttttt tgcggcgggt aatgttgctt tcgctaaaaa atggctaaat   1080
aaatccggtt tctttgatga ggaatttaat cactggggtg gagaagatgt ggaatttgga   1140
tatcgcttat tccgttacgg tagtttcttt aaaactattg atggcattat ggcctaccat   1200
caagagccac caggtaaaga aaatgaaacc gatcgtgaag cgggaaaaaa tattacgctc   1260
gatattatga gagaaaaggt cccttatatc tatagaaaac ttttaccaat agaagattcg   1320
catatcaata gagtaccttt agtttcaatt tatatcccag cttataactg tgcaaactat   1380
attcaacgtt gcgtagatag tgcactgaat cagactgttg ttgatctcga ggtttgtatt   1440
tgtaacgatg gttcaacaga taatacctta gaagtgatca ataagcttta tggtaataat   1500
cctagggtac gcatcatgtc taaaccaaat ggcggaatag cctcagcatc aaatgcagcc   1560
gtttcttttg ctaaaggtta ttacattggg cagttagatt cagatgatta tcttgagcct   1620
gatgcagttg aactgtgttt aaaagaattt ttaaaagata aaacgctagc ttgtgtttat   1680
accactaata gaaacgtcaa tccggatggt agcttaatcg ctaatggtta caattggcca   1740
```

```
gaattttcac gagaaaaact cacaacggct atgattgctc accactttag aatgttcacg    1800
attagagctt ggcatttaac tgatggattc aatgaaaaaa ttgaaaatgc cgtagactat    1860
gacatgttcc tcaaactcag tgaagttgga aaatttaaac atcttaataa aatctgctat    1920
aaccgtgtat tacatggtga taacacatca attaagaaac ttggcattca aagaaaaac    1980 cattttgttg tagtcaatca gtcattaaat agacaaggca taacttatta taattatgac    2040
gaatttgatg atttagatga agtagaaag tatattttca ataaaaccgc tgaatatcaa    2100
gaagagattg atatcttaaa agatattaaa atcatccaga ataaagatgc caaaatcgca    2160
gtcagtattt tttatcccaa tacattaaac ggcttagtga aaaaactaaa caatattatt    2220
gaatataata aaaatatatt cgttattgtt ctacatgttg ataagaatca tcttacacca    2280
gatatcaaaa aagaaatact agccttctat cataaacatc aagtgaatat tttactaaat    2340
aatgatatct catattacac gagtaataga ttaataaaaa ctgaggcgca tttaagtaat    2400
attaataaat taagtcagtt aaatctaaat tgtgaataca tcattttga taatcatgac    2460 agcctattcg ttaaaaatga cagctatgct tatatgaaaa aatatgatgt cggcatgaat    2520
ttctcagcat taacacatga ttggatcgag aaaatcaatg cgcatccacc atttaaaaag    2580
ctcattaaaa cttatttaa tgacaatgac ttaaaaagta tgaatgtgaa agggcatca    2640 caaggtatgt ttatgacgta tgcgctagcg catgagcttc tgacgattat taaagaagtc    2700
atcacatctt gccagtcaat tgatagtgtg ccagaatata acactgagga tatttggttc    2760
caatttgcac ttttaatctt agaaagaaa accggccatg tatttaataa aacatcgacc    2820
ctgacttata tgccttggga acgaaaatta caatggacaa atgaacaaat tgaaagtgca    2880
aaaagaggag aaaatatacc tgttaacaag ttcattatta atagtataac tctataa     2937

<210> SEQ ID NO 8
<211> LENGTH: 972
<212> TYPE: PRT
<213> ORGANISM: Pasteurella multocida

<400> SEQUENCE: 8

Met Asn Thr Leu Ser Gln Ala Ile Lys Ala Tyr Asn Ser Asn Asp Tyr
1               5                   10                  15

Gln Leu Ala Leu Lys Leu Phe Glu Lys Ser Ala Glu Ile Tyr Gly Arg
            20                  25                  30

Lys Ile Val Glu Phe Gln Ile Thr Lys Cys Gln Glu Lys Leu Ser Ala
        35                  40                  45

His Pro Ser Val Asn Ser Ala His Leu Ser Val Asn Lys Glu Glu Lys
    50                  55                  60

Val Asn Val Cys Asp Ser Pro Leu Asp Ile Ala Thr Gln Leu Leu Leu
65                  70                  75                  80

Ser Asn Val Lys Lys Leu Val Leu Ser Asp Ser Glu Lys Asn Thr Leu
                85                  90                  95

Lys Asn Lys Trp Lys Leu Leu Thr Glu Lys Lys Ser Glu Asn Ala Glu
            100                 105                 110

Val Arg Ala Val Ala Leu Val Pro Lys Asp Phe Pro Lys Asp Leu Val
        115                 120                 125

Leu Ala Pro Leu Pro Asp His Val Asn Asp Phe Thr Trp Tyr Lys Lys
    130                 135                 140

Arg Lys Lys Arg Leu Gly Ile Lys Pro Glu His Gln His Val Gly Leu
145                 150                 155                 160
```

-continued

```
Ser Ile Ile Val Thr Thr Phe Asn Arg Pro Ala Ile Leu Ser Ile Thr
                165                 170                 175
Leu Ala Cys Leu Val Asn Gln Lys Thr His Tyr Pro Phe Glu Val Ile
            180                 185                 190
Val Thr Asp Asp Gly Ser Gln Glu Asp Leu Ser Pro Ile Ile Arg Gln
        195                 200                 205
Tyr Glu Asn Lys Leu Asp Ile Arg Tyr Val Arg Gln Lys Asp Asn Gly
    210                 215                 220
Phe Gln Ala Ser Ala Ala Arg Asn Met Gly Leu Arg Leu Ala Lys Tyr
225                 230                 235                 240
Asp Phe Ile Gly Leu Leu Asp Cys Asp Met Ala Pro Asn Pro Leu Trp
                245                 250                 255
Val His Ser Tyr Val Ala Glu Leu Leu Glu Asp Asp Asp Leu Thr Ile
            260                 265                 270
Ile Gly Pro Arg Lys Tyr Ile Asp Thr Gln His Ile Asp Pro Lys Asp
        275                 280                 285
Phe Leu Asn Asn Ala Ser Leu Leu Glu Ser Leu Pro Glu Val Lys Thr
    290                 295                 300
Asn Asn Ser Val Ala Ala Lys Gly Glu Gly Thr Val Ser Leu Asp Trp
305                 310                 315                 320
Arg Leu Glu Gln Phe Glu Lys Thr Glu Asn Leu Arg Leu Ser Asp Ser
                325                 330                 335
Pro Phe Arg Phe Phe Ala Ala Gly Asn Val Ala Phe Ala Lys Lys Trp
            340                 345                 350
Leu Asn Lys Ser Gly Phe Phe Asp Glu Glu Phe Asn His Trp Gly Gly
        355                 360                 365
Glu Asp Val Glu Phe Gly Tyr Arg Leu Phe Arg Tyr Gly Ser Phe Phe
    370                 375                 380
Lys Thr Ile Asp Gly Ile Met Ala Tyr His Gln Glu Pro Pro Gly Lys
385                 390                 395                 400
Glu Asn Glu Thr Asp Arg Glu Ala Gly Lys Asn Ile Thr Leu Asp Ile
                405                 410                 415
Met Arg Glu Lys Val Pro Tyr Ile Tyr Arg Lys Leu Leu Pro Ile Glu
            420                 425                 430
Asp Ser His Ile Asn Arg Val Pro Leu Val Ser Ile Tyr Ile Pro Ala
        435                 440                 445
Tyr Asn Cys Ala Asn Tyr Ile Gln Arg Cys Val Asp Ser Ala Leu Asn
    450                 455                 460
Gln Thr Val Val Asp Leu Glu Val Cys Ile Cys Asn Asp Gly Ser Thr
465                 470                 475                 480
Asp Asn Thr Leu Glu Val Ile Asn Lys Leu Tyr Gly Asn Asn Pro Arg
                485                 490                 495
Val Arg Ile Met Ser Lys Pro Asn Gly Gly Ile Ala Ser Ala Ser Asn
            500                 505                 510
Ala Ala Val Ser Phe Ala Lys Gly Tyr Tyr Ile Gly Gln Leu Asp Ser
        515                 520                 525
Asp Asp Tyr Leu Glu Pro Asp Ala Val Glu Leu Cys Leu Lys Glu Phe
    530                 535                 540
Leu Lys Asp Lys Thr Leu Ala Cys Val Tyr Thr Thr Asn Arg Asn Val
545                 550                 555                 560
Asn Pro Asp Gly Ser Leu Ile Ala Asn Gly Tyr Asn Trp Pro Glu Phe
                565                 570                 575
Ser Arg Glu Lys Leu Thr Thr Ala Met Ile Ala His His Phe Arg Met
```

-continued

```
                580                 585                 590
        Phe Thr Ile Arg Ala Trp His Leu Thr Asp Gly Phe Asn Glu Lys Ile
            595                 600                 605
        Glu Asn Ala Val Asp Tyr Asp Met Phe Leu Lys Leu Ser Glu Val Gly
            610                 615                 620
        Lys Phe Lys His Leu Asn Lys Ile Cys Tyr Asn Arg Val Leu His Gly
        625                 630                 635                 640
        Asp Asn Thr Ser Ile Lys Lys Leu Gly Ile Gln Lys Lys Asn His Phe
                        645                 650                 655
        Val Val Val Asn Gln Ser Leu Asn Arg Gln Gly Ile Thr Tyr Tyr Asn
                    660                 665                 670
        Tyr Asp Glu Phe Asp Asp Leu Asp Glu Ser Arg Lys Tyr Ile Phe Asn
                    675                 680                 685
        Lys Thr Ala Glu Tyr Gln Glu Glu Ile Asp Ile Leu Lys Asp Ile Lys
                    690                 695                 700
        Ile Ile Gln Asn Lys Asp Ala Lys Ile Ala Val Ser Ile Phe Tyr Pro
        705                 710                 715                 720
        Asn Thr Leu Asn Gly Leu Val Lys Lys Leu Asn Asn Ile Ile Glu Tyr
                        725                 730                 735
        Asn Lys Asn Ile Phe Val Ile Val Leu His Val Asp Lys Asn His Leu
                    740                 745                 750
        Thr Pro Asp Ile Lys Lys Glu Ile Leu Ala Phe Tyr His Lys His Gln
                    755                 760                 765
        Val Asn Ile Leu Leu Asn Asn Asp Ile Ser Tyr Tyr Thr Ser Asn Arg
                    770                 775                 780
        Leu Ile Lys Thr Glu Ala His Leu Ser Asn Ile Asn Lys Leu Ser Gln
        785                 790                 795                 800
        Leu Asn Leu Asn Cys Glu Tyr Ile Ile Phe Asp Asn His Asp Ser Leu
                        805                 810                 815
        Phe Val Lys Asn Asp Ser Tyr Ala Tyr Met Lys Lys Tyr Asp Val Gly
                    820                 825                 830
        Met Asn Phe Ser Ala Leu Thr His Asp Trp Ile Glu Lys Ile Asn Ala
                    835                 840                 845
        His Pro Pro Phe Lys Lys Leu Ile Lys Thr Tyr Phe Asn Asp Asn Asp
        850                 855                 860
        Leu Lys Ser Met Asn Val Lys Gly Ala Ser Gln Gly Met Phe Met Thr
        865                 870                 875                 880
        Tyr Ala Leu Ala His Glu Leu Leu Thr Ile Ile Lys Glu Val Ile Thr
                        885                 890                 895
        Ser Cys Gln Ser Ile Asp Ser Val Pro Glu Tyr Asn Thr Glu Asp Ile
                    900                 905                 910
        Trp Phe Gln Phe Ala Leu Leu Ile Leu Glu Lys Lys Thr Gly His Val
                    915                 920                 925
        Phe Asn Lys Thr Ser Thr Leu Thr Tyr Met Pro Trp Glu Arg Lys Leu
                    930                 935                 940
        Gln Trp Thr Asn Glu Gln Ile Glu Ser Ala Lys Arg Gly Glu Asn Ile
        945                 950                 955                 960
        Pro Val Asn Lys Phe Ile Ile Asn Ser Ile Thr Leu
                        965                 970

<210> SEQ ID NO 9
<211> LENGTH: 1767
<212> TYPE: DNA
<213> ORGANISM: Xenopus laevis
```

-continued

```
<400> SEQUENCE: 9
atgaaggaaa aagctgcaga acaatggag attcctgaag ggatcccaa agatctagag      60
ccaaaacacc ccacccttg gaggataatt tattattctt ttggtgtggt gctattagct    120
accattacag cagcctatgt ggcagagttc caggtcctca acatgaagc cattctcttc    180
tcccttgggc tttatggtct tgcaatgctt ctccacctga tgcagag cctctttgcc     240
ttcctggaga tacgcagggt aaataagagt gagcttcctt gcagctttaa aagacagtg    300
gctctgacca ttgctgggta tcaggagaac cctgagtacc tgataaagtg cttggaatcc   360
tgcaagtatg tgaaataccc caagataaa ctcaagatca ttttggtcat cgatgggaac    420
acagaggatg atgcctacat gatggagatg ttcaaagacg tgttccacgg tgaagatgta   480
ggcacctacg tatggaaggg aaattaccac actgttaaaa agcctgagga gaccaataag   540
ggatcctgtc ctgaggtttc taagcccttg aatgaagatg aagtatcaa atggtggaa     600
gaacttgtta gaaacaagag atgtgtgtgc atcatgcaac agtgggcgg aaaaagagag    660
gtcatgtaca cagcattcca ggccattggg acttctgtgg actatgtaca ggtctgtgac   720
tcggacacca aactggatga actggcaaca gtggaaatgg tgaaggttct ggaatccaat   780
gacatgtacg cgcagtggg aggagacgtt cgcattctga acccttatga ttccttcatt   840
agtttcatga gcagcctgcg ttactggatg cgtttaacg tggagagggc ctgccagtct   900
tacttcgact gcgtgtcctg tataagtgga ccctctggga atgtaccgaa caacattctc   960
caggtgtttt tggaagcctg gtacagacag aaatttttgg gaacctattg tactttggga  1020
gatgatagac atcctgacaa accgagtgctc agcatgggat atcgcaccaa atacacccac  1080
aaatccagag cattctccga aactccatcc ctgtatctcc ggtggttgaa ccagcaaacc  1140
cggtggacca agtcctactt ccgagagtgg ctgtataatg cccagtggtg gcacaagcat  1200
cacatctgga tgacctatga gtctgtggtg tccttcatct ttcccttctt catcactgcc  1260
actgttatcc gcctcatcta tgccggcacc atatggaatg ttgtgtggct cctcctgtgc  1320
atccagatca tgtctctctt caaatccatc tatgcctgct ggctccgcgg caacttcatt  1380
atgctcctga tgtctctcta ctccatgctg tacatgactg ggcttctgcc atccaagtac  1440
tttgccttgt tgaccttaaa caagaccggt tggggaacat ctgggcgcaa gaagatagta  1500
ggcaactaca tgccaatact gccctgtcc atatgggcag ctgttctgtg tggaggggtg  1560
ggttatagta tctatatgga ctgtcaaaat gactggagca cccctgaaaa gcaaaaggag  1620
atgtaccatc tattgtatgg gtgtgtgggc tatgtaatgt actgggtaat catggctgtg  1680
atgtactggg tctgggtgaa gaggtgctgc aggaagaggt cccaaactgt caccctggtc  1740
catgacattc ctgatatgtg tgtttaa                                       1767
```

<210> SEQ ID NO 10
<211> LENGTH: 588
<212> TYPE: PRT
<213> ORGANISM: Xenopus laevis

<400> SEQUENCE: 10

```
Met Lys Glu Lys Ala Ala Glu Thr Met Glu Ile Pro Glu Gly Ile Pro
1               5                   10                  15

Lys Asp Leu Glu Pro Lys His Pro Thr Leu Trp Arg Ile Ile Tyr Tyr
            20                  25                  30

Ser Phe Gly Val Val Leu Leu Ala Thr Ile Thr Ala Ala Tyr Val Ala
        35                  40                  45
```

```
Glu Phe Gln Val Leu Lys His Glu Ala Ile Leu Phe Ser Leu Gly Leu
    50                  55                  60

Tyr Gly Leu Ala Met Leu Leu His Leu Met Met Gln Ser Leu Phe Ala
65                  70                  75                  80

Phe Leu Glu Ile Arg Arg Val Asn Lys Ser Glu Leu Pro Cys Ser Phe
                85                  90                  95

Lys Lys Thr Val Ala Leu Thr Ile Ala Gly Tyr Gln Glu Asn Pro Glu
            100                 105                 110

Tyr Leu Ile Lys Cys Leu Glu Ser Cys Lys Tyr Val Lys Tyr Pro Lys
        115                 120                 125

Asp Lys Leu Lys Ile Ile Leu Val Ile Asp Gly Asn Thr Glu Asp Asp
    130                 135                 140

Ala Tyr Met Met Glu Met Phe Lys Asp Val Phe His Gly Glu Asp Val
145                 150                 155                 160

Gly Thr Tyr Val Trp Lys Gly Asn Tyr His Thr Val Lys Lys Pro Glu
                165                 170                 175

Glu Thr Asn Lys Gly Ser Cys Pro Glu Val Ser Lys Pro Leu Asn Glu
            180                 185                 190

Asp Glu Gly Ile Asn Met Val Glu Glu Leu Val Arg Asn Lys Arg Cys
        195                 200                 205

Val Cys Ile Met Gln Gln Trp Gly Gly Lys Arg Glu Val Met Tyr Thr
    210                 215                 220

Ala Phe Gln Ala Ile Gly Thr Ser Val Asp Tyr Val Gln Val Cys Asp
225                 230                 235                 240

Ser Asp Thr Lys Leu Asp Glu Leu Ala Thr Val Glu Met Val Lys Val
                245                 250                 255

Leu Glu Ser Asn Asp Met Tyr Gly Ala Val Gly Gly Asp Val Arg Ile
            260                 265                 270

Leu Asn Pro Tyr Asp Ser Phe Ile Ser Phe Met Ser Ser Leu Arg Tyr
        275                 280                 285

Trp Met Ala Phe Asn Val Glu Arg Ala Cys Gln Ser Tyr Phe Asp Cys
    290                 295                 300

Val Ser Cys Ile Ser Gly Pro Leu Gly Met Tyr Arg Asn Asn Ile Leu
305                 310                 315                 320

Gln Val Phe Leu Glu Ala Trp Tyr Arg Gln Lys Phe Leu Gly Thr Tyr
                325                 330                 335

Cys Thr Leu Gly Asp Asp Arg His Leu Thr Asn Arg Val Leu Ser Met
            340                 345                 350

Gly Tyr Arg Thr Lys Tyr Thr His Lys Ser Arg Ala Phe Ser Glu Thr
        355                 360                 365

Pro Ser Leu Tyr Leu Arg Trp Leu Asn Gln Gln Thr Arg Trp Thr Lys
    370                 375                 380

Ser Tyr Phe Arg Glu Trp Leu Tyr Asn Ala Gln Trp His Lys His
385                 390                 395                 400

His Ile Trp Met Thr Tyr Glu Ser Val Val Ser Phe Ile Pro Phe
                405                 410                 415

Phe Ile Thr Ala Thr Val Ile Arg Leu Ile Tyr Ala Gly Thr Ile Trp
            420                 425                 430

Asn Val Val Trp Leu Leu Leu Cys Ile Gln Ile Met Ser Leu Phe Lys
        435                 440                 445

Ser Ile Tyr Ala Cys Trp Leu Arg Gly Asn Phe Ile Met Leu Leu Met
    450                 455                 460
```

```
Ser Leu Tyr Ser Met Leu Tyr Met Thr Gly Leu Leu Pro Ser Lys Tyr
465                 470                 475                 480

Phe Ala Leu Leu Thr Leu Asn Lys Thr Gly Trp Gly Thr Ser Gly Arg
                485                 490                 495

Lys Lys Ile Val Gly Asn Tyr Met Pro Ile Leu Pro Leu Ser Ile Trp
            500                 505                 510

Ala Ala Val Leu Cys Gly Gly Val Gly Tyr Ser Ile Tyr Met Asp Cys
        515                 520                 525

Gln Asn Asp Trp Ser Thr Pro Glu Lys Gln Lys Glu Met Tyr His Leu
    530                 535                 540

Leu Tyr Gly Cys Val Gly Tyr Val Met Tyr Trp Val Ile Met Ala Val
545                 550                 555                 560

Met Tyr Trp Val Trp Val Lys Arg Cys Cys Arg Lys Arg Ser Gln Thr
                565                 570                 575

Val Thr Leu Val His Asp Ile Pro Asp Met Cys Val
            580                 585

<210> SEQ ID NO 11
<211> LENGTH: 1740
<212> TYPE: DNA
<213> ORGANISM: Chlorella virus PBCV-1

<400> SEQUENCE: 11
aagacttctt gaaagttaca atgggtaaaa atataatcat aatggtttcg tggtacacca      60
tcataacttc aaatctaatc gcggttggag gagcctctct aatcttggct ccggcaatta     120
ctgggtatgt tctacattgg aatattgctc tctcgacaat ctggggagta tcagcttatg     180
gtattttcgt ttttgggttt ttccttgcac aagtttatt ttcagaactg aacaggaaac      240
gtcttcgcaa gtggatttct ctcagaccta agggttggaa tgatgttcgt ttggctgtga     300
tcattgctgg atatcgcgag gatccttata tgttccagaa gtgcctcgag tctgtacgtg     360
actctgatta tggcaacgtt gcccgtctga tttgtgtgat tgacggtgat gaggacgatg     420
atatgaggat ggctgccgtt tacaaggcga tctacaatga taatatcaag aagcccgagt     480
tgttctgtg tgagtcagac gacaaggaag gtgaacgcat cgactctgat ttctctcgcg     540
acatttgtgt cctccagcct catcgtggaa acgggagtg tctttatact ggctttcaac      600
ttgcaaagat ggaccccagt gtcaatgctg tcgttctgat tgacagcgat accgttctcg     660
agaaggatgc tattctggaa gttgtatacc cacttgcatg cgatcccgag atccaagccg     720
ttgcaggtga gtgtaagatt tggaacacag acactctttt gagtcttctc gtcgcttggc     780
ggtactattc tgcgttttgt gtggagagga gtgcccagtc ttttttcagg actgttcagt     840
gcgttggggg gccactggt gcctacaaga ttgatatcat taaggagatt aaggaccct      900
ggatttccca gcgctttctt ggtcagaagt gtacttacgg tgacgaccgc cggctaacca     960
acgagatctt gatgcgtggt aaaaaggttg tgttcactcc atttgctgtt ggttggtctg    1020
acagtccgac caatgtgttt cggtacatcg ttcagcagac ccgctggagt aagtcgtggt    1080
gccgcgaaat ttggtacacc ctcttcgccg cgtggaagca cggtttgtct ggaatttggc    1140
tggcctttga atgtttgtat caaattacat acttcttcct cgtgatttac ctcttttctc    1200
gcctagccgt tgaggccgac cctcgcgccc agacagccac ggtgattgtg agcaccacgg    1260
ttgcattgat taagtgtggg tatttttcat tccgagccaa ggatattcgg gcgttttact    1320
ttgtgcttta tacatttgtt tactttttct gtatgattcc ggccaggatt actgcaatga    1380
tgacgctttg ggacattggc tgggatactc gcggtggaaa cgagaagcct tccgttggca    1440
```

-continued

```
cccgggtcgc tctgtgggca agcaatatc tcattgcata tatgtggtgg gccgcggttg    1500
ttggcgctgg agtttacagc atcgtccata actggatgtt cgattggaat tctctttctt    1560
atcgttttgc tttggttggt atttgttctt acattgtttt tattgttatt gtgctggtgg    1620
tttatttcac cggcaaaatt acgacttgga atttcacgaa gcttcagaag gagctaatcg    1680
aggatcgcgt tctgtacgat gcaactacca atgctcagtc tgtgtgattt ttcctgcaag    1740
```

<210> SEQ ID NO 12
<211> LENGTH: 567
<212> TYPE: PRT
<213> ORGANISM: Chlorella virus PBCV-1

<400> SEQUENCE: 12

```
Met Gly Lys Asn Ile Ile Ile Met Val Ser Trp Tyr Thr Ile Ile Thr
1               5                   10                  15

Ser Asn Leu Ile Ala Val Gly Gly Ala Ser Leu Ile Leu Ala Pro Ala
                20                  25                  30

Ile Thr Gly Tyr Val Leu His Trp Asn Ile Ala Leu Ser Thr Ile Trp
            35                  40                  45

Gly Val Ser Ala Tyr Gly Ile Phe Val Phe Gly Phe Phe Leu Ala Gln
        50                  55                  60

Val Leu Phe Ser Glu Leu Asn Arg Lys Arg Leu Arg Lys Trp Ile Ser
65                  70                  75                  80

Leu Arg Pro Lys Gly Trp Asn Asp Val Arg Leu Ala Val Ile Ile Ala
                85                  90                  95

Gly Tyr Arg Glu Asp Pro Tyr Met Phe Gln Lys Cys Leu Glu Ser Val
            100                 105                 110

Arg Asp Ser Asp Tyr Gly Asn Val Ala Arg Leu Ile Cys Val Ile Asp
        115                 120                 125

Gly Asp Glu Asp Asp Met Arg Met Ala Ala Val Tyr Lys Ala Ile
    130                 135                 140

Tyr Asn Asp Asn Ile Lys Lys Pro Glu Phe Val Leu Cys Glu Ser Asp
145                 150                 155                 160

Asp Lys Glu Gly Glu Arg Ile Asp Ser Asp Phe Ser Arg Asp Ile Cys
                165                 170                 175

Val Leu Gln Pro His Arg Gly Lys Arg Glu Cys Leu Tyr Thr Gly Phe
            180                 185                 190

Gln Leu Ala Lys Met Asp Pro Ser Val Asn Ala Val Leu Ile Asp
        195                 200                 205

Ser Asp Thr Val Leu Glu Lys Asp Ala Ile Leu Glu Val Val Tyr Pro
    210                 215                 220

Leu Ala Cys Asp Pro Glu Ile Gln Ala Val Ala Gly Glu Cys Lys Ile
225                 230                 235                 240

Trp Asn Thr Asp Thr Leu Leu Ser Leu Leu Val Ala Trp Arg Tyr Tyr
                245                 250                 255

Ser Ala Phe Cys Val Glu Arg Ser Ala Gln Ser Phe Phe Arg Thr Val
            260                 265                 270

Gln Cys Val Gly Gly Pro Leu Gly Ala Tyr Lys Asp Ile Ile Lys Glu
        275                 280                 285

Ile Lys Asp Pro Trp Ile Ser Gln Arg Phe Leu Gly Gln Lys Cys Thr
    290                 295                 300

Tyr Gly Asp Asp Arg Arg Leu Thr Asn Glu Ile Leu Met Arg Gly Lys
305                 310                 315                 320
```

-continued

Lys Val Val Phe Thr Pro Phe Ala Val Gly Trp Ser Asp Ser Pro Thr
            325                 330                 335

Asn Val Phe Arg Tyr Ile Val Gln Gln Thr Arg Trp Ser Lys Ser Trp
            340                 345                 350

Cys Arg Glu Ile Trp Tyr Thr Leu Phe Ala Ala Trp Lys His Gly Leu
            355                 360                 365

Ser Gly Ile Trp Leu Ala Phe Glu Cys Leu Tyr Gln Ile Thr Tyr Phe
    370                 375                 380

Phe Leu Val Ile Tyr Leu Phe Ser Arg Leu Ala Val Glu Ala Asp Pro
385                 390                 395                 400

Arg Ala Gln Thr Ala Thr Val Ile Val Ser Thr Val Ala Leu Ile
                405                 410                 415

Lys Cys Gly Tyr Phe Ser Phe Arg Ala Lys Asp Ile Arg Ala Phe Tyr
                420                 425                 430

Phe Val Leu Tyr Thr Phe Val Tyr Phe Cys Met Ile Pro Ala Arg
                435                 440                 445

Ile Thr Ala Met Met Thr Leu Trp Asp Ile Gly Trp Asp Thr Arg Gly
            450                 455                 460

Gly Asn Glu Lys Pro Ser Val Gly Thr Arg Val Ala Leu Trp Ala Lys
465                 470                 475                 480

Gln Tyr Leu Ile Ala Tyr Met Trp Trp Ala Ala Val Val Gly Ala Gly
                485                 490                 495

Val Tyr Ser Ile Val His Asn Trp Met Phe Asp Trp Asn Ser Leu Ser
                500                 505                 510

Tyr Arg Phe Ala Leu Val Gly Ile Cys Ser Tyr Ile Val Phe Ile Val
            515                 520                 525

Ile Val Leu Val Val Tyr Phe Thr Gly Lys Ile Thr Thr Trp Asn Phe
            530                 535                 540

Thr Lys Leu Gln Lys Glu Leu Ile Glu Asp Arg Val Leu Tyr Asp Ala
545                 550                 555                 560

Thr Thr Asn Ala Gln Ser Val
                565

<210> SEQ ID NO 13
<211> LENGTH: 1380
<212> TYPE: DNA
<213> ORGANISM: Sulfolobus solfataricus

<400> SEQUENCE: 13
tgccctcatg cggttaagct tgaaatggcc ttttttagaa agagaaagga gttatctagt      60
taaccaatct tgccaccaga aagttatcat agcatatagg gaagcaatat attgcactgc     120
tagtgcgata gaaccgtata ttagagtttt caatttatct tctggaatta ataaaatcat     180
ggtcattaca aagggtatta tagctataaa tcctccgtaa tgcaagaata ataaaaagat     240
aaagaagtcg gaatggtaac gggttggcag atacaatagt aataagagct tagtattaat     300
tacattaatt gaggaataga tcttaagaat tctagtgaaa ctcatataaa ggaacaagag     360
cgtaaataat ggtaacagat tggtgtatat catattaaaa acgtataatg aacccctttt     420
acttatacta ccgtcagcta tctcccttat aaaattaaga taatttgctc ttgtccatct     480
agttacttgt ttcgtaaaca ttttttatgtc tctaggggt tttgtatatg ccactgcatc     540
aaagactttt acagccctat acccttttt tataacaaaa tcggttaaat ctctatcatc     600
ggaattttta attggtcttc caaacatttt cggctctaaa aactctttag ataaatatata     660 tggttttacg agttcggtcc tatatattac acattgtcca cttaatatta tagcacttcc     720

```
aaaatagttt accgccctgt ttactatctc acttattctc tcaaagaatt caccataata      780
atatgcatat ttattttct cgtcatacat aattctaata tttggcccta ctccacctac       840
tgactcatca aaaacactta acatctttag tatagagtct ttataaataa tcgtatcact      900
atctagaaac atcactagag gagatcttac atacttaact ccctcggcta acgcgtatct     960
tttcccctta tgttcacgca tataaataaa tttaccacca tatctttccg taattgattt    1020
gtatggttct agaacactat cccctacaac aataaattct aaccttgtgt catataaagt    1080
ccttatcact ttttcaaaaa tatctatttc ctccttataa actggtatca caactgtaag    1140
atcagagaga ttataaaaac ttgagtgttg agttttcta ttattactta ttactgcaaa     1200
aaatgaattc aaaagaaat aaagaatagt tataattgtg aatgaaagag ataaatgaa      1260 atatgagact ccgtgaaata agtgaaacat aatcaccact ataatgctcg atatcgaaat   1320
atataacgat ttttcctaat tcaccattcg aattctccgt tcaaaaaggg gttagttaac   1380
```

<210> SEQ ID NO 14
<211> LENGTH: 415
<212> TYPE: PRT
<213> ORGANISM: Sulfolobus solfataricus

<400> SEQUENCE: 14

```
Met Val Ile Met Phe His Leu Phe His Gly Val Ser Tyr Phe Ile Tyr
1               5                   10                  15

Ser Leu Ser Phe Thr Ile Ile Thr Ile Leu Tyr Phe Phe Leu Asn Ser
            20                  25                  30

Phe Phe Ala Val Ile Ser Asn Asn Arg Lys Thr Gln His Ser Ser Phe
        35                  40                  45

Tyr Asn Leu Ser Asp Leu Thr Val Val Ile Pro Val Tyr Lys Glu Glu
    50                  55                  60

Ile Asp Ile Phe Glu Lys Val Ile Arg Thr Leu Tyr Asp Thr Arg Leu
65                  70                  75                  80

Glu Phe Ile Val Val Gly Asp Ser Val Leu Glu Pro Tyr Lys Ser Ile
                85                  90                  95

Thr Glu Arg Tyr Gly Gly Lys Phe Ile Tyr Met Arg Glu His Lys Gly
            100                 105                 110

Lys Arg Tyr Ala Leu Ala Glu Gly Val Lys Tyr Val Arg Ser Pro Leu
        115                 120                 125

Val Met Phe Leu Asp Ser Asp Thr Ile Ile Tyr Lys Asp Ser Ile Leu
    130                 135                 140

Lys Met Leu Ser Val Phe Asp Glu Ser Val Gly Gly Val Gly Pro Asn
145                 150                 155                 160

Ile Arg Ile Met Tyr Asp Glu Lys Asn Lys Tyr Ala Tyr Tyr Tyr Gly
                165                 170                 175

Glu Phe Phe Glu Arg Ile Ser Glu Ile Val Asn Arg Ala Val Asn Tyr
            180                 185                 190

Phe Gly Ser Ala Ile Ile Leu Ser Gly Gln Cys Val Ile Tyr Arg Thr
        195                 200                 205

Glu Leu Val Lys Pro Tyr Ile Leu Ser Lys Glu Phe Leu Glu Pro Lys
    210                 215                 220

Met Phe Gly Arg Pro Ile Lys Ile Ser Asp Asp Arg Asp Leu Thr Asp
225                 230                 235                 240

Phe Val Ile Lys Lys Gly Tyr Arg Ala Val Lys Val Phe Asp Ala Val
                245                 250                 255
```

-continued

```
Ala Tyr Thr Lys Pro Pro Arg Asp Ile Lys Met Phe Thr Lys Gln Val
            260                 265                 270

Thr Arg Trp Thr Arg Ala Asn Tyr Leu Asn Phe Ile Arg Glu Ile Ala
        275                 280                 285

Asp Gly Ser Ile Ser Lys Arg Gly Ser Leu Tyr Val Phe Asn Met Ile
    290                 295                 300

Tyr Thr Asn Leu Leu Pro Leu Phe Thr Leu Leu Phe Leu Tyr Met Ser
305                 310                 315                 320

Phe Thr Arg Ile Leu Lys Ile Tyr Ser Ser Ile Asn Val Ile Asn Thr
                325                 330                 335

Lys Leu Leu Leu Leu Tyr Leu Pro Thr Arg Tyr His Ser Asp Phe
                340                 345                 350

Phe Ile Phe Tyr Leu Phe Leu His Tyr Gly Gly Phe Ile Ala Ile Ile
            355                 360                 365

Pro Phe Val Met Thr Met Ile Tyr Leu Ile Pro Glu Asp Lys Leu Lys
        370                 375                 380

Thr Leu Ile Tyr Gly Ser Ile Ala Leu Ala Val Gln Tyr Ile Ala Ser
385                 390                 395                 400

Leu Tyr Ala Met Ile Thr Phe Trp Trp Gln Asp Trp Leu Thr Arg
                405                 410                 415
```

```
<210> SEQ ID NO 15
<211> LENGTH: 417
<212> TYPE: PRT
<213> ORGANISM: Streptococcus equisimilis
<220> FEATURE:
<221> NAME/KEY: MISC_FEATURE
<222> LOCATION: (226)..(226)
<223> OTHER INFORMATION: Xaa = Ala, Ser, or any other amino acid

<400> SEQUENCE: 15
```

```
Met Arg Thr Leu Lys Asn Leu Ile Thr Val Val Ala Phe Ser Ile Phe
1               5                   10                  15

Trp Val Leu Leu Ile Tyr Val Asn Val Tyr Leu Phe Gly Ala Lys Gly
            20                  25                  30

Ser Leu Ser Ile Tyr Gly Phe Leu Leu Ile Ala Tyr Leu Leu Val Lys
        35                  40                  45

Met Ser Leu Ser Phe Phe Tyr Lys Pro Phe Lys Gly Arg Ala Gly Gln
    50                  55                  60

Tyr Lys Val Ala Ala Ile Ile Pro Ser Tyr Asn Glu Asp Ala Glu Ser
65                  70                  75                  80

Leu Leu Glu Thr Leu Lys Ser Val Gln Gln Gln Thr Tyr Pro Leu Ala
                85                  90                  95

Glu Ile Tyr Val Val Asp Asp Gly Ser Ala Asp Glu Thr Gly Ile Lys
            100                 105                 110

Arg Ile Glu Asp Tyr Val Arg Asp Thr Gly Asp Leu Ser Ser Asn Val
        115                 120                 125

Ile Val His Arg Ser Glu Lys Asn Gln Gly Lys Arg His Ala Gln Ala
    130                 135                 140

Trp Ala Phe Glu Arg Ser Asp Ala Asp Val Phe Leu Thr Val Asp Ser
145                 150                 155                 160

Asp Thr Tyr Ile Tyr Pro Asp Ala Leu Glu Glu Leu Leu Lys Thr Phe
                165                 170                 175

Asn Asp Pro Thr Val Phe Ala Ala Thr Gly His Leu Asn Val Arg Asn
            180                 185                 190

Arg Gln Thr Asn Leu Leu Thr Arg Leu Thr Asp Ile Arg Tyr Asp Asn
```

```
                    195                 200                 205
Ala Phe Gly Val Glu Arg Ala Gln Ser Val Thr Gly Asn Ile Leu
    210                 215                 220

Val Xaa Ser Gly Pro Leu Ser Val Tyr Arg Arg Glu Val Val Pro
225                 230                 235                 240

Asn Ile Asp Arg Tyr Ile Asn Gln Thr Phe Leu Gly Ile Pro Val Ser
                245                 250                 255

Ile Gly Asp Asp Arg Cys Leu Thr Asn Tyr Ala Thr Asp Leu Gly Lys
                260                 265                 270

Thr Val Tyr Gln Ser Thr Ala Lys Cys Ile Thr Asp Val Pro Asp Lys
            275                 280                 285

Met Ser Thr Tyr Leu Lys Gln Gln Asn Arg Trp Asn Lys Ser Phe Phe
    290                 295                 300

Arg Glu Ser Ile Ile Ser Val Lys Lys Ile Met Asn Asn Pro Phe Val
305                 310                 315                 320

Ala Leu Trp Thr Ile Leu Glu Val Ser Met Phe Met Met Leu Val Tyr
                325                 330                 335

Ser Val Val Asp Phe Phe Val Gly Asn Val Arg Glu Phe Asp Trp Leu
            340                 345                 350

Arg Val Leu Ala Phe Leu Val Ile Ile Phe Ile Val Ala Leu Cys Arg
        355                 360                 365

Asn Ile His Tyr Met Leu Lys His Pro Leu Ser Phe Leu Leu Ser Pro
    370                 375                 380

Phe Tyr Gly Val Leu His Leu Phe Val Leu Gln Pro Leu Lys Leu Tyr
385                 390                 395                 400

Ser Leu Phe Thr Ile Arg Asn Ala Asp Trp Gly Thr Arg Lys Lys Leu
                405                 410                 415

Leu
```

```
<210> SEQ ID NO 16
<211> LENGTH: 417
<212> TYPE: PRT
<213> ORGANISM: Streptococcus equisimilis
<220> FEATURE:
<221> NAME/KEY: MISC_FEATURE
<222> LOCATION: (262)..(262)
<223> OTHER INFORMATION: Xaa = Ala, Ser or any other amino acid

<400> SEQUENCE: 16
```

```
Met Arg Thr Leu Lys Asn Leu Ile Thr Val Val Ala Phe Ser Ile Phe
1               5                   10                  15

Trp Val Leu Leu Ile Tyr Val Asn Val Tyr Leu Phe Gly Ala Lys Gly
                20                  25                  30

Ser Leu Ser Ile Tyr Gly Phe Leu Leu Ile Ala Tyr Leu Leu Val Lys
            35                  40                  45

Met Ser Leu Ser Phe Phe Tyr Lys Pro Phe Lys Gly Arg Ala Gly Gln
    50                  55                  60

Tyr Lys Val Ala Ala Ile Ile Pro Ser Tyr Asn Glu Asp Ala Glu Ser
65                  70                  75                  80

Leu Leu Glu Thr Leu Lys Ser Val Gln Gln Gln Thr Tyr Pro Leu Ala
                85                  90                  95

Glu Ile Tyr Val Val Asp Asp Gly Ser Ala Asp Glu Thr Gly Ile Lys
                100                 105                 110

Arg Ile Glu Asp Tyr Val Arg Asp Thr Gly Asp Leu Ser Ser Asn Val
            115                 120                 125
```

```
Ile Val His Arg Ser Glu Lys Asn Gln Gly Lys Arg His Ala Gln Ala
        130                 135                 140

Trp Ala Phe Glu Arg Ser Asp Ala Asp Val Phe Leu Thr Val Asp Ser
145                 150                 155                 160

Asp Thr Tyr Ile Tyr Pro Asp Ala Leu Glu Glu Leu Leu Lys Thr Phe
                165                 170                 175

Asn Asp Pro Thr Val Phe Ala Ala Thr Gly His Leu Asn Val Arg Asn
            180                 185                 190

Arg Gln Thr Asn Leu Leu Thr Arg Leu Thr Asp Ile Arg Tyr Asp Asn
        195                 200                 205

Ala Phe Gly Val Glu Arg Ala Ala Gln Ser Val Thr Gly Asn Ile Leu
    210                 215                 220

Val Cys Ser Gly Pro Leu Ser Val Tyr Arg Arg Glu Val Val Pro
225                 230                 235                 240

Asn Ile Asp Arg Tyr Ile Asn Gln Thr Phe Leu Gly Ile Pro Val Ser
                245                 250                 255

Ile Gly Asp Asp Arg Xaa Leu Thr Asn Tyr Ala Thr Asp Leu Gly Lys
            260                 265                 270

Thr Val Tyr Gln Ser Thr Ala Lys Cys Ile Thr Asp Val Pro Asp Lys
        275                 280                 285

Met Ser Thr Tyr Leu Lys Gln Gln Asn Arg Trp Asn Lys Ser Phe Phe
    290                 295                 300

Arg Glu Ser Ile Ile Ser Val Lys Lys Ile Met Asn Asn Pro Phe Val
305                 310                 315                 320

Ala Leu Trp Thr Ile Leu Glu Val Ser Met Phe Met Leu Val Tyr
                325                 330                 335

Ser Val Val Asp Phe Val Gly Asn Val Arg Glu Phe Asp Trp Leu
            340                 345                 350

Arg Val Leu Ala Phe Leu Val Ile Phe Ile Val Ala Leu Cys Arg
        355                 360                 365

Asn Ile His Tyr Met Leu Lys His Pro Leu Ser Phe Leu Leu Ser Pro
370                 375                 380

Phe Tyr Gly Val Leu His Leu Phe Val Leu Gln Pro Leu Lys Leu Tyr
385                 390                 395                 400

Ser Leu Phe Thr Ile Arg Asn Ala Asp Trp Gly Thr Arg Lys Lys Leu
                405                 410                 415

Leu
```

<210> SEQ ID NO 17
<211> LENGTH: 417
<212> TYPE: PRT
<213> ORGANISM: Streptococcus equisimilis
<220> FEATURE:
<221> NAME/KEY: MISC_FEATURE
<222> LOCATION: (281)..(281)
<223> OTHER INFORMATION: Xaa = Ala, Ser or any other amino acid

<400> SEQUENCE: 17

```
Met Arg Thr Leu Lys Asn Leu Ile Thr Val Ala Phe Ser Ile Phe
1               5                   10                  15

Trp Val Leu Leu Ile Tyr Val Asn Val Tyr Leu Phe Gly Ala Lys Gly
                20                  25                  30

Ser Leu Ser Ile Tyr Gly Phe Leu Leu Ile Ala Tyr Leu Leu Val Lys
            35                  40                  45

Met Ser Leu Ser Phe Phe Tyr Lys Pro Phe Lys Gly Arg Ala Gly Gln
        50                  55                  60
```

```
Tyr Lys Val Ala Ala Ile Ile Pro Ser Tyr Asn Glu Asp Ala Glu Ser
 65                  70                  75                  80

Leu Leu Glu Thr Leu Lys Ser Val Gln Gln Gln Thr Tyr Pro Leu Ala
             85                  90                  95

Glu Ile Tyr Val Val Asp Asp Gly Ser Ala Asp Glu Thr Gly Ile Lys
         100                 105                 110

Arg Ile Glu Asp Tyr Val Arg Asp Thr Gly Asp Leu Ser Ser Asn Val
     115                 120                 125

Ile Val His Arg Ser Glu Lys Asn Gln Gly Lys Arg His Ala Gln Ala
 130                 135                 140

Trp Ala Phe Glu Arg Ser Asp Ala Asp Val Phe Leu Thr Val Asp Ser
145                 150                 155                 160

Asp Thr Tyr Ile Tyr Pro Asp Ala Leu Glu Leu Leu Lys Thr Phe
             165                 170                 175

Asn Asp Pro Thr Val Phe Ala Ala Thr Gly His Leu Asn Val Arg Asn
         180                 185                 190

Arg Gln Thr Asn Leu Leu Thr Arg Leu Thr Asp Ile Arg Tyr Asp Asn
     195                 200                 205

Ala Phe Gly Val Glu Arg Ala Ala Gln Ser Val Thr Gly Asn Ile Leu
210                 215                 220

Val Cys Ser Gly Pro Leu Ser Val Tyr Arg Arg Glu Val Val Val Pro
225                 230                 235                 240

Asn Ile Asp Arg Tyr Ile Asn Gln Thr Phe Leu Gly Ile Pro Val Ser
             245                 250                 255

Ile Gly Asp Asp Arg Cys Leu Thr Asn Tyr Ala Thr Asp Leu Gly Lys
         260                 265                 270

Thr Val Tyr Gln Ser Thr Ala Lys Xaa Ile Thr Asp Val Pro Asp Lys
     275                 280                 285

Met Ser Thr Tyr Leu Lys Gln Gln Asn Arg Trp Asn Lys Ser Phe Phe
290                 295                 300

Arg Glu Ser Ile Ile Ser Val Lys Lys Ile Met Asn Asn Pro Phe Val
305                 310                 315                 320

Ala Leu Trp Thr Ile Leu Glu Val Ser Met Phe Met Met Leu Val Tyr
             325                 330                 335

Ser Val Val Asp Phe Phe Val Gly Asn Val Arg Glu Phe Asp Trp Leu
         340                 345                 350

Arg Val Leu Ala Phe Leu Val Ile Ile Phe Ile Val Ala Leu Cys Arg
     355                 360                 365

Asn Ile His Tyr Met Leu Lys His Pro Leu Ser Phe Leu Leu Ser Pro
370                 375                 380

Phe Tyr Gly Val Leu His Leu Phe Val Leu Gln Pro Leu Lys Leu Tyr
385                 390                 395                 400

Ser Leu Phe Thr Ile Arg Asn Ala Asp Trp Gly Thr Arg Lys Lys Leu
             405                 410                 415

Leu

<210> SEQ ID NO 18
<211> LENGTH: 417
<212> TYPE: PRT
<213> ORGANISM: Streptococcus equisimilis
<220> FEATURE:
<221> NAME/KEY: MISC_FEATURE
<222> LOCATION: (367)..(367)
<223> OTHER INFORMATION: Xaa = Ala, Ser or any other amino acid
```

<400> SEQUENCE: 18

```
Met Arg Thr Leu Lys Asn Leu Ile Thr Val Val Ala Phe Ser Ile Phe
1               5                   10                  15

Trp Val Leu Leu Ile Tyr Val Asn Val Tyr Leu Phe Gly Ala Lys Gly
            20                  25                  30

Ser Leu Ser Ile Tyr Gly Phe Leu Leu Ile Ala Tyr Leu Leu Val Lys
        35                  40                  45

Met Ser Leu Ser Phe Phe Tyr Lys Pro Phe Lys Gly Arg Ala Gly Gln
    50                  55                  60

Tyr Lys Val Ala Ala Ile Ile Pro Ser Tyr Asn Glu Asp Ala Glu Ser
65                  70                  75                  80

Leu Leu Glu Thr Leu Lys Ser Val Gln Gln Gln Thr Tyr Pro Leu Ala
                85                  90                  95

Glu Ile Tyr Val Val Asp Asp Gly Ser Ala Asp Glu Thr Gly Ile Lys
            100                 105                 110

Arg Ile Glu Asp Tyr Val Arg Asp Thr Gly Asp Leu Ser Ser Asn Val
        115                 120                 125

Ile Val His Arg Ser Glu Lys Asn Gln Gly Lys Arg His Ala Gln Ala
    130                 135                 140

Trp Ala Phe Glu Arg Ser Asp Ala Asp Val Phe Leu Thr Val Asp Ser
145                 150                 155                 160

Asp Thr Tyr Ile Tyr Pro Asp Ala Leu Glu Glu Leu Leu Lys Thr Phe
                165                 170                 175

Asn Asp Pro Thr Val Phe Ala Ala Thr Gly His Leu Asn Val Arg Asn
            180                 185                 190

Arg Gln Thr Asn Leu Leu Thr Arg Leu Thr Asp Ile Arg Tyr Asp Asn
        195                 200                 205

Ala Phe Gly Val Glu Arg Ala Ala Gln Ser Val Thr Gly Asn Ile Leu
    210                 215                 220

Val Cys Ser Gly Pro Leu Ser Val Tyr Arg Arg Glu Val Val Val Pro
225                 230                 235                 240

Asn Ile Asp Arg Tyr Ile Asn Gln Thr Phe Leu Gly Ile Pro Val Ser
                245                 250                 255

Ile Gly Asp Asp Arg Cys Leu Thr Asn Tyr Ala Thr Asp Leu Gly Lys
            260                 265                 270

Thr Val Tyr Gln Ser Thr Ala Lys Cys Ile Thr Asp Val Pro Asp Lys
        275                 280                 285

Met Ser Thr Tyr Leu Lys Gln Gln Asn Arg Trp Asn Lys Ser Phe Phe
    290                 295                 300

Arg Glu Ser Ile Ile Ser Val Lys Lys Ile Met Asn Asn Pro Phe Val
305                 310                 315                 320

Ala Leu Trp Thr Ile Leu Glu Val Ser Met Phe Met Met Leu Val Tyr
                325                 330                 335

Ser Val Val Asp Phe Phe Val Gly Asn Val Arg Glu Phe Asp Trp Leu
            340                 345                 350

Arg Val Leu Ala Phe Leu Val Ile Ile Phe Ile Val Ala Leu Xaa Arg
        355                 360                 365

Asn Ile His Tyr Met Leu Lys His Pro Leu Ser Phe Leu Leu Ser Pro
    370                 375                 380

Phe Tyr Gly Val Leu His Leu Phe Val Leu Gln Pro Leu Lys Leu Tyr
385                 390                 395                 400

Ser Leu Phe Thr Ile Arg Asn Ala Asp Trp Gly Thr Arg Lys Lys Leu
                405                 410                 415
```

Leu

<210> SEQ ID NO 19
<211> LENGTH: 417
<212> TYPE: PRT
<213> ORGANISM: Streptococcus equisimilis
<220> FEATURE:
<221> NAME/KEY: MISC_FEATURE
<222> LOCATION: (226)..(226)
<223> OTHER INFORMATION: Xaa = Ala, Ser or any other amino acid
<220> FEATURE:
<221> NAME/KEY: MISC_FEATURE
<222> LOCATION: (262)..(262)
<223> OTHER INFORMATION: Xaa = Ala, Ser or any other amino acid

<400> SEQUENCE: 19

```
Met Arg Thr Leu Lys Asn Leu Ile Thr Val Ala Phe Ser Ile Phe
1               5                   10                  15

Trp Val Leu Leu Ile Tyr Val Asn Val Tyr Leu Phe Gly Ala Lys Gly
                20                  25                  30

Ser Leu Ser Ile Tyr Gly Phe Leu Leu Ile Ala Tyr Leu Leu Val Lys
            35                  40                  45

Met Ser Leu Ser Phe Phe Tyr Lys Pro Phe Lys Gly Arg Ala Gly Gln
    50                  55                  60

Tyr Lys Val Ala Ala Ile Ile Pro Ser Tyr Asn Glu Asp Ala Glu Ser
65                  70                  75                  80

Leu Leu Glu Thr Leu Lys Ser Val Gln Gln Gln Thr Tyr Pro Leu Ala
                85                  90                  95

Glu Ile Tyr Val Val Asp Asp Gly Ser Ala Asp Glu Thr Gly Ile Lys
            100                 105                 110

Arg Ile Glu Asp Tyr Val Arg Asp Thr Gly Asp Leu Ser Ser Asn Val
        115                 120                 125

Ile Val His Arg Ser Glu Lys Asn Gln Gly Lys Arg His Ala Gln Ala
    130                 135                 140

Trp Ala Phe Glu Arg Ser Asp Ala Asp Val Phe Leu Thr Val Asp Ser
145                 150                 155                 160

Asp Thr Tyr Ile Tyr Pro Asp Ala Leu Glu Glu Leu Leu Lys Thr Phe
                165                 170                 175

Asn Asp Pro Thr Val Phe Ala Ala Thr Gly His Leu Asn Val Arg Asn
            180                 185                 190

Arg Gln Thr Asn Leu Leu Thr Arg Leu Thr Asp Ile Arg Tyr Asp Asn
        195                 200                 205

Ala Phe Gly Val Glu Arg Ala Ala Gln Ser Val Thr Gly Asn Ile Leu
    210                 215                 220

Val Xaa Ser Gly Pro Leu Ser Val Tyr Arg Arg Glu Val Val Val Pro
225                 230                 235                 240

Asn Ile Asp Arg Tyr Ile Asn Gln Thr Phe Leu Gly Ile Pro Val Ser
                245                 250                 255

Ile Gly Asp Asp Arg Xaa Leu Thr Asn Tyr Ala Thr Asp Leu Gly Lys
            260                 265                 270

Thr Val Tyr Gln Ser Thr Ala Lys Cys Ile Thr Asp Val Pro Asp Lys
        275                 280                 285

Met Ser Thr Tyr Leu Lys Gln Gln Asn Arg Trp Asn Lys Ser Phe Phe
    290                 295                 300

Arg Glu Ser Ile Ile Ser Val Lys Lys Ile Met Asn Asn Pro Phe Val
305                 310                 315                 320
```

```
Ala Leu Trp Thr Ile Leu Glu Val Ser Met Phe Met Met Leu Val Tyr
                325                 330                 335

Ser Val Val Asp Phe Phe Val Gly Asn Val Arg Glu Phe Asp Trp Leu
                340                 345                 350

Arg Val Leu Ala Phe Leu Val Ile Ile Phe Ile Val Ala Leu Cys Arg
                355                 360                 365

Asn Ile His Tyr Met Leu Lys His Pro Leu Ser Phe Leu Leu Ser Pro
                370                 375                 380

Phe Tyr Gly Val Leu His Leu Phe Val Leu Gln Pro Leu Lys Leu Tyr
385                 390                 395                 400

Ser Leu Phe Thr Ile Arg Asn Ala Asp Trp Gly Thr Arg Lys Lys Leu
                405                 410                 415

Leu

<210> SEQ ID NO 20
<211> LENGTH: 417
<212> TYPE: PRT
<213> ORGANISM: Streptococcus equisimilis
<220> FEATURE:
<221> NAME/KEY: MISC_FEATURE
<222> LOCATION: (226)..(226)
<223> OTHER INFORMATION: Xaa = Ala, Ser or any other amino acid
<220> FEATURE:
<221> NAME/KEY: MISC_FEATURE
<222> LOCATION: (281)..(281)
<223> OTHER INFORMATION: Xaa = Ala, Ser or any other amino acid

<400> SEQUENCE: 20

Met Arg Thr Leu Lys Asn Leu Ile Thr Val Ala Phe Ser Ile Phe
1               5                   10                  15

Trp Val Leu Leu Ile Tyr Val Asn Val Tyr Leu Phe Gly Ala Lys Gly
                20                  25                  30

Ser Leu Ser Ile Tyr Gly Phe Leu Leu Ile Ala Tyr Leu Leu Val Lys
                35                  40                  45

Met Ser Leu Ser Phe Phe Tyr Lys Pro Phe Lys Gly Arg Ala Gly Gln
50                  55                  60

Tyr Lys Val Ala Ala Ile Ile Pro Ser Tyr Asn Glu Asp Ala Glu Ser
65                  70                  75                  80

Leu Leu Glu Thr Leu Lys Ser Val Gln Gln Gln Thr Tyr Pro Leu Ala
                85                  90                  95

Glu Ile Tyr Val Val Asp Asp Gly Ser Ala Asp Glu Thr Gly Ile Lys
                100                 105                 110

Arg Ile Glu Asp Tyr Val Arg Asp Thr Gly Asp Leu Ser Ser Asn Val
                115                 120                 125

Ile Val His Arg Ser Glu Lys Asn Gln Gly Lys Arg His Ala Gln Ala
            130                 135                 140

Trp Ala Phe Glu Arg Ser Asp Ala Asp Val Phe Leu Thr Val Asp Ser
145                 150                 155                 160

Asp Thr Tyr Ile Tyr Pro Asp Ala Leu Glu Glu Leu Leu Lys Thr Phe
                165                 170                 175

Asn Asp Pro Thr Val Phe Ala Ala Thr Gly His Leu Asn Val Arg Asn
                180                 185                 190

Arg Gln Thr Asn Leu Leu Thr Arg Leu Thr Asp Ile Arg Tyr Asp Asn
            195                 200                 205

Ala Phe Gly Val Glu Arg Ala Ala Gln Ser Val Thr Gly Asn Ile Leu
        210                 215                 220

Val Xaa Ser Gly Pro Leu Ser Val Tyr Arg Arg Glu Val Val Val Pro
```

-continued

```
                225                 230                 235                 240
    Asn Ile Asp Arg Tyr Ile Asn Gln Thr Phe Leu Gly Ile Pro Val Ser
                        245                 250                 255

Ile Gly Asp Asp Arg Cys Leu Thr Asn Tyr Ala Thr Asp Leu Gly Lys
                260                 265                 270

Thr Val Tyr Gln Ser Thr Ala Lys Xaa Ile Thr Asp Val Pro Asp Lys
                    275                 280                 285

Met Ser Thr Tyr Leu Lys Gln Gln Asn Arg Trp Asn Lys Ser Phe Phe
                290                 295                 300

Arg Glu Ser Ile Ile Ser Val Lys Lys Ile Met Asn Asn Pro Phe Val
    305                 310                 315                 320

Ala Leu Trp Thr Ile Leu Glu Val Ser Met Phe Met Met Leu Val Tyr
                        325                 330                 335

Ser Val Val Asp Phe Phe Val Gly Asn Val Arg Glu Phe Asp Trp Leu
                    340                 345                 350

Arg Val Leu Ala Phe Leu Val Ile Ile Phe Ile Val Ala Leu Cys Arg
                355                 360                 365

Asn Ile His Tyr Met Leu Lys His Pro Leu Ser Phe Leu Leu Ser Pro
                370                 375                 380

Phe Tyr Gly Val Leu His Leu Phe Val Leu Gln Pro Leu Lys Leu Tyr
    385                 390                 395                 400

Ser Leu Phe Thr Ile Arg Asn Ala Asp Trp Gly Thr Arg Lys Lys Leu
                        405                 410                 415

Leu

<210> SEQ ID NO 21
    <211> LENGTH: 417
    <212> TYPE: PRT
    <213> ORGANISM: Streptococcus equisimilis
    <220> FEATURE:
    <221> NAME/KEY: MISC_FEATURE
    <222> LOCATION: (226)..(226)
    <223> OTHER INFORMATION: Xaa = Ala, Ser or any other amino acid
    <220> FEATURE:
    <221> NAME/KEY: MISC_FEATURE
    <222> LOCATION: (367)..(367)
    <223> OTHER INFORMATION: Xaa = Ala, Ser or any other amino acid

<400> SEQUENCE: 21

Met Arg Thr Leu Lys Asn Leu Ile Thr Val Val Ala Phe Ser Ile Phe
    1               5                   10                  15

Trp Val Leu Leu Ile Tyr Val Asn Val Tyr Leu Phe Gly Ala Lys Gly
                    20                  25                  30

Ser Leu Ser Ile Tyr Gly Phe Leu Leu Ile Ala Tyr Leu Leu Val Lys
                35                  40                  45

Met Ser Leu Ser Phe Phe Tyr Lys Pro Phe Lys Gly Arg Ala Gly Gln
        50                  55                  60

Tyr Lys Val Ala Ala Ile Ile Pro Ser Tyr Asn Glu Asp Ala Glu Ser
    65                  70                  75                  80

Leu Leu Glu Thr Leu Lys Ser Val Gln Gln Gln Thr Tyr Pro Leu Ala
                        85                  90                  95

Glu Ile Tyr Val Val Asp Asp Gly Ser Ala Asp Glu Thr Gly Ile Lys
                    100                 105                 110

Arg Ile Glu Asp Tyr Val Arg Asp Thr Gly Asp Leu Ser Ser Asn Val
                115                 120                 125

Ile Val His Arg Ser Glu Lys Asn Gln Gly Lys Arg His Ala Gln Ala
        130                 135                 140
```

```
Trp Ala Phe Glu Arg Ser Asp Ala Asp Val Phe Leu Thr Val Asp Ser
145                 150                 155                 160

Asp Thr Tyr Ile Tyr Pro Asp Ala Leu Glu Glu Leu Lys Thr Phe
                165                 170                 175

Asn Asp Pro Thr Val Phe Ala Ala Thr Gly His Leu Asn Val Arg Asn
            180                 185                 190

Arg Gln Thr Asn Leu Leu Thr Arg Leu Thr Asp Ile Arg Tyr Asp Asn
        195                 200                 205

Ala Phe Gly Val Glu Arg Ala Ala Gln Ser Val Thr Gly Asn Ile Leu
    210                 215                 220

Val Xaa Ser Gly Pro Leu Ser Val Tyr Arg Arg Glu Val Val Pro
225                 230                 235                 240

Asn Ile Asp Arg Tyr Ile Asn Gln Thr Phe Leu Gly Ile Pro Val Ser
                245                 250                 255

Ile Gly Asp Asp Arg Cys Leu Thr Asn Tyr Ala Thr Asp Leu Gly Lys
            260                 265                 270

Thr Val Tyr Gln Ser Thr Ala Lys Cys Ile Thr Asp Val Pro Asp Lys
        275                 280                 285

Met Ser Thr Tyr Leu Lys Gln Gln Asn Arg Trp Asn Lys Ser Phe Phe
    290                 295                 300

Arg Glu Ser Ile Ile Ser Val Lys Lys Ile Met Asn Asn Pro Phe Val
305                 310                 315                 320

Ala Leu Trp Thr Ile Leu Glu Val Ser Met Phe Met Met Leu Val Tyr
                325                 330                 335

Ser Val Val Asp Phe Phe Val Gly Asn Val Arg Glu Phe Asp Trp Leu
            340                 345                 350

Arg Val Leu Ala Phe Leu Val Ile Ile Phe Ile Val Ala Leu Xaa Arg
        355                 360                 365

Asn Ile His Tyr Met Leu Lys His Pro Leu Ser Phe Leu Leu Ser Pro
    370                 375                 380

Phe Tyr Gly Val Leu His Leu Phe Val Leu Gln Pro Leu Lys Leu Tyr
385                 390                 395                 400

Ser Leu Phe Thr Ile Arg Asn Ala Asp Trp Gly Thr Arg Lys Lys Leu
                405                 410                 415

Leu
```

<210> SEQ ID NO 22
<211> LENGTH: 417
<212> TYPE: PRT
<213> ORGANISM: Streptococcus equisimilis
<220> FEATURE:
<221> NAME/KEY: MISC_FEATURE
<222> LOCATION: (262)..(262)
<223> OTHER INFORMATION: Xaa = Ala, Ser or any other amino acid
<220> FEATURE:
<221> NAME/KEY: MISC_FEATURE
<222> LOCATION: (281)..(281)
<223> OTHER INFORMATION: Xaa = Ala, Ser or any other amino acid

<400> SEQUENCE: 22

```
Met Arg Thr Leu Lys Asn Leu Ile Thr Val Val Ala Phe Ser Ile Phe
1               5                   10                  15

Trp Val Leu Leu Ile Tyr Val Asn Val Tyr Leu Phe Gly Ala Lys Gly
            20                  25                  30

Ser Leu Ser Ile Tyr Gly Phe Leu Leu Ile Ala Tyr Leu Leu Val Lys
        35                  40                  45
```

```
Met Ser Leu Ser Phe Phe Tyr Lys Pro Phe Lys Gly Arg Ala Gly Gln
 50                  55                  60

Tyr Lys Val Ala Ala Ile Ile Pro Ser Tyr Asn Glu Asp Ala Glu Ser
 65                  70                  75                  80

Leu Leu Glu Thr Leu Lys Ser Val Gln Gln Thr Tyr Pro Leu Ala
                 85                  90                  95

Glu Ile Tyr Val Val Asp Asp Gly Ser Ala Asp Glu Thr Gly Ile Lys
                100                 105                 110

Arg Ile Glu Asp Tyr Val Arg Asp Thr Gly Asp Leu Ser Ser Asn Val
            115                 120                 125

Ile Val His Arg Ser Glu Lys Asn Gln Gly Lys Arg His Ala Gln Ala
    130                 135                 140

Trp Ala Phe Glu Arg Ser Asp Ala Asp Val Phe Leu Thr Val Asp Ser
145                 150                 155                 160

Asp Thr Tyr Ile Tyr Pro Asp Ala Leu Glu Glu Leu Leu Lys Thr Phe
                165                 170                 175

Asn Asp Pro Thr Val Phe Ala Ala Thr Gly His Leu Asn Val Arg Asn
            180                 185                 190

Arg Gln Thr Asn Leu Leu Thr Arg Leu Thr Asp Ile Arg Tyr Asp Asn
        195                 200                 205

Ala Phe Gly Val Glu Arg Ala Ala Gln Ser Val Thr Gly Asn Ile Leu
210                 215                 220

Val Cys Ser Gly Pro Leu Ser Val Tyr Arg Arg Glu Val Val Val Pro
225                 230                 235                 240

Asn Ile Asp Arg Tyr Ile Asn Gln Thr Phe Leu Gly Ile Pro Val Ser
                245                 250                 255

Ile Gly Asp Asp Arg Xaa Leu Thr Asn Tyr Ala Thr Asp Leu Gly Lys
            260                 265                 270

Thr Val Tyr Gln Ser Thr Ala Lys Xaa Ile Thr Asp Val Pro Asp Lys
        275                 280                 285

Met Ser Thr Tyr Leu Lys Gln Gln Asn Arg Trp Asn Lys Ser Phe Phe
290                 295                 300

Arg Glu Ser Ile Ile Ser Val Lys Lys Ile Met Asn Asn Pro Phe Val
305                 310                 315                 320

Ala Leu Trp Thr Ile Leu Glu Val Ser Met Phe Met Met Leu Val Tyr
                325                 330                 335

Ser Val Val Asp Phe Phe Val Gly Asn Val Arg Glu Phe Asp Trp Leu
            340                 345                 350

Arg Val Leu Ala Phe Leu Val Ile Ile Phe Ile Val Ala Leu Cys Arg
        355                 360                 365

Asn Ile His Tyr Met Leu Lys His Pro Leu Ser Phe Leu Leu Ser Pro
370                 375                 380

Phe Tyr Gly Val Leu His Leu Phe Val Leu Gln Pro Leu Lys Leu Tyr
385                 390                 395                 400

Ser Leu Phe Thr Ile Arg Asn Ala Asp Trp Gly Thr Arg Lys Lys Leu
                405                 410                 415

Leu

<210> SEQ ID NO 23
<211> LENGTH: 417
<212> TYPE: PRT
<213> ORGANISM: Streptococcus equisimilis
<220> FEATURE:
<221> NAME/KEY: MISC_FEATURE
<222> LOCATION: (262)..(262)
```

-continued

<223> OTHER INFORMATION: Xaa = Ala, Ser or any other amino acid
<220> FEATURE:
<221> NAME/KEY: MISC_FEATURE
<222> LOCATION: (367)..(367)
<223> OTHER INFORMATION: Xaa = Ala, Ser or any other amino acid

<400> SEQUENCE: 23

```
Met Arg Thr Leu Lys Asn Leu Ile Thr Val Ala Phe Ser Ile Phe
1               5                   10                  15

Trp Val Leu Leu Ile Tyr Val Asn Val Tyr Leu Phe Gly Ala Lys Gly
            20                  25                  30

Ser Leu Ser Ile Tyr Gly Phe Leu Leu Ile Ala Tyr Leu Leu Val Lys
        35                  40                  45

Met Ser Leu Ser Phe Phe Tyr Lys Pro Phe Lys Gly Arg Ala Gly Gln
50                  55                  60

Tyr Lys Val Ala Ala Ile Ile Pro Ser Tyr Asn Glu Asp Ala Glu Ser
65                  70                  75                  80

Leu Leu Glu Thr Leu Lys Ser Val Gln Gln Gln Thr Tyr Pro Leu Ala
            85                  90                  95

Glu Ile Tyr Val Val Asp Asp Gly Ser Ala Asp Glu Thr Gly Ile Lys
            100                 105                 110

Arg Ile Glu Asp Tyr Val Arg Asp Thr Gly Asp Leu Ser Ser Asn Val
            115                 120                 125

Ile Val His Arg Ser Glu Lys Asn Gln Gly Lys Arg His Ala Gln Ala
130                 135                 140

Trp Ala Phe Glu Arg Ser Asp Ala Asp Val Phe Leu Thr Val Asp Ser
145                 150                 155                 160

Asp Thr Tyr Ile Tyr Pro Asp Ala Leu Glu Glu Leu Leu Lys Thr Phe
            165                 170                 175

Asn Asp Pro Thr Val Phe Ala Ala Thr Gly His Leu Asn Val Arg Asn
            180                 185                 190

Arg Gln Thr Asn Leu Leu Thr Arg Leu Thr Asp Ile Arg Tyr Asp Asn
            195                 200                 205

Ala Phe Gly Val Glu Arg Ala Ala Gln Ser Val Thr Gly Asn Ile Leu
210                 215                 220

Val Cys Ser Gly Pro Leu Ser Val Tyr Arg Arg Glu Val Val Pro
225                 230                 235                 240

Asn Ile Asp Arg Tyr Ile Asn Gln Thr Phe Leu Gly Ile Pro Val Ser
            245                 250                 255

Ile Gly Asp Asp Arg Xaa Leu Thr Asn Tyr Ala Thr Asp Leu Gly Lys
            260                 265                 270

Thr Val Tyr Gln Ser Thr Ala Lys Cys Ile Thr Asp Val Pro Asp Lys
            275                 280                 285

Met Ser Thr Tyr Leu Lys Gln Gln Asn Arg Trp Asn Lys Ser Phe Phe
290                 295                 300

Arg Glu Ser Ile Ile Ser Val Lys Lys Ile Met Asn Asn Pro Phe Val
305                 310                 315                 320

Ala Leu Trp Thr Ile Leu Glu Val Ser Met Phe Met Met Leu Val Tyr
            325                 330                 335

Ser Val Val Asp Phe Phe Val Gly Asn Val Arg Glu Phe Asp Trp Leu
            340                 345                 350

Arg Val Leu Ala Phe Leu Val Ile Phe Ile Val Ala Leu Xaa Arg
            355                 360                 365

Asn Ile His Tyr Met Leu Lys His Pro Leu Ser Phe Leu Leu Ser Pro
            370                 375                 380
```

-continued

Phe Tyr Gly Val Leu His Leu Phe Val Leu Gln Pro Leu Lys Leu Tyr
385                 390                 395                 400

Ser Leu Phe Thr Ile Arg Asn Ala Asp Trp Gly Thr Arg Lys Lys Leu
            405                 410                 415

Leu

<210> SEQ ID NO 24
<211> LENGTH: 417
<212> TYPE: PRT
<213> ORGANISM: Streptococcus equisimilis
<220> FEATURE:
<221> NAME/KEY: MISC_FEATURE
<222> LOCATION: (281)..(281)
<223> OTHER INFORMATION: Xaa = Ala, Ser or any other amino acid
<220> FEATURE:
<221> NAME/KEY: MISC_FEATURE
<222> LOCATION: (367)..(367)
<223> OTHER INFORMATION: Xaa = Ala, Ser or any other amino acid

<400> SEQUENCE: 24

Met Arg Thr Leu Lys Asn Leu Ile Thr Val Val Ala Phe Ser Ile Phe
1               5                   10                  15

Trp Val Leu Leu Ile Tyr Val Asn Val Tyr Leu Phe Gly Ala Lys Gly
            20                  25                  30

Ser Leu Ser Ile Tyr Gly Phe Leu Leu Ile Ala Tyr Leu Leu Val Lys
        35                  40                  45

Met Ser Leu Ser Phe Phe Tyr Lys Pro Phe Lys Gly Arg Ala Gly Gln
    50                  55                  60

Tyr Lys Val Ala Ala Ile Ile Pro Ser Tyr Asn Glu Asp Ala Glu Ser
65                  70                  75                  80

Leu Leu Glu Thr Leu Lys Ser Val Gln Gln Gln Thr Tyr Pro Leu Ala
                85                  90                  95

Glu Ile Tyr Val Val Asp Asp Gly Ser Ala Asp Glu Thr Gly Ile Lys
            100                 105                 110

Arg Ile Glu Asp Tyr Val Arg Asp Thr Gly Asp Leu Ser Ser Asn Val
        115                 120                 125

Ile Val His Arg Ser Glu Lys Asn Gln Gly Lys Arg His Ala Gln Ala
    130                 135                 140

Trp Ala Phe Glu Arg Ser Asp Ala Asp Val Phe Leu Thr Val Asp Ser
145                 150                 155                 160

Asp Thr Tyr Ile Tyr Pro Asp Ala Leu Glu Glu Leu Leu Lys Thr Phe
                165                 170                 175

Asn Asp Pro Thr Val Phe Ala Ala Thr Gly His Leu Asn Val Arg Asn
            180                 185                 190

Arg Gln Thr Asn Leu Leu Thr Arg Leu Thr Asp Ile Arg Tyr Asp Asn
        195                 200                 205

Ala Phe Gly Val Glu Arg Ala Ala Gln Ser Val Thr Gly Asn Ile Leu
    210                 215                 220

Val Cys Ser Gly Pro Leu Ser Val Tyr Arg Arg Glu Val Val Val Pro
225                 230                 235                 240

Asn Ile Asp Arg Tyr Ile Asn Gln Thr Phe Leu Gly Ile Pro Val Ser
                245                 250                 255

Ile Gly Asp Asp Arg Cys Leu Thr Asn Tyr Ala Thr Asp Leu Gly Lys
            260                 265                 270

Thr Val Tyr Gln Ser Thr Ala Lys Xaa Ile Thr Asp Val Pro Asp Lys
        275                 280                 285

```
Met Ser Thr Tyr Leu Lys Gln Gln Asn Arg Trp Asn Lys Ser Phe Phe
    290                 295                 300

Arg Glu Ser Ile Ile Ser Val Lys Lys Ile Met Asn Asn Pro Phe Val
305                 310                 315                 320

Ala Leu Trp Thr Ile Leu Glu Val Ser Met Phe Met Met Leu Val Tyr
                325                 330                 335

Ser Val Val Asp Phe Phe Val Gly Asn Val Arg Glu Phe Asp Trp Leu
            340                 345                 350

Arg Val Leu Ala Phe Leu Val Ile Phe Ile Val Ala Leu Xaa Arg
        355                 360                 365

Asn Ile His Tyr Met Leu Lys His Pro Leu Ser Phe Leu Leu Ser Pro
    370                 375                 380

Phe Tyr Gly Val Leu His Leu Phe Val Leu Gln Pro Leu Lys Leu Tyr
385                 390                 395                 400

Ser Leu Phe Thr Ile Arg Asn Ala Asp Trp Gly Thr Arg Lys Lys Leu
                405                 410                 415

Leu

<210> SEQ ID NO 25
<211> LENGTH: 417
<212> TYPE: PRT
<213> ORGANISM: Streptococcus equisimilis
<220> FEATURE:
<221> NAME/KEY: MISC_FEATURE
<222> LOCATION: (262)..(262)
<223> OTHER INFORMATION: Xaa = Ala, Ser or any other amino acid
<220> FEATURE:
<221> NAME/KEY: MISC_FEATURE
<222> LOCATION: (281)..(281)
<223> OTHER INFORMATION: Xaa = Ala, Ser or any other amino acid
<220> FEATURE:
<221> NAME/KEY: MISC_FEATURE
<222> LOCATION: (367)..(367)
<223> OTHER INFORMATION: Xaa = Ala, Ser or any other amino acid

<400> SEQUENCE: 25

Met Arg Thr Leu Lys Asn Leu Ile Thr Val Val Ala Phe Ser Ile Phe
1               5                   10                  15

Trp Val Leu Leu Ile Tyr Val Asn Val Tyr Leu Phe Gly Ala Lys Gly
            20                  25                  30

Ser Leu Ser Ile Tyr Gly Phe Leu Leu Ile Ala Tyr Leu Leu Val Lys
        35                  40                  45

Met Ser Leu Ser Phe Phe Tyr Lys Pro Phe Lys Gly Arg Ala Gly Gln
    50                  55                  60

Tyr Lys Val Ala Ala Ile Ile Pro Ser Tyr Asn Glu Asp Ala Glu Ser
65                  70                  75                  80

Leu Leu Glu Thr Leu Lys Ser Val Gln Gln Thr Tyr Pro Leu Ala
            85                  90                  95

Glu Ile Tyr Val Val Asp Asp Gly Ser Ala Asp Glu Thr Gly Ile Lys
            100                 105                 110

Arg Ile Glu Asp Tyr Val Arg Asp Thr Gly Asp Leu Ser Ser Asn Val
        115                 120                 125

Ile Val His Arg Ser Glu Lys Asn Gln Gly Lys Arg His Ala Gln Ala
    130                 135                 140

Trp Ala Phe Glu Arg Ser Asp Ala Asp Val Phe Leu Thr Val Asp Ser
145                 150                 155                 160

Asp Thr Tyr Ile Tyr Pro Asp Ala Leu Glu Glu Leu Leu Lys Thr Phe
                165                 170                 175
```

```
Asn Asp Pro Thr Val Phe Ala Ala Thr Gly His Leu Asn Val Arg Asn
            180                 185                 190

Arg Gln Thr Asn Leu Leu Thr Arg Leu Thr Asp Ile Arg Tyr Asp Asn
        195                 200                 205

Ala Phe Gly Val Glu Arg Ala Ala Gln Ser Val Thr Gly Asn Ile Leu
    210                 215                 220

Val Cys Ser Gly Pro Leu Ser Val Tyr Arg Arg Glu Val Val Val Pro
225                 230                 235                 240

Asn Ile Asp Arg Tyr Ile Asn Gln Thr Phe Leu Gly Ile Pro Val Ser
            245                 250                 255

Ile Gly Asp Asp Arg Xaa Leu Thr Asn Tyr Ala Thr Asp Leu Gly Lys
            260                 265                 270

Thr Val Tyr Gln Ser Thr Ala Lys Xaa Ile Thr Asp Val Pro Asp Lys
        275                 280                 285

Met Ser Thr Tyr Leu Lys Gln Gln Asn Arg Trp Asn Lys Ser Phe Phe
290                 295                 300

Arg Glu Ser Ile Ile Ser Val Lys Lys Ile Met Asn Asn Pro Phe Val
305                 310                 315                 320

Ala Leu Trp Thr Ile Leu Glu Val Ser Met Phe Met Met Leu Val Tyr
            325                 330                 335

Ser Val Val Asp Phe Phe Val Gly Asn Val Arg Glu Phe Asp Trp Leu
            340                 345                 350

Arg Val Leu Ala Phe Leu Val Ile Ile Phe Ile Val Ala Leu Xaa Arg
        355                 360                 365

Asn Ile His Tyr Met Leu Lys His Pro Leu Ser Phe Leu Leu Ser Pro
    370                 375                 380

Phe Tyr Gly Val Leu His Leu Phe Val Leu Gln Pro Leu Lys Leu Tyr
385                 390                 395                 400

Ser Leu Phe Thr Ile Arg Asn Ala Asp Trp Gly Thr Arg Lys Lys Leu
            405                 410                 415

Leu

<210> SEQ ID NO 26
<211> LENGTH: 417
<212> TYPE: PRT
<213> ORGANISM: Streptococcus equisimilis
<220> FEATURE:
<221> NAME/KEY: MISC_FEATURE
<222> LOCATION: (226)..(226)
<223> OTHER INFORMATION: Xaa = Ala, Ser or any other amino acid
<220> FEATURE:
<221> NAME/KEY: MISC_FEATURE
<222> LOCATION: (281)..(281)
<223> OTHER INFORMATION: Xaa = Ala, Ser or any other amino acid
<220> FEATURE:
<221> NAME/KEY: MISC_FEATURE
<222> LOCATION: (367)..(367)
<223> OTHER INFORMATION: Xaa = Ala, Ser or any other amino acid

<400> SEQUENCE: 26

Met Arg Thr Leu Lys Asn Leu Ile Thr Val Val Ala Phe Ser Ile Phe
1               5                   10                  15

Trp Val Leu Leu Ile Tyr Val Asn Val Tyr Leu Phe Gly Ala Lys Gly
            20                  25                  30

Ser Leu Ser Ile Tyr Gly Phe Leu Leu Ile Ala Tyr Leu Leu Val Lys
        35                  40                  45

Met Ser Leu Ser Phe Phe Tyr Lys Pro Phe Lys Gly Arg Ala Gly Gln
    50                  55                  60
```

```
Tyr Lys Val Ala Ala Ile Ile Pro Ser Tyr Asn Glu Asp Ala Glu Ser
 65                  70                  75                  80

Leu Leu Glu Thr Leu Lys Ser Val Gln Gln Thr Tyr Pro Leu Ala
             85                  90                  95

Glu Ile Tyr Val Val Asp Asp Gly Ser Ala Asp Glu Thr Gly Ile Lys
            100                 105                 110

Arg Ile Glu Asp Tyr Val Arg Asp Thr Gly Asp Leu Ser Ser Asn Val
        115                 120                 125

Ile Val His Arg Ser Glu Lys Asn Gln Gly Lys Arg His Ala Gln Ala
    130                 135                 140

Trp Ala Phe Glu Arg Ser Asp Ala Asp Val Phe Leu Thr Val Asp Ser
145                 150                 155                 160

Asp Thr Tyr Ile Tyr Pro Asp Ala Leu Glu Glu Leu Leu Lys Thr Phe
                165                 170                 175

Asn Asp Pro Thr Val Phe Ala Ala Thr Gly His Leu Asn Val Arg Asn
            180                 185                 190

Arg Gln Thr Asn Leu Leu Thr Arg Leu Thr Asp Ile Arg Tyr Asp Asn
        195                 200                 205

Ala Phe Gly Val Glu Arg Ala Ala Gln Ser Val Thr Gly Asn Ile Leu
    210                 215                 220

Val Xaa Ser Gly Pro Leu Ser Val Tyr Arg Arg Glu Val Val Pro
225                 230                 235                 240

Asn Ile Asp Arg Tyr Ile Asn Gln Thr Phe Leu Gly Ile Pro Val Ser
                245                 250                 255

Ile Gly Asp Asp Arg Cys Leu Thr Asn Tyr Ala Thr Asp Leu Gly Lys
            260                 265                 270

Thr Val Tyr Gln Ser Thr Ala Lys Xaa Ile Thr Asp Val Pro Asp Lys
        275                 280                 285

Met Ser Thr Tyr Leu Lys Gln Gln Asn Arg Trp Asn Lys Ser Phe Phe
    290                 295                 300

Arg Glu Ser Ile Ile Ser Val Lys Lys Ile Met Asn Asn Pro Phe Val
305                 310                 315                 320

Ala Leu Trp Thr Ile Leu Glu Val Ser Met Phe Met Met Leu Val Tyr
                325                 330                 335

Ser Val Val Asp Phe Phe Val Gly Asn Val Arg Glu Phe Asp Trp Leu
            340                 345                 350

Arg Val Leu Ala Phe Leu Val Ile Ile Phe Ile Val Ala Leu Xaa Arg
        355                 360                 365

Asn Ile His Tyr Met Leu Lys His Pro Leu Ser Phe Leu Leu Ser Pro
    370                 375                 380

Phe Tyr Gly Val Leu His Leu Phe Val Leu Gln Pro Leu Lys Leu Tyr
385                 390                 395                 400

Ser Leu Phe Thr Ile Arg Asn Ala Asp Trp Gly Thr Arg Lys Lys Leu
                405                 410                 415

Leu
```

<210> SEQ ID NO 27
<211> LENGTH: 417
<212> TYPE: PRT
<213> ORGANISM: Streptococcus equisimilis
<220> FEATURE:
<221> NAME/KEY: MISC_FEATURE
<222> LOCATION: (226)..(226)
<223> OTHER INFORMATION: Xaa = Ala, Ser or any other amino acid
<220> FEATURE:
<221> NAME/KEY: MISC_FEATURE -continued

```
<222> LOCATION: (262)..(262)
<223> OTHER INFORMATION: Xaa = Ala, Ser or any other amino acid
<220> FEATURE:
<221> NAME/KEY: MISC_FEATURE
<222> LOCATION: (367)..(367)
<223> OTHER INFORMATION: Xaa = Ala, Ser or any other amino acid

<400> SEQUENCE: 27
```

| | | | | | | | | | | | | | | | |
|---|---|---|---|---|---|---|---|---|---|---|---|---|---|---|---|
| Met | Arg | Thr | Leu | Lys | Asn | Leu | Ile | Thr | Val | Val | Ala | Phe | Ser | Ile | Phe |
| 1 | | | | 5 | | | | | 10 | | | | | 15 | |
| Trp | Val | Leu | Leu | Ile | Tyr | Val | Asn | Val | Tyr | Leu | Phe | Gly | Ala | Lys | Gly |
| | | | 20 | | | | | 25 | | | | | 30 | | |
| Ser | Leu | Ser | Ile | Tyr | Gly | Phe | Leu | Leu | Ile | Ala | Tyr | Leu | Leu | Val | Lys |
| | | 35 | | | | | 40 | | | | | 45 | | | |
| Met | Ser | Leu | Ser | Phe | Phe | Tyr | Lys | Pro | Phe | Lys | Gly | Arg | Ala | Gly | Gln |
| | 50 | | | | | 55 | | | | | 60 | | | | |
| Tyr | Lys | Val | Ala | Ala | Ile | Ile | Pro | Ser | Tyr | Asn | Glu | Asp | Ala | Glu | Ser |
| 65 | | | | | 70 | | | | | 75 | | | | | 80 |
| Leu | Leu | Glu | Thr | Leu | Lys | Ser | Val | Gln | Gln | Gln | Thr | Tyr | Pro | Leu | Ala |
| | | | | 85 | | | | | 90 | | | | | 95 | |
| Glu | Ile | Tyr | Val | Val | Asp | Asp | Gly | Ser | Ala | Asp | Glu | Thr | Gly | Ile | Lys |
| | | | 100 | | | | | 105 | | | | | 110 | | |
| Arg | Ile | Glu | Asp | Tyr | Val | Arg | Asp | Thr | Gly | Asp | Leu | Ser | Ser | Asn | Val |
| | | 115 | | | | | 120 | | | | | 125 | | | |
| Ile | Val | His | Arg | Ser | Glu | Lys | Asn | Gln | Gly | Lys | Arg | His | Ala | Gln | Ala |
| | 130 | | | | | 135 | | | | | 140 | | | | |
| Trp | Ala | Phe | Glu | Arg | Ser | Asp | Ala | Asp | Val | Phe | Leu | Thr | Val | Asp | Ser |
| 145 | | | | | 150 | | | | | 155 | | | | | 160 |
| Asp | Thr | Tyr | Ile | Tyr | Pro | Asp | Ala | Leu | Glu | Glu | Leu | Leu | Lys | Thr | Phe |
| | | | | 165 | | | | | 170 | | | | | 175 | |
| Asn | Asp | Pro | Thr | Val | Phe | Ala | Ala | Thr | Gly | His | Leu | Asn | Val | Arg | Asn |
| | | | 180 | | | | | 185 | | | | | 190 | | |
| Arg | Gln | Thr | Asn | Leu | Leu | Thr | Arg | Leu | Thr | Asp | Ile | Arg | Tyr | Asp | Asn |
| | | 195 | | | | | 200 | | | | | 205 | | | |
| Ala | Phe | Gly | Val | Glu | Arg | Ala | Ala | Gln | Ser | Val | Thr | Gly | Asn | Ile | Leu |
| | 210 | | | | | 215 | | | | | 220 | | | | |
| Val | Xaa | Ser | Gly | Pro | Leu | Ser | Val | Tyr | Arg | Arg | Glu | Val | Val | Pro |
| 225 | | | | | 230 | | | | | 235 | | | | | 240 |
| Asn | Ile | Asp | Arg | Tyr | Ile | Asn | Gln | Thr | Phe | Leu | Gly | Ile | Pro | Val | Ser |
| | | | | 245 | | | | | 250 | | | | | 255 | |
| Ile | Gly | Asp | Asp | Arg | Xaa | Leu | Thr | Asn | Tyr | Ala | Thr | Asp | Leu | Gly | Lys |
| | | | 260 | | | | | 265 | | | | | 270 | | |
| Thr | Val | Tyr | Gln | Ser | Thr | Ala | Lys | Cys | Ile | Thr | Asp | Val | Pro | Asp | Lys |
| | | 275 | | | | | 280 | | | | | 285 | | | |
| Met | Ser | Thr | Tyr | Leu | Lys | Gln | Gln | Asn | Arg | Trp | Asn | Lys | Ser | Phe | Phe |
| | 290 | | | | | 295 | | | | | 300 | | | | |
| Arg | Glu | Ser | Ile | Ile | Ser | Val | Lys | Lys | Ile | Met | Asn | Asn | Pro | Phe | Val |
| 305 | | | | | 310 | | | | | 315 | | | | | 320 |
| Ala | Leu | Trp | Thr | Ile | Leu | Glu | Val | Ser | Met | Phe | Met | Met | Leu | Val | Tyr |
| | | | | 325 | | | | | 330 | | | | | 335 | |
| Ser | Val | Val | Asp | Phe | Phe | Val | Gly | Asn | Val | Arg | Glu | Phe | Asp | Trp | Leu |
| | | | 340 | | | | | 345 | | | | | 350 | | |
| Arg | Val | Leu | Ala | Phe | Leu | Val | Ile | Ile | Phe | Ile | Val | Ala | Leu | Xaa | Arg |
| | | 355 | | | | | 360 | | | | | 365 | | | |
| Asn | Ile | His | Tyr | Met | Leu | Lys | His | Pro | Leu | Ser | Phe | Leu | Leu | Ser | Pro |

-continued

```
                370                 375                 380
Phe Tyr Gly Val Leu His Leu Phe Val Leu Gln Pro Leu Lys Leu Tyr
385                 390                 395                 400

Ser Leu Phe Thr Ile Arg Asn Ala Asp Trp Gly Thr Arg Lys Lys Leu
                405                 410                 415

Leu

<210> SEQ ID NO 28
<211> LENGTH: 417
<212> TYPE: PRT
<213> ORGANISM: Streptococcus equisimilis
<220> FEATURE:
<221> NAME/KEY: MISC_FEATURE
<222> LOCATION: (226)..(226)
<223> OTHER INFORMATION: Xaa = Ala, Ser or any other amino acid
<220> FEATURE:
<221> NAME/KEY: MISC_FEATURE
<222> LOCATION: (262)..(262)
<223> OTHER INFORMATION: Xaa = Ala, Ser or any other amino acid
<220> FEATURE:
<221> NAME/KEY: MISC_FEATURE
<222> LOCATION: (281)..(281)
<223> OTHER INFORMATION: Xaa = Ala, Ser or any other amino acid

<400> SEQUENCE: 28

Met Arg Thr Leu Lys Asn Leu Ile Thr Val Ala Phe Ser Ile Phe
1               5                   10                  15

Trp Val Leu Leu Ile Tyr Val Asn Val Tyr Leu Phe Gly Ala Lys Gly
                20                  25                  30

Ser Leu Ser Ile Tyr Gly Phe Leu Ile Ala Tyr Leu Leu Val Lys
                35                  40                  45

Met Ser Leu Ser Phe Phe Tyr Lys Pro Phe Lys Gly Arg Ala Gly Gln
50                  55                  60

Tyr Lys Val Ala Ala Ile Ile Pro Ser Tyr Asn Glu Asp Ala Glu Ser
65                  70                  75                  80

Leu Leu Glu Thr Leu Lys Ser Val Gln Gln Gln Thr Tyr Pro Leu Ala
                85                  90                  95

Glu Ile Tyr Val Val Asp Asp Gly Ser Ala Asp Glu Thr Gly Ile Lys
                100                 105                 110

Arg Ile Glu Asp Tyr Val Arg Asp Thr Gly Asp Leu Ser Ser Asn Val
                115                 120                 125

Ile Val His Arg Ser Glu Lys Asn Gln Gly Lys Arg His Ala Gln Ala
130                 135                 140

Trp Ala Phe Glu Arg Ser Asp Ala Asp Val Phe Leu Thr Val Asp Ser
145                 150                 155                 160

Asp Thr Tyr Ile Tyr Pro Asp Ala Leu Glu Glu Leu Leu Lys Thr Phe
                165                 170                 175

Asn Asp Pro Thr Val Phe Ala Ala Thr Gly His Leu Asn Val Arg Asn
                180                 185                 190

Arg Gln Thr Asn Leu Leu Thr Arg Leu Thr Asp Ile Arg Tyr Asp Asn
                195                 200                 205

Ala Phe Gly Val Glu Arg Ala Ala Gln Ser Val Thr Gly Asn Ile Leu
                210                 215                 220

Val Xaa Ser Gly Pro Leu Ser Val Tyr Arg Arg Glu Val Val Pro
225                 230                 235                 240

Asn Ile Asp Arg Tyr Ile Asn Gln Thr Phe Leu Gly Ile Pro Val Ser
                245                 250                 255

Ile Gly Asp Asp Arg Xaa Leu Thr Asn Tyr Ala Thr Asp Leu Gly Lys
```

-continued

```
                    260                 265                 270
Thr Val Tyr Gln Ser Thr Ala Lys Xaa Ile Thr Asp Val Pro Asp Lys
            275                 280                 285

Met Ser Thr Tyr Leu Lys Gln Gln Asn Arg Trp Asn Lys Ser Phe Phe
        290                 295                 300

Arg Glu Ser Ile Ile Ser Val Lys Lys Ile Met Asn Asn Pro Phe Val
305                 310                 315                 320

Ala Leu Trp Thr Ile Leu Glu Val Ser Met Phe Met Leu Val Tyr
                325                 330                 335

Ser Val Val Asp Phe Phe Val Gly Asn Val Arg Glu Phe Asp Trp Leu
                340                 345                 350

Arg Val Leu Ala Phe Leu Val Ile Ile Phe Ile Val Ala Leu Cys Arg
                355                 360                 365

Asn Ile His Tyr Met Leu Lys His Pro Leu Ser Phe Leu Leu Ser Pro
            370                 375                 380

Phe Tyr Gly Val Leu His Leu Phe Val Leu Gln Pro Leu Lys Leu Tyr
385                 390                 395                 400

Ser Leu Phe Thr Ile Arg Asn Ala Asp Trp Gly Thr Arg Lys Lys Leu
                405                 410                 415

Leu
```

```
<210> SEQ ID NO 29
<211> LENGTH: 417
<212> TYPE: PRT
<213> ORGANISM: Streptococcus equisimilis
<220> FEATURE:
<221> NAME/KEY: MISC_FEATURE
<222> LOCATION: (226)..(226)
<223> OTHER INFORMATION: Xaa = Ala, Ser or any other amino acid
<220> FEATURE:
<221> NAME/KEY: MISC_FEATURE
<222> LOCATION: (262)..(262)
<223> OTHER INFORMATION: Xaa = Ala, Ser or any other amino acid
<220> FEATURE:
<221> NAME/KEY: MISC_FEATURE
<222> LOCATION: (281)..(281)
<223> OTHER INFORMATION: Xaa = Ala, Ser or any other amino acid
<220> FEATURE:
<221> NAME/KEY: MISC_FEATURE
<222> LOCATION: (367)..(367)
<223> OTHER INFORMATION: Xaa = Ala, Ser or any other amino acid

<400> SEQUENCE: 29
```

```
Met Arg Thr Leu Lys Asn Leu Ile Thr Val Val Ala Phe Ser Ile Phe
1               5                   10                  15

Trp Val Leu Leu Ile Tyr Val Asn Val Tyr Leu Phe Gly Ala Lys Gly
            20                  25                  30

Ser Leu Ser Ile Tyr Gly Phe Leu Leu Ile Ala Tyr Leu Leu Val Lys
        35                  40                  45

Met Ser Leu Ser Phe Phe Tyr Lys Pro Phe Lys Gly Arg Ala Gly Gln
    50                  55                  60

Tyr Lys Val Ala Ala Ile Ile Pro Ser Tyr Asn Glu Asp Ala Glu Ser
65                  70                  75                  80

Leu Leu Glu Thr Leu Lys Ser Val Gln Gln Gln Thr Tyr Pro Leu Ala
                85                  90                  95

Glu Ile Tyr Val Val Asp Asp Gly Ser Ala Asp Glu Thr Gly Ile Lys
            100                 105                 110

Arg Ile Glu Asp Tyr Val Arg Asp Thr Gly Asp Leu Ser Ser Asn Val
        115                 120                 125
```

-continued

Ile Val His Arg Ser Glu Lys Asn Gln Gly Lys Arg His Ala Gln Ala
            130                 135                 140
Trp Ala Phe Glu Arg Ser Asp Ala Asp Val Phe Leu Thr Val Asp Ser
145                 150                 155                 160
Asp Thr Tyr Ile Tyr Pro Asp Ala Leu Glu Glu Leu Leu Lys Thr Phe
                165                 170                 175
Asn Asp Pro Thr Val Phe Ala Ala Thr Gly His Leu Asn Val Arg Asn
            180                 185                 190
Arg Gln Thr Asn Leu Leu Thr Arg Leu Thr Asp Ile Arg Tyr Asp Asn
        195                 200                 205
Ala Phe Gly Val Glu Arg Ala Ala Gln Ser Val Thr Gly Asn Ile Leu
    210                 215                 220
Val Xaa Ser Gly Pro Leu Ser Val Tyr Arg Arg Glu Val Val Pro
225                 230                 235                 240
Asn Ile Asp Arg Tyr Ile Asn Gln Thr Phe Leu Gly Ile Pro Val Ser
                245                 250                 255
Ile Gly Asp Asp Arg Xaa Leu Thr Asn Tyr Ala Thr Asp Leu Gly Lys
            260                 265                 270
Thr Val Tyr Gln Ser Thr Ala Lys Xaa Ile Thr Asp Val Pro Asp Lys
        275                 280                 285
Met Ser Thr Tyr Leu Lys Gln Gln Asn Arg Trp Asn Lys Ser Phe Phe
    290                 295                 300
Arg Glu Ser Ile Ile Ser Val Lys Lys Ile Met Asn Asn Pro Phe Val
305                 310                 315                 320
Ala Leu Trp Thr Ile Leu Glu Val Ser Met Phe Met Leu Val Tyr
                325                 330                 335
Ser Val Val Asp Phe Phe Val Gly Asn Val Arg Glu Phe Asp Trp Leu
            340                 345                 350
Arg Val Leu Ala Phe Leu Val Ile Phe Ile Val Ala Leu Xaa Arg
        355                 360                 365
Asn Ile His Tyr Met Leu Lys His Pro Leu Ser Phe Leu Leu Ser Pro
    370                 375                 380
Phe Tyr Gly Val Leu His Leu Phe Val Leu Gln Pro Leu Lys Leu Tyr
385                 390                 395                 400
Ser Leu Phe Thr Ile Arg Asn Ala Asp Trp Gly Thr Arg Lys Lys Leu
                405                 410                 415
Leu

<210> SEQ ID NO 30
<211> LENGTH: 419
<212> TYPE: PRT
<213> ORGANISM: Streptococcus pyogenes
<220> FEATURE:
<221> NAME/KEY: MISC_FEATURE
<222> LOCATION: (124)..(124)
<223> OTHER INFORMATION: Xaa = Ala, Ser or any other amino acid

<400> SEQUENCE: 30

Met Pro Ile Phe Lys Lys Thr Leu Ile Val Leu Ser Phe Ile Phe Leu
1               5                   10                  15
Ile Ser Ile Leu Ile Tyr Leu Asn Met Tyr Leu Phe Gly Thr Ser Thr
            20                  25                  30
Val Gly Ile Tyr Gly Val Ile Leu Ile Thr Tyr Leu Val Ile Lys Leu
        35                  40                  45
Gly Leu Ser Phe Leu Tyr Glu Pro Phe Lys Gly Asn Pro His Asp Tyr
    50                  55                  60

Lys Val Ala Val Ile Pro Ser Tyr Asn Glu Asp Ala Glu Ser Leu
65                  70                  75                  80

Leu Glu Thr Leu Lys Ser Val Leu Ala Gln Thr Tyr Pro Leu Ser Glu
            85                  90                  95

Ile Tyr Ile Val Asp Asp Gly Ser Ser Asn Thr Asp Ala Ile Gln Leu
            100                 105                 110

Ile Glu Glu Tyr Val Asn Arg Glu Val Asp Ile Xaa Arg Asn Val Ile
            115                 120                 125

Val His Arg Ser Leu Val Asn Lys Gly Lys Arg His Ala Gln Ala Trp
130                 135                 140

Ala Phe Glu Arg Ser Asp Ala Asp Val Phe Leu Thr Val Asp Ser Asp
145                 150                 155                 160

Thr Tyr Ile Tyr Pro Asn Ala Leu Glu Glu Leu Leu Lys Ser Phe Asn
            165                 170                 175

Asp Glu Thr Val Tyr Ala Ala Thr Gly His Leu Asn Ala Arg Asn Arg
            180                 185                 190

Gln Thr Asn Leu Leu Thr Arg Leu Thr Asp Ile Arg Tyr Asp Asn Ala
            195                 200                 205

Phe Gly Val Glu Arg Ala Ala Gln Ser Leu Thr Gly Asn Ile Leu Val
210                 215                 220

Cys Ser Gly Pro Leu Ser Ile Tyr Arg Arg Glu Val Ile Ile Pro Asn
225                 230                 235                 240

Leu Glu Arg Tyr Lys Asn Gln Thr Phe Leu Gly Leu Pro Val Ser Ile
            245                 250                 255

Gly Asp Asp Arg Cys Leu Thr Asn Tyr Ala Ile Asp Leu Gly Arg Thr
            260                 265                 270

Val Tyr Gln Ser Thr Ala Arg Cys Asp Thr Asp Val Pro Phe Gln Leu
            275                 280                 285

Lys Ser Tyr Leu Lys Gln Gln Asn Arg Trp Asn Lys Ser Phe Phe Arg
290                 295                 300

Glu Ser Ile Ile Ser Val Lys Lys Ile Leu Ser Asn Pro Ile Val Ala
305                 310                 315                 320

Leu Trp Thr Ile Phe Glu Val Val Met Phe Met Leu Ile Val Ala
            325                 330                 335

Ile Gly Asn Leu Leu Phe Asn Gln Ala Ile Gln Leu Asp Leu Ile Lys
            340                 345                 350

Leu Phe Ala Phe Leu Ser Ile Ile Phe Ile Val Ala Leu Cys Arg Asn
            355                 360                 365

Val His Tyr Met Val Lys His Pro Ala Ser Phe Leu Leu Ser Pro Leu
370                 375                 380

Tyr Gly Ile Leu His Leu Phe Val Leu Gln Pro Leu Lys Leu Tyr Ser
385                 390                 395                 400

Leu Cys Thr Ile Lys Asn Thr Glu Trp Gly Thr Arg Lys Lys Val Thr
            405                 410                 415

Ile Phe Lys

<210> SEQ ID NO 31
<211> LENGTH: 419
<212> TYPE: PRT
<213> ORGANISM: Streptococcus pyogenes
<220> FEATURE:
<221> NAME/KEY: MISC_FEATURE
<222> LOCATION: (225)..(225)
<223> OTHER INFORMATION: Xaa = Ala, Ser or any other amino acid

<400> SEQUENCE: 31

```
Met Pro Ile Phe Lys Lys Thr Leu Ile Val Leu Ser Phe Ile Phe Leu
1               5                   10                  15

Ile Ser Ile Leu Ile Tyr Leu Asn Met Tyr Leu Phe Gly Thr Ser Thr
            20                  25                  30

Val Gly Ile Tyr Gly Val Ile Leu Ile Thr Tyr Leu Val Ile Lys Leu
        35                  40                  45

Gly Leu Ser Phe Leu Tyr Glu Pro Phe Lys Gly Asn Pro His Asp Tyr
    50                  55                  60

Lys Val Ala Ala Val Ile Pro Ser Tyr Asn Glu Asp Ala Glu Ser Leu
65                  70                  75                  80

Leu Glu Thr Leu Lys Ser Val Leu Ala Gln Thr Tyr Pro Leu Ser Glu
                85                  90                  95

Ile Tyr Ile Val Asp Asp Gly Ser Ser Asn Thr Asp Ala Ile Gln Leu
            100                 105                 110

Ile Glu Glu Tyr Val Asn Arg Glu Val Asp Ile Cys Arg Asn Val Ile
        115                 120                 125

Val His Arg Ser Leu Val Asn Lys Gly Lys Arg His Ala Gln Ala Trp
130                 135                 140

Ala Phe Glu Arg Ser Asp Ala Asp Val Phe Leu Thr Val Asp Ser Asp
145                 150                 155                 160

Thr Tyr Ile Tyr Pro Asn Ala Leu Glu Glu Leu Leu Lys Ser Phe Asn
                165                 170                 175

Asp Glu Thr Val Tyr Ala Ala Thr Gly His Leu Asn Ala Arg Asn Arg
            180                 185                 190

Gln Thr Asn Leu Leu Thr Arg Leu Thr Asp Ile Arg Tyr Asp Asn Ala
        195                 200                 205

Phe Gly Val Glu Arg Ala Ala Gln Ser Leu Thr Gly Asn Ile Leu Val
210                 215                 220

Xaa Ser Gly Pro Leu Ser Ile Tyr Arg Arg Glu Val Ile Ile Pro Asn
225                 230                 235                 240

Leu Glu Arg Tyr Lys Asn Gln Thr Phe Leu Gly Leu Pro Val Ser Ile
                245                 250                 255

Gly Asp Asp Arg Cys Leu Thr Asn Tyr Ala Ile Asp Leu Gly Arg Thr
            260                 265                 270

Val Tyr Gln Ser Thr Ala Arg Cys Asp Thr Asp Val Pro Phe Gln Leu
        275                 280                 285

Lys Ser Tyr Leu Lys Gln Gln Asn Arg Trp Asn Lys Ser Phe Phe Arg
290                 295                 300

Glu Ser Ile Ile Ser Val Lys Lys Ile Leu Ser Asn Pro Ile Val Ala
305                 310                 315                 320

Leu Trp Thr Ile Phe Glu Val Val Met Phe Met Met Leu Ile Val Ala
                325                 330                 335

Ile Gly Asn Leu Leu Phe Asn Gln Ala Ile Gln Leu Asp Leu Ile Lys
            340                 345                 350

Leu Phe Ala Phe Leu Ser Ile Ile Phe Ile Val Ala Leu Cys Arg Asn
        355                 360                 365

Val His Tyr Met Val Lys His Pro Ala Ser Phe Leu Leu Ser Pro Leu
370                 375                 380

Tyr Gly Ile Leu His Leu Phe Val Leu Gln Pro Leu Lys Leu Tyr Ser
385                 390                 395                 400

Leu Cys Thr Ile Lys Asn Thr Glu Trp Gly Thr Arg Lys Lys Val Thr
                405                 410                 415
```

Ile Phe Lys

<210> SEQ ID NO 32
<211> LENGTH: 419
<212> TYPE: PRT
<213> ORGANISM: Streptococcus pyogenes
<220> FEATURE:
<221> NAME/KEY: MISC_FEATURE
<222> LOCATION: (261)..(261)
<223> OTHER INFORMATION: Xaa = Ala, Ser or any other amino acid

<400> SEQUENCE: 32

```
Met Pro Ile Phe Lys Lys Thr Leu Ile Val Leu Ser Phe Ile Phe Leu
1               5                   10                  15

Ile Ser Ile Leu Ile Tyr Leu Asn Met Tyr Leu Phe Gly Thr Ser Thr
            20                  25                  30

Val Gly Ile Tyr Gly Val Ile Leu Ile Thr Tyr Leu Val Ile Lys Leu
        35                  40                  45

Gly Leu Ser Phe Leu Tyr Glu Pro Phe Lys Gly Asn Pro His Asp Tyr
    50                  55                  60

Lys Val Ala Ala Val Ile Pro Ser Tyr Asn Glu Asp Ala Glu Ser Leu
65                  70                  75                  80

Leu Glu Thr Leu Lys Ser Val Leu Ala Gln Thr Tyr Pro Leu Ser Glu
                85                  90                  95

Ile Tyr Ile Val Asp Asp Gly Ser Ser Asn Thr Asp Ala Ile Gln Leu
            100                 105                 110

Ile Glu Glu Tyr Val Asn Arg Glu Val Asp Ile Cys Arg Asn Val Ile
        115                 120                 125

Val His Arg Ser Leu Val Asn Lys Gly Lys Arg His Ala Gln Ala Trp
    130                 135                 140

Ala Phe Glu Arg Ser Asp Ala Asp Val Phe Leu Thr Val Asp Ser Asp
145                 150                 155                 160

Thr Tyr Ile Tyr Pro Asn Ala Leu Glu Glu Leu Leu Lys Ser Phe Asn
                165                 170                 175

Asp Glu Thr Val Tyr Ala Ala Thr Gly His Leu Asn Ala Arg Asn Arg
            180                 185                 190

Gln Thr Asn Leu Leu Thr Arg Leu Thr Asp Ile Arg Tyr Asp Asn Ala
        195                 200                 205

Phe Gly Val Glu Arg Ala Ala Gln Ser Leu Thr Gly Asn Ile Leu Val
    210                 215                 220

Cys Ser Gly Pro Leu Ser Ile Tyr Arg Arg Glu Val Ile Ile Pro Asn
225                 230                 235                 240

Leu Glu Arg Tyr Lys Asn Gln Thr Phe Leu Gly Leu Pro Val Ser Ile
                245                 250                 255

Gly Asp Asp Arg Xaa Leu Thr Asn Tyr Ala Ile Asp Leu Gly Arg Thr
            260                 265                 270

Val Tyr Gln Ser Thr Ala Arg Cys Asp Thr Asp Val Pro Phe Gln Leu
        275                 280                 285

Lys Ser Tyr Leu Lys Gln Gln Asn Arg Trp Asn Lys Ser Phe Phe Arg
    290                 295                 300

Glu Ser Ile Ile Ser Val Lys Lys Ile Leu Ser Asn Pro Ile Val Ala
305                 310                 315                 320

Leu Trp Thr Ile Phe Glu Val Val Met Phe Met Met Leu Ile Val Ala
                325                 330                 335

Ile Gly Asn Leu Leu Phe Asn Gln Ala Ile Gln Leu Asp Leu Ile Lys
```

```
                    340                 345                 350
Leu Phe Ala Phe Leu Ser Ile Ile Phe Ile Val Ala Leu Cys Arg Asn
                355                 360                 365
Val His Tyr Met Val Lys His Pro Ala Ser Phe Leu Leu Ser Pro Leu
            370                 375                 380
Tyr Gly Ile Leu His Leu Phe Val Leu Gln Pro Leu Lys Leu Tyr Ser
385                 390                 395                 400
Leu Cys Thr Ile Lys Asn Thr Glu Trp Gly Thr Arg Lys Lys Val Thr
                405                 410                 415
Ile Phe Lys

<210> SEQ ID NO 33
<211> LENGTH: 419
<212> TYPE: PRT
<213> ORGANISM: Streptococcus pyogenes
<220> FEATURE:
<221> NAME/KEY: MISC_FEATURE
<222> LOCATION: (280)..(280)
<223> OTHER INFORMATION: Xaa = Ala, Ser or any other amino acid

<400> SEQUENCE: 33

Met Pro Ile Phe Lys Lys Thr Leu Ile Val Leu Ser Phe Ile Phe Leu
1               5                   10                  15
Ile Ser Ile Leu Ile Tyr Leu Asn Met Tyr Leu Phe Gly Thr Ser Thr
            20                  25                  30
Val Gly Ile Tyr Gly Val Ile Leu Ile Thr Tyr Leu Val Ile Lys Leu
        35                  40                  45
Gly Leu Ser Phe Leu Tyr Glu Pro Phe Lys Gly Asn Pro His Asp Tyr
    50                  55                  60
Lys Val Ala Ala Val Ile Pro Ser Tyr Asn Glu Asp Ala Glu Ser Leu
65                  70                  75                  80
Leu Glu Thr Leu Lys Ser Val Leu Ala Gln Thr Tyr Pro Leu Ser Glu
                85                  90                  95
Ile Tyr Ile Val Asp Asp Gly Ser Ser Asn Thr Asp Ala Ile Gln Leu
            100                 105                 110
Ile Glu Glu Tyr Val Asn Arg Glu Val Asp Ile Cys Arg Asn Val Ile
        115                 120                 125
Val His Arg Ser Leu Val Asn Lys Gly Lys Arg His Ala Gln Ala Trp
    130                 135                 140
Ala Phe Glu Arg Ser Asp Ala Asp Val Phe Leu Thr Val Asp Ser Asp
145                 150                 155                 160
Thr Tyr Ile Tyr Pro Asn Ala Leu Glu Glu Leu Leu Lys Ser Phe Asn
                165                 170                 175
Asp Glu Thr Val Tyr Ala Ala Thr Gly His Leu Asn Ala Arg Asn Arg
            180                 185                 190
Gln Thr Asn Leu Leu Thr Arg Leu Thr Asp Ile Arg Tyr Asp Asn Ala
        195                 200                 205
Phe Gly Val Glu Arg Ala Ala Gln Ser Leu Thr Gly Asn Ile Leu Val
    210                 215                 220
Cys Ser Gly Pro Leu Ser Ile Tyr Arg Arg Glu Val Ile Ile Pro Asn
225                 230                 235                 240
Leu Glu Arg Tyr Lys Asn Gln Thr Phe Leu Gly Leu Pro Val Ser Ile
                245                 250                 255
Gly Asp Asp Arg Cys Leu Thr Asn Tyr Ala Ile Asp Leu Gly Arg Thr
            260                 265                 270
```

```
Val Tyr Gln Ser Thr Ala Arg Xaa Asp Thr Asp Val Pro Phe Gln Leu
            275                 280                 285

Lys Ser Tyr Leu Lys Gln Gln Asn Arg Trp Asn Lys Ser Phe Phe Arg
            290                 295                 300

Glu Ser Ile Ile Ser Val Lys Lys Ile Leu Ser Asn Pro Ile Val Ala
305                 310                 315                 320

Leu Trp Thr Ile Phe Glu Val Val Met Phe Met Met Leu Ile Val Ala
                325                 330                 335

Ile Gly Asn Leu Leu Phe Asn Gln Ala Ile Gln Leu Asp Leu Ile Lys
                340                 345                 350

Leu Phe Ala Phe Leu Ser Ile Ile Phe Ile Val Ala Leu Cys Arg Asn
            355                 360                 365

Val His Tyr Met Val Lys His Pro Ala Ser Phe Leu Leu Ser Pro Leu
            370                 375                 380

Tyr Gly Ile Leu His Leu Phe Val Leu Gln Pro Leu Lys Leu Tyr Ser
385                 390                 395                 400

Leu Cys Thr Ile Lys Asn Thr Glu Trp Gly Thr Arg Lys Lys Val Thr
                405                 410                 415

Ile Phe Lys

<210> SEQ ID NO 34
<211> LENGTH: 419
<212> TYPE: PRT
<213> ORGANISM: Streptococcus pyogenes
<220> FEATURE:
<221> NAME/KEY: MISC_FEATURE
<222> LOCATION: (366)..(366)
<223> OTHER INFORMATION: Xaa = Ala, Ser or any other amino acid

<400> SEQUENCE: 34

Met Pro Ile Phe Lys Lys Thr Leu Ile Val Leu Ser Phe Ile Phe Leu
1               5                   10                  15

Ile Ser Ile Leu Ile Tyr Leu Asn Met Tyr Leu Phe Gly Thr Ser Thr
                20                  25                  30

Val Gly Ile Tyr Gly Val Ile Leu Ile Thr Tyr Leu Val Ile Lys Leu
            35                  40                  45

Gly Leu Ser Phe Leu Tyr Glu Pro Phe Lys Gly Asn Pro His Asp Tyr
50                  55                  60

Lys Val Ala Ala Val Ile Pro Ser Tyr Asn Glu Asp Ala Glu Ser Leu
65                  70                  75                  80

Leu Glu Thr Leu Lys Ser Val Leu Ala Gln Thr Tyr Pro Leu Ser Glu
                85                  90                  95

Ile Tyr Ile Val Asp Asp Gly Ser Ser Asn Thr Asp Ala Ile Gln Leu
                100                 105                 110

Ile Glu Glu Tyr Val Asn Arg Glu Val Asp Ile Cys Arg Asn Val Ile
            115                 120                 125

Val His Arg Ser Leu Val Asn Lys Gly Lys Arg His Ala Gln Ala Trp
            130                 135                 140

Ala Phe Glu Arg Ser Asp Ala Asp Val Phe Leu Thr Val Asp Ser Asp
145                 150                 155                 160

Thr Tyr Ile Tyr Pro Asn Ala Leu Glu Glu Leu Leu Lys Ser Phe Asn
                165                 170                 175

Asp Glu Thr Val Tyr Ala Ala Thr Gly His Leu Asn Ala Arg Asn Arg
                180                 185                 190

Gln Thr Asn Leu Leu Thr Arg Leu Thr Asp Ile Arg Tyr Asp Asn Ala
            195                 200                 205
```

```
Phe Gly Val Glu Arg Ala Ala Gln Ser Leu Thr Gly Asn Ile Leu Val
    210                 215                 220

Cys Ser Gly Pro Leu Ser Ile Tyr Arg Arg Glu Val Ile Ile Pro Asn
225                 230                 235                 240

Leu Glu Arg Tyr Lys Asn Gln Thr Phe Leu Gly Leu Pro Val Ser Ile
                245                 250                 255

Gly Asp Asp Arg Cys Leu Thr Asn Tyr Ala Ile Asp Leu Gly Arg Thr
                260                 265                 270

Val Tyr Gln Ser Thr Ala Arg Cys Asp Thr Asp Val Pro Phe Gln Leu
            275                 280                 285

Lys Ser Tyr Leu Lys Gln Gln Asn Arg Trp Asn Lys Ser Phe Phe Arg
    290                 295                 300

Glu Ser Ile Ile Ser Val Lys Lys Ile Leu Ser Asn Pro Ile Val Ala
305                 310                 315                 320

Leu Trp Thr Ile Phe Glu Val Val Met Phe Met Met Leu Ile Val Ala
                325                 330                 335

Ile Gly Asn Leu Leu Phe Asn Gln Ala Ile Gln Leu Asp Leu Ile Lys
                340                 345                 350

Leu Phe Ala Phe Leu Ser Ile Ile Phe Ile Val Ala Leu Xaa Arg Asn
            355                 360                 365

Val His Tyr Met Val Lys His Pro Ala Ser Phe Leu Leu Ser Pro Leu
    370                 375                 380

Tyr Gly Ile Leu His Leu Phe Val Leu Gln Pro Leu Lys Leu Tyr Ser
385                 390                 395                 400

Leu Cys Thr Ile Lys Asn Thr Glu Trp Gly Thr Arg Lys Lys Val Thr
                405                 410                 415

Ile Phe Lys

<210> SEQ ID NO 35
<211> LENGTH: 419
<212> TYPE: PRT
<213> ORGANISM: Streptococcus pyogenes
<220> FEATURE:
<221> NAME/KEY: MISC_FEATURE
<222> LOCATION: (402)..(402)
<223> OTHER INFORMATION: Xaa = Ala, Ser or any other amino acid

<400> SEQUENCE: 35

Met Pro Ile Phe Lys Lys Thr Leu Ile Val Leu Ser Phe Ile Phe Leu
1               5                   10                  15

Ile Ser Ile Leu Ile Tyr Leu Asn Met Tyr Leu Phe Gly Thr Ser Thr
                20                  25                  30

Val Gly Ile Tyr Gly Val Ile Leu Ile Thr Tyr Leu Val Ile Lys Leu
            35                  40                  45

Gly Leu Ser Phe Leu Tyr Glu Pro Phe Lys Gly Asn Pro His Asp Tyr
    50                  55                  60

Lys Val Ala Ala Val Ile Pro Ser Tyr Asn Glu Asp Ala Glu Ser Leu
65                  70                  75                  80

Leu Glu Thr Leu Lys Ser Val Leu Ala Gln Thr Tyr Pro Leu Ser Glu
                85                  90                  95

Ile Tyr Ile Val Asp Asp Gly Ser Ser Asn Thr Asp Ala Ile Gln Leu
                100                 105                 110

Ile Glu Glu Tyr Val Asn Arg Glu Val Asp Ile Cys Arg Asn Val Ile
            115                 120                 125

Val His Arg Ser Leu Val Asn Lys Gly Lys Arg His Ala Gln Ala Trp
```

```
                130                 135                 140
Ala Phe Glu Arg Ser Asp Ala Asp Val Phe Leu Thr Val Asp Ser Asp
145                 150                 155                 160

Thr Tyr Ile Tyr Pro Asn Ala Leu Glu Glu Leu Leu Lys Ser Phe Asn
                165                 170                 175

Asp Glu Thr Val Tyr Ala Ala Thr Gly His Leu Asn Ala Arg Asn Arg
            180                 185                 190

Gln Thr Asn Leu Leu Thr Arg Leu Thr Asp Ile Arg Tyr Asp Asn Ala
        195                 200                 205

Phe Gly Val Glu Arg Ala Ala Gln Ser Leu Thr Gly Asn Ile Leu Val
    210                 215                 220

Cys Ser Gly Pro Leu Ser Ile Tyr Arg Arg Glu Val Ile Ile Pro Asn
225                 230                 235                 240

Leu Glu Arg Tyr Lys Asn Gln Thr Phe Leu Gly Leu Pro Val Ser Ile
                245                 250                 255

Gly Asp Asp Arg Cys Leu Thr Asn Tyr Ala Ile Asp Leu Gly Arg Thr
            260                 265                 270

Val Tyr Gln Ser Thr Ala Arg Cys Asp Thr Asp Val Pro Phe Gln Leu
        275                 280                 285

Lys Ser Tyr Leu Lys Gln Gln Asn Arg Trp Asn Lys Ser Phe Phe Arg
    290                 295                 300

Glu Ser Ile Ile Ser Val Lys Lys Ile Leu Ser Asn Pro Ile Val Ala
305                 310                 315                 320

Leu Trp Thr Ile Phe Glu Val Val Met Phe Met Met Leu Ile Val Ala
                325                 330                 335

Ile Gly Asn Leu Leu Phe Asn Gln Ala Ile Gln Leu Asp Leu Ile Lys
            340                 345                 350

Leu Phe Ala Phe Leu Ser Ile Ile Phe Ile Val Ala Leu Cys Arg Asn
        355                 360                 365

Val His Tyr Met Val Lys His Pro Ala Ser Phe Leu Leu Ser Pro Leu
    370                 375                 380

Tyr Gly Ile Leu His Leu Phe Val Leu Gln Pro Leu Lys Leu Tyr Ser
385                 390                 395                 400

Leu Xaa Thr Ile Lys Asn Thr Glu Trp Gly Thr Arg Lys Lys Val Thr
                405                 410                 415

Ile Phe Lys

<210> SEQ ID NO 36
<211> LENGTH: 419
<212> TYPE: PRT
<213> ORGANISM: Streptococcus pyogenes
<220> FEATURE:
<221> NAME/KEY: MISC_FEATURE
<222> LOCATION: (225)..(225)
<223> OTHER INFORMATION: Xaa = Ala, Ser or any other amino acid
<220> FEATURE:
<221> NAME/KEY: MISC_FEATURE
<222> LOCATION: (124)..(124)
<223> OTHER INFORMATION: Xaa = Ala, Ser or any other amino acid

<400> SEQUENCE: 36

Met Pro Ile Phe Lys Lys Thr Leu Ile Val Leu Ser Phe Ile Phe Leu
1               5                   10                  15

Ile Ser Ile Leu Ile Tyr Leu Asn Met Tyr Leu Phe Gly Thr Ser Thr
            20                  25                  30

Val Gly Ile Tyr Gly Val Ile Leu Ile Thr Tyr Leu Val Ile Lys Leu
        35                  40                  45
```

-continued

```
Gly Leu Ser Phe Leu Tyr Glu Pro Phe Lys Gly Asn Pro His Asp Tyr
 50                  55                  60
Lys Val Ala Ala Val Ile Pro Ser Tyr Asn Glu Asp Ala Glu Ser Leu
 65                  70                  75                  80
Leu Glu Thr Leu Lys Ser Val Leu Ala Gln Thr Tyr Pro Leu Ser Glu
                 85                  90                  95
Ile Tyr Ile Val Asp Asp Gly Ser Ser Asn Thr Asp Ala Ile Gln Leu
            100                 105                 110
Ile Glu Glu Tyr Val Asn Arg Glu Val Asp Ile Xaa Arg Asn Val Ile
        115                 120                 125
Val His Arg Ser Leu Val Asn Lys Gly Lys Arg His Ala Gln Ala Trp
130                 135                 140
Ala Phe Glu Arg Ser Asp Ala Asp Val Phe Leu Thr Val Asp Ser Asp
145                 150                 155                 160
Thr Tyr Ile Tyr Pro Asn Ala Leu Glu Glu Leu Leu Lys Ser Phe Asn
                165                 170                 175
Asp Glu Thr Val Tyr Ala Ala Thr Gly His Leu Asn Ala Arg Asn Arg
            180                 185                 190
Gln Thr Asn Leu Leu Thr Arg Leu Thr Asp Ile Arg Tyr Asp Asn Ala
        195                 200                 205
Phe Gly Val Glu Arg Ala Ala Gln Ser Leu Thr Gly Asn Ile Leu Val
210                 215                 220
Xaa Ser Gly Pro Leu Ser Ile Tyr Arg Arg Glu Val Ile Ile Pro Asn
225                 230                 235                 240
Leu Glu Arg Tyr Lys Asn Gln Thr Phe Leu Gly Leu Pro Val Ser Ile
                245                 250                 255
Gly Asp Asp Arg Cys Leu Thr Asn Tyr Ala Ile Asp Leu Gly Arg Thr
            260                 265                 270
Val Tyr Gln Ser Thr Ala Arg Cys Asp Thr Asp Val Pro Phe Gln Leu
        275                 280                 285
Lys Ser Tyr Leu Lys Gln Gln Asn Arg Trp Asn Lys Ser Phe Phe Arg
290                 295                 300
Glu Ser Ile Ile Ser Val Lys Lys Ile Leu Ser Asn Pro Ile Val Ala
305                 310                 315                 320
Leu Trp Thr Ile Phe Glu Val Val Met Phe Met Met Leu Ile Val Ala
                325                 330                 335
Ile Gly Asn Leu Leu Phe Asn Gln Ala Ile Gln Leu Asp Leu Ile Lys
            340                 345                 350
Leu Phe Ala Phe Leu Ser Ile Ile Phe Ile Val Ala Leu Cys Arg Asn
        355                 360                 365
Val His Tyr Met Val Lys His Pro Ala Ser Phe Leu Leu Ser Pro Leu
370                 375                 380
Tyr Gly Ile Leu His Leu Phe Val Leu Gln Pro Leu Lys Leu Tyr Ser
385                 390                 395                 400
Leu Cys Thr Ile Lys Asn Thr Glu Trp Gly Thr Arg Lys Lys Val Thr
                405                 410                 415
Ile Phe Lys
```

<210> SEQ ID NO 37
<211> LENGTH: 419
<212> TYPE: PRT
<213> ORGANISM: Streptococcus pyogenes
<220> FEATURE:
<221> NAME/KEY: MISC_FEATURE

```
<222> LOCATION: (124)..(124)
<223> OTHER INFORMATION: Xaa = Ala, Ser or any other amino acid
<220> FEATURE:
<221> NAME/KEY: MISC_FEATURE
<222> LOCATION: (261)..(261)
<223> OTHER INFORMATION: Xaa = Ala, Ser or any other amino acid

<400> SEQUENCE: 37
```

| | | | | | | | | | | | | | | |
|---|---|---|---|---|---|---|---|---|---|---|---|---|---|---|
| Met | Pro | Ile | Phe | Lys | Lys | Thr | Leu | Ile | Val | Leu | Ser | Phe | Ile | Phe | Leu |
| 1 | | | | 5 | | | | | 10 | | | | | 15 | |

Ile Ser Ile Leu Ile Tyr Leu Asn Met Tyr Leu Phe Gly Thr Ser Thr
              20              25                 30

Val Gly Ile Tyr Gly Val Ile Leu Ile Thr Tyr Leu Val Ile Lys Leu
       35               40              45

Gly Leu Ser Phe Leu Tyr Glu Pro Phe Lys Gly Asn Pro His Asp Tyr
50                  55                  60

Lys Val Ala Ala Val Ile Pro Ser Tyr Asn Glu Asp Ala Glu Ser Leu
65              70              75              80

Leu Glu Thr Leu Lys Ser Val Leu Ala Gln Thr Tyr Pro Leu Ser Glu
              85              90              95

Ile Tyr Ile Val Asp Asp Gly Ser Asn Thr Asp Ala Ile Gln Leu
        100              105            110

Ile Glu Glu Tyr Val Asn Arg Glu Val Asp Ile Xaa Arg Asn Val Ile
       115               120            125

Val His Arg Ser Leu Val Asn Lys Gly Lys Arg His Ala Gln Ala Trp
130                135              140

Ala Phe Glu Arg Ser Asp Ala Asp Val Phe Leu Thr Val Asp Ser Asp
145              150              155            160

Thr Tyr Ile Tyr Pro Asn Ala Leu Glu Glu Leu Leu Lys Ser Phe Asn
              165              170            175

Asp Glu Thr Val Tyr Ala Ala Thr Gly His Leu Asn Ala Arg Asn Arg
        180              185            190

Gln Thr Asn Leu Leu Thr Arg Leu Thr Asp Ile Arg Tyr Asp Asn Ala
       195               200            205

Phe Gly Val Glu Arg Ala Ala Gln Ser Leu Thr Gly Asn Ile Leu Val
210                215              220

Cys Ser Gly Pro Leu Ser Ile Tyr Arg Arg Glu Val Ile Ile Pro Asn
225              230              235            240

Leu Glu Arg Tyr Lys Asn Gln Thr Phe Leu Gly Leu Pro Val Ser Ile
              245              250            255

Gly Asp Asp Arg Xaa Leu Thr Asn Tyr Ala Ile Asp Leu Gly Arg Thr
        260              265            270

Val Tyr Gln Ser Thr Ala Arg Cys Asp Thr Asp Val Pro Phe Gln Leu
       275               280            285

Lys Ser Tyr Leu Lys Gln Gln Asn Arg Trp Asn Lys Ser Phe Phe Arg
290                295              300

Glu Ser Ile Ile Ser Val Lys Lys Ile Leu Ser Asn Pro Ile Val Ala
305              310              315            320

Leu Trp Thr Ile Phe Glu Val Val Met Phe Met Met Leu Ile Val Ala
              325              330            335

Ile Gly Asn Leu Leu Phe Asn Gln Ala Ile Gln Leu Asp Leu Ile Lys
        340              345            350

Leu Phe Ala Phe Leu Ser Ile Ile Phe Ile Val Ala Leu Cys Arg Asn
       355               360            365

Val His Tyr Met Val Lys His Pro Ala Ser Phe Leu Leu Ser Pro Leu

```
                      370                 375                 380
Tyr Gly Ile Leu His Leu Phe Val Leu Gln Pro Leu Lys Leu Tyr Ser
385                 390                 395                 400

Leu Cys Thr Ile Lys Asn Thr Glu Trp Gly Thr Arg Lys Lys Val Thr
                405                 410                 415

Ile Phe Lys

<210> SEQ ID NO 38
<211> LENGTH: 419
<212> TYPE: PRT
<213> ORGANISM: Streptococcus pyogenes
<220> FEATURE:
<221> NAME/KEY: MISC_FEATURE
<222> LOCATION: (124)..(124)
<223> OTHER INFORMATION: Xaa = Ala, Ser or any other amino acid
<220> FEATURE:
<221> NAME/KEY: MISC_FEATURE
<222> LOCATION: (280)..(280)
<223> OTHER INFORMATION: Xaa = Ala, Ser or any other amino acid

<400> SEQUENCE: 38

Met Pro Ile Phe Lys Lys Thr Leu Ile Val Leu Ser Phe Ile Phe Leu
1               5                  10                  15

Ile Ser Ile Leu Ile Tyr Leu Asn Met Tyr Leu Phe Gly Thr Ser Thr
                20                  25                  30

Val Gly Ile Tyr Gly Val Ile Leu Ile Thr Tyr Leu Val Ile Lys Leu
            35                  40                  45

Gly Leu Ser Phe Leu Tyr Glu Pro Phe Lys Gly Asn Pro His Asp Tyr
50                  55                  60

Lys Val Ala Ala Val Ile Pro Ser Tyr Asn Glu Asp Ala Glu Ser Leu
65                  70                  75                  80

Leu Glu Thr Leu Lys Ser Val Leu Ala Gln Thr Tyr Pro Leu Ser Glu
                85                  90                  95

Ile Tyr Ile Val Asp Asp Gly Ser Ser Asn Thr Asp Ala Ile Gln Leu
            100                 105                 110

Ile Glu Glu Tyr Val Asn Arg Glu Val Asp Ile Xaa Arg Asn Val Ile
        115                 120                 125

Val His Arg Ser Leu Val Asn Lys Gly Lys Arg His Ala Gln Ala Trp
130                 135                 140

Ala Phe Glu Arg Ser Asp Ala Asp Val Phe Leu Thr Val Asp Ser Asp
145                 150                 155                 160

Thr Tyr Ile Tyr Pro Asn Ala Leu Glu Glu Leu Leu Lys Ser Phe Asn
                165                 170                 175

Asp Glu Thr Val Tyr Ala Ala Thr Gly His Leu Asn Ala Arg Asn Arg
            180                 185                 190

Gln Thr Asn Leu Leu Thr Arg Leu Thr Asp Ile Arg Tyr Asp Asn Ala
        195                 200                 205

Phe Gly Val Glu Arg Ala Ala Gln Ser Leu Thr Gly Asn Ile Leu Val
    210                 215                 220

Cys Ser Gly Pro Leu Ser Ile Tyr Arg Arg Glu Val Ile Ile Pro Asn
225                 230                 235                 240

Leu Glu Arg Tyr Lys Asn Gln Thr Phe Leu Gly Leu Pro Val Ser Ile
                245                 250                 255

Gly Asp Asp Arg Cys Leu Thr Asn Tyr Ala Ile Asp Leu Gly Arg Thr
            260                 265                 270

Val Tyr Gln Ser Thr Ala Arg Xaa Asp Thr Asp Val Pro Phe Gln Leu
        275                 280                 285
```

-continued

```
Lys Ser Tyr Leu Lys Gln Gln Asn Arg Trp Asn Lys Ser Phe Phe Arg
            290                 295                 300

Glu Ser Ile Ile Ser Val Lys Lys Ile Leu Ser Asn Pro Ile Val Ala
305                 310                 315                 320

Leu Trp Thr Ile Phe Glu Val Val Met Phe Met Met Leu Ile Val Ala
                325                 330                 335

Ile Gly Asn Leu Leu Phe Asn Gln Ala Ile Gln Leu Asp Leu Ile Lys
                340                 345                 350

Leu Phe Ala Phe Leu Ser Ile Ile Phe Ile Val Ala Leu Cys Arg Asn
            355                 360                 365

Val His Tyr Met Val Lys His Pro Ala Ser Phe Leu Leu Ser Pro Leu
    370                 375                 380

Tyr Gly Ile Leu His Leu Phe Val Leu Gln Pro Leu Lys Leu Tyr Ser
385                 390                 395                 400

Leu Cys Thr Ile Lys Asn Thr Glu Trp Gly Thr Arg Lys Lys Val Thr
                405                 410                 415

Ile Phe Lys
```

<210> SEQ ID NO 39
<211> LENGTH: 419
<212> TYPE: PRT
<213> ORGANISM: Streptococcus pyogenes
<220> FEATURE:
<221> NAME/KEY: MISC_FEATURE
<222> LOCATION: (124)..(124)
<223> OTHER INFORMATION: Xaa = Ala, Ser or any other amino acid
<220> FEATURE:
<221> NAME/KEY: MISC_FEATURE
<222> LOCATION: (366)..(366)
<223> OTHER INFORMATION: Xaa = Ala, Ser or any other amino acid

<400> SEQUENCE: 39

```
Met Pro Ile Phe Lys Lys Thr Leu Ile Val Leu Ser Phe Ile Phe Leu
1               5                   10                  15

Ile Ser Ile Leu Ile Tyr Leu Asn Met Tyr Leu Phe Gly Thr Ser Thr
            20                  25                  30

Val Gly Ile Tyr Gly Val Ile Leu Ile Thr Tyr Leu Val Ile Lys Leu
        35                  40                  45

Gly Leu Ser Phe Leu Tyr Glu Pro Phe Lys Gly Asn Pro His Asp Tyr
    50                  55                  60

Lys Val Ala Ala Val Ile Pro Ser Tyr Asn Glu Asp Ala Glu Ser Leu
65                  70                  75                  80

Leu Glu Thr Leu Lys Ser Val Leu Ala Gln Thr Tyr Pro Leu Ser Glu
                85                  90                  95

Ile Tyr Ile Val Asp Asp Gly Ser Ser Asn Thr Asp Ala Ile Gln Leu
                100                 105                 110

Ile Glu Glu Tyr Val Asn Arg Glu Val Asp Ile Xaa Arg Asn Val Ile
            115                 120                 125

Val His Arg Ser Leu Val Asn Lys Gly Lys Arg His Ala Gln Ala Trp
    130                 135                 140

Ala Phe Glu Arg Ser Asp Ala Asp Val Phe Leu Thr Val Asp Ser Asp
145                 150                 155                 160

Thr Tyr Ile Tyr Pro Asn Ala Leu Glu Glu Leu Leu Lys Ser Phe Asn
                165                 170                 175

Asp Glu Thr Val Tyr Ala Ala Thr Gly His Leu Asn Ala Arg Asn Arg
                180                 185                 190
```

-continued

```
Gln Thr Asn Leu Leu Thr Arg Leu Thr Asp Ile Arg Tyr Asp Asn Ala
            195                 200                 205

Phe Gly Val Glu Arg Ala Ala Gln Ser Leu Thr Gly Asn Ile Leu Val
        210                 215                 220

Cys Ser Gly Pro Leu Ser Ile Tyr Arg Arg Glu Val Ile Ile Pro Asn
225                 230                 235                 240

Leu Glu Arg Tyr Lys Asn Gln Thr Phe Leu Gly Leu Pro Val Ser Ile
                245                 250                 255

Gly Asp Asp Arg Cys Leu Thr Asn Tyr Ala Ile Asp Leu Gly Arg Thr
            260                 265                 270

Val Tyr Gln Ser Thr Ala Arg Cys Asp Thr Asp Val Pro Phe Gln Leu
        275                 280                 285

Lys Ser Tyr Leu Lys Gln Gln Asn Arg Trp Asn Lys Ser Phe Phe Arg
    290                 295                 300

Glu Ser Ile Ile Ser Val Lys Lys Ile Leu Ser Asn Pro Ile Val Ala
305                 310                 315                 320

Leu Trp Thr Ile Phe Glu Val Met Phe Met Met Leu Ile Val Ala
                325                 330                 335

Ile Gly Asn Leu Leu Phe Asn Gln Ala Ile Gln Leu Asp Leu Ile Lys
            340                 345                 350

Leu Phe Ala Phe Leu Ser Ile Ile Phe Ile Val Ala Leu Xaa Arg Asn
        355                 360                 365

Val His Tyr Met Val Lys His Pro Ala Ser Phe Leu Leu Ser Pro Leu
    370                 375                 380

Tyr Gly Ile Leu His Leu Phe Val Leu Gln Pro Leu Lys Leu Tyr Ser
385                 390                 395                 400

Leu Cys Thr Ile Lys Asn Thr Glu Trp Gly Thr Arg Lys Lys Val Thr
                405                 410                 415

Ile Phe Lys

<210> SEQ ID NO 40
<211> LENGTH: 419
<212> TYPE: PRT
<213> ORGANISM: Streptococcus pyogenes
<220> FEATURE:
<221> NAME/KEY: MISC_FEATURE
<222> LOCATION: (124)..(124)
<223> OTHER INFORMATION: Xaa = Ala, Ser or any other amino acid
<220> FEATURE:
<221> NAME/KEY: MISC_FEATURE
<222> LOCATION: (402)..(402)
<223> OTHER INFORMATION: Xaa = Ala, Ser or any other amino acid

<400> SEQUENCE: 40

Met Pro Ile Phe Lys Lys Thr Leu Ile Val Leu Ser Phe Ile Phe Leu
1               5                   10                  15

Ile Ser Ile Leu Ile Tyr Leu Asn Met Tyr Leu Phe Gly Thr Ser Thr
            20                  25                  30

Val Gly Ile Tyr Gly Val Ile Leu Ile Thr Tyr Leu Val Ile Lys Leu
        35                  40                  45

Gly Leu Ser Phe Leu Tyr Glu Pro Phe Lys Gly Asn Pro His Asp Tyr
    50                  55                  60

Lys Val Ala Ala Val Ile Pro Ser Tyr Asn Glu Asp Ala Glu Ser Leu
65                  70                  75                  80

Leu Glu Thr Leu Lys Ser Val Leu Ala Gln Thr Tyr Pro Leu Ser Glu
                85                  90                  95

Ile Tyr Ile Val Asp Asp Gly Ser Ser Asn Thr Asp Ala Ile Gln Leu
```

```
                100                 105                 110
Ile Glu Glu Tyr Val Asn Arg Glu Val Asp Ile Xaa Arg Asn Val Ile
            115                 120                 125

Val His Arg Ser Leu Val Asn Lys Gly Lys Arg His Ala Gln Ala Trp
130                 135                 140

Ala Phe Glu Arg Ser Asp Ala Asp Val Phe Leu Thr Val Asp Ser Asp
145                 150                 155                 160

Thr Tyr Ile Tyr Pro Asn Ala Leu Glu Leu Leu Lys Ser Phe Asn
                165                 170                 175

Asp Glu Thr Val Tyr Ala Ala Thr Gly His Leu Asn Ala Arg Asn Arg
            180                 185                 190

Gln Thr Asn Leu Leu Thr Arg Leu Thr Asp Ile Arg Tyr Asp Asn Ala
            195                 200                 205

Phe Gly Val Glu Arg Ala Ala Gln Ser Leu Thr Gly Asn Ile Leu Val
            210                 215                 220

Cys Ser Gly Pro Leu Ser Ile Tyr Arg Arg Glu Val Ile Ile Pro Asn
225                 230                 235                 240

Leu Glu Arg Tyr Lys Asn Gln Thr Phe Leu Gly Leu Pro Val Ser Ile
                245                 250                 255

Gly Asp Asp Arg Cys Leu Thr Asn Tyr Ala Ile Asp Leu Gly Arg Thr
            260                 265                 270

Val Tyr Gln Ser Thr Ala Arg Cys Asp Thr Asp Val Pro Phe Gln Leu
            275                 280                 285

Lys Ser Tyr Leu Lys Gln Gln Asn Arg Trp Asn Lys Ser Phe Phe Arg
            290                 295                 300

Glu Ser Ile Ile Ser Val Lys Lys Ile Leu Ser Asn Pro Ile Val Ala
305                 310                 315                 320

Leu Trp Thr Ile Phe Glu Val Val Met Phe Met Leu Ile Val Ala
                325                 330                 335

Ile Gly Asn Leu Leu Phe Asn Gln Ala Ile Gln Leu Asp Leu Ile Lys
            340                 345                 350

Leu Phe Ala Phe Leu Ser Ile Ile Phe Ile Val Ala Leu Cys Arg Asn
            355                 360                 365

Val His Tyr Met Val Lys His Pro Ala Ser Phe Leu Leu Ser Pro Leu
370                 375                 380

Tyr Gly Ile Leu His Leu Phe Val Leu Gln Pro Leu Lys Leu Tyr Ser
385                 390                 395                 400

Leu Xaa Thr Ile Lys Asn Thr Glu Trp Gly Thr Arg Lys Lys Val Thr
                405                 410                 415

Ile Phe Lys

<210> SEQ ID NO 41
<211> LENGTH: 419
<212> TYPE: PRT
<213> ORGANISM: Streptococcus pyogenes
<220> FEATURE:
<221> NAME/KEY: MISC_FEATURE
<222> LOCATION: (225)..(225)
<223> OTHER INFORMATION: Xaa = Ala, Ser or any other amino acid
<220> FEATURE:
<221> NAME/KEY: MISC_FEATURE
<222> LOCATION: (261)..(261)
<223> OTHER INFORMATION: Xaa = Ala, Ser or any other amino acid

<400> SEQUENCE: 41

Met Pro Ile Phe Lys Lys Thr Leu Ile Val Leu Ser Phe Ile Phe Leu
1               5                   10                  15
```

```
Ile Ser Ile Leu Ile Tyr Leu Asn Met Tyr Leu Phe Gly Thr Ser Thr
             20                  25                  30

Val Gly Ile Tyr Gly Val Ile Leu Ile Thr Tyr Leu Val Ile Lys Leu
             35                  40                  45

Gly Leu Ser Phe Leu Tyr Glu Pro Phe Lys Gly Asn Pro His Asp Tyr
             50                  55                  60

Lys Val Ala Ala Val Ile Pro Ser Tyr Asn Glu Asp Ala Glu Ser Leu
 65                  70                  75                  80

Leu Glu Thr Leu Lys Ser Val Leu Ala Gln Thr Tyr Pro Leu Ser Glu
                 85                  90                  95

Ile Tyr Ile Val Asp Asp Gly Ser Ser Asn Thr Asp Ala Ile Gln Leu
            100                 105                 110

Ile Glu Glu Tyr Val Asn Arg Glu Val Asp Ile Cys Arg Asn Val Ile
            115                 120                 125

Val His Arg Ser Leu Val Asn Lys Gly Lys Arg His Ala Gln Ala Trp
        130                 135                 140

Ala Phe Glu Arg Ser Asp Ala Asp Val Phe Leu Thr Val Asp Ser Asp
145                 150                 155                 160

Thr Tyr Ile Tyr Pro Asn Ala Leu Glu Glu Leu Leu Lys Ser Phe Asn
                165                 170                 175

Asp Glu Thr Val Tyr Ala Ala Thr Gly His Leu Asn Ala Arg Asn Arg
            180                 185                 190

Gln Thr Asn Leu Leu Thr Arg Leu Thr Asp Ile Arg Tyr Asp Asn Ala
        195                 200                 205

Phe Gly Val Glu Arg Ala Ala Gln Ser Leu Thr Gly Asn Ile Leu Val
            210                 215                 220

Xaa Ser Gly Pro Leu Ser Ile Tyr Arg Arg Glu Val Ile Ile Pro Asn
225                 230                 235                 240

Leu Glu Arg Tyr Lys Asn Gln Thr Phe Leu Gly Leu Pro Val Ser Ile
                245                 250                 255

Gly Asp Asp Arg Xaa Leu Thr Asn Tyr Ala Ile Asp Leu Gly Arg Thr
            260                 265                 270

Val Tyr Gln Ser Thr Ala Arg Cys Asp Thr Asp Val Pro Phe Gln Leu
        275                 280                 285

Lys Ser Tyr Leu Lys Gln Gln Asn Arg Trp Asn Lys Ser Phe Phe Arg
        290                 295                 300

Glu Ser Ile Ile Ser Val Lys Lys Ile Leu Ser Asn Pro Ile Val Ala
305                 310                 315                 320

Leu Trp Thr Ile Phe Glu Val Val Met Phe Met Met Leu Ile Val Ala
                325                 330                 335

Ile Gly Asn Leu Leu Phe Asn Gln Ala Ile Gln Leu Asp Leu Ile Lys
            340                 345                 350

Leu Phe Ala Phe Leu Ser Ile Ile Phe Ile Val Ala Leu Cys Arg Asn
        355                 360                 365

Val His Tyr Met Val Lys His Pro Ala Ser Phe Leu Leu Ser Pro Leu
    370                 375                 380

Tyr Gly Ile Leu His Leu Phe Val Leu Gln Pro Leu Lys Leu Tyr Ser
385                 390                 395                 400

Leu Cys Thr Ile Lys Asn Thr Glu Trp Gly Thr Arg Lys Lys Val Thr
                405                 410                 415

Ile Phe Lys
```

```
<210> SEQ ID NO 42
<211> LENGTH: 419
<212> TYPE: PRT
<213> ORGANISM: Streptococcus pyogenes
<220> FEATURE:
<221> NAME/KEY: MISC_FEATURE
<222> LOCATION: (225)..(280)
<223> OTHER INFORMATION: Xaa = Ala, Ser or any other amino acid
<220> FEATURE:
<221> NAME/KEY: MISC_FEATURE
<222> LOCATION: (280)..(280)
<223> OTHER INFORMATION: Xaa = Ala, Ser or any other amino acid

<400> SEQUENCE: 42

Met Pro Ile Phe Lys Lys Thr Leu Ile Val Leu Ser Phe Ile Phe Leu
1               5                   10                  15

Ile Ser Ile Leu Ile Tyr Leu Asn Met Tyr Leu Phe Gly Thr Ser Thr
            20                  25                  30

Val Gly Ile Tyr Gly Val Ile Leu Ile Thr Tyr Leu Val Ile Lys Leu
        35                  40                  45

Gly Leu Ser Phe Leu Tyr Glu Pro Phe Lys Gly Asn Pro His Asp Tyr
    50                  55                  60

Lys Val Ala Ala Val Ile Pro Ser Tyr Asn Asp Ala Glu Ser Leu
65                  70                  75                  80

Leu Glu Thr Leu Lys Ser Val Leu Ala Gln Thr Tyr Pro Leu Ser Glu
                85                  90                  95

Ile Tyr Ile Val Asp Asp Gly Ser Ser Asn Thr Asp Ala Ile Gln Leu
            100                 105                 110

Ile Glu Glu Tyr Val Asn Arg Glu Val Asp Ile Cys Arg Asn Val Ile
        115                 120                 125

Val His Arg Ser Leu Val Asn Lys Gly Lys Arg His Ala Gln Ala Trp
    130                 135                 140

Ala Phe Glu Arg Ser Asp Ala Asp Val Phe Leu Thr Val Asp Ser Asp
145                 150                 155                 160

Thr Tyr Ile Tyr Pro Asn Ala Leu Glu Glu Leu Leu Lys Ser Phe Asn
                165                 170                 175

Asp Glu Thr Val Tyr Ala Ala Thr Gly His Leu Asn Ala Arg Asn Arg
            180                 185                 190

Gln Thr Asn Leu Leu Thr Arg Leu Thr Asp Ile Arg Tyr Asp Asn Ala
        195                 200                 205

Phe Gly Val Glu Arg Ala Ala Gln Ser Leu Thr Gly Asn Ile Leu Val
    210                 215                 220

Xaa Ser Gly Pro Leu Ser Ile Tyr Arg Arg Glu Val Ile Ile Pro Asn
225                 230                 235                 240

Leu Glu Arg Tyr Lys Asn Gln Thr Phe Leu Gly Leu Pro Val Ser Ile
                245                 250                 255

Gly Asp Asp Arg Cys Leu Thr Asn Tyr Ala Ile Asp Leu Gly Arg Thr
            260                 265                 270

Val Tyr Gln Ser Thr Ala Arg Xaa Asp Thr Asp Val Pro Phe Gln Leu
        275                 280                 285

Lys Ser Tyr Leu Lys Gln Gln Asn Arg Trp Asn Lys Ser Phe Phe Arg
    290                 295                 300

Glu Ser Ile Ile Ser Val Lys Lys Ile Leu Ser Asn Pro Ile Val Ala
305                 310                 315                 320

Leu Trp Thr Ile Phe Glu Val Val Met Phe Met Met Leu Ile Val Ala
                325                 330                 335

Ile Gly Asn Leu Leu Phe Asn Gln Ala Ile Gln Leu Asp Leu Ile Lys
```

-continued

```
                340                 345                 350
Leu Phe Ala Phe Leu Ser Ile Ile Phe Ile Val Ala Leu Cys Arg Asn
            355                 360                 365

Val His Tyr Met Val Lys His Pro Ala Ser Phe Leu Leu Ser Pro Leu
        370                 375                 380

Tyr Gly Ile Leu His Leu Phe Val Leu Gln Pro Leu Lys Leu Tyr Ser
385                 390                 395                 400

Leu Cys Thr Ile Lys Asn Thr Glu Trp Gly Thr Arg Lys Lys Val Thr
                405                 410                 415

Ile Phe Lys

<210> SEQ ID NO 43
<211> LENGTH: 419
<212> TYPE: PRT
<213> ORGANISM: Streptococcus pyogenes
<220> FEATURE:
<221> NAME/KEY: MISC_FEATURE
<222> LOCATION: (225)..(225)
<223> OTHER INFORMATION: Xaa = Ala, Ser or any other amino acid
<220> FEATURE:
<221> NAME/KEY: MISC_FEATURE
<222> LOCATION: (366)..(366)
<223> OTHER INFORMATION: Xaa = Ala, Ser or any other amino acid

<400> SEQUENCE: 43

Met Pro Ile Phe Lys Lys Thr Leu Ile Val Leu Ser Phe Ile Phe Leu
1               5                   10                  15

Ile Ser Ile Leu Ile Tyr Leu Asn Met Tyr Leu Phe Gly Thr Ser Thr
            20                  25                  30

Val Gly Ile Tyr Gly Val Ile Leu Ile Thr Tyr Leu Val Ile Lys Leu
        35                  40                  45

Gly Leu Ser Phe Leu Tyr Glu Pro Phe Lys Gly Asn Pro His Asp Tyr
    50                  55                  60

Lys Val Ala Ala Val Ile Pro Ser Tyr Asn Glu Asp Ala Glu Ser Leu
65                  70                  75                  80

Leu Glu Thr Leu Lys Ser Val Leu Ala Gln Thr Tyr Pro Leu Ser Glu
                85                  90                  95

Ile Tyr Ile Val Asp Asp Gly Ser Ser Asn Thr Asp Ala Ile Gln Leu
            100                 105                 110

Ile Glu Glu Tyr Val Asn Arg Glu Val Asp Ile Cys Arg Asn Val Ile
        115                 120                 125

Val His Arg Ser Leu Val Asn Lys Gly Lys Arg His Ala Gln Ala Trp
    130                 135                 140

Ala Phe Glu Arg Ser Asp Ala Asp Val Phe Leu Thr Val Asp Ser Asp
145                 150                 155                 160

Thr Tyr Ile Tyr Pro Asn Ala Leu Glu Glu Leu Leu Lys Ser Phe Asn
                165                 170                 175

Asp Glu Thr Val Tyr Ala Ala Thr Gly His Leu Asn Ala Arg Asn Arg
            180                 185                 190

Gln Thr Asn Leu Leu Thr Arg Leu Thr Asp Ile Arg Tyr Asp Asn Ala
        195                 200                 205

Phe Gly Val Glu Arg Ala Ala Gln Ser Leu Thr Gly Asn Ile Leu Val
    210                 215                 220

Xaa Ser Gly Pro Leu Ser Ile Tyr Arg Arg Glu Val Ile Ile Pro Asn
225                 230                 235                 240

Leu Glu Arg Tyr Lys Asn Gln Thr Phe Leu Gly Leu Pro Val Ser Ile
                245                 250                 255
```

-continued

```
Gly Asp Asp Arg Cys Leu Thr Asn Tyr Ala Ile Asp Leu Gly Arg Thr
            260                 265                 270

Val Tyr Gln Ser Thr Ala Arg Cys Asp Thr Asp Val Pro Phe Gln Leu
        275                 280                 285

Lys Ser Tyr Leu Lys Gln Gln Asn Arg Trp Asn Lys Ser Phe Phe Arg
    290                 295                 300

Glu Ser Ile Ile Ser Val Lys Lys Ile Leu Ser Asn Pro Ile Val Ala
305                 310                 315                 320

Leu Trp Thr Ile Phe Glu Val Val Met Phe Met Met Leu Ile Val Ala
                325                 330                 335

Ile Gly Asn Leu Leu Phe Asn Gln Ala Ile Gln Leu Asp Leu Ile Lys
            340                 345                 350

Leu Phe Ala Phe Leu Ser Ile Ile Phe Ile Val Ala Leu Xaa Arg Asn
        355                 360                 365

Val His Tyr Met Val Lys His Pro Ala Ser Phe Leu Leu Ser Pro Leu
    370                 375                 380

Tyr Gly Ile Leu His Leu Phe Val Leu Gln Pro Leu Lys Leu Tyr Ser
385                 390                 395                 400

Leu Cys Thr Ile Lys Asn Thr Glu Trp Gly Thr Arg Lys Lys Val Thr
                405                 410                 415

Ile Phe Lys

<210> SEQ ID NO 44
<211> LENGTH: 419
<212> TYPE: PRT
<213> ORGANISM: Streptococcus pyogenes
<220> FEATURE:
<221> NAME/KEY: MISC_FEATURE
<222> LOCATION: (225)..(225)
<223> OTHER INFORMATION: Xaa = Ala, Ser or any other amino acid
<220> FEATURE:
<221> NAME/KEY: MISC_FEATURE
<222> LOCATION: (402)..(402)
<223> OTHER INFORMATION: Xaa = Ala, Ser or any other amino acid

<400> SEQUENCE: 44

Met Pro Ile Phe Lys Lys Thr Leu Ile Val Leu Ser Phe Ile Phe Leu
1               5                   10                  15

Ile Ser Ile Leu Ile Tyr Leu Asn Met Tyr Leu Phe Gly Thr Ser Thr
            20                  25                  30

Val Gly Ile Tyr Gly Val Ile Leu Ile Thr Tyr Leu Val Ile Lys Leu
        35                  40                  45

Gly Leu Ser Phe Leu Tyr Glu Pro Phe Lys Gly Asn Pro His Asp Tyr
    50                  55                  60

Lys Val Ala Ala Val Ile Pro Ser Tyr Asn Glu Asp Ala Glu Ser Leu
65                  70                  75                  80

Leu Glu Thr Leu Lys Ser Val Leu Ala Gln Thr Tyr Pro Leu Ser Glu
                85                  90                  95

Ile Tyr Ile Val Asp Asp Gly Ser Ser Asn Thr Asp Ala Ile Gln Leu
            100                 105                 110

Ile Glu Glu Tyr Val Asn Arg Glu Val Asp Ile Cys Arg Asn Val Ile
        115                 120                 125

Val His Arg Ser Leu Val Asn Lys Gly Lys Arg His Ala Gln Ala Trp
    130                 135                 140

Ala Phe Glu Arg Ser Asp Ala Asp Val Phe Leu Thr Val Asp Ser Asp
145                 150                 155                 160
```

```
Thr Tyr Ile Tyr Pro Asn Ala Leu Glu Glu Leu Leu Lys Ser Phe Asn
                165                 170                 175

Asp Glu Thr Val Tyr Ala Ala Thr Gly His Leu Asn Ala Arg Asn Arg
            180                 185                 190

Gln Thr Asn Leu Leu Thr Arg Leu Thr Asp Ile Arg Tyr Asp Asn Ala
        195                 200                 205

Phe Gly Val Glu Arg Ala Ala Gln Ser Leu Thr Gly Asn Ile Leu Val
    210                 215                 220

Xaa Ser Gly Pro Leu Ser Ile Tyr Arg Arg Glu Val Ile Ile Pro Asn
225                 230                 235                 240

Leu Glu Arg Tyr Lys Asn Gln Thr Phe Leu Gly Leu Pro Val Ser Ile
                245                 250                 255

Gly Asp Asp Arg Cys Leu Thr Asn Tyr Ala Ile Asp Leu Gly Arg Thr
            260                 265                 270

Val Tyr Gln Ser Thr Ala Arg Cys Asp Thr Asp Val Pro Phe Gln Leu
        275                 280                 285

Lys Ser Tyr Leu Lys Gln Gln Asn Arg Trp Asn Lys Ser Phe Phe Arg
    290                 295                 300

Glu Ser Ile Ile Ser Val Lys Lys Ile Leu Ser Asn Pro Ile Val Ala
305                 310                 315                 320

Leu Trp Thr Ile Phe Glu Val Val Met Phe Met Met Leu Ile Val Ala
                325                 330                 335

Ile Gly Asn Leu Leu Phe Asn Gln Ala Ile Gln Leu Asp Leu Ile Lys
            340                 345                 350

Leu Phe Ala Phe Leu Ser Ile Ile Phe Ile Val Ala Leu Cys Arg Asn
        355                 360                 365

Val His Tyr Met Val Lys His Pro Ala Ser Phe Leu Leu Ser Pro Leu
    370                 375                 380

Tyr Gly Ile Leu His Leu Phe Val Leu Gln Pro Leu Lys Leu Tyr Ser
385                 390                 395                 400

Leu Xaa Thr Ile Lys Asn Thr Glu Trp Gly Thr Arg Lys Lys Val Thr
                405                 410                 415

Ile Phe Lys

<210> SEQ ID NO 45
<211> LENGTH: 419
<212> TYPE: PRT
<213> ORGANISM: Streptococcus pyogenes
<220> FEATURE:
<221> NAME/KEY: MISC_FEATURE
<222> LOCATION: (261)..(261)
<223> OTHER INFORMATION: Xaa = Ala, Ser or any other amino acid
<220> FEATURE:
<221> NAME/KEY: MISC_FEATURE
<222> LOCATION: (280)..(280)
<223> OTHER INFORMATION: Xaa = Ala, Ser or any other amino acid

<400> SEQUENCE: 45

Met Pro Ile Phe Lys Lys Thr Leu Ile Val Leu Ser Phe Ile Phe Leu
1               5                   10                  15

Ile Ser Ile Leu Ile Tyr Leu Asn Met Tyr Leu Phe Gly Thr Ser Thr
            20                  25                  30

Val Gly Ile Tyr Gly Val Ile Leu Ile Thr Tyr Leu Val Ile Lys Leu
        35                  40                  45

Gly Leu Ser Phe Leu Tyr Glu Pro Phe Lys Gly Asn Pro His Asp Tyr
    50                  55                  60

Lys Val Ala Ala Val Ile Pro Ser Tyr Asn Glu Asp Ala Glu Ser Leu
```

```
              65                  70                  75                  80
Leu Glu Thr Leu Lys Ser Val Leu Ala Gln Thr Tyr Pro Leu Ser Glu
                    85                  90                  95

Ile Tyr Ile Val Asp Asp Gly Ser Ser Asn Thr Asp Ala Ile Gln Leu
                100                 105                 110

Ile Glu Glu Tyr Val Asn Arg Glu Val Asp Ile Cys Arg Asn Val Ile
                115                 120                 125

Val His Arg Ser Leu Val Asn Lys Gly Lys Arg His Ala Gln Ala Trp
    130                 135                 140

Ala Phe Glu Arg Ser Asp Ala Asp Val Phe Leu Thr Val Asp Ser Asp
145                 150                 155                 160

Thr Tyr Ile Tyr Pro Asn Ala Leu Glu Glu Leu Leu Lys Ser Phe Asn
                165                 170                 175

Asp Glu Thr Val Tyr Ala Ala Thr Gly His Leu Asn Ala Arg Asn Arg
                180                 185                 190

Gln Thr Asn Leu Leu Thr Arg Leu Thr Asp Ile Arg Tyr Asp Asn Ala
                195                 200                 205

Phe Gly Val Glu Arg Ala Ala Gln Ser Leu Thr Gly Asn Ile Leu Val
    210                 215                 220

Cys Ser Gly Pro Leu Ser Ile Tyr Arg Arg Glu Val Ile Ile Pro Asn
225                 230                 235                 240

Leu Glu Arg Tyr Lys Asn Gln Thr Phe Leu Gly Leu Pro Val Ser Ile
                245                 250                 255

Gly Asp Asp Arg Xaa Leu Thr Asn Tyr Ala Ile Asp Leu Gly Arg Thr
                260                 265                 270

Val Tyr Gln Ser Thr Ala Arg Xaa Asp Thr Asp Val Pro Phe Gln Leu
                275                 280                 285

Lys Ser Tyr Leu Lys Gln Gln Asn Arg Trp Asn Lys Ser Phe Phe Arg
    290                 295                 300

Glu Ser Ile Ile Ser Val Lys Lys Ile Leu Ser Asn Pro Ile Val Ala
305                 310                 315                 320

Leu Trp Thr Ile Phe Glu Val Val Met Phe Met Met Leu Ile Val Ala
                325                 330                 335

Ile Gly Asn Leu Leu Phe Asn Gln Ala Ile Gln Leu Asp Leu Ile Lys
                340                 345                 350

Leu Phe Ala Phe Leu Ser Ile Ile Phe Ile Val Ala Leu Cys Arg Asn
                355                 360                 365

Val His Tyr Met Val Lys His Pro Ala Ser Phe Leu Leu Ser Pro Leu
    370                 375                 380

Tyr Gly Ile Leu His Leu Phe Val Leu Gln Pro Leu Lys Leu Tyr Ser
385                 390                 395                 400

Leu Cys Thr Ile Lys Asn Thr Glu Trp Gly Thr Arg Lys Lys Val Thr
                405                 410                 415

Ile Phe Lys

<210> SEQ ID NO 46
<211> LENGTH: 419
<212> TYPE: PRT
<213> ORGANISM: Streptococcus pyogenes
<220> FEATURE:
<221> NAME/KEY: MISC_FEATURE
<222> LOCATION: (261)..(261)
<223> OTHER INFORMATION: Xaa = Ala, Ser or any other amino acid
<220> FEATURE:
<221> NAME/KEY: MISC_FEATURE
<222> LOCATION: (366)..(366)
```

<223> OTHER INFORMATION: Xaa = Ala, Ser or any other amino acid

<400> SEQUENCE: 46

```
Met Pro Ile Phe Lys Lys Thr Leu Ile Val Leu Ser Phe Ile Phe Leu
1               5                   10                  15
Ile Ser Ile Leu Ile Tyr Leu Asn Met Tyr Leu Phe Gly Thr Ser Thr
            20                  25                  30
Val Gly Ile Tyr Gly Val Ile Leu Ile Thr Tyr Leu Val Ile Lys Leu
        35                  40                  45
Gly Leu Ser Phe Leu Tyr Glu Pro Phe Lys Gly Asn Pro His Asp Tyr
50                  55                  60
Lys Val Ala Ala Val Ile Pro Ser Tyr Asn Glu Asp Ala Glu Ser Leu
65                  70                  75                  80
Leu Glu Thr Leu Lys Ser Val Leu Ala Gln Thr Tyr Pro Leu Ser Glu
                85                  90                  95
Ile Tyr Ile Val Asp Asp Gly Ser Ser Asn Thr Asp Ala Ile Gln Leu
            100                 105                 110
Ile Glu Glu Tyr Val Asn Arg Glu Val Asp Ile Cys Arg Asn Val Ile
        115                 120                 125
Val His Arg Ser Leu Val Asn Lys Gly Lys Arg His Ala Gln Ala Trp
130                 135                 140
Ala Phe Glu Arg Ser Asp Ala Asp Val Phe Leu Thr Val Asp Ser Asp
145                 150                 155                 160
Thr Tyr Ile Tyr Pro Asn Ala Leu Glu Glu Leu Leu Lys Ser Phe Asn
                165                 170                 175
Asp Glu Thr Val Tyr Ala Ala Thr Gly His Leu Asn Ala Arg Asn Arg
            180                 185                 190
Gln Thr Asn Leu Leu Thr Arg Leu Thr Asp Ile Arg Tyr Asp Asn Ala
        195                 200                 205
Phe Gly Val Glu Arg Ala Ala Gln Ser Leu Thr Gly Asn Ile Leu Val
210                 215                 220
Cys Ser Gly Pro Leu Ser Ile Tyr Arg Arg Glu Val Ile Ile Pro Asn
225                 230                 235                 240
Leu Glu Arg Tyr Lys Asn Gln Thr Phe Leu Gly Leu Pro Val Ser Ile
                245                 250                 255
Gly Asp Asp Arg Xaa Leu Thr Asn Tyr Ala Ile Asp Leu Gly Arg Thr
            260                 265                 270
Val Tyr Gln Ser Thr Ala Arg Cys Asp Thr Asp Val Pro Phe Gln Leu
        275                 280                 285
Lys Ser Tyr Leu Lys Gln Gln Asn Arg Trp Asn Lys Ser Phe Phe Arg
290                 295                 300
Glu Ser Ile Ile Ser Val Lys Lys Ile Leu Ser Asn Pro Ile Val Ala
305                 310                 315                 320
Leu Trp Thr Ile Phe Glu Val Val Met Phe Met Met Leu Ile Val Ala
                325                 330                 335
Ile Gly Asn Leu Leu Phe Asn Gln Ala Ile Gln Leu Asp Leu Ile Lys
            340                 345                 350
Leu Phe Ala Phe Leu Ser Ile Ile Phe Ile Val Ala Leu Xaa Arg Asn
        355                 360                 365
Val His Tyr Met Val Lys His Pro Ala Ser Phe Leu Leu Ser Pro Leu
370                 375                 380
Tyr Gly Ile Leu His Leu Phe Val Leu Gln Pro Leu Lys Leu Tyr Ser
385                 390                 395                 400
```

-continued

```
Leu Cys Thr Ile Lys Asn Thr Glu Trp Gly Thr Arg Lys Val Thr
                405                 410                 415

Ile Phe Lys

<210> SEQ ID NO 47
<211> LENGTH: 419
<212> TYPE: PRT
<213> ORGANISM: Streptococcus pyogenes
<220> FEATURE:
<221> NAME/KEY: MISC_FEATURE
<222> LOCATION: (261)..(261)
<223> OTHER INFORMATION: Xaa = Ala, Ser or any other amino acid
<220> FEATURE:
<221> NAME/KEY: MISC_FEATURE
<222> LOCATION: (402)..(402)
<223> OTHER INFORMATION: Xaa = Ala, Ser or any other amino acid

<400> SEQUENCE: 47

Met Pro Ile Phe Lys Lys Thr Leu Ile Val Leu Ser Phe Ile Phe Leu
1               5                   10                  15

Ile Ser Ile Leu Ile Tyr Leu Asn Met Tyr Leu Phe Gly Thr Ser Thr
            20                  25                  30

Val Gly Ile Tyr Gly Val Ile Leu Ile Thr Tyr Leu Val Ile Lys Leu
        35                  40                  45

Gly Leu Ser Phe Leu Tyr Glu Pro Phe Lys Gly Asn Pro His Asp Tyr
    50                  55                  60

Lys Val Ala Ala Val Ile Pro Ser Tyr Asn Glu Asp Ala Glu Ser Leu
65                  70                  75                  80

Leu Glu Thr Leu Lys Ser Val Leu Ala Gln Thr Tyr Pro Leu Ser Glu
                85                  90                  95

Ile Tyr Ile Val Asp Asp Gly Ser Ser Asn Thr Asp Ala Ile Gln Leu
            100                 105                 110

Ile Glu Glu Tyr Val Asn Arg Glu Val Asp Ile Cys Arg Asn Val Ile
        115                 120                 125

Val His Arg Ser Leu Val Asn Lys Gly Lys Arg His Ala Gln Ala Trp
    130                 135                 140

Ala Phe Glu Arg Ser Asp Ala Asp Val Phe Leu Thr Val Asp Ser Asp
145                 150                 155                 160

Thr Tyr Ile Tyr Pro Asn Ala Leu Glu Glu Leu Leu Lys Ser Phe Asn
                165                 170                 175

Asp Glu Thr Val Tyr Ala Ala Thr Gly His Leu Asn Ala Arg Asn Arg
            180                 185                 190

Gln Thr Asn Leu Leu Thr Arg Leu Thr Asp Ile Arg Tyr Asp Asn Ala
        195                 200                 205

Phe Gly Val Glu Arg Ala Ala Gln Ser Leu Thr Gly Asn Ile Leu Val
    210                 215                 220

Cys Ser Gly Pro Leu Ser Ile Tyr Arg Arg Glu Val Ile Ile Pro Asn
225                 230                 235                 240

Leu Glu Arg Tyr Lys Asn Gln Thr Phe Leu Gly Leu Pro Val Ser Ile
                245                 250                 255

Gly Asp Asp Arg Xaa Leu Thr Asn Tyr Ala Ile Asp Leu Gly Arg Thr
            260                 265                 270

Val Tyr Gln Ser Thr Ala Arg Cys Asp Thr Asp Val Pro Phe Gln Leu
        275                 280                 285

Lys Ser Tyr Leu Lys Gln Gln Asn Arg Trp Asn Lys Ser Phe Phe Arg
    290                 295                 300

Glu Ser Ile Ile Ser Val Lys Lys Ile Leu Ser Asn Pro Ile Val Ala
```

```
                        305                 310                 315                 320
Leu Trp Thr Ile Phe Glu Val Val Met Phe Met Met Leu Ile Val Ala
                325                 330                 335
Ile Gly Asn Leu Leu Phe Asn Gln Ala Ile Gln Leu Asp Leu Ile Lys
                340                 345                 350
Leu Phe Ala Phe Leu Ser Ile Ile Phe Ile Val Ala Leu Cys Arg Asn
                355                 360                 365
Val His Tyr Met Val Lys His Pro Ala Ser Phe Leu Leu Ser Pro Leu
        370                 375                 380
Tyr Gly Ile Leu His Leu Phe Val Leu Gln Pro Leu Lys Leu Tyr Ser
385                 390                 395                 400
Leu Xaa Thr Ile Lys Asn Thr Glu Trp Gly Thr Arg Lys Lys Val Thr
                405                 410                 415

Ile Phe Lys

<210> SEQ ID NO 48
<211> LENGTH: 419
<212> TYPE: PRT
<213> ORGANISM: Streptococcus pyogenes
<220> FEATURE:
<221> NAME/KEY: MISC_FEATURE
<222> LOCATION: (280)..(280)
<223> OTHER INFORMATION: Xaa = Ala, Ser or any other amino acid
<220> FEATURE:
<221> NAME/KEY: MISC_FEATURE
<222> LOCATION: (366)..(366)
<223> OTHER INFORMATION: Xaa = Ala, Ser or any other amino acid

<400> SEQUENCE: 48

Met Pro Ile Phe Lys Lys Thr Leu Ile Val Leu Ser Phe Ile Phe Leu
1               5                   10                  15
Ile Ser Ile Leu Ile Tyr Leu Asn Met Tyr Leu Phe Gly Thr Ser Thr
                20                  25                  30
Val Gly Ile Tyr Gly Val Ile Leu Ile Thr Tyr Leu Val Ile Lys Leu
            35                  40                  45
Gly Leu Ser Phe Leu Tyr Glu Pro Phe Lys Gly Asn Pro His Asp Tyr
    50                  55                  60
Lys Val Ala Ala Val Ile Pro Ser Tyr Asn Glu Asp Ala Glu Ser Leu
65                  70                  75                  80
Leu Glu Thr Leu Lys Ser Val Leu Ala Gln Thr Tyr Pro Leu Ser Glu
                85                  90                  95
Ile Tyr Ile Val Asp Asp Gly Ser Ser Asn Thr Asp Ala Ile Gln Leu
            100                 105                 110
Ile Glu Glu Tyr Val Asn Arg Glu Val Asp Ile Cys Arg Asn Val Ile
        115                 120                 125
Val His Arg Ser Leu Val Asn Lys Gly Lys Arg His Ala Gln Ala Trp
    130                 135                 140
Ala Phe Glu Arg Ser Asp Ala Asp Val Phe Leu Thr Val Asp Ser Asp
145                 150                 155                 160
Thr Tyr Ile Tyr Pro Asn Ala Leu Glu Glu Leu Leu Lys Ser Phe Asn
                165                 170                 175
Asp Glu Thr Val Tyr Ala Ala Thr Gly His Leu Asn Ala Arg Asn Arg
            180                 185                 190
Gln Thr Asn Leu Leu Thr Arg Leu Thr Asp Ile Arg Tyr Asp Asn Ala
        195                 200                 205
Phe Gly Val Glu Arg Ala Ala Gln Ser Leu Thr Gly Asn Ile Leu Val
    210                 215                 220
```

-continued

```
Cys Ser Gly Pro Leu Ser Ile Tyr Arg Arg Glu Val Ile Ile Pro Asn
225                 230                 235                 240

Leu Glu Arg Tyr Lys Asn Gln Thr Phe Leu Gly Leu Pro Val Ser Ile
            245                 250                 255

Gly Asp Asp Arg Cys Leu Thr Asn Tyr Ala Ile Asp Leu Gly Arg Thr
            260                 265                 270

Val Tyr Gln Ser Thr Ala Arg Xaa Asp Thr Asp Val Pro Phe Gln Leu
        275                 280                 285

Lys Ser Tyr Leu Lys Gln Gln Asn Arg Trp Asn Lys Ser Phe Phe Arg
    290                 295                 300

Glu Ser Ile Ile Ser Val Lys Lys Ile Leu Ser Asn Pro Ile Val Ala
305                 310                 315                 320

Leu Trp Thr Ile Phe Glu Val Val Met Phe Met Met Leu Ile Val Ala
                325                 330                 335

Ile Gly Asn Leu Leu Phe Asn Gln Ala Ile Gln Leu Asp Leu Ile Lys
            340                 345                 350

Leu Phe Ala Phe Leu Ser Ile Ile Phe Ile Val Ala Leu Xaa Arg Asn
        355                 360                 365

Val His Tyr Met Val Lys His Pro Ala Ser Phe Leu Leu Ser Pro Leu
    370                 375                 380

Tyr Gly Ile Leu His Leu Phe Val Leu Gln Pro Leu Lys Leu Tyr Ser
385                 390                 395                 400

Leu Cys Thr Ile Lys Asn Thr Glu Trp Gly Thr Arg Lys Lys Val Thr
                405                 410                 415

Ile Phe Lys

<210> SEQ ID NO 49
<211> LENGTH: 419
<212> TYPE: PRT
<213> ORGANISM: Streptococcus pyogenes
<220> FEATURE:
<221> NAME/KEY: MISC_FEATURE
<222> LOCATION: (280)..(280)
<223> OTHER INFORMATION: Xaa = Ala, Ser or any other amino acid
<220> FEATURE:
<221> NAME/KEY: MISC_FEATURE
<222> LOCATION: (402)..(402)
<223> OTHER INFORMATION: Xaa = Ala, Ser or any other amino acid

<400> SEQUENCE: 49

Met Pro Ile Phe Lys Lys Thr Leu Ile Val Leu Ser Phe Ile Phe Leu
1               5                   10                  15

Ile Ser Ile Leu Ile Tyr Leu Asn Met Tyr Leu Phe Gly Thr Ser Thr
            20                  25                  30

Val Gly Ile Tyr Gly Val Ile Leu Ile Thr Tyr Leu Val Ile Lys Leu
        35                  40                  45

Gly Leu Ser Phe Leu Tyr Glu Pro Phe Lys Gly Asn Pro His Asp Tyr
    50                  55                  60

Lys Val Ala Ala Val Ile Pro Ser Tyr Asn Glu Asp Ala Glu Ser Leu
65                  70                  75                  80

Leu Glu Thr Leu Lys Ser Val Leu Ala Gln Thr Tyr Pro Leu Ser Glu
                85                  90                  95

Ile Tyr Ile Val Asp Asp Gly Ser Ser Asn Thr Asp Ala Ile Gln Leu
            100                 105                 110

Ile Glu Glu Tyr Val Asn Arg Glu Val Asp Ile Cys Arg Asn Val Ile
        115                 120                 125
```

-continued

```
Val His Arg Ser Leu Val Asn Lys Gly Lys Arg His Ala Gln Ala Trp
    130                 135                 140
Ala Phe Glu Arg Ser Asp Ala Asp Val Phe Leu Thr Val Asp Ser Asp
145                 150                 155                 160
Thr Tyr Ile Tyr Pro Asn Ala Leu Glu Glu Leu Leu Lys Ser Phe Asn
                165                 170                 175
Asp Glu Thr Val Tyr Ala Ala Thr Gly His Leu Asn Ala Arg Asn Arg
            180                 185                 190
Gln Thr Asn Leu Leu Thr Arg Leu Thr Asp Ile Arg Tyr Asp Asn Ala
        195                 200                 205
Phe Gly Val Glu Arg Ala Ala Gln Ser Leu Thr Gly Asn Ile Leu Val
    210                 215                 220
Cys Ser Gly Pro Leu Ser Ile Tyr Arg Arg Glu Val Ile Ile Pro Asn
225                 230                 235                 240
Leu Glu Arg Tyr Lys Asn Gln Thr Phe Leu Gly Leu Pro Val Ser Ile
                245                 250                 255
Gly Asp Asp Arg Cys Leu Thr Asn Tyr Ala Ile Asp Leu Gly Arg Thr
            260                 265                 270
Val Tyr Gln Ser Thr Ala Arg Xaa Asp Thr Asp Val Pro Phe Gln Leu
        275                 280                 285
Lys Ser Tyr Leu Lys Gln Gln Asn Arg Trp Asn Lys Ser Phe Arg
    290                 295                 300
Glu Ser Ile Ile Ser Val Lys Lys Ile Leu Ser Asn Pro Ile Val Ala
305                 310                 315                 320
Leu Trp Thr Ile Phe Glu Val Val Met Phe Met Met Leu Ile Val Ala
                325                 330                 335
Ile Gly Asn Leu Leu Phe Asn Gln Ala Ile Gln Leu Asp Leu Ile Lys
            340                 345                 350
Leu Phe Ala Phe Leu Ser Ile Ile Phe Ile Val Ala Leu Cys Arg Asn
        355                 360                 365
Val His Tyr Met Val Lys His Pro Ala Ser Phe Leu Leu Ser Pro Leu
    370                 375                 380
Tyr Gly Ile Leu His Leu Phe Val Leu Gln Pro Leu Lys Leu Tyr Ser
385                 390                 395                 400
Leu Xaa Thr Ile Lys Asn Thr Glu Trp Gly Thr Arg Lys Lys Val Thr
                405                 410                 415
Ile Phe Lys
```

```
<210> SEQ ID NO 50
<211> LENGTH: 419
<212> TYPE: PRT
<213> ORGANISM: Streptococcus pyogenes
<220> FEATURE:
<221> NAME/KEY: MISC_FEATURE
<222> LOCATION: (366)..(366)
<223> OTHER INFORMATION: Xaa= Ala, Ser or any other amino acid
<220> FEATURE:
<221> NAME/KEY: MISC_FEATURE
<222> LOCATION: (402)..(402)
<223> OTHER INFORMATION: Xaa= Ala, Ser or any other amino acid

<400> SEQUENCE: 50
```

```
Met Pro Ile Phe Lys Lys Thr Leu Ile Val Leu Ser Phe Ile Phe Leu
1               5                   10                  15
Ile Ser Ile Leu Ile Tyr Leu Asn Met Tyr Leu Phe Gly Thr Ser Thr
            20                  25                  30
Val Gly Ile Tyr Gly Val Ile Leu Ile Thr Tyr Leu Val Ile Lys Leu
```

```
            35                  40                  45
Gly Leu Ser Phe Leu Tyr Glu Pro Phe Lys Gly Asn Pro His Asp Tyr
 50                  55                  60

Lys Val Ala Val Ile Pro Ser Tyr Asn Glu Asp Ala Glu Ser Leu
 65                  70                  75                  80

Leu Glu Thr Leu Lys Ser Val Leu Ala Gln Thr Tyr Pro Leu Ser Glu
                 85                  90                  95

Ile Tyr Ile Val Asp Asp Gly Ser Ser Asn Thr Asp Ala Ile Gln Leu
                100                 105                 110

Ile Glu Glu Tyr Val Asn Arg Glu Val Asp Ile Cys Arg Asn Val Ile
                115                 120                 125

Val His Arg Ser Leu Val Asn Lys Gly Lys Arg His Ala Gln Ala Trp
130                 135                 140

Ala Phe Glu Arg Ser Asp Ala Asp Val Phe Leu Thr Val Asp Ser Asp
145                 150                 155                 160

Thr Tyr Ile Tyr Pro Asn Ala Leu Glu Glu Leu Leu Lys Ser Phe Asn
                165                 170                 175

Asp Glu Thr Val Tyr Ala Ala Thr Gly His Leu Asn Ala Arg Asn Arg
                180                 185                 190

Gln Thr Asn Leu Leu Thr Arg Leu Thr Asp Ile Arg Tyr Asp Asn Ala
                195                 200                 205

Phe Gly Val Glu Arg Ala Ala Gln Ser Leu Thr Gly Asn Ile Leu Val
210                 215                 220

Cys Ser Gly Pro Leu Ser Ile Tyr Arg Arg Glu Val Ile Ile Pro Asn
225                 230                 235                 240

Leu Glu Arg Tyr Lys Asn Gln Thr Phe Leu Gly Leu Pro Val Ser Ile
                245                 250                 255

Gly Asp Asp Arg Cys Leu Thr Asn Tyr Ala Ile Asp Leu Gly Arg Thr
                260                 265                 270

Val Tyr Gln Ser Thr Ala Arg Cys Asp Thr Asp Val Pro Phe Gln Leu
                275                 280                 285

Lys Ser Tyr Leu Lys Gln Gln Asn Arg Trp Asn Lys Ser Phe Phe Arg
290                 295                 300

Glu Ser Ile Ile Ser Val Lys Lys Ile Leu Ser Asn Pro Ile Val Ala
305                 310                 315                 320

Leu Trp Thr Ile Phe Glu Val Val Met Phe Met Leu Ile Val Ala
                325                 330                 335

Ile Gly Asn Leu Leu Phe Asn Gln Ala Ile Gln Leu Asp Leu Ile Lys
                340                 345                 350

Leu Phe Ala Phe Leu Ser Ile Ile Phe Ile Val Ala Leu Xaa Arg Asn
                355                 360                 365

Val His Tyr Met Val Lys His Pro Ala Ser Phe Leu Leu Ser Pro Leu
370                 375                 380

Tyr Gly Ile Leu His Leu Phe Val Leu Gln Pro Leu Lys Leu Tyr Ser
385                 390                 395                 400

Leu Xaa Thr Ile Lys Asn Thr Glu Trp Gly Thr Arg Lys Lys Val Thr
                405                 410                 415

Ile Phe Lys

<210> SEQ ID NO 51
<211> LENGTH: 419
<212> TYPE: PRT
<213> ORGANISM: Streptococcus pyogenes
<220> FEATURE:
```

```
<221> NAME/KEY: MISC_FEATURE
<222> LOCATION: (124)..(124)
<223> OTHER INFORMATION: Xaa = Ala, Ser or any other amino acid
<220> FEATURE:
<221> NAME/KEY: MISC_FEATURE
<222> LOCATION: (261)..(261)
<223> OTHER INFORMATION: Xaa = Ala, Ser or any other amino acid
<220> FEATURE:
<221> NAME/KEY: MISC_FEATURE
<222> LOCATION: (225)..(225)
<223> OTHER INFORMATION: Xaa = Ala, Ser or any other amino acid

<400> SEQUENCE: 51

Met Pro Ile Phe Lys Lys Thr Leu Ile Val Leu Ser Phe Ile Phe Leu
1               5                   10                  15

Ile Ser Ile Leu Ile Tyr Leu Asn Met Tyr Leu Phe Gly Thr Ser Thr
            20                  25                  30

Val Gly Ile Tyr Gly Val Ile Leu Ile Thr Tyr Leu Val Ile Lys Leu
        35                  40                  45

Gly Leu Ser Phe Leu Tyr Glu Pro Phe Lys Gly Asn Pro His Asp Tyr
50                  55                  60

Lys Val Ala Ala Val Ile Pro Ser Tyr Asn Glu Asp Ala Glu Ser Leu
65                  70                  75                  80

Leu Glu Thr Leu Lys Ser Val Leu Ala Gln Thr Tyr Pro Leu Ser Glu
                85                  90                  95

Ile Tyr Ile Val Asp Asp Gly Ser Ser Asn Thr Asp Ala Ile Gln Leu
            100                 105                 110

Ile Glu Glu Tyr Val Asn Arg Glu Val Asp Ile Xaa Arg Asn Val Ile
        115                 120                 125

Val His Arg Ser Leu Val Asn Lys Gly Lys Arg His Ala Gln Ala Trp
130                 135                 140

Ala Phe Glu Arg Ser Asp Ala Asp Val Phe Leu Thr Val Asp Ser Asp
145                 150                 155                 160

Thr Tyr Ile Tyr Pro Asn Ala Leu Glu Glu Leu Leu Lys Ser Phe Asn
                165                 170                 175

Asp Glu Thr Val Tyr Ala Ala Thr Gly His Leu Asn Ala Arg Asn Arg
            180                 185                 190

Gln Thr Asn Leu Leu Thr Arg Leu Thr Asp Ile Arg Tyr Asp Asn Ala
        195                 200                 205

Phe Gly Val Glu Arg Ala Ala Gln Ser Leu Thr Gly Asn Ile Leu Val
210                 215                 220

Xaa Ser Gly Pro Leu Ser Ile Tyr Arg Arg Glu Val Ile Ile Pro Asn
225                 230                 235                 240

Leu Glu Arg Tyr Lys Asn Gln Thr Phe Leu Gly Leu Pro Val Ser Ile
                245                 250                 255

Gly Asp Asp Arg Xaa Leu Thr Asn Tyr Ala Ile Asp Leu Gly Arg Thr
            260                 265                 270

Val Tyr Gln Ser Thr Ala Arg Cys Asp Thr Asp Val Pro Phe Gln Leu
        275                 280                 285

Lys Ser Tyr Leu Lys Gln Gln Asn Arg Trp Asn Lys Ser Phe Phe Arg
290                 295                 300

Glu Ser Ile Ile Ser Val Lys Lys Ile Leu Ser Asn Pro Ile Val Ala
305                 310                 315                 320

Leu Trp Thr Ile Phe Glu Val Met Phe Met Leu Ile Val Ala
                325                 330                 335

Ile Gly Asn Leu Leu Phe Asn Gln Ala Ile Gln Leu Asp Leu Ile Lys
            340                 345                 350
```

-continued

```
Leu Phe Ala Phe Leu Ser Ile Ile Phe Ile Val Ala Leu Cys Arg Asn
            355                 360                 365

Val His Tyr Met Val Lys His Pro Ala Ser Phe Leu Leu Ser Pro Leu
    370                 375                 380

Tyr Gly Ile Leu His Leu Phe Val Leu Gln Pro Leu Lys Leu Tyr Ser
385                 390                 395                 400

Leu Cys Thr Ile Lys Asn Thr Glu Trp Gly Thr Arg Lys Lys Val Thr
                405                 410                 415

Ile Phe Lys

<210> SEQ ID NO 52
<211> LENGTH: 419
<212> TYPE: PRT
<213> ORGANISM: Streptococcus pyogenes
<220> FEATURE:
<221> NAME/KEY: MISC_FEATURE
<222> LOCATION: (124)..(124)
<223> OTHER INFORMATION: Xaa = Ala, Ser or any other amino acid
<220> FEATURE:
<221> NAME/KEY: MISC_FEATURE
<222> LOCATION: (225)..(225)
<223> OTHER INFORMATION: Xaa = Ala, Ser or any other amino acid
<220> FEATURE:
<221> NAME/KEY: MISC_FEATURE
<222> LOCATION: (280)..(280)
<223> OTHER INFORMATION: Xaa = Ala, Ser or any other amino acid

<400> SEQUENCE: 52

Met Pro Ile Phe Lys Lys Thr Leu Ile Val Leu Ser Phe Ile Phe Leu
1               5                   10                  15

Ile Ser Ile Leu Ile Tyr Leu Asn Met Tyr Leu Phe Gly Thr Ser Thr
            20                  25                  30

Val Gly Ile Tyr Gly Val Ile Leu Ile Thr Tyr Leu Val Ile Lys Leu
        35                  40                  45

Gly Leu Ser Phe Leu Tyr Glu Pro Phe Lys Gly Asn Pro His Asp Tyr
    50                  55                  60

Lys Val Ala Ala Val Ile Pro Ser Tyr Asn Glu Asp Ala Glu Ser Leu
65                  70                  75                  80

Leu Glu Thr Leu Lys Ser Val Leu Ala Gln Thr Tyr Pro Leu Ser Glu
                85                  90                  95

Ile Tyr Ile Val Asp Asp Gly Ser Ser Asn Thr Asp Ala Ile Gln Leu
            100                 105                 110

Ile Glu Glu Tyr Val Asn Arg Glu Val Asp Ile Xaa Arg Asn Val Ile
        115                 120                 125

Val His Arg Ser Leu Val Asn Lys Gly Lys Arg His Ala Gln Ala Trp
    130                 135                 140

Ala Phe Glu Arg Ser Asp Ala Asp Val Phe Leu Thr Val Asp Ser Asp
145                 150                 155                 160

Thr Tyr Ile Tyr Pro Asn Ala Leu Glu Glu Leu Leu Lys Ser Phe Asn
                165                 170                 175

Asp Glu Thr Val Tyr Ala Ala Thr Gly His Leu Asn Ala Arg Asn Arg
            180                 185                 190

Gln Thr Asn Leu Leu Thr Arg Leu Thr Asp Ile Arg Tyr Asp Asn Ala
        195                 200                 205

Phe Gly Val Glu Arg Ala Ala Gln Ser Leu Thr Gly Asn Ile Leu Val
    210                 215                 220

Xaa Ser Gly Pro Leu Ser Ile Tyr Arg Arg Glu Val Ile Ile Pro Asn
225                 230                 235                 240
```

```
Leu Glu Arg Tyr Lys Asn Gln Thr Phe Leu Gly Leu Pro Val Ser Ile
                245                 250                 255

Gly Asp Asp Arg Cys Leu Thr Asn Tyr Ala Ile Asp Leu Gly Arg Thr
            260                 265                 270

Val Tyr Gln Ser Thr Ala Arg Xaa Asp Thr Asp Val Pro Phe Gln Leu
        275                 280                 285

Lys Ser Tyr Leu Lys Gln Gln Asn Arg Trp Asn Lys Ser Phe Phe Arg
    290                 295                 300

Glu Ser Ile Ile Ser Val Lys Lys Ile Leu Ser Asn Pro Ile Val Ala
305                 310                 315                 320

Leu Trp Thr Ile Phe Glu Val Met Phe Met Met Leu Ile Val Ala
                325                 330                 335

Ile Gly Asn Leu Leu Phe Asn Gln Ala Ile Gln Leu Asp Leu Ile Lys
                340                 345                 350

Leu Phe Ala Phe Leu Ser Ile Ile Phe Ile Val Ala Leu Cys Arg Asn
            355                 360                 365

Val His Tyr Met Val Lys His Pro Ala Ser Phe Leu Leu Ser Pro Leu
    370                 375                 380

Tyr Gly Ile Leu His Leu Phe Val Leu Gln Pro Leu Lys Leu Tyr Ser
385                 390                 395                 400

Leu Cys Thr Ile Lys Asn Thr Glu Trp Gly Thr Arg Lys Lys Val Thr
                405                 410                 415

Ile Phe Lys

<210> SEQ ID NO 53
<211> LENGTH: 419
<212> TYPE: PRT
<213> ORGANISM: Streptococcus pyogenes
<220> FEATURE:
<221> NAME/KEY: MISC_FEATURE
<222> LOCATION: (124)..(124)
<223> OTHER INFORMATION: Xaa = Ala, Ser or any other amino acid
<220> FEATURE:
<221> NAME/KEY: MISC_FEATURE
<222> LOCATION: (225)..(225)
<223> OTHER INFORMATION: Xaa = Ala, Ser or any other amino acid
<220> FEATURE:
<221> NAME/KEY: MISC_FEATURE
<222> LOCATION: (366)..(366)
<223> OTHER INFORMATION: Xaa = Ala, Ser or any other amino acid

<400> SEQUENCE: 53

Met Pro Ile Phe Lys Lys Thr Leu Ile Val Leu Ser Phe Ile Phe Leu
1               5                   10                  15

Ile Ser Ile Leu Ile Tyr Leu Asn Met Tyr Leu Phe Gly Thr Ser Thr
                20                  25                  30

Val Gly Ile Tyr Gly Val Ile Leu Ile Thr Tyr Leu Val Ile Lys Leu
            35                  40                  45

Gly Leu Ser Phe Leu Tyr Glu Pro Phe Lys Gly Asn Pro His Asp Tyr
        50                  55                  60

Lys Val Ala Ala Val Ile Pro Ser Tyr Asn Glu Asp Ala Glu Ser Leu
65                  70                  75                  80

Leu Glu Thr Leu Lys Ser Val Leu Ala Gln Thr Tyr Pro Leu Ser Glu
                85                  90                  95

Ile Tyr Ile Val Asp Asp Gly Ser Ser Asn Thr Asp Ala Ile Gln Leu
            100                 105                 110

Ile Glu Glu Tyr Val Asn Arg Glu Val Asp Ile Xaa Arg Asn Val Ile
        115                 120                 125
```

```
Val His Arg Ser Leu Val Asn Lys Gly Lys Arg His Ala Gln Ala Trp
    130                 135                 140
Ala Phe Glu Arg Ser Asp Ala Asp Val Phe Leu Thr Val Asp Ser Asp
145                 150                 155                 160
Thr Tyr Ile Tyr Pro Asn Ala Leu Glu Leu Leu Lys Ser Phe Asn
                    165                 170                 175
Asp Glu Thr Val Tyr Ala Ala Thr Gly His Leu Asn Ala Arg Asn Arg
                180                 185                 190
Gln Thr Asn Leu Leu Thr Arg Leu Thr Asp Ile Arg Tyr Asp Asn Ala
                195                 200                 205
Phe Gly Val Glu Arg Ala Ala Gln Ser Leu Thr Gly Asn Ile Leu Val
    210                 215                 220
Xaa Ser Gly Pro Leu Ser Ile Tyr Arg Arg Glu Val Ile Ile Pro Asn
225                 230                 235                 240
Leu Glu Arg Tyr Lys Asn Gln Thr Phe Leu Gly Leu Pro Val Ser Ile
                    245                 250                 255
Gly Asp Asp Arg Cys Leu Thr Asn Tyr Ala Ile Asp Leu Gly Arg Thr
                260                 265                 270
Val Tyr Gln Ser Thr Ala Arg Cys Asp Thr Asp Val Pro Phe Gln Leu
    275                 280                 285
Lys Ser Tyr Leu Lys Gln Gln Asn Arg Trp Asn Lys Ser Phe Phe Arg
290                 295                 300
Glu Ser Ile Ile Ser Val Lys Lys Ile Leu Ser Asn Pro Ile Val Ala
305                 310                 315                 320
Leu Trp Thr Ile Phe Glu Val Val Met Phe Met Leu Ile Val Ala
                    325                 330                 335
Ile Gly Asn Leu Leu Phe Asn Gln Ala Ile Gln Leu Asp Leu Ile Lys
                340                 345                 350
Leu Phe Ala Phe Leu Ser Ile Ile Phe Ile Val Ala Leu Xaa Arg Asn
                355                 360                 365
Val His Tyr Met Val Lys His Pro Ala Ser Phe Leu Leu Ser Pro Leu
    370                 375                 380
Tyr Gly Ile Leu His Leu Phe Val Leu Gln Pro Leu Lys Leu Tyr Ser
385                 390                 395                 400
Leu Cys Thr Ile Lys Asn Thr Glu Trp Gly Thr Arg Lys Lys Val Thr
                405                 410                 415
Ile Phe Lys

<210> SEQ ID NO 54
<211> LENGTH: 419
<212> TYPE: PRT
<213> ORGANISM: Streptococcus pyogenes
<220> FEATURE:
<221> NAME/KEY: MISC_FEATURE
<222> LOCATION: (124)..(124)
<223> OTHER INFORMATION: Xaa = Ala, Ser or any other amino acid
<220> FEATURE:
<221> NAME/KEY: MISC_FEATURE
<222> LOCATION: (225)..(225)
<223> OTHER INFORMATION: Xaa = Ala, Ser or any other amino acid
<220> FEATURE:
<221> NAME/KEY: MISC_FEATURE
<222> LOCATION: (402)..(402)
<223> OTHER INFORMATION: Xaa = Ala, Ser or any other amino acid

<400> SEQUENCE: 54

Met Pro Ile Phe Lys Lys Thr Leu Ile Val Leu Ser Phe Ile Phe Leu
1               5                   10                  15
```

```
Ile Ser Ile Leu Ile Tyr Leu Asn Met Tyr Leu Phe Gly Thr Ser Thr
            20                  25                  30

Val Gly Ile Tyr Gly Val Ile Leu Ile Thr Tyr Leu Val Ile Lys Leu
            35                  40                  45

Gly Leu Ser Phe Leu Tyr Glu Pro Phe Lys Gly Asn Pro His Asp Tyr
            50                  55                  60

Lys Val Ala Ala Val Ile Pro Ser Tyr Asn Glu Asp Ala Glu Ser Leu
65                  70                  75                  80

Leu Glu Thr Leu Lys Ser Val Leu Ala Gln Thr Tyr Pro Leu Ser Glu
                85                  90                  95

Ile Tyr Ile Val Asp Asp Gly Ser Ser Asn Thr Asp Ala Ile Gln Leu
            100                 105                 110

Ile Glu Glu Tyr Val Asn Arg Glu Val Asp Ile Xaa Arg Asn Val Ile
            115                 120                 125

Val His Arg Ser Leu Val Asn Lys Gly Lys Arg His Ala Gln Ala Trp
    130                 135                 140

Ala Phe Glu Arg Ser Asp Ala Asp Val Phe Leu Thr Val Asp Ser Asp
145                 150                 155                 160

Thr Tyr Ile Tyr Pro Asn Ala Leu Glu Glu Leu Leu Lys Ser Phe Asn
                165                 170                 175

Asp Glu Thr Val Tyr Ala Ala Thr Gly His Leu Asn Ala Arg Asn Arg
            180                 185                 190

Gln Thr Asn Leu Leu Thr Arg Leu Thr Asp Ile Arg Tyr Asp Asn Ala
    195                 200                 205

Phe Gly Val Glu Arg Ala Ala Gln Ser Leu Thr Gly Asn Ile Leu Val
    210                 215                 220

Xaa Ser Gly Pro Leu Ser Ile Tyr Arg Arg Glu Val Ile Ile Pro Asn
225                 230                 235                 240

Leu Glu Arg Tyr Lys Asn Gln Thr Phe Leu Gly Leu Pro Val Ser Ile
                245                 250                 255

Gly Asp Asp Arg Cys Leu Thr Asn Tyr Ala Ile Asp Leu Gly Arg Thr
            260                 265                 270

Val Tyr Gln Ser Thr Ala Arg Cys Asp Thr Asp Val Pro Phe Gln Leu
    275                 280                 285

Lys Ser Tyr Leu Lys Gln Gln Asn Arg Trp Asn Lys Ser Phe Phe Arg
290                 295                 300

Glu Ser Ile Ile Ser Val Lys Lys Ile Leu Ser Asn Pro Ile Val Ala
305                 310                 315                 320

Leu Trp Thr Ile Phe Glu Val Val Met Phe Met Met Leu Ile Val Ala
                325                 330                 335

Ile Gly Asn Leu Leu Phe Asn Gln Ala Ile Gln Leu Asp Leu Ile Lys
            340                 345                 350

Leu Phe Ala Phe Leu Ser Ile Ile Phe Ile Val Ala Leu Cys Arg Asn
    355                 360                 365

Val His Tyr Met Val Lys His Pro Ala Ser Phe Leu Leu Ser Pro Leu
    370                 375                 380

Tyr Gly Ile Leu His Leu Phe Val Leu Gln Pro Leu Lys Leu Tyr Ser
385                 390                 395                 400

Leu Xaa Thr Ile Lys Asn Thr Glu Trp Gly Thr Arg Lys Lys Val Thr
                405                 410                 415

Ile Phe Lys
```

```
<210> SEQ ID NO 55
<211> LENGTH: 419
<212> TYPE: PRT
<213> ORGANISM: Streptococcus pyogenes
<220> FEATURE:
<221> NAME/KEY: MISC_FEATURE
<222> LOCATION: (124)..(124)
<223> OTHER INFORMATION: Xaa = Ala, Ser or any other amino acid
<220> FEATURE:
<221> NAME/KEY: MISC_FEATURE
<222> LOCATION: (261)..(261)
<223> OTHER INFORMATION: Xaa = Ala, Ser or any other amino acid
<220> FEATURE:
<221> NAME/KEY: MISC_FEATURE
<222> LOCATION: (280)..(280)
<223> OTHER INFORMATION: Xaa = Ala, Ser or any other amino acid

<400> SEQUENCE: 55

Met Pro Ile Phe Lys Lys Thr Leu Ile Val Leu Ser Phe Ile Phe Leu
1               5                   10                  15

Ile Ser Ile Leu Ile Tyr Leu Asn Met Tyr Leu Phe Gly Thr Ser Thr
            20                  25                  30

Val Gly Ile Tyr Gly Val Ile Leu Ile Thr Tyr Leu Val Ile Lys Leu
        35                  40                  45

Gly Leu Ser Phe Leu Tyr Glu Pro Phe Lys Gly Asn Pro His Asp Tyr
    50                  55                  60

Lys Val Ala Ala Val Ile Pro Ser Tyr Asn Glu Asp Ala Glu Ser Leu
65                  70                  75                  80

Leu Glu Thr Leu Lys Ser Val Leu Ala Gln Thr Tyr Pro Leu Ser Glu
                85                  90                  95

Ile Tyr Ile Val Asp Asp Gly Ser Ser Asn Thr Asp Ala Ile Gln Leu
            100                 105                 110

Ile Glu Glu Tyr Val Asn Arg Glu Val Asp Ile Xaa Arg Asn Val Ile
        115                 120                 125

Val His Arg Ser Leu Val Asn Lys Gly Lys Arg His Ala Gln Ala Trp
    130                 135                 140

Ala Phe Glu Arg Ser Asp Ala Asp Val Phe Leu Thr Val Asp Ser Asp
145                 150                 155                 160

Thr Tyr Ile Tyr Pro Asn Ala Leu Glu Glu Leu Leu Lys Ser Phe Asn
                165                 170                 175

Asp Glu Thr Val Tyr Ala Ala Thr Gly His Leu Asn Ala Arg Asn Arg
            180                 185                 190

Gln Thr Asn Leu Leu Thr Arg Leu Thr Asp Ile Arg Tyr Asp Asn Ala
        195                 200                 205

Phe Gly Val Glu Arg Ala Ala Gln Ser Leu Thr Gly Asn Ile Leu Val
    210                 215                 220

Cys Ser Gly Pro Leu Ser Ile Tyr Arg Arg Glu Val Ile Ile Pro Asn
225                 230                 235                 240

Leu Glu Arg Tyr Lys Asn Gln Thr Phe Leu Gly Leu Pro Val Ser Ile
                245                 250                 255

Gly Asp Asp Arg Xaa Leu Thr Asn Tyr Ala Ile Asp Leu Gly Arg Thr
            260                 265                 270

Val Tyr Gln Ser Thr Ala Arg Xaa Asp Thr Asp Val Pro Phe Gln Leu
        275                 280                 285

Lys Ser Tyr Leu Lys Gln Gln Asn Arg Trp Asn Lys Ser Phe Phe Arg
    290                 295                 300

Glu Ser Ile Ile Ser Val Lys Lys Ile Leu Ser Asn Pro Ile Val Ala
305                 310                 315                 320
```

-continued

```
Leu Trp Thr Ile Phe Glu Val Met Phe Met Met Leu Ile Val Ala
                325                 330                 335

Ile Gly Asn Leu Leu Phe Asn Gln Ala Ile Gln Leu Asp Leu Ile Lys
            340                 345                 350

Leu Phe Ala Phe Leu Ser Ile Ile Phe Ile Val Ala Leu Cys Arg Asn
            355                 360                 365

Val His Tyr Met Val Lys His Pro Ala Ser Phe Leu Leu Ser Pro Leu
    370                 375                 380

Tyr Gly Ile Leu His Leu Phe Val Leu Gln Pro Leu Lys Leu Tyr Ser
385                 390                 395                 400

Leu Cys Thr Ile Lys Asn Thr Glu Trp Gly Thr Arg Lys Lys Val Thr
                405                 410                 415

Ile Phe Lys

<210> SEQ ID NO 56
<211> LENGTH: 419
<212> TYPE: PRT
<213> ORGANISM: Streptococcus pyogenes
<220> FEATURE:
<221> NAME/KEY: MISC_FEATURE
<222> LOCATION: (124)..(124)
<223> OTHER INFORMATION: Xaa = Ala, Ser or any other amino acid
<220> FEATURE:
<221> NAME/KEY: MISC_FEATURE
<222> LOCATION: (261)..(261)
<223> OTHER INFORMATION: Xaa = Ala, Ser or any other amino acid
<220> FEATURE:
<221> NAME/KEY: MISC_FEATURE
<222> LOCATION: (366)..(366)
<223> OTHER INFORMATION: Xaa = Ala, Ser or any other amino acid

<400> SEQUENCE: 56

Met Pro Ile Phe Lys Lys Thr Leu Ile Val Leu Ser Phe Ile Phe Leu
1               5                   10                  15

Ile Ser Ile Leu Ile Tyr Leu Asn Met Tyr Leu Phe Gly Thr Ser Thr
            20                  25                  30

Val Gly Ile Tyr Gly Val Ile Leu Ile Thr Tyr Leu Val Ile Lys Leu
        35                  40                  45

Gly Leu Ser Phe Leu Tyr Glu Pro Phe Lys Gly Asn Pro His Asp Tyr
    50                  55                  60

Lys Val Ala Ala Val Ile Pro Ser Tyr Asn Glu Asp Ala Glu Ser Leu
65                  70                  75                  80

Leu Glu Thr Leu Lys Ser Val Leu Ala Gln Thr Tyr Pro Leu Ser Glu
                85                  90                  95

Ile Tyr Ile Val Asp Asp Gly Ser Ser Asn Thr Asp Ala Ile Gln Leu
            100                 105                 110

Ile Glu Glu Tyr Val Asn Arg Glu Val Asp Ile Xaa Arg Asn Val Ile
        115                 120                 125

Val His Arg Ser Leu Val Asn Lys Gly Lys His Ala Gln Ala Trp
    130                 135                 140

Ala Phe Glu Arg Ser Asp Ala Asp Val Phe Leu Thr Val Asp Ser Asp
145                 150                 155                 160

Thr Tyr Ile Tyr Pro Asn Ala Leu Glu Glu Leu Leu Lys Ser Phe Asn
                165                 170                 175

Asp Glu Thr Val Tyr Ala Ala Thr Gly His Leu Asn Ala Arg Asn Arg
            180                 185                 190

Gln Thr Asn Leu Leu Thr Arg Leu Thr Asp Ile Arg Tyr Asp Asn Ala
        195                 200                 205
```

```
                                    -continued

Phe Gly Val Glu Arg Ala Ala Gln Ser Leu Thr Gly Asn Ile Leu Val
    210                 215                 220

Cys Ser Gly Pro Leu Ser Ile Tyr Arg Arg Glu Val Ile Pro Asn
225                 230                 235                 240

Leu Glu Arg Tyr Lys Asn Gln Thr Phe Leu Gly Leu Pro Val Ser Ile
                245                 250                 255

Gly Asp Asp Arg Xaa Leu Thr Asn Tyr Ala Ile Asp Leu Gly Arg Thr
                260                 265                 270

Val Tyr Gln Ser Thr Ala Arg Cys Asp Thr Asp Val Pro Phe Gln Leu
                275                 280                 285

Lys Ser Tyr Leu Lys Gln Gln Asn Arg Trp Asn Lys Ser Phe Phe Arg
    290                 295                 300

Glu Ser Ile Ile Ser Val Lys Lys Ile Leu Ser Asn Pro Ile Val Ala
305                 310                 315                 320

Leu Trp Thr Ile Phe Glu Val Val Met Phe Met Leu Ile Val Ala
                    325                 330                 335

Ile Gly Asn Leu Leu Phe Asn Gln Ala Ile Gln Leu Asp Leu Ile Lys
                340                 345                 350

Leu Phe Ala Phe Leu Ser Ile Ile Phe Ile Val Ala Leu Xaa Arg Asn
    355                 360                 365

Val His Tyr Met Val Lys His Pro Ala Ser Phe Leu Leu Ser Pro Leu
    370                 375                 380

Tyr Gly Ile Leu His Leu Phe Val Leu Gln Pro Leu Lys Leu Tyr Ser
385                 390                 395                 400

Leu Cys Thr Ile Lys Asn Thr Glu Trp Gly Thr Arg Lys Lys Val Thr
                405                 410                 415

Ile Phe Lys

<210> SEQ ID NO 57
<211> LENGTH: 419
<212> TYPE: PRT
<213> ORGANISM: Streptococcus pyogenes
<220> FEATURE:
<221> NAME/KEY: MISC_FEATURE
<222> LOCATION: (124)..(124)
<223> OTHER INFORMATION: Xaa = Ala, Ser or any other amino acid
<220> FEATURE:
<221> NAME/KEY: MISC_FEATURE
<222> LOCATION: (261)..(261)
<223> OTHER INFORMATION: Xaa = Ala, Ser or any other amino acid
<220> FEATURE:
<221> NAME/KEY: MISC_FEATURE
<222> LOCATION: (402)..(402)
<223> OTHER INFORMATION: Xaa = Ala, Ser or any other amino acid

<400> SEQUENCE: 57

Met Pro Ile Phe Lys Lys Thr Leu Ile Val Leu Ser Phe Ile Phe Leu
1               5                   10                  15

Ile Ser Ile Leu Ile Tyr Leu Asn Met Tyr Leu Phe Gly Thr Ser Thr
                20                  25                  30

Val Gly Ile Tyr Gly Val Ile Leu Ile Thr Tyr Leu Val Ile Lys Leu
            35                  40                  45

Gly Leu Ser Phe Leu Tyr Glu Pro Phe Lys Gly Asn Pro His Asp Tyr
    50                  55                  60

Lys Val Ala Ala Val Ile Pro Ser Tyr Asn Glu Asp Ala Glu Ser Leu
65                  70                  75                  80

Leu Glu Thr Leu Lys Ser Val Leu Ala Gln Thr Tyr Pro Leu Ser Glu
                85                  90                  95
```

```
Ile Tyr Ile Val Asp Asp Gly Ser Ser Asn Thr Asp Ala Ile Gln Leu
            100                 105                 110

Ile Glu Glu Tyr Val Asn Arg Glu Val Asp Ile Xaa Arg Asn Val Ile
        115                 120                 125

Val His Arg Ser Leu Val Asn Lys Gly Lys Arg His Ala Gln Ala Trp
    130                 135                 140

Ala Phe Glu Arg Ser Asp Ala Asp Val Phe Leu Thr Val Asp Ser Asp
145                 150                 155                 160

Thr Tyr Ile Tyr Pro Asn Ala Leu Glu Glu Leu Leu Lys Ser Phe Asn
                165                 170                 175

Asp Glu Thr Val Tyr Ala Ala Thr Gly His Leu Asn Ala Arg Asn Arg
            180                 185                 190

Gln Thr Asn Leu Leu Thr Arg Leu Thr Asp Ile Arg Tyr Asp Asn Ala
        195                 200                 205

Phe Gly Val Glu Arg Ala Ala Gln Ser Leu Thr Gly Asn Ile Leu Val
    210                 215                 220

Cys Ser Gly Pro Leu Ser Ile Tyr Arg Arg Glu Val Ile Ile Pro Asn
225                 230                 235                 240

Leu Glu Arg Tyr Lys Asn Gln Thr Phe Leu Gly Leu Pro Val Ser Ile
                245                 250                 255

Gly Asp Asp Arg Xaa Leu Thr Asn Tyr Ala Ile Asp Leu Gly Arg Thr
            260                 265                 270

Val Tyr Gln Ser Thr Ala Arg Cys Asp Thr Asp Val Pro Phe Gln Leu
        275                 280                 285

Lys Ser Tyr Leu Lys Gln Gln Asn Arg Trp Asn Lys Ser Phe Phe Arg
    290                 295                 300

Glu Ser Ile Ile Ser Val Lys Lys Ile Leu Ser Asn Pro Ile Val Ala
305                 310                 315                 320

Leu Trp Thr Ile Phe Glu Val Val Met Phe Met Met Leu Ile Val Ala
                325                 330                 335

Ile Gly Asn Leu Leu Phe Asn Gln Ala Ile Gln Leu Asp Leu Ile Lys
            340                 345                 350

Leu Phe Ala Phe Leu Ser Ile Ile Phe Ile Val Ala Leu Cys Arg Asn
        355                 360                 365

Val His Tyr Met Val Lys His Pro Ala Ser Phe Leu Leu Ser Pro Leu
    370                 375                 380

Tyr Gly Ile Leu His Leu Phe Val Leu Gln Pro Leu Lys Leu Tyr Ser
385                 390                 395                 400

Leu Xaa Thr Ile Lys Asn Thr Glu Trp Gly Thr Arg Lys Lys Val Thr
                405                 410                 415

Ile Phe Lys

<210> SEQ ID NO 58
<211> LENGTH: 419
<212> TYPE: PRT
<213> ORGANISM: Streptococcus pyogenes
<220> FEATURE:
<221> NAME/KEY: MISC_FEATURE
<222> LOCATION: (124)..(124)
<223> OTHER INFORMATION: Xaa = Ala, Ser or any other amino acid
<220> FEATURE:
<221> NAME/KEY: MISC_FEATURE
<222> LOCATION: (280)..(280)
<223> OTHER INFORMATION: Xaa = Ala, Ser or any other amino acid
<220> FEATURE:
<221> NAME/KEY: MISC_FEATURE
<222> LOCATION: (366)..(366)
<223> OTHER INFORMATION: Xaa = Ala, Ser or any other amino acid
```

<400> SEQUENCE: 58

```
Met Pro Ile Phe Lys Lys Thr Leu Ile Val Leu Ser Phe Ile Phe Leu
1               5                   10                  15

Ile Ser Ile Leu Ile Tyr Leu Asn Met Tyr Leu Phe Gly Thr Ser Thr
            20                  25                  30

Val Gly Ile Tyr Gly Val Ile Leu Ile Thr Tyr Leu Val Ile Lys Leu
        35                  40                  45

Gly Leu Ser Phe Leu Tyr Glu Pro Phe Lys Gly Asn Pro His Asp Tyr
50                  55                  60

Lys Val Ala Ala Val Ile Pro Ser Tyr Asn Glu Asp Ala Glu Ser Leu
65                  70                  75                  80

Leu Glu Thr Leu Lys Ser Val Leu Ala Gln Thr Tyr Pro Leu Ser Glu
                85                  90                  95

Ile Tyr Ile Val Asp Asp Gly Ser Ser Asn Thr Asp Ala Ile Gln Leu
            100                 105                 110

Ile Glu Glu Tyr Val Asn Arg Glu Val Asp Ile Xaa Arg Asn Val Ile
        115                 120                 125

Val His Arg Ser Leu Val Asn Lys Gly Lys Arg His Ala Gln Ala Trp
130                 135                 140

Ala Phe Glu Arg Ser Asp Ala Asp Val Phe Leu Thr Val Asp Ser Asp
145                 150                 155                 160

Thr Tyr Ile Tyr Pro Asn Ala Leu Glu Glu Leu Leu Lys Ser Phe Asn
                165                 170                 175

Asp Glu Thr Val Tyr Ala Ala Thr Gly His Leu Asn Ala Arg Asn Arg
            180                 185                 190

Gln Thr Asn Leu Leu Thr Arg Leu Thr Asp Ile Arg Tyr Asp Asn Ala
        195                 200                 205

Phe Gly Val Glu Arg Ala Ala Gln Ser Leu Thr Gly Asn Ile Leu Val
210                 215                 220

Cys Ser Gly Pro Leu Ser Ile Tyr Arg Arg Glu Val Ile Ile Pro Asn
225                 230                 235                 240

Leu Glu Arg Tyr Lys Asn Gln Thr Phe Leu Gly Leu Pro Val Ser Ile
                245                 250                 255

Gly Asp Asp Arg Cys Leu Thr Asn Tyr Ala Ile Asp Leu Gly Arg Thr
            260                 265                 270

Val Tyr Gln Ser Thr Ala Arg Xaa Asp Thr Asp Val Pro Phe Gln Leu
        275                 280                 285

Lys Ser Tyr Leu Lys Gln Gln Asn Arg Trp Asn Lys Ser Phe Phe Arg
290                 295                 300

Glu Ser Ile Ile Ser Val Lys Lys Ile Leu Ser Asn Pro Ile Val Ala
305                 310                 315                 320

Leu Trp Thr Ile Phe Glu Val Val Met Phe Met Met Leu Ile Val Ala
                325                 330                 335

Ile Gly Asn Leu Leu Phe Asn Gln Ala Ile Gln Leu Asp Leu Ile Lys
            340                 345                 350

Leu Phe Ala Phe Leu Ser Ile Phe Ile Val Ala Leu Xaa Arg Asn
        355                 360                 365

Val His Tyr Met Val Lys His Pro Ala Ser Phe Leu Leu Ser Pro Leu
370                 375                 380

Tyr Gly Ile Leu His Leu Phe Val Leu Gln Pro Leu Lys Leu Tyr Ser
385                 390                 395                 400

Leu Cys Thr Ile Lys Asn Thr Glu Trp Gly Thr Arg Lys Lys Val Thr
```

```
                    405                 410                 415

Ile Phe Lys

<210> SEQ ID NO 59
<211> LENGTH: 419
<212> TYPE: PRT
<213> ORGANISM: Streptococcus pyogenes
<220> FEATURE:
<221> NAME/KEY: MISC_FEATURE
<222> LOCATION: (124)..(124)
<223> OTHER INFORMATION: Xaa = Ala, Ser or any other amino acid
<220> FEATURE:
<221> NAME/KEY: MISC_FEATURE
<222> LOCATION: (280)..(280)
<223> OTHER INFORMATION: Xaa = Ala, Ser or any other amino acid
<220> FEATURE:
<221> NAME/KEY: MISC_FEATURE
<222> LOCATION: (402)..(402)
<223> OTHER INFORMATION: Xaa = Ala, Ser or any other amino acid

<400> SEQUENCE: 59

Met Pro Ile Phe Lys Lys Thr Leu Ile Val Leu Ser Phe Ile Phe Leu
1               5                   10                  15

Ile Ser Ile Leu Ile Tyr Leu Asn Met Tyr Leu Phe Gly Thr Ser Thr
            20                  25                  30

Val Gly Ile Tyr Gly Val Ile Leu Ile Thr Tyr Leu Val Ile Lys Leu
        35                  40                  45

Gly Leu Ser Phe Leu Tyr Glu Pro Phe Lys Gly Asn Pro His Asp Tyr
    50                  55                  60

Lys Val Ala Ala Val Ile Pro Ser Tyr Asn Glu Asp Ala Glu Ser Leu
65                  70                  75                  80

Leu Glu Thr Leu Lys Ser Val Leu Ala Gln Thr Tyr Pro Leu Ser Glu
                85                  90                  95

Ile Tyr Ile Val Asp Asp Gly Ser Ser Asn Thr Asp Ala Ile Gln Leu
            100                 105                 110

Ile Glu Glu Tyr Val Asn Arg Glu Val Asp Ile Xaa Arg Asn Val Ile
        115                 120                 125

Val His Arg Ser Leu Val Asn Lys Gly Lys Arg His Ala Gln Ala Trp
    130                 135                 140

Ala Phe Glu Arg Ser Asp Ala Asp Val Phe Leu Thr Val Asp Ser Asp
145                 150                 155                 160

Thr Tyr Ile Tyr Pro Asn Ala Leu Glu Glu Leu Leu Lys Ser Phe Asn
                165                 170                 175

Asp Glu Thr Val Tyr Ala Ala Thr Gly His Leu Asn Ala Arg Asn Arg
            180                 185                 190

Gln Thr Asn Leu Leu Thr Arg Leu Thr Asp Ile Arg Tyr Asp Asn Ala
        195                 200                 205

Phe Gly Val Glu Arg Ala Ala Gln Ser Leu Thr Gly Asn Ile Leu Val
    210                 215                 220

Cys Ser Gly Pro Leu Ser Ile Tyr Arg Arg Glu Val Ile Ile Pro Asn
225                 230                 235                 240

Leu Glu Arg Tyr Lys Asn Gln Thr Phe Leu Gly Leu Pro Val Ser Ile
                245                 250                 255

Gly Asp Asp Arg Cys Leu Thr Asn Tyr Ala Ile Asp Leu Gly Arg Thr
            260                 265                 270

Val Tyr Gln Ser Thr Ala Arg Xaa Asp Thr Asp Val Pro Phe Gln Leu
        275                 280                 285

Lys Ser Tyr Leu Lys Gln Gln Asn Arg Trp Asn Lys Ser Phe Phe Arg
```

```
             290                 295                 300
Glu Ser Ile Ile Ser Val Lys Lys Ile Leu Ser Asn Pro Ile Val Ala
305                 310                 315                 320

Leu Trp Thr Ile Phe Glu Val Val Met Phe Met Met Leu Ile Val Ala
                325                 330                 335

Ile Gly Asn Leu Leu Phe Asn Gln Ala Ile Gln Leu Asp Leu Ile Lys
                340                 345                 350

Leu Phe Ala Phe Leu Ser Ile Ile Phe Ile Val Ala Leu Cys Arg Asn
                355                 360                 365

Val His Tyr Met Val Lys His Pro Ala Ser Phe Leu Leu Ser Pro Leu
                370                 375                 380

Tyr Gly Ile Leu His Leu Phe Val Leu Gln Pro Leu Lys Leu Tyr Ser
385                 390                 395                 400

Leu Xaa Thr Ile Lys Asn Thr Glu Trp Gly Thr Arg Lys Lys Val Thr
                405                 410                 415

Ile Phe Lys

<210> SEQ ID NO 60
<211> LENGTH: 419
<212> TYPE: PRT
<213> ORGANISM: Streptococcus pyogenes
<220> FEATURE:
<221> NAME/KEY: MISC_FEATURE
<222> LOCATION: (124)..(124)
<223> OTHER INFORMATION: Xaa = Ala, Ser or any other amino acid
<220> FEATURE:
<221> NAME/KEY: MISC_FEATURE
<222> LOCATION: (366)..(366)
<223> OTHER INFORMATION: Xaa = Ala, Ser or any other amino acid
<220> FEATURE:
<221> NAME/KEY: MISC_FEATURE
<222> LOCATION: (402)..(402)
<223> OTHER INFORMATION: Xaa = Ala, Ser or any other amino acid

<400> SEQUENCE: 60

Met Pro Ile Phe Lys Lys Thr Leu Ile Val Leu Ser Phe Ile Phe Leu
1               5                   10                  15

Ile Ser Ile Leu Ile Tyr Leu Asn Met Tyr Leu Phe Gly Thr Ser Thr
                20                  25                  30

Val Gly Ile Tyr Gly Val Ile Leu Ile Thr Tyr Leu Val Ile Lys Leu
                35                  40                  45

Gly Leu Ser Phe Leu Tyr Glu Pro Phe Lys Gly Asn Pro His Asp Tyr
            50                  55                  60

Lys Val Ala Ala Val Ile Pro Ser Tyr Asn Glu Asp Ala Glu Ser Leu
65                  70                  75                  80

Leu Glu Thr Leu Lys Ser Val Leu Ala Gln Thr Tyr Pro Leu Ser Glu
                85                  90                  95

Ile Tyr Ile Val Asp Asp Gly Ser Ser Asn Thr Asp Ala Ile Gln Leu
                100                 105                 110

Ile Glu Glu Tyr Val Asn Arg Glu Val Asp Ile Xaa Arg Asn Val Ile
                115                 120                 125

Val His Arg Ser Leu Val Asn Lys Gly Lys Arg His Ala Gln Ala Trp
                130                 135                 140

Ala Phe Glu Arg Ser Asp Ala Asp Val Phe Leu Thr Val Asp Ser Asp
145                 150                 155                 160

Thr Tyr Ile Tyr Pro Asn Ala Leu Glu Glu Leu Leu Lys Ser Phe Asn
                165                 170                 175

Asp Glu Thr Val Tyr Ala Ala Thr Gly His Leu Asn Ala Arg Asn Arg
```

-continued

```
                180                 185                 190
Gln Thr Asn Leu Leu Thr Arg Leu Thr Asp Ile Arg Tyr Asp Asn Ala
            195                 200                 205

Phe Gly Val Glu Arg Ala Ala Gln Ser Leu Thr Gly Asn Ile Leu Val
210                 215                 220

Cys Ser Gly Pro Leu Ser Ile Tyr Arg Arg Glu Val Ile Ile Pro Asn
225                 230                 235                 240

Leu Glu Arg Tyr Lys Asn Gln Thr Phe Leu Gly Leu Pro Val Ser Ile
                245                 250                 255

Gly Asp Asp Arg Cys Leu Thr Asn Tyr Ala Ile Asp Leu Gly Arg Thr
            260                 265                 270

Val Tyr Gln Ser Thr Ala Arg Cys Asp Thr Asp Val Pro Phe Gln Leu
        275                 280                 285

Lys Ser Tyr Leu Lys Gln Gln Asn Arg Trp Asn Lys Ser Phe Phe Arg
    290                 295                 300

Glu Ser Ile Ile Ser Val Lys Lys Ile Leu Ser Asn Pro Ile Val Ala
305                 310                 315                 320

Leu Trp Thr Ile Phe Glu Val Val Met Phe Met Met Leu Ile Val Ala
                325                 330                 335

Ile Gly Asn Leu Leu Phe Asn Gln Ala Ile Gln Leu Asp Leu Ile Lys
            340                 345                 350

Leu Phe Ala Phe Leu Ser Ile Ile Phe Ile Val Ala Leu Xaa Arg Asn
        355                 360                 365

Val His Tyr Met Val Lys His Pro Ala Ser Phe Leu Leu Ser Pro Leu
    370                 375                 380

Tyr Gly Ile Leu His Leu Phe Val Leu Gln Pro Leu Lys Leu Tyr Ser
385                 390                 395                 400

Leu Xaa Thr Ile Lys Asn Thr Glu Trp Gly Thr Arg Lys Lys Val Thr
                405                 410                 415

Ile Phe Lys

<210> SEQ ID NO 61
<211> LENGTH: 419
<212> TYPE: PRT
<213> ORGANISM: Streptococcus pyogenes
<220> FEATURE:
<221> NAME/KEY: MISC_FEATURE
<222> LOCATION: (225)..(225)
<223> OTHER INFORMATION: Xaa = Ala, Ser or any other amino acid
<220> FEATURE:
<221> NAME/KEY: MISC_FEATURE
<222> LOCATION: (261)..(261)
<223> OTHER INFORMATION: Xaa = Ala, Ser or any other amino acid
<220> FEATURE:
<221> NAME/KEY: MISC_FEATURE
<222> LOCATION: (280)..(280)
<223> OTHER INFORMATION: Xaa = Ala, Ser or any other amino acid

<400> SEQUENCE: 61

Met Pro Ile Phe Lys Lys Thr Leu Ile Val Leu Ser Phe Ile Phe Leu
1               5                   10                  15

Ile Ser Ile Leu Ile Tyr Leu Asn Met Tyr Leu Phe Gly Thr Ser Thr
            20                  25                  30

Val Gly Ile Tyr Gly Val Ile Leu Ile Thr Tyr Leu Val Ile Lys Leu
        35                  40                  45

Gly Leu Ser Phe Leu Tyr Glu Pro Phe Lys Gly Asn Pro His Asp Tyr
    50                  55                  60

Lys Val Ala Ala Val Ile Pro Ser Tyr Asn Glu Asp Ala Glu Ser Leu
```

```
                65                  70                  75                  80
Leu Glu Thr Leu Lys Ser Val Leu Ala Gln Thr Tyr Pro Leu Ser Glu
                    85                  90                  95
Ile Tyr Ile Val Asp Asp Gly Ser Ser Asn Thr Asp Ala Ile Gln Leu
                100                 105                 110
Ile Glu Glu Tyr Val Asn Arg Glu Val Asp Ile Cys Arg Asn Val Ile
                115                 120                 125
Val His Arg Ser Leu Val Asn Lys Gly Lys Arg His Ala Gln Ala Trp
130                 135                 140
Ala Phe Glu Arg Ser Asp Ala Asp Val Phe Leu Thr Val Asp Ser Asp
145                 150                 155                 160
Thr Tyr Ile Tyr Pro Asn Ala Leu Glu Glu Leu Leu Lys Ser Phe Asn
                165                 170                 175
Asp Glu Thr Val Tyr Ala Ala Thr Gly His Leu Asn Ala Arg Asn Arg
                180                 185                 190
Gln Thr Asn Leu Leu Thr Arg Leu Thr Asp Ile Arg Tyr Asp Asn Ala
                195                 200                 205
Phe Gly Val Glu Arg Ala Ala Gln Ser Leu Thr Gly Asn Ile Leu Val
210                 215                 220
Xaa Ser Gly Pro Leu Ser Ile Tyr Arg Arg Glu Val Ile Ile Pro Asn
225                 230                 235                 240
Leu Glu Arg Tyr Lys Asn Gln Thr Phe Leu Gly Leu Pro Val Ser Ile
                245                 250                 255
Gly Asp Asp Arg Xaa Leu Thr Asn Tyr Ala Ile Asp Leu Gly Arg Thr
                260                 265                 270
Val Tyr Gln Ser Thr Ala Arg Xaa Asp Thr Asp Val Pro Phe Gln Leu
                275                 280                 285
Lys Ser Tyr Leu Lys Gln Gln Asn Arg Trp Asn Lys Ser Phe Phe Arg
                290                 295                 300
Glu Ser Ile Ile Ser Val Lys Lys Ile Leu Ser Asn Pro Ile Val Ala
305                 310                 315                 320
Leu Trp Thr Ile Phe Glu Val Val Met Phe Met Met Leu Ile Val Ala
                325                 330                 335
Ile Gly Asn Leu Leu Phe Asn Gln Ala Ile Gln Leu Asp Leu Ile Lys
                340                 345                 350
Leu Phe Ala Phe Leu Ser Ile Ile Phe Ile Val Ala Leu Cys Arg Asn
                355                 360                 365
Val His Tyr Met Val Lys His Pro Ala Ser Phe Leu Leu Ser Pro Leu
                370                 375                 380
Tyr Gly Ile Leu His Leu Phe Val Leu Gln Pro Leu Lys Leu Tyr Ser
385                 390                 395                 400
Leu Cys Thr Ile Lys Asn Thr Glu Trp Gly Thr Arg Lys Lys Val Thr
                405                 410                 415
Ile Phe Lys

<210> SEQ ID NO 62
<211> LENGTH: 419
<212> TYPE: PRT
<213> ORGANISM: Streptococcus pyogenes
<220> FEATURE:
<221> NAME/KEY: MISC_FEATURE
<222> LOCATION: (225)..(225)
<223> OTHER INFORMATION: Xaa = Ala, Ser or any other amino acid
<220> FEATURE:
<221> NAME/KEY: MISC_FEATURE
<222> LOCATION: (261)..(261)
```

```
<223> OTHER INFORMATION: Xaa = Ala, Ser or any other amino acid
<220> FEATURE:
<221> NAME/KEY: MISC_FEATURE
<222> LOCATION: (366)..(366)
<223> OTHER INFORMATION: Xaa = Ala, Ser or any other amino acid

<400> SEQUENCE: 62

Met Pro Ile Phe Lys Lys Thr Leu Ile Val Leu Ser Phe Ile Phe Leu
1               5                   10                  15

Ile Ser Ile Leu Ile Tyr Leu Asn Met Tyr Leu Phe Gly Thr Ser Thr
            20                  25                  30

Val Gly Ile Tyr Gly Val Ile Leu Ile Thr Tyr Leu Val Ile Lys Leu
        35                  40                  45

Gly Leu Ser Phe Leu Tyr Glu Pro Phe Lys Gly Asn Pro His Asp Tyr
    50                  55                  60

Lys Val Ala Ala Val Ile Pro Ser Tyr Asn Glu Asp Ala Glu Ser Leu
65                  70                  75                  80

Leu Glu Thr Leu Lys Ser Val Leu Ala Gln Thr Tyr Pro Leu Ser Glu
                85                  90                  95

Ile Tyr Ile Val Asp Asp Gly Ser Ser Asn Thr Asp Ala Ile Gln Leu
            100                 105                 110

Ile Glu Glu Tyr Val Asn Arg Glu Val Asp Ile Cys Arg Asn Val Ile
        115                 120                 125

Val His Arg Ser Leu Val Asn Lys Gly Lys Arg His Ala Gln Ala Trp
130                 135                 140

Ala Phe Glu Arg Ser Asp Ala Asp Val Phe Leu Thr Val Asp Ser Asp
145                 150                 155                 160

Thr Tyr Ile Tyr Pro Asn Ala Leu Glu Glu Leu Leu Lys Ser Phe Asn
                165                 170                 175

Asp Glu Thr Val Tyr Ala Ala Thr Gly His Leu Asn Ala Arg Asn Arg
            180                 185                 190

Gln Thr Asn Leu Leu Thr Arg Leu Thr Asp Ile Arg Tyr Asp Asn Ala
        195                 200                 205

Phe Gly Val Glu Arg Ala Ala Gln Ser Leu Thr Gly Asn Ile Leu Val
210                 215                 220

Xaa Ser Gly Pro Leu Ser Ile Tyr Arg Arg Glu Val Ile Ile Pro Asn
225                 230                 235                 240

Leu Glu Arg Tyr Lys Asn Gln Thr Phe Leu Gly Leu Pro Val Ser Ile
                245                 250                 255

Gly Asp Asp Arg Xaa Leu Thr Asn Tyr Ala Ile Asp Leu Gly Arg Thr
            260                 265                 270

Val Tyr Gln Ser Thr Ala Arg Cys Asp Thr Asp Val Pro Phe Gln Leu
        275                 280                 285

Lys Ser Tyr Leu Lys Gln Gln Asn Arg Trp Asn Lys Ser Phe Phe Arg
290                 295                 300

Glu Ser Ile Ile Ser Val Lys Lys Ile Leu Ser Asn Pro Ile Val Ala
305                 310                 315                 320

Leu Trp Thr Ile Phe Glu Val Val Met Phe Met Met Leu Ile Val Ala
                325                 330                 335

Ile Gly Asn Leu Leu Phe Asn Gln Ala Ile Gln Leu Asp Leu Ile Lys
            340                 345                 350

Leu Phe Ala Phe Leu Ser Ile Ile Phe Ile Val Ala Leu Xaa Arg Asn
        355                 360                 365

Val His Tyr Met Val Lys His Pro Ala Ser Phe Leu Leu Ser Pro Leu
370                 375                 380
```

-continued

Tyr Gly Ile Leu His Leu Phe Val Leu Gln Pro Leu Lys Leu Tyr Ser
385                 390                 395                 400

Leu Cys Thr Ile Lys Asn Thr Glu Trp Gly Thr Arg Lys Lys Val Thr
                405                 410                 415

Ile Phe Lys

<210> SEQ ID NO 63
<211> LENGTH: 419
<212> TYPE: PRT
<213> ORGANISM: Streptococcus pyogenes
<220> FEATURE:
<221> NAME/KEY: MISC_FEATURE
<222> LOCATION: (225)..(225)
<223> OTHER INFORMATION: Xaa = Ala, Ser or any other amino acid
<220> FEATURE:
<221> NAME/KEY: MISC_FEATURE
<222> LOCATION: (261)..(261)
<223> OTHER INFORMATION: Xaa = Ala, Ser or any other amino acid
<220> FEATURE:
<221> NAME/KEY: MISC_FEATURE
<222> LOCATION: (402)..(402)
<223> OTHER INFORMATION: Xaa = Ala, Ser or any other amino acid

<400> SEQUENCE: 63

Met Pro Ile Phe Lys Lys Thr Leu Ile Val Leu Ser Phe Ile Phe Leu
1               5                   10                  15

Ile Ser Ile Leu Ile Tyr Leu Asn Met Tyr Leu Phe Gly Thr Ser Thr
            20                  25                  30

Val Gly Ile Tyr Gly Val Ile Leu Ile Thr Tyr Leu Val Ile Lys Leu
        35                  40                  45

Gly Leu Ser Phe Leu Tyr Glu Pro Phe Lys Gly Asn Pro His Asp Tyr
50                  55                  60

Lys Val Ala Ala Val Ile Pro Ser Tyr Asn Glu Asp Ala Glu Ser Leu
65                  70                  75                  80

Leu Glu Thr Leu Lys Ser Val Leu Ala Gln Thr Tyr Pro Leu Ser Glu
                85                  90                  95

Ile Tyr Ile Val Asp Asp Gly Ser Ser Asn Thr Asp Ala Ile Gln Leu
            100                 105                 110

Ile Glu Glu Tyr Val Asn Arg Glu Val Asp Ile Cys Arg Asn Val Ile
        115                 120                 125

Val His Arg Ser Leu Val Asn Lys Gly Lys Arg His Ala Gln Ala Trp
130                 135                 140

Ala Phe Glu Arg Ser Asp Ala Asp Val Phe Leu Thr Val Asp Ser Asp
145                 150                 155                 160

Thr Tyr Ile Tyr Pro Asn Ala Leu Glu Glu Leu Leu Lys Ser Phe Asn
                165                 170                 175

Asp Glu Thr Val Tyr Ala Ala Thr Gly His Leu Asn Ala Arg Asn Arg
            180                 185                 190

Gln Thr Asn Leu Leu Thr Arg Leu Thr Asp Ile Arg Tyr Asp Asn Ala
        195                 200                 205

Phe Gly Val Glu Arg Ala Ala Gln Ser Leu Thr Gly Asn Ile Leu Val
    210                 215                 220

Xaa Ser Gly Pro Leu Ser Ile Tyr Arg Arg Glu Val Ile Ile Pro Asn
225                 230                 235                 240

Leu Glu Arg Tyr Lys Asn Gln Thr Phe Leu Gly Leu Pro Val Ser Ile
                245                 250                 255

Gly Asp Asp Arg Xaa Leu Thr Asn Tyr Ala Ile Asp Leu Gly Arg Thr
            260                 265                 270

```
Val Tyr Gln Ser Thr Ala Arg Cys Asp Thr Asp Val Pro Phe Gln Leu
        275                 280                 285

Lys Ser Tyr Leu Lys Gln Gln Asn Arg Trp Asn Lys Ser Phe Phe Arg
    290                 295                 300

Glu Ser Ile Ile Ser Val Lys Lys Ile Leu Ser Asn Pro Ile Val Ala
305                 310                 315                 320

Leu Trp Thr Ile Phe Glu Val Val Met Phe Met Leu Ile Val Ala
                325                 330                 335

Ile Gly Asn Leu Leu Phe Asn Gln Ala Ile Gln Leu Asp Leu Ile Lys
                340                 345                 350

Leu Phe Ala Phe Leu Ser Ile Ile Phe Ile Val Ala Leu Cys Arg Asn
                355                 360                 365

Val His Tyr Met Val Lys His Pro Ala Ser Phe Leu Leu Ser Pro Leu
        370                 375                 380

Tyr Gly Ile Leu His Leu Phe Val Leu Gln Pro Leu Lys Leu Tyr Ser
385                 390                 395                 400

Leu Xaa Thr Ile Lys Asn Thr Glu Trp Gly Thr Arg Lys Lys Val Thr
                405                 410                 415

Ile Phe Lys

<210> SEQ ID NO 64
<211> LENGTH: 419
<212> TYPE: PRT
<213> ORGANISM: Streptococcus pyogenes
<220> FEATURE:
<221> NAME/KEY: MISC_FEATURE
<222> LOCATION: (225)..(225)
<223> OTHER INFORMATION: Xaa = Ala, Ser or any other amino acid
<220> FEATURE:
<221> NAME/KEY: MISC_FEATURE
<222> LOCATION: (280)..(280)
<223> OTHER INFORMATION: Xaa = Ala, Ser or any other amino acid
<220> FEATURE:
<221> NAME/KEY: MISC_FEATURE
<222> LOCATION: (366)..(366)
<223> OTHER INFORMATION: Xaa = Ala, Ser or any other amino acid

<400> SEQUENCE: 64

Met Pro Ile Phe Lys Lys Thr Leu Ile Val Leu Ser Phe Ile Phe Leu
1               5                   10                  15

Ile Ser Ile Leu Ile Tyr Leu Asn Met Tyr Leu Phe Gly Thr Ser Thr
                20                  25                  30

Val Gly Ile Tyr Gly Val Ile Leu Ile Thr Tyr Leu Val Ile Lys Leu
            35                  40                  45

Gly Leu Ser Phe Leu Tyr Glu Pro Phe Lys Gly Asn Pro His Asp Tyr
50                  55                  60

Lys Val Ala Ala Val Ile Pro Ser Tyr Asn Glu Asp Ala Glu Ser Leu
65                  70                  75                  80

Leu Glu Thr Leu Lys Ser Val Leu Ala Gln Thr Tyr Pro Leu Ser Glu
                85                  90                  95

Ile Tyr Ile Val Asp Asp Gly Ser Ser Asn Thr Asp Ala Ile Gln Leu
            100                 105                 110

Ile Glu Glu Tyr Val Asn Arg Glu Val Asp Ile Cys Arg Asn Val Ile
        115                 120                 125

Val His Arg Ser Leu Val Asn Lys Gly Lys Arg His Ala Gln Ala Trp
130                 135                 140

Ala Phe Glu Arg Ser Asp Ala Asp Val Phe Leu Thr Val Asp Ser Asp
145                 150                 155                 160
```

-continued

```
Thr Tyr Ile Tyr Pro Asn Ala Leu Glu Glu Leu Leu Lys Ser Phe Asn
            165                 170                 175

Asp Glu Thr Val Tyr Ala Ala Thr Gly His Leu Asn Ala Arg Asn Arg
        180                 185                 190

Gln Thr Asn Leu Leu Thr Arg Leu Thr Asp Ile Arg Tyr Asp Asn Ala
    195                 200                 205

Phe Gly Val Glu Arg Ala Ala Gln Ser Leu Thr Gly Asn Ile Leu Val
210                 215                 220

Xaa Ser Gly Pro Leu Ser Ile Tyr Arg Arg Glu Val Ile Ile Pro Asn
225                 230                 235                 240

Leu Glu Arg Tyr Lys Asn Gln Thr Phe Leu Gly Leu Pro Val Ser Ile
            245                 250                 255

Gly Asp Asp Arg Cys Leu Thr Asn Tyr Ala Ile Asp Leu Gly Arg Thr
        260                 265                 270

Val Tyr Gln Ser Thr Ala Arg Xaa Asp Thr Asp Val Pro Phe Gln Leu
    275                 280                 285

Lys Ser Tyr Leu Lys Gln Gln Asn Arg Trp Asn Lys Ser Phe Phe Arg
290                 295                 300

Glu Ser Ile Ile Ser Val Lys Lys Ile Leu Ser Asn Pro Ile Val Ala
305                 310                 315                 320

Leu Trp Thr Ile Phe Glu Val Val Met Phe Met Met Leu Ile Val Ala
            325                 330                 335

Ile Gly Asn Leu Leu Phe Asn Gln Ala Ile Gln Leu Asp Leu Ile Lys
        340                 345                 350

Leu Phe Ala Phe Leu Ser Ile Ile Phe Ile Val Ala Leu Xaa Arg Asn
    355                 360                 365

Val His Tyr Met Val Lys His Pro Ala Ser Phe Leu Leu Ser Pro Leu
370                 375                 380

Tyr Gly Ile Leu His Leu Phe Val Leu Gln Pro Leu Lys Leu Tyr Ser
385                 390                 395                 400

Leu Cys Thr Ile Lys Asn Thr Glu Trp Gly Thr Arg Lys Lys Val Thr
            405                 410                 415

Ile Phe Lys

<210> SEQ ID NO 65
<211> LENGTH: 419
<212> TYPE: PRT
<213> ORGANISM: Streptococcus pyogenes
<220> FEATURE:
<221> NAME/KEY: MISC_FEATURE
<222> LOCATION: (225)..(225)
<223> OTHER INFORMATION: Xaa = Ala, Ser or any other amino acid
<220> FEATURE:
<221> NAME/KEY: MISC_FEATURE
<222> LOCATION: (280)..(280)
<223> OTHER INFORMATION: Xaa = Ala, Ser or any other amino acid
<220> FEATURE:
<221> NAME/KEY: MISC_FEATURE
<222> LOCATION: (402)..(402)
<223> OTHER INFORMATION: Xaa = Ala, Ser or any other amino acid

<400> SEQUENCE: 65

Met Pro Ile Phe Lys Lys Thr Leu Ile Val Leu Ser Phe Ile Phe Leu
1               5                   10                  15

Ile Ser Ile Leu Ile Tyr Leu Asn Met Tyr Leu Phe Gly Thr Ser Thr
            20                  25                  30

Val Gly Ile Tyr Gly Val Ile Leu Ile Thr Tyr Leu Val Ile Lys Leu
        35                  40                  45
```

-continued

```
Gly Leu Ser Phe Leu Tyr Glu Pro Phe Lys Gly Asn Pro His Asp Tyr
 50                  55                  60

Lys Val Ala Ala Val Ile Pro Ser Tyr Asn Glu Asp Ala Glu Ser Leu
 65                  70                  75                  80

Leu Glu Thr Leu Lys Ser Val Leu Ala Gln Thr Tyr Pro Leu Ser Glu
                 85                  90                  95

Ile Tyr Ile Val Asp Asp Gly Ser Ser Asn Thr Asp Ala Ile Gln Leu
            100                 105                 110

Ile Glu Glu Tyr Val Asn Arg Glu Val Asp Ile Cys Arg Asn Val Ile
            115                 120                 125

Val His Arg Ser Leu Val Asn Lys Gly Lys Arg His Ala Gln Ala Trp
130                 135                 140

Ala Phe Glu Arg Ser Asp Ala Asp Val Phe Leu Thr Val Asp Ser Asp
145                 150                 155                 160

Thr Tyr Ile Tyr Pro Asn Ala Leu Glu Glu Leu Leu Lys Ser Phe Asn
                165                 170                 175

Asp Glu Thr Val Tyr Ala Ala Thr Gly His Leu Asn Ala Arg Asn Arg
            180                 185                 190

Gln Thr Asn Leu Leu Thr Arg Leu Thr Asp Ile Arg Tyr Asp Asn Ala
            195                 200                 205

Phe Gly Val Glu Arg Ala Ala Gln Ser Leu Thr Gly Asn Ile Leu Val
210                 215                 220

Xaa Ser Gly Pro Leu Ser Ile Tyr Arg Arg Glu Val Ile Ile Pro Asn
225                 230                 235                 240

Leu Glu Arg Tyr Lys Asn Gln Thr Phe Leu Gly Leu Pro Val Ser Ile
                245                 250                 255

Gly Asp Asp Arg Cys Leu Thr Asn Tyr Ala Ile Asp Leu Gly Arg Thr
            260                 265                 270

Val Tyr Gln Ser Thr Ala Arg Xaa Asp Thr Asp Val Pro Phe Gln Leu
            275                 280                 285

Lys Ser Tyr Leu Lys Gln Gln Asn Arg Trp Asn Lys Ser Phe Phe Arg
290                 295                 300

Glu Ser Ile Ile Ser Val Lys Lys Ile Leu Ser Asn Pro Ile Val Ala
305                 310                 315                 320

Leu Trp Thr Ile Phe Glu Val Val Met Phe Met Met Leu Ile Val Ala
                325                 330                 335

Ile Gly Asn Leu Leu Phe Asn Gln Ala Ile Gln Leu Asp Leu Ile Lys
            340                 345                 350

Leu Phe Ala Phe Leu Ser Ile Ile Phe Ile Val Ala Leu Cys Arg Asn
            355                 360                 365

Val His Tyr Met Val Lys His Pro Ala Ser Phe Leu Leu Ser Pro Leu
370                 375                 380

Tyr Gly Ile Leu His Leu Phe Val Leu Gln Pro Leu Lys Leu Tyr Ser
385                 390                 395                 400

Leu Xaa Thr Ile Lys Asn Thr Glu Trp Gly Thr Arg Lys Lys Val Thr
                405                 410                 415

Ile Phe Lys
```

<210> SEQ ID NO 66
<211> LENGTH: 419
<212> TYPE: PRT
<213> ORGANISM: Streptococcus pyogenes
<220> FEATURE:
<221> NAME/KEY: MISC_FEATURE

```
<222> LOCATION: (225)..(225)
<223> OTHER INFORMATION: Xaa = Ala, Ser or any other amino acid
<220> FEATURE:
<221> NAME/KEY: MISC_FEATURE
<222> LOCATION: (366)..(366)
<223> OTHER INFORMATION: Xaa = Ala, Ser or any other amino acid
<220> FEATURE:
<221> NAME/KEY: MISC_FEATURE
<222> LOCATION: (402)..(402)
<223> OTHER INFORMATION: Xaa = Ala, Ser or any other amino acid

<400> SEQUENCE: 66
```

| | | | | | | | | | | | | | | |
|---|---|---|---|---|---|---|---|---|---|---|---|---|---|---|
| Met | Pro | Ile | Phe | Lys | Lys | Thr | Leu | Ile | Val | Leu | Ser | Phe | Ile | Phe Leu |
| 1 | | | | 5 | | | | | 10 | | | | | 15 |
| Ile | Ser | Ile | Leu | Ile | Tyr | Leu | Asn | Met | Tyr | Leu | Phe | Gly | Thr | Ser Thr |
| | | | 20 | | | | | 25 | | | | | 30 | |
| Val | Gly | Ile | Tyr | Gly | Val | Ile | Leu | Ile | Thr | Tyr | Leu | Val | Ile | Lys Leu |
| | | 35 | | | | | 40 | | | | | 45 | | |
| Gly | Leu | Ser | Phe | Leu | Tyr | Glu | Pro | Phe | Lys | Gly | Asn | Pro | His | Asp Tyr |
| | 50 | | | | | 55 | | | | | 60 | | | |
| Lys | Val | Ala | Ala | Val | Ile | Pro | Ser | Tyr | Asn | Glu | Asp | Ala | Glu | Ser Leu |
| 65 | | | | | 70 | | | | | 75 | | | | | 80 |
| Leu | Glu | Thr | Leu | Lys | Ser | Val | Leu | Ala | Gln | Thr | Tyr | Pro | Leu | Ser Glu |
| | | | | 85 | | | | | 90 | | | | | 95 |
| Ile | Tyr | Ile | Val | Asp | Asp | Gly | Ser | Ser | Asn | Thr | Asp | Ala | Ile | Gln Leu |
| | | | 100 | | | | | 105 | | | | | 110 | |
| Ile | Glu | Glu | Tyr | Val | Asn | Arg | Glu | Val | Asp | Ile | Cys | Arg | Asn | Val Ile |
| | | 115 | | | | | 120 | | | | | 125 | | |
| Val | His | Arg | Ser | Leu | Val | Asn | Lys | Gly | Lys | Arg | His | Ala | Gln | Ala Trp |
| | 130 | | | | | 135 | | | | | 140 | | | |
| Ala | Phe | Glu | Arg | Ser | Asp | Ala | Asp | Val | Phe | Leu | Thr | Val | Asp | Ser Asp |
| 145 | | | | | 150 | | | | | 155 | | | | | 160 |
| Thr | Tyr | Ile | Tyr | Pro | Asn | Ala | Leu | Glu | Glu | Leu | Leu | Lys | Ser | Phe Asn |
| | | | | 165 | | | | | 170 | | | | | 175 |
| Asp | Glu | Thr | Val | Tyr | Ala | Ala | Thr | Gly | His | Leu | Asn | Ala | Arg | Asn Arg |
| | | | 180 | | | | | 185 | | | | | 190 | |
| Gln | Thr | Asn | Leu | Leu | Thr | Arg | Leu | Thr | Asp | Ile | Arg | Tyr | Asp | Asn Ala |
| | | 195 | | | | | 200 | | | | | 205 | | |
| Phe | Gly | Val | Glu | Arg | Ala | Ala | Gln | Ser | Leu | Thr | Gly | Asn | Ile | Leu Val |
| | 210 | | | | | 215 | | | | | 220 | | | |
| Xaa | Ser | Gly | Pro | Leu | Ser | Ile | Tyr | Arg | Arg | Glu | Val | Ile | Ile | Pro Asn |
| 225 | | | | | 230 | | | | | 235 | | | | | 240 |
| Leu | Glu | Arg | Tyr | Lys | Asn | Gln | Thr | Phe | Leu | Gly | Leu | Pro | Val | Ser Ile |
| | | | | 245 | | | | | 250 | | | | | 255 |
| Gly | Asp | Asp | Arg | Cys | Leu | Thr | Asn | Tyr | Ala | Ile | Asp | Leu | Gly | Arg Thr |
| | | | 260 | | | | | 265 | | | | | 270 | |
| Val | Tyr | Gln | Ser | Thr | Ala | Arg | Cys | Asp | Thr | Asp | Val | Pro | Phe | Gln Leu |
| | | 275 | | | | | 280 | | | | | 285 | | |
| Lys | Ser | Tyr | Leu | Lys | Gln | Gln | Asn | Arg | Trp | Asn | Lys | Ser | Phe | Phe Arg |
| | 290 | | | | | 295 | | | | | 300 | | | |
| Glu | Ser | Ile | Ile | Ser | Val | Lys | Lys | Ile | Leu | Ser | Asn | Pro | Ile | Val Ala |
| 305 | | | | | 310 | | | | | 315 | | | | | 320 |
| Leu | Trp | Thr | Ile | Phe | Glu | Val | Val | Met | Phe | Met | Met | Leu | Ile | Val Ala |
| | | | | 325 | | | | | 330 | | | | | 335 |
| Ile | Gly | Asn | Leu | Leu | Phe | Asn | Gln | Ala | Ile | Gln | Leu | Asp | Leu | Ile Lys |
| | | | 340 | | | | | 345 | | | | | 350 | |

```
Leu Phe Ala Phe Leu Ser Ile Ile Phe Ile Val Ala Leu Xaa Arg Asn
              355                 360                 365

Val His Tyr Met Val Lys His Pro Ala Ser Phe Leu Leu Ser Pro Leu
    370                 375                 380

Tyr Gly Ile Leu His Leu Phe Val Leu Gln Pro Leu Lys Leu Tyr Ser
385                 390                 395                 400

Leu Xaa Thr Ile Lys Asn Thr Glu Trp Gly Thr Arg Lys Lys Val Thr
                405                 410                 415

Ile Phe Lys

<210> SEQ ID NO 67
<211> LENGTH: 419
<212> TYPE: PRT
<213> ORGANISM: Streptococcus pyogenes
<220> FEATURE:
<221> NAME/KEY: MISC_FEATURE
<222> LOCATION: (261)..(261)
<223> OTHER INFORMATION: Xaa = Ala, Ser or any other amino acid
<220> FEATURE:
<221> NAME/KEY: MISC_FEATURE
<222> LOCATION: (280)..(280)
<223> OTHER INFORMATION: Xaa = Ala, Ser or any other amino acid
<220> FEATURE:
<221> NAME/KEY: MISC_FEATURE
<222> LOCATION: (366)..(366)
<223> OTHER INFORMATION: Xaa = Ala, Ser or any other amino acid

<400> SEQUENCE: 67

Met Pro Ile Phe Lys Lys Thr Leu Ile Val Leu Ser Phe Ile Phe Leu
1               5                   10                  15

Ile Ser Ile Leu Ile Tyr Leu Asn Met Tyr Leu Phe Gly Thr Ser Thr
                20                  25                  30

Val Gly Ile Tyr Gly Val Ile Leu Ile Thr Tyr Leu Val Ile Lys Leu
            35                  40                  45

Gly Leu Ser Phe Leu Tyr Glu Pro Phe Lys Gly Asn Pro His Asp Tyr
    50                  55                  60

Lys Val Ala Ala Val Ile Pro Ser Tyr Asn Glu Asp Ala Glu Ser Leu
65                  70                  75                  80

Leu Glu Thr Leu Lys Ser Val Leu Ala Gln Thr Tyr Pro Leu Ser Glu
                85                  90                  95

Ile Tyr Ile Val Asp Asp Gly Ser Ser Asn Thr Asp Ala Ile Gln Leu
            100                 105                 110

Ile Glu Glu Tyr Val Asn Arg Glu Val Asp Ile Cys Arg Asn Val Ile
        115                 120                 125

Val His Arg Ser Leu Val Asn Lys Gly Lys Arg His Ala Gln Ala Trp
    130                 135                 140

Ala Phe Glu Arg Ser Asp Ala Asp Val Phe Leu Thr Val Asp Ser Asp
145                 150                 155                 160

Thr Tyr Ile Tyr Pro Asn Ala Leu Glu Glu Leu Leu Lys Ser Phe Asn
                165                 170                 175

Asp Glu Thr Val Tyr Ala Ala Thr Gly His Leu Asn Ala Arg Asn Arg
            180                 185                 190

Gln Thr Asn Leu Leu Thr Arg Leu Thr Asp Ile Arg Tyr Asp Asn Ala
        195                 200                 205

Phe Gly Val Glu Arg Ala Ala Gln Ser Leu Thr Gly Asn Ile Leu Val
    210                 215                 220

Cys Ser Gly Pro Leu Ser Ile Tyr Arg Arg Glu Val Ile Ile Pro Asn
225                 230                 235                 240
```

```
Leu Glu Arg Tyr Lys Asn Gln Thr Phe Leu Gly Leu Pro Val Ser Ile
                245                 250                 255

Gly Asp Asp Arg Xaa Leu Thr Asn Tyr Ala Ile Asp Leu Gly Arg Thr
            260                 265                 270

Val Tyr Gln Ser Thr Ala Arg Xaa Asp Thr Asp Val Pro Phe Gln Leu
        275                 280                 285

Lys Ser Tyr Leu Lys Gln Gln Asn Arg Trp Asn Lys Ser Phe Phe Arg
    290                 295                 300

Glu Ser Ile Ile Ser Val Lys Lys Ile Leu Ser Asn Pro Ile Val Ala
305                 310                 315                 320

Leu Trp Thr Ile Phe Glu Val Met Phe Met Leu Ile Val Ala
                325                 330                 335

Ile Gly Asn Leu Leu Phe Asn Gln Ala Ile Gln Leu Asp Leu Ile Lys
                340                 345                 350

Leu Phe Ala Phe Leu Ser Ile Ile Phe Ile Val Ala Leu Xaa Arg Asn
            355                 360                 365

Val His Tyr Met Val Lys His Pro Ala Ser Phe Leu Leu Ser Pro Leu
        370                 375                 380

Tyr Gly Ile Leu His Leu Phe Val Leu Gln Pro Leu Lys Leu Tyr Ser
385                 390                 395                 400

Leu Cys Thr Ile Lys Asn Thr Glu Trp Gly Thr Arg Lys Lys Val Thr
                405                 410                 415

Ile Phe Lys

<210> SEQ ID NO 68
<211> LENGTH: 419
<212> TYPE: PRT
<213> ORGANISM: Streptococcus pyogenes
<220> FEATURE:
<221> NAME/KEY: MISC_FEATURE
<222> LOCATION: (261)..(261)
<223> OTHER INFORMATION: Xaa = Ala, Ser or any other amino acid
<220> FEATURE:
<221> NAME/KEY: MISC_FEATURE
<222> LOCATION: (280)..(280)
<223> OTHER INFORMATION: Xaa = Ala, Ser or any other amino acid
<220> FEATURE:
<221> NAME/KEY: MISC_FEATURE
<222> LOCATION: (402)..(402)
<223> OTHER INFORMATION: Xaa = Ala, Ser or any other amino acid

<400> SEQUENCE: 68

Met Pro Ile Phe Lys Lys Thr Leu Ile Val Leu Ser Phe Ile Phe Leu
1               5                   10                  15

Ile Ser Ile Leu Ile Tyr Leu Asn Met Tyr Leu Phe Gly Thr Ser Thr
            20                  25                  30

Val Gly Ile Tyr Gly Val Ile Leu Ile Thr Tyr Leu Val Ile Lys Leu
        35                  40                  45

Gly Leu Ser Phe Leu Tyr Glu Pro Phe Lys Gly Asn Pro His Asp Tyr
    50                  55                  60

Lys Val Ala Ala Val Ile Pro Ser Tyr Asn Glu Asp Ala Glu Ser Leu
65                  70                  75                  80

Leu Glu Thr Leu Lys Ser Val Leu Ala Gln Thr Tyr Pro Leu Ser Glu
                85                  90                  95

Ile Tyr Ile Val Asp Asp Gly Ser Ser Asn Thr Asp Ala Ile Gln Leu
            100                 105                 110

Ile Glu Glu Tyr Val Asn Arg Glu Val Asp Ile Cys Arg Asn Val Ile
        115                 120                 125
```

```
Val His Arg Ser Leu Val Asn Lys Gly Lys Arg His Ala Gln Ala Trp
    130                 135                 140

Ala Phe Glu Arg Ser Asp Ala Asp Val Phe Leu Thr Val Asp Ser Asp
145                 150                 155                 160

Thr Tyr Ile Tyr Pro Asn Ala Leu Glu Glu Leu Leu Lys Ser Phe Asn
                165                 170                 175

Asp Glu Thr Val Tyr Ala Ala Thr Gly His Leu Asn Ala Arg Asn Arg
            180                 185                 190

Gln Thr Asn Leu Leu Thr Arg Leu Thr Asp Ile Arg Tyr Asp Asn Ala
        195                 200                 205

Phe Gly Val Glu Arg Ala Ala Gln Ser Leu Thr Gly Asn Ile Leu Val
    210                 215                 220

Cys Ser Gly Pro Leu Ser Ile Tyr Arg Arg Glu Val Ile Ile Pro Asn
225                 230                 235                 240

Leu Glu Arg Tyr Lys Asn Gln Thr Phe Leu Gly Leu Pro Val Ser Ile
                245                 250                 255

Gly Asp Asp Arg Xaa Leu Thr Asn Tyr Ala Ile Asp Leu Gly Arg Thr
            260                 265                 270

Val Tyr Gln Ser Thr Ala Arg Xaa Asp Thr Asp Val Pro Phe Gln Leu
        275                 280                 285

Lys Ser Tyr Leu Lys Gln Gln Asn Arg Trp Asn Lys Ser Phe Arg
290                 295                 300

Glu Ser Ile Ile Ser Val Lys Lys Ile Leu Ser Asn Pro Ile Val Ala
305                 310                 315                 320

Leu Trp Thr Ile Phe Glu Val Val Met Phe Met Leu Ile Val Ala
                325                 330                 335

Ile Gly Asn Leu Leu Phe Asn Gln Ala Ile Gln Leu Asp Leu Ile Lys
            340                 345                 350

Leu Phe Ala Phe Leu Ser Ile Ile Phe Ile Val Ala Leu Cys Arg Asn
        355                 360                 365

Val His Tyr Met Val Lys His Pro Ala Ser Phe Leu Leu Ser Pro Leu
    370                 375                 380

Tyr Gly Ile Leu His Leu Phe Val Leu Gln Pro Leu Lys Leu Tyr Ser
385                 390                 395                 400

Leu Xaa Thr Ile Lys Asn Thr Glu Trp Gly Thr Arg Lys Lys Val Thr
                405                 410                 415

Ile Phe Lys

<210> SEQ ID NO 69
<211> LENGTH: 419
<212> TYPE: PRT
<213> ORGANISM: Streptococcus pyogenes
<220> FEATURE:
<221> NAME/KEY: MISC_FEATURE
<222> LOCATION: (261)..(261)
<223> OTHER INFORMATION: Xaa = Ala, Ser or any other amino acid
<220> FEATURE:
<221> NAME/KEY: MISC_FEATURE
<222> LOCATION: (366)..(366)
<223> OTHER INFORMATION: Xaa = Ala, Ser or any other amino acid
<220> FEATURE:
<221> NAME/KEY: MISC_FEATURE
<222> LOCATION: (402)..(402)
<223> OTHER INFORMATION: Xaa = Ala, Ser or any other amino acid

<400> SEQUENCE: 69

Met Pro Ile Phe Lys Lys Thr Leu Ile Val Leu Ser Phe Ile Phe Leu
1               5                   10                  15
```

```
Ile Ser Ile Leu Ile Tyr Leu Asn Met Tyr Leu Phe Gly Thr Ser Thr
             20                  25                  30

Val Gly Ile Tyr Gly Val Ile Leu Ile Thr Tyr Leu Val Ile Lys Leu
                 35                  40                  45

Gly Leu Ser Phe Leu Tyr Glu Pro Phe Lys Gly Asn Pro His Asp Tyr
 50                  55                  60

Lys Val Ala Ala Val Ile Pro Ser Tyr Asn Glu Asp Ala Glu Ser Leu
 65                  70                  75                  80

Leu Glu Thr Leu Lys Ser Val Leu Ala Gln Thr Tyr Pro Leu Ser Glu
                 85                  90                  95

Ile Tyr Ile Val Asp Asp Gly Ser Ser Asn Thr Asp Ala Ile Gln Leu
                100                 105                 110

Ile Glu Glu Tyr Val Asn Arg Glu Val Asp Ile Cys Arg Asn Val Ile
            115                 120                 125

Val His Arg Ser Leu Val Asn Lys Gly Lys Arg His Ala Gln Ala Trp
130                 135                 140

Ala Phe Glu Arg Ser Asp Ala Asp Val Phe Leu Thr Val Asp Ser Asp
145                 150                 155                 160

Thr Tyr Ile Tyr Pro Asn Ala Leu Glu Glu Leu Leu Lys Ser Phe Asn
                165                 170                 175

Asp Glu Thr Val Tyr Ala Ala Thr Gly His Leu Asn Ala Arg Asn Arg
            180                 185                 190

Gln Thr Asn Leu Leu Thr Arg Leu Thr Asp Ile Arg Tyr Asp Asn Ala
        195                 200                 205

Phe Gly Val Glu Arg Ala Ala Gln Ser Leu Thr Gly Asn Ile Leu Val
210                 215                 220

Cys Ser Gly Pro Leu Ser Ile Tyr Arg Arg Glu Val Ile Ile Pro Asn
225                 230                 235                 240

Leu Glu Arg Tyr Lys Asn Gln Thr Phe Leu Gly Leu Pro Val Ser Ile
                245                 250                 255

Gly Asp Asp Arg Xaa Leu Thr Asn Tyr Ala Ile Asp Leu Gly Arg Thr
            260                 265                 270

Val Tyr Gln Ser Thr Ala Arg Cys Asp Thr Asp Val Pro Phe Gln Leu
        275                 280                 285

Lys Ser Tyr Leu Lys Gln Gln Asn Arg Trp Asn Lys Ser Phe Phe Arg
    290                 295                 300

Glu Ser Ile Ile Ser Val Lys Lys Ile Leu Ser Asn Pro Ile Val Ala
305                 310                 315                 320

Leu Trp Thr Ile Phe Glu Val Val Met Phe Met Leu Ile Val Ala
                325                 330                 335

Ile Gly Asn Leu Leu Phe Asn Gln Ala Ile Gln Leu Asp Leu Ile Lys
            340                 345                 350

Leu Phe Ala Phe Leu Ser Ile Ile Phe Ile Val Ala Leu Xaa Arg Asn
        355                 360                 365

Val His Tyr Met Val Lys His Pro Ala Ser Phe Leu Leu Ser Pro Leu
    370                 375                 380

Tyr Gly Ile Leu His Leu Phe Val Leu Gln Pro Leu Lys Leu Tyr Ser
385                 390                 395                 400

Leu Xaa Thr Ile Lys Asn Thr Glu Trp Gly Thr Arg Lys Lys Val Thr
                405                 410                 415

Ile Phe Lys

<210> SEQ ID NO 70
```

```
<211> LENGTH: 419
<212> TYPE: PRT
<213> ORGANISM: Streptococcus pyogenes
<220> FEATURE:
<221> NAME/KEY: MISC_FEATURE
<222> LOCATION: (280)..(280)
<223> OTHER INFORMATION: Xaa = Ala, Ser or any other amino acid
<220> FEATURE:
<221> NAME/KEY: MISC_FEATURE
<222> LOCATION: (366)..(366)
<223> OTHER INFORMATION: Xaa = Ala, Ser or any other amino acid
<220> FEATURE:
<221> NAME/KEY: MISC_FEATURE
<222> LOCATION: (402)..(402)
<223> OTHER INFORMATION: Xaa = Ala, Ser or any other amino acid

<400> SEQUENCE: 70
```

Met Pro Ile Phe Lys Lys Thr Leu Ile Val Leu Ser Phe Ile Phe Leu
1               5                   10                  15

Ile Ser Ile Leu Ile Tyr Leu Asn Met Tyr Leu Phe Gly Thr Ser Thr
            20                  25                  30

Val Gly Ile Tyr Gly Val Ile Leu Ile Thr Tyr Leu Val Ile Lys Leu
        35                  40                  45

Gly Leu Ser Phe Leu Tyr Glu Pro Phe Lys Gly Asn Pro His Asp Tyr
    50                  55                  60

Lys Val Ala Ala Val Ile Pro Ser Tyr Asn Glu Asp Ala Glu Ser Leu
65                  70                  75                  80

Leu Glu Thr Leu Lys Ser Val Leu Ala Gln Thr Tyr Pro Leu Ser Glu
                85                  90                  95

Ile Tyr Ile Val Asp Asp Gly Ser Ser Asn Thr Asp Ala Ile Gln Leu
            100                 105                 110

Ile Glu Glu Tyr Val Asn Arg Glu Val Asp Ile Cys Arg Asn Val Ile
        115                 120                 125

Val His Arg Ser Leu Val Asn Lys Gly Lys Arg His Ala Gln Ala Trp
130                 135                 140

Ala Phe Glu Arg Ser Asp Ala Asp Val Phe Leu Thr Val Asp Ser Asp
145                 150                 155                 160

Thr Tyr Ile Tyr Pro Asn Ala Leu Glu Glu Leu Leu Lys Ser Phe Asn
                165                 170                 175

Asp Glu Thr Val Tyr Ala Ala Thr Gly His Leu Asn Ala Arg Asn Arg
            180                 185                 190

Gln Thr Asn Leu Leu Thr Arg Leu Thr Asp Ile Arg Tyr Asp Asn Ala
        195                 200                 205

Phe Gly Val Glu Arg Ala Ala Gln Ser Leu Thr Gly Asn Ile Leu Val
210                 215                 220

Cys Ser Gly Pro Leu Ser Ile Tyr Arg Arg Glu Val Ile Ile Pro Asn
225                 230                 235                 240

Leu Glu Arg Tyr Lys Asn Gln Thr Phe Leu Gly Leu Pro Val Ser Ile
                245                 250                 255

Gly Asp Asp Arg Cys Leu Thr Asn Tyr Ala Ile Asp Leu Gly Arg Thr
            260                 265                 270

Val Tyr Gln Ser Thr Ala Arg Xaa Asp Thr Asp Val Pro Phe Gln Leu
        275                 280                 285

Lys Ser Tyr Leu Lys Gln Gln Asn Arg Trp Asn Lys Ser Phe Phe Arg
290                 295                 300

Glu Ser Ile Ile Ser Val Lys Lys Ile Leu Ser Asn Pro Ile Val Ala
305                 310                 315                 320

Leu Trp Thr Ile Phe Glu Val Val Met Phe Met Met Leu Ile Val Ala

-continued

```
                325                 330                 335
Ile Gly Asn Leu Leu Phe Asn Gln Ala Ile Gln Leu Asp Leu Ile Lys
            340                 345                 350

Leu Phe Ala Phe Leu Ser Ile Ile Phe Ile Val Ala Leu Xaa Arg Asn
            355                 360                 365

Val His Tyr Met Val Lys His Pro Ala Ser Phe Leu Leu Ser Pro Leu
        370                 375                 380

Tyr Gly Ile Leu His Leu Phe Val Leu Gln Pro Leu Lys Leu Tyr Ser
385                 390                 395                 400

Leu Xaa Thr Ile Lys Asn Thr Glu Trp Gly Thr Arg Lys Lys Val Thr
                405                 410                 415

Ile Phe Lys

<210> SEQ ID NO 71
<211> LENGTH: 419
<212> TYPE: PRT
<213> ORGANISM: Streptococcus pyogenes
<220> FEATURE:
<221> NAME/KEY: MISC_FEATURE
<222> LOCATION: (124)..(124)
<223> OTHER INFORMATION: Xaa = Ala, Ser or any other amino acid
<220> FEATURE:
<221> NAME/KEY: MISC_FEATURE
<222> LOCATION: (225)..(225)
<223> OTHER INFORMATION: Xaa = Ala, Ser or any other amino acid
<220> FEATURE:
<221> NAME/KEY: MISC_FEATURE
<222> LOCATION: (261)..(261)
<223> OTHER INFORMATION: Xaa = Ala, Ser or any other amino acid
<220> FEATURE:
<221> NAME/KEY: MISC_FEATURE
<222> LOCATION: (280)..(280)
<223> OTHER INFORMATION: Xaa = Ala, Ser or any other amino acid

<400> SEQUENCE: 71

Met Pro Ile Phe Lys Lys Thr Leu Ile Val Leu Ser Phe Ile Phe Leu
1               5                   10                  15

Ile Ser Ile Leu Ile Tyr Leu Asn Met Tyr Leu Phe Gly Thr Ser Thr
            20                  25                  30

Val Gly Ile Tyr Gly Val Ile Leu Ile Thr Tyr Leu Val Ile Lys Leu
        35                  40                  45

Gly Leu Ser Phe Leu Tyr Glu Pro Phe Lys Gly Asn Pro His Asp Tyr
    50                  55                  60

Lys Val Ala Ala Val Ile Pro Ser Tyr Asn Glu Asp Ala Glu Ser Leu
65                  70                  75                  80

Leu Glu Thr Leu Lys Ser Val Leu Ala Gln Thr Tyr Pro Leu Ser Glu
                85                  90                  95

Ile Tyr Ile Val Asp Asp Gly Ser Ser Asn Thr Asp Ala Ile Gln Leu
            100                 105                 110

Ile Glu Glu Tyr Val Asn Arg Glu Val Asp Ile Xaa Arg Asn Val Ile
        115                 120                 125

Val His Arg Ser Leu Val Asn Lys Gly Lys Arg His Ala Gln Ala Trp
    130                 135                 140

Ala Phe Glu Arg Ser Asp Ala Asp Val Phe Leu Thr Val Asp Ser Asp
145                 150                 155                 160

Thr Tyr Ile Tyr Pro Asn Ala Leu Glu Glu Leu Leu Lys Ser Phe Asn
                165                 170                 175

Asp Glu Thr Val Tyr Ala Ala Thr Gly His Leu Asn Ala Arg Asn Arg
            180                 185                 190
```

```
Gln Thr Asn Leu Leu Thr Arg Leu Thr Asp Ile Arg Tyr Asp Asn Ala
            195                 200                 205

Phe Gly Val Glu Arg Ala Ala Gln Ser Leu Thr Gly Asn Ile Leu Val
        210                 215                 220

Xaa Ser Gly Pro Leu Ser Ile Tyr Arg Arg Glu Val Ile Ile Pro Asn
225                 230                 235                 240

Leu Glu Arg Tyr Lys Asn Gln Thr Phe Leu Gly Leu Pro Val Ser Ile
                245                 250                 255

Gly Asp Asp Arg Xaa Leu Thr Asn Tyr Ala Ile Asp Leu Gly Arg Thr
            260                 265                 270

Val Tyr Gln Ser Thr Ala Arg Xaa Asp Thr Asp Val Pro Phe Gln Leu
        275                 280                 285

Lys Ser Tyr Leu Lys Gln Gln Asn Arg Trp Asn Lys Ser Phe Phe Arg
    290                 295                 300

Glu Ser Ile Ile Ser Val Lys Lys Ile Leu Ser Asn Pro Ile Val Ala
305                 310                 315                 320

Leu Trp Thr Ile Phe Glu Val Val Met Phe Met Met Leu Ile Val Ala
                325                 330                 335

Ile Gly Asn Leu Leu Phe Asn Gln Ala Ile Gln Leu Asp Leu Ile Lys
            340                 345                 350

Leu Phe Ala Phe Leu Ser Ile Ile Phe Ile Val Ala Leu Cys Arg Asn
        355                 360                 365

Val His Tyr Met Val Lys His Pro Ala Ser Phe Leu Leu Ser Pro Leu
    370                 375                 380

Tyr Gly Ile Leu His Leu Phe Val Leu Gln Pro Leu Lys Leu Tyr Ser
385                 390                 395                 400

Leu Cys Thr Ile Lys Asn Thr Glu Trp Gly Thr Arg Lys Lys Val Thr
                405                 410                 415

Ile Phe Lys

<210> SEQ ID NO 72
<211> LENGTH: 419
<212> TYPE: PRT
<213> ORGANISM: Streptococcus pyogenes
<220> FEATURE:
<221> NAME/KEY: MISC_FEATURE
<222> LOCATION: (124)..(124)
<223> OTHER INFORMATION: Xaa = Ala, Ser or any other amino acid
<220> FEATURE:
<221> NAME/KEY: MISC_FEATURE
<222> LOCATION: (225)..(225)
<223> OTHER INFORMATION: Xaa = Ala, Ser or any other amino acid
<220> FEATURE:
<221> NAME/KEY: MISC_FEATURE
<222> LOCATION: (261)..(261)
<223> OTHER INFORMATION: Xaa = Ala, Ser or any other amino acid
<220> FEATURE:
<221> NAME/KEY: MISC_FEATURE
<222> LOCATION: (366)..(366)
<223> OTHER INFORMATION: Xaa = Ala, Ser or any other amino acid

<400> SEQUENCE: 72

Met Pro Ile Phe Lys Lys Thr Leu Ile Val Leu Ser Phe Ile Phe Leu
1               5                   10                  15

Ile Ser Ile Leu Ile Tyr Leu Asn Met Tyr Leu Phe Gly Thr Ser Thr
            20                  25                  30

Val Gly Ile Tyr Gly Val Ile Leu Ile Thr Tyr Leu Val Ile Lys Leu
        35                  40                  45

Gly Leu Ser Phe Leu Tyr Glu Pro Phe Lys Gly Asn Pro His Asp Tyr
    50                  55                  60
```

```
Lys Val Ala Ala Val Ile Pro Ser Tyr Asn Glu Asp Ala Glu Ser Leu
 65                  70                  75                  80

Leu Glu Thr Leu Lys Ser Val Leu Ala Gln Thr Tyr Pro Leu Ser Glu
                 85                  90                  95

Ile Tyr Ile Val Asp Asp Gly Ser Ser Asn Thr Asp Ala Ile Gln Leu
                100                 105                 110

Ile Glu Glu Tyr Val Asn Arg Glu Val Asp Ile Xaa Arg Asn Val Ile
                115                 120                 125

Val His Arg Ser Leu Val Asn Lys Gly Lys Arg His Ala Gln Ala Trp
        130                 135                 140

Ala Phe Glu Arg Ser Asp Ala Asp Val Phe Leu Thr Val Asp Ser Asp
145                 150                 155                 160

Thr Tyr Ile Tyr Pro Asn Ala Leu Glu Glu Leu Leu Lys Ser Phe Asn
                165                 170                 175

Asp Glu Thr Val Tyr Ala Ala Thr Gly His Leu Asn Ala Arg Asn Arg
                180                 185                 190

Gln Thr Asn Leu Leu Thr Arg Leu Thr Asp Ile Arg Tyr Asp Asn Ala
        195                 200                 205

Phe Gly Val Glu Arg Ala Ala Gln Ser Leu Thr Gly Asn Ile Leu Val
210                 215                 220

Xaa Ser Gly Pro Leu Ser Ile Tyr Arg Arg Glu Val Ile Ile Pro Asn
225                 230                 235                 240

Leu Glu Arg Tyr Lys Asn Gln Thr Phe Leu Gly Leu Pro Val Ser Ile
                245                 250                 255

Gly Asp Asp Arg Xaa Leu Thr Asn Tyr Ala Ile Asp Leu Gly Arg Thr
                260                 265                 270

Val Tyr Gln Ser Thr Ala Arg Cys Asp Thr Asp Val Pro Phe Gln Leu
        275                 280                 285

Lys Ser Tyr Leu Lys Gln Gln Asn Arg Trp Asn Lys Ser Phe Arg
290                 295                 300

Glu Ser Ile Ile Ser Val Lys Lys Ile Leu Ser Asn Pro Ile Val Ala
305                 310                 315                 320

Leu Trp Thr Ile Phe Glu Val Val Met Phe Met Leu Ile Val Ala
                325                 330                 335

Ile Gly Asn Leu Leu Phe Asn Gln Ala Ile Gln Leu Asp Leu Ile Lys
                340                 345                 350

Leu Phe Ala Phe Leu Ser Ile Ile Phe Ile Val Ala Leu Xaa Arg Asn
        355                 360                 365

Val His Tyr Met Val Lys His Pro Ala Ser Phe Leu Leu Ser Pro Leu
        370                 375                 380

Tyr Gly Ile Leu His Leu Phe Val Leu Gln Pro Leu Lys Leu Tyr Ser
385                 390                 395                 400

Leu Cys Thr Ile Lys Asn Thr Glu Trp Gly Thr Arg Lys Lys Val Thr
                405                 410                 415

Ile Phe Lys

<210> SEQ ID NO 73
<211> LENGTH: 419
<212> TYPE: PRT
<213> ORGANISM: Streptococcus pyogenes
<220> FEATURE:
<221> NAME/KEY: MISC_FEATURE
<222> LOCATION: (124)..(124)
<223> OTHER INFORMATION: Xaa = Ala, Ser or any other amino acid
<220> FEATURE:
```

-continued

```
<221> NAME/KEY: MISC_FEATURE
<222> LOCATION: (225)..(225)
<223> OTHER INFORMATION: Xaa = Ala, Ser or any other amino acid
<220> FEATURE:
<221> NAME/KEY: MISC_FEATURE
<222> LOCATION: (261)..(261)
<223> OTHER INFORMATION: Xaa = Ala, Ser or any other amino acid
<220> FEATURE:
<221> NAME/KEY: MISC_FEATURE
<222> LOCATION: (402)..(402)
<223> OTHER INFORMATION: Xaa = Ala, Ser or any other amino acid

<400> SEQUENCE: 73

Met Pro Ile Phe Lys Lys Thr Leu Ile Val Leu Ser Phe Ile Phe Leu
1               5                   10                  15

Ile Ser Ile Leu Ile Tyr Leu Asn Met Tyr Leu Phe Gly Thr Ser Thr
            20                  25                  30

Val Gly Ile Tyr Gly Val Ile Leu Ile Thr Tyr Leu Val Ile Lys Leu
        35                  40                  45

Gly Leu Ser Phe Leu Tyr Glu Pro Phe Lys Gly Asn Pro His Asp Tyr
50                  55                  60

Lys Val Ala Ala Val Ile Pro Ser Tyr Asn Glu Asp Ala Glu Ser Leu
65                  70                  75                  80

Leu Glu Thr Leu Lys Ser Val Leu Ala Gln Thr Tyr Pro Leu Ser Glu
                85                  90                  95

Ile Tyr Ile Val Asp Asp Gly Ser Ser Asn Thr Asp Ala Ile Gln Leu
            100                 105                 110

Ile Glu Glu Tyr Val Asn Arg Glu Val Asp Ile Xaa Arg Asn Val Ile
        115                 120                 125

Val His Arg Ser Leu Val Asn Lys Gly Lys Arg His Ala Gln Ala Trp
130                 135                 140

Ala Phe Glu Arg Ser Asp Ala Asp Val Phe Leu Thr Val Asp Ser Asp
145                 150                 155                 160

Thr Tyr Ile Tyr Pro Asn Ala Leu Glu Glu Leu Leu Lys Ser Phe Asn
                165                 170                 175

Asp Glu Thr Val Tyr Ala Ala Thr Gly His Leu Asn Ala Arg Asn Arg
            180                 185                 190

Gln Thr Asn Leu Leu Thr Arg Leu Thr Asp Ile Arg Tyr Asp Asn Ala
        195                 200                 205

Phe Gly Val Glu Arg Ala Ala Gln Ser Leu Thr Gly Asn Ile Leu Val
210                 215                 220

Xaa Ser Gly Pro Leu Ser Ile Tyr Arg Arg Glu Val Ile Ile Pro Asn
225                 230                 235                 240

Leu Glu Arg Tyr Lys Asn Gln Thr Phe Leu Gly Leu Pro Val Ser Ile
                245                 250                 255

Gly Asp Asp Arg Xaa Leu Thr Asn Tyr Ala Ile Asp Leu Gly Arg Thr
            260                 265                 270

Val Tyr Gln Ser Thr Ala Arg Cys Asp Thr Asp Val Pro Phe Gln Leu
        275                 280                 285

Lys Ser Tyr Leu Lys Gln Gln Asn Arg Trp Asn Lys Ser Phe Phe Arg
290                 295                 300

Glu Ser Ile Ile Ser Val Lys Lys Ile Leu Ser Asn Pro Ile Val Ala
305                 310                 315                 320

Leu Trp Thr Ile Phe Glu Val Met Phe Met Leu Ile Val Ala
                325                 330                 335

Ile Gly Asn Leu Leu Phe Asn Gln Ala Ile Gln Leu Asp Leu Ile Lys
            340                 345                 350
```

-continued

```
Leu Phe Ala Phe Leu Ser Ile Ile Phe Ile Val Ala Leu Cys Arg Asn
            355                 360                 365

Val His Tyr Met Val Lys His Pro Ala Ser Phe Leu Leu Ser Pro Leu
    370                 375                 380

Tyr Gly Ile Leu His Leu Phe Val Leu Gln Pro Leu Lys Leu Tyr Ser
385                 390                 395                 400

Leu Xaa Thr Ile Lys Asn Thr Glu Trp Gly Thr Arg Lys Lys Val Thr
                405                 410                 415

Ile Phe Lys

<210> SEQ ID NO 74
<211> LENGTH: 419
<212> TYPE: PRT
<213> ORGANISM: Streptococcus pyogenes
<220> FEATURE:
<221> NAME/KEY: MISC_FEATURE
<222> LOCATION: (124)..(124)
<223> OTHER INFORMATION: Xaa = Ala, Ser or any other amino acid
<220> FEATURE:
<221> NAME/KEY: MISC_FEATURE
<222> LOCATION: (225)..(225)
<223> OTHER INFORMATION: Xaa = Ala, Ser or any other amino acid
<220> FEATURE:
<221> NAME/KEY: MISC_FEATURE
<222> LOCATION: (280)..(280)
<223> OTHER INFORMATION: Xaa = Ala, Ser or any other amino acid
<220> FEATURE:
<221> NAME/KEY: MISC_FEATURE
<222> LOCATION: (366)..(366)
<223> OTHER INFORMATION: Xaa = Ala, Ser or any other amino acid

<400> SEQUENCE: 74

Met Pro Ile Phe Lys Lys Thr Leu Ile Val Leu Ser Phe Ile Phe Leu
1               5                   10                  15

Ile Ser Ile Leu Ile Tyr Leu Asn Met Tyr Leu Phe Gly Thr Ser Thr
                20                  25                  30

Val Gly Ile Tyr Gly Val Ile Leu Ile Thr Tyr Leu Val Ile Lys Leu
            35                  40                  45

Gly Leu Ser Phe Leu Tyr Glu Pro Phe Lys Gly Asn Pro His Asp Tyr
50                  55                  60

Lys Val Ala Ala Val Ile Pro Ser Tyr Asn Glu Asp Ala Glu Ser Leu
65                  70                  75                  80

Leu Glu Thr Leu Lys Ser Val Leu Ala Gln Thr Tyr Pro Leu Ser Glu
                85                  90                  95

Ile Tyr Ile Val Asp Asp Gly Ser Ser Asn Thr Asp Ala Ile Gln Leu
            100                 105                 110

Ile Glu Glu Tyr Val Asn Arg Glu Val Asp Ile Xaa Arg Asn Val Ile
            115                 120                 125

Val His Arg Ser Leu Val Asn Lys Gly Lys Arg His Ala Gln Ala Trp
130                 135                 140

Ala Phe Glu Arg Ser Asp Ala Asp Val Phe Leu Thr Val Asp Ser Asp
145                 150                 155                 160

Thr Tyr Ile Tyr Pro Asn Ala Leu Glu Glu Leu Leu Lys Ser Phe Asn
                165                 170                 175

Asp Glu Thr Val Tyr Ala Ala Thr Gly His Leu Asn Ala Arg Asn Arg
            180                 185                 190

Gln Thr Asn Leu Leu Thr Arg Leu Thr Asp Ile Arg Tyr Asp Asn Ala
            195                 200                 205

Phe Gly Val Glu Arg Ala Ala Gln Ser Leu Thr Gly Asn Ile Leu Val
```

-continued

```
                210                 215                 220
Xaa Ser Gly Pro Leu Ser Ile Tyr Arg Arg Glu Val Ile Ile Pro Asn
225                 230                 235                 240

Leu Glu Arg Tyr Lys Asn Gln Thr Phe Leu Gly Leu Pro Val Ser Ile
                245                 250                 255

Gly Asp Asp Arg Cys Leu Thr Asn Tyr Ala Ile Asp Leu Gly Arg Thr
                260                 265                 270

Val Tyr Gln Ser Thr Ala Arg Xaa Asp Thr Asp Val Pro Phe Gln Leu
                275                 280                 285

Lys Ser Tyr Leu Lys Gln Gln Asn Arg Trp Asn Lys Ser Phe Phe Arg
290                 295                 300

Glu Ser Ile Ile Ser Val Lys Lys Ile Leu Ser Asn Pro Ile Val Ala
305                 310                 315                 320

Leu Trp Thr Ile Phe Glu Val Val Met Phe Met Met Leu Ile Val Ala
                325                 330                 335

Ile Gly Asn Leu Leu Phe Asn Gln Ala Ile Gln Leu Asp Leu Ile Lys
                340                 345                 350

Leu Phe Ala Phe Leu Ser Ile Ile Phe Ile Val Ala Leu Xaa Arg Asn
                355                 360                 365

Val His Tyr Met Val Lys His Pro Ala Ser Phe Leu Leu Ser Pro Leu
                370                 375                 380

Tyr Gly Ile Leu His Leu Phe Val Leu Gln Pro Leu Lys Leu Tyr Ser
385                 390                 395                 400

Leu Cys Thr Ile Lys Asn Thr Glu Trp Gly Thr Arg Lys Lys Val Thr
                405                 410                 415

Ile Phe Lys

<210> SEQ ID NO 75
<211> LENGTH: 419
<212> TYPE: PRT
<213> ORGANISM: Streptococcus pyogenes
<220> FEATURE:
<221> NAME/KEY: MISC_FEATURE
<222> LOCATION: (124)..(124)
<223> OTHER INFORMATION: Xaa = Ala, Ser or any other amino acid
<220> FEATURE:
<221> NAME/KEY: MISC_FEATURE
<222> LOCATION: (225)..(225)
<223> OTHER INFORMATION: Xaa = Ala, Ser or any other amino acid
<220> FEATURE:
<221> NAME/KEY: MISC_FEATURE
<222> LOCATION: (280)..(280)
<223> OTHER INFORMATION: Xaa = Ala, Ser or any other amino acid
<220> FEATURE:
<221> NAME/KEY: MISC_FEATURE
<222> LOCATION: (402)..(402)
<223> OTHER INFORMATION: Xaa = Ala, Ser or any other amino acid

<400> SEQUENCE: 75

Met Pro Ile Phe Lys Lys Thr Leu Ile Val Leu Ser Phe Ile Phe Leu
1               5                   10                  15

Ile Ser Ile Leu Ile Tyr Leu Asn Met Tyr Leu Phe Gly Thr Ser Thr
                20                  25                  30

Val Gly Ile Tyr Gly Val Ile Leu Ile Thr Tyr Leu Val Ile Lys Leu
                35                  40                  45

Gly Leu Ser Phe Leu Tyr Glu Pro Phe Lys Gly Asn Pro His Asp Tyr
                50                  55                  60

Lys Val Ala Ala Val Ile Pro Ser Tyr Asn Glu Asp Ala Glu Ser Leu
65                  70                  75                  80
```

-continued

```
Leu Glu Thr Leu Lys Ser Val Leu Ala Gln Thr Tyr Pro Leu Ser Glu
                 85                  90                  95
Ile Tyr Ile Val Asp Asp Gly Ser Ser Asn Thr Asp Ala Ile Gln Leu
            100                 105                 110
Ile Glu Glu Tyr Val Asn Arg Glu Val Asp Ile Xaa Arg Asn Val Ile
        115                 120                 125
Val His Arg Ser Leu Val Asn Lys Gly Lys Arg His Ala Gln Ala Trp
130                 135                 140
Ala Phe Glu Arg Ser Asp Ala Asp Val Phe Leu Thr Val Asp Ser Asp
145                 150                 155                 160
Thr Tyr Ile Tyr Pro Asn Ala Leu Glu Glu Leu Leu Lys Ser Phe Asn
                165                 170                 175
Asp Glu Thr Val Tyr Ala Ala Thr Gly His Leu Asn Ala Arg Asn Arg
            180                 185                 190
Gln Thr Asn Leu Leu Thr Arg Leu Thr Asp Ile Arg Tyr Asp Asn Ala
        195                 200                 205
Phe Gly Val Glu Arg Ala Ala Gln Ser Leu Thr Gly Asn Ile Leu Val
210                 215                 220
Xaa Ser Gly Pro Leu Ser Ile Tyr Arg Arg Glu Val Ile Ile Pro Asn
225                 230                 235                 240
Leu Glu Arg Tyr Lys Asn Gln Thr Phe Leu Gly Leu Pro Val Ser Ile
                245                 250                 255
Gly Asp Asp Arg Cys Leu Thr Asn Tyr Ala Ile Asp Leu Gly Arg Thr
            260                 265                 270
Val Tyr Gln Ser Thr Ala Arg Xaa Asp Thr Asp Val Pro Phe Gln Leu
        275                 280                 285
Lys Ser Tyr Leu Lys Gln Gln Asn Arg Trp Asn Lys Ser Phe Phe Arg
290                 295                 300
Glu Ser Ile Ile Ser Val Lys Lys Ile Leu Ser Asn Pro Ile Val Ala
305                 310                 315                 320
Leu Trp Thr Ile Phe Glu Val Val Met Phe Met Leu Ile Val Ala
                325                 330                 335
Ile Gly Asn Leu Leu Phe Asn Gln Ala Ile Gln Leu Asp Leu Ile Lys
            340                 345                 350
Leu Phe Ala Phe Leu Ser Ile Ile Phe Ile Val Ala Leu Cys Arg Asn
        355                 360                 365
Val His Tyr Met Val Lys His Pro Ala Ser Phe Leu Leu Ser Pro Leu
370                 375                 380
Tyr Gly Ile Leu His Leu Phe Val Leu Gln Pro Leu Lys Leu Tyr Ser
385                 390                 395                 400
Leu Xaa Thr Ile Lys Asn Thr Glu Trp Gly Thr Arg Lys Lys Val Thr
                405                 410                 415
Ile Phe Lys
```

<210> SEQ ID NO 76  
<211> LENGTH: 419  
<212> TYPE: PRT  
<213> ORGANISM: Streptococcus pyogenes  
<220> FEATURE:  
<221> NAME/KEY: MISC_FEATURE  
<222> LOCATION: (124)..(124)  
<223> OTHER INFORMATION: Xaa = Ala, Ser or any other amino acid  
<220> FEATURE:  
<221> NAME/KEY: MISC_FEATURE  
<222> LOCATION: (225)..(225)  
<223> OTHER INFORMATION: Xaa = Ala, Ser or any other amino acid  
<220> FEATURE:

```
<221> NAME/KEY: MISC_FEATURE
<222> LOCATION: (366)..(366)
<223> OTHER INFORMATION: Xaa = Ala, Ser or any other amino acid
<220> FEATURE:
<221> NAME/KEY: MISC_FEATURE
<222> LOCATION: (402)..(402)
<223> OTHER INFORMATION: Xaa = Ala, Ser or any other amino acid

<400> SEQUENCE: 76
```

| | | | | | | | | | | | | | | | |
|---|---|---|---|---|---|---|---|---|---|---|---|---|---|---|---|
| Met | Pro | Ile | Phe | Lys | Lys | Thr | Leu | Ile | Val | Leu | Ser | Phe | Ile | Phe | Leu |
| 1 | | | | 5 | | | | | 10 | | | | | 15 | |
| Ile | Ser | Ile | Leu | Ile | Tyr | Leu | Asn | Met | Tyr | Leu | Phe | Gly | Thr | Ser | Thr |
| | | | 20 | | | | | 25 | | | | | 30 | | |
| Val | Gly | Ile | Tyr | Gly | Val | Ile | Leu | Ile | Thr | Tyr | Leu | Val | Ile | Lys | Leu |
| | | 35 | | | | | 40 | | | | | 45 | | | |
| Gly | Leu | Ser | Phe | Leu | Tyr | Glu | Pro | Phe | Lys | Gly | Asn | Pro | His | Asp | Tyr |
| 50 | | | | | 55 | | | | | 60 | | | | | |
| Lys | Val | Ala | Ala | Val | Ile | Pro | Ser | Tyr | Asn | Glu | Asp | Ala | Glu | Ser | Leu |
| 65 | | | | 70 | | | | | 75 | | | | | 80 | |
| Leu | Glu | Thr | Leu | Lys | Ser | Val | Leu | Ala | Gln | Thr | Tyr | Pro | Leu | Ser | Glu |
| | | | | 85 | | | | | 90 | | | | | 95 | |
| Ile | Tyr | Ile | Val | Asp | Asp | Gly | Ser | Ser | Asn | Thr | Asp | Ala | Ile | Gln | Leu |
| | | | 100 | | | | | 105 | | | | | 110 | | |
| Ile | Glu | Glu | Tyr | Val | Asn | Arg | Glu | Val | Asp | Ile | Xaa | Arg | Asn | Val | Ile |
| | | 115 | | | | | 120 | | | | | 125 | | | |
| Val | His | Arg | Ser | Leu | Val | Asn | Lys | Gly | Lys | Arg | His | Ala | Gln | Ala | Trp |
| 130 | | | | | 135 | | | | | 140 | | | | | |
| Ala | Phe | Glu | Arg | Ser | Asp | Ala | Asp | Val | Phe | Leu | Thr | Val | Asp | Ser | Asp |
| 145 | | | | 150 | | | | | 155 | | | | | 160 | |
| Thr | Tyr | Ile | Tyr | Pro | Asn | Ala | Leu | Glu | Glu | Leu | Leu | Lys | Ser | Phe | Asn |
| | | | | 165 | | | | | 170 | | | | | 175 | |
| Asp | Glu | Thr | Val | Tyr | Ala | Ala | Thr | Gly | His | Leu | Asn | Ala | Arg | Asn | Arg |
| | | | 180 | | | | | 185 | | | | | 190 | | |
| Gln | Thr | Asn | Leu | Leu | Thr | Arg | Leu | Thr | Asp | Ile | Arg | Tyr | Asp | Asn | Ala |
| | | 195 | | | | | 200 | | | | | 205 | | | |
| Phe | Gly | Val | Glu | Arg | Ala | Ala | Gln | Ser | Leu | Thr | Gly | Asn | Ile | Leu | Val |
| 210 | | | | | 215 | | | | | 220 | | | | | |
| Xaa | Ser | Gly | Pro | Leu | Ser | Ile | Tyr | Arg | Arg | Glu | Val | Ile | Ile | Pro | Asn |
| 225 | | | | | 230 | | | | | 235 | | | | | 240 |
| Leu | Glu | Arg | Tyr | Lys | Asn | Gln | Thr | Phe | Leu | Gly | Leu | Pro | Val | Ser | Ile |
| | | | | 245 | | | | | 250 | | | | | 255 | |
| Gly | Asp | Asp | Arg | Cys | Leu | Thr | Asn | Tyr | Ala | Ile | Asp | Leu | Gly | Arg | Thr |
| | | | 260 | | | | | 265 | | | | | 270 | | |
| Val | Tyr | Gln | Ser | Thr | Ala | Arg | Cys | Asp | Thr | Asp | Val | Pro | Phe | Gln | Leu |
| | | 275 | | | | | 280 | | | | | 285 | | | |
| Lys | Ser | Tyr | Leu | Lys | Gln | Gln | Asn | Arg | Trp | Asn | Lys | Ser | Phe | Phe | Arg |
| | | | 290 | | | | | 295 | | | | | 300 | | |
| Glu | Ser | Ile | Ile | Ser | Val | Lys | Lys | Ile | Leu | Ser | Asn | Pro | Ile | Val | Ala |
| 305 | | | | | 310 | | | | | 315 | | | | | 320 |
| Leu | Trp | Thr | Ile | Phe | Glu | Val | Val | Met | Phe | Met | Met | Leu | Ile | Val | Ala |
| | | | | 325 | | | | | 330 | | | | | 335 | |
| Ile | Gly | Asn | Leu | Leu | Phe | Asn | Gln | Ala | Ile | Gln | Leu | Asp | Leu | Ile | Lys |
| | | | 340 | | | | | 345 | | | | | 350 | | |
| Leu | Phe | Ala | Phe | Leu | Ser | Ile | Ile | Phe | Ile | Val | Ala | Leu | Xaa | Arg | Asn |
| | | 355 | | | | | 360 | | | | | 365 | | | |

-continued

```
Val His Tyr Met Val Lys His Pro Ala Ser Phe Leu Leu Ser Pro Leu
        370                 375                 380

Tyr Gly Ile Leu His Leu Phe Val Leu Gln Pro Leu Lys Leu Tyr Ser
385                 390                 395                 400

Leu Xaa Thr Ile Lys Asn Thr Glu Trp Gly Thr Arg Lys Lys Val Thr
                405                 410                 415

Ile Phe Lys

<210> SEQ ID NO 77
<211> LENGTH: 419
<212> TYPE: PRT
<213> ORGANISM: Streptococcus pyogenes
<220> FEATURE:
<221> NAME/KEY: MISC_FEATURE
<222> LOCATION: (124)..(124)
<223> OTHER INFORMATION: Xaa = Ala, Ser or any other amino acid
<220> FEATURE:
<221> NAME/KEY: MISC_FEATURE
<222> LOCATION: (261)..(261)
<223> OTHER INFORMATION: Xaa = Ala, Ser or any other amino acid
<220> FEATURE:
<221> NAME/KEY: MISC_FEATURE
<222> LOCATION: (280)..(280)
<223> OTHER INFORMATION: Xaa = Ala, Ser or any other amino acid
<220> FEATURE:
<221> NAME/KEY: MISC_FEATURE
<222> LOCATION: (366)..(366)
<223> OTHER INFORMATION: Xaa = Ala, Ser or any other amino acid

<400> SEQUENCE: 77

Met Pro Ile Phe Lys Lys Thr Leu Ile Val Leu Ser Phe Ile Phe Leu
1               5                   10                  15

Ile Ser Ile Leu Ile Tyr Leu Asn Met Tyr Leu Phe Gly Thr Ser Thr
                20                  25                  30

Val Gly Ile Tyr Gly Val Ile Leu Ile Thr Tyr Leu Val Ile Lys Leu
            35                  40                  45

Gly Leu Ser Phe Leu Tyr Glu Pro Phe Lys Gly Asn Pro His Asp Tyr
50                  55                  60

Lys Val Ala Ala Val Ile Pro Ser Tyr Asn Glu Asp Ala Glu Ser Leu
65                  70                  75                  80

Leu Glu Thr Leu Lys Ser Val Leu Ala Gln Thr Tyr Pro Leu Ser Glu
                85                  90                  95

Ile Tyr Ile Val Asp Asp Gly Ser Ser Asn Thr Asp Ala Ile Gln Leu
            100                 105                 110

Ile Glu Glu Tyr Val Asn Arg Glu Val Asp Ile Xaa Arg Asn Val Ile
        115                 120                 125

Val His Arg Ser Leu Val Asn Lys Gly Lys Arg His Ala Gln Ala Trp
130                 135                 140

Ala Phe Glu Arg Ser Asp Ala Asp Val Phe Leu Thr Val Asp Ser Asp
145                 150                 155                 160

Thr Tyr Ile Tyr Pro Asn Ala Leu Glu Glu Leu Leu Lys Ser Phe Asn
                165                 170                 175

Asp Glu Thr Val Tyr Ala Ala Thr Gly His Leu Asn Ala Arg Asn Arg
            180                 185                 190

Gln Thr Asn Leu Leu Thr Arg Leu Thr Asp Ile Arg Tyr Asp Asn Ala
        195                 200                 205

Phe Gly Val Glu Arg Ala Ala Gln Ser Leu Thr Gly Asn Ile Leu Val
210                 215                 220

Cys Ser Gly Pro Leu Ser Ile Tyr Arg Arg Glu Val Ile Ile Pro Asn
225                 230                 235                 240
```

-continued

```
Leu Glu Arg Tyr Lys Asn Gln Thr Phe Leu Gly Leu Pro Val Ser Ile
                245                 250                 255

Gly Asp Asp Arg Xaa Leu Thr Asn Tyr Ala Ile Asp Leu Gly Arg Thr
            260                 265                 270

Val Tyr Gln Ser Thr Ala Arg Xaa Asp Thr Asp Val Pro Phe Gln Leu
            275                 280                 285

Lys Ser Tyr Leu Lys Gln Gln Asn Arg Trp Asn Lys Ser Phe Phe Arg
        290                 295                 300

Glu Ser Ile Ile Ser Val Lys Lys Ile Leu Ser Asn Pro Ile Val Ala
305                 310                 315                 320

Leu Trp Thr Ile Phe Glu Val Val Met Phe Met Leu Ile Val Ala
                325                 330                 335

Ile Gly Asn Leu Leu Phe Asn Gln Ala Ile Gln Leu Asp Leu Ile Lys
            340                 345                 350

Leu Phe Ala Phe Leu Ser Ile Ile Phe Ile Val Ala Leu Xaa Arg Asn
        355                 360                 365

Val His Tyr Met Val Lys His Pro Ala Ser Phe Leu Leu Ser Pro Leu
    370                 375                 380

Tyr Gly Ile Leu His Leu Phe Val Leu Gln Pro Leu Lys Leu Tyr Ser
385                 390                 395                 400

Leu Cys Thr Ile Lys Asn Thr Glu Trp Gly Thr Arg Lys Lys Val Thr
                405                 410                 415

Ile Phe Lys

<210> SEQ ID NO 78
<211> LENGTH: 419
<212> TYPE: PRT
<213> ORGANISM: Streptococcus pyogenes
<220> FEATURE:
<221> NAME/KEY: MISC_FEATURE
<222> LOCATION: (124)..(124)
<223> OTHER INFORMATION: Xaa = Ala, Ser or any other amino acid
<220> FEATURE:
<221> NAME/KEY: MISC_FEATURE
<222> LOCATION: (261)..(261)
<223> OTHER INFORMATION: Xaa = Ala, Ser or any other amino acid
<220> FEATURE:
<221> NAME/KEY: MISC_FEATURE
<222> LOCATION: (280)..(280)
<223> OTHER INFORMATION: Xaa = Ala, Ser or any other amino acid
<220> FEATURE:
<221> NAME/KEY: MISC_FEATURE
<222> LOCATION: (402)..(402)
<223> OTHER INFORMATION: Xaa = Ala, Ser or any other amino acid

<400> SEQUENCE: 78

Met Pro Ile Phe Lys Lys Thr Leu Ile Val Leu Ser Phe Ile Phe Leu
1               5                   10                  15

Ile Ser Ile Leu Ile Tyr Leu Asn Met Tyr Leu Phe Gly Thr Ser Thr
            20                  25                  30

Val Gly Ile Tyr Gly Val Ile Leu Ile Thr Tyr Leu Val Ile Lys Leu
        35                  40                  45

Gly Leu Ser Phe Leu Tyr Glu Pro Phe Lys Gly Asn Pro His Asp Tyr
    50                  55                  60

Lys Val Ala Ala Val Ile Pro Ser Tyr Asn Glu Asp Ala Glu Ser Leu
65                  70                  75                  80

Leu Glu Thr Leu Lys Ser Val Leu Ala Gln Thr Tyr Pro Leu Ser Glu
                85                  90                  95

Ile Tyr Ile Val Asp Asp Gly Ser Ser Asn Thr Asp Ala Ile Gln Leu
```

```
                    100                 105                 110
Ile Glu Glu Tyr Val Asn Arg Glu Val Asp Ile Xaa Arg Asn Val Ile
            115                 120                 125
Val His Arg Ser Leu Val Asn Lys Gly Lys Arg His Ala Gln Ala Trp
    130                 135                 140
Ala Phe Glu Arg Ser Asp Ala Asp Val Phe Leu Thr Val Asp Ser Asp
145                 150                 155                 160
Thr Tyr Ile Tyr Pro Asn Ala Leu Glu Leu Leu Lys Ser Phe Asn
                165                 170                 175
Asp Glu Thr Val Tyr Ala Ala Thr Gly His Leu Asn Ala Arg Asn Arg
            180                 185                 190
Gln Thr Asn Leu Leu Thr Arg Leu Thr Asp Ile Arg Tyr Asp Asn Ala
            195                 200                 205
Phe Gly Val Glu Arg Ala Ala Gln Ser Leu Thr Gly Asn Ile Leu Val
    210                 215                 220
Cys Ser Gly Pro Leu Ser Ile Tyr Arg Arg Glu Val Ile Ile Pro Asn
225                 230                 235                 240
Leu Glu Arg Tyr Lys Asn Gln Thr Phe Leu Gly Leu Pro Val Ser Ile
                245                 250                 255
Gly Asp Asp Arg Xaa Leu Thr Asn Tyr Ala Ile Asp Leu Gly Arg Thr
            260                 265                 270
Val Tyr Gln Ser Thr Ala Arg Xaa Asp Thr Asp Val Pro Phe Gln Leu
            275                 280                 285
Lys Ser Tyr Leu Lys Gln Gln Asn Arg Trp Asn Lys Ser Phe Phe Arg
    290                 295                 300
Glu Ser Ile Ile Ser Val Lys Lys Ile Leu Ser Asn Pro Ile Val Ala
305                 310                 315                 320
Leu Trp Thr Ile Phe Glu Val Val Met Phe Met Leu Ile Val Ala
                325                 330                 335
Ile Gly Asn Leu Leu Phe Asn Gln Ala Ile Gln Leu Asp Leu Ile Lys
            340                 345                 350
Leu Phe Ala Phe Leu Ser Ile Ile Phe Ile Val Ala Leu Cys Arg Asn
            355                 360                 365
Val His Tyr Met Val Lys His Pro Ala Ser Phe Leu Leu Ser Pro Leu
    370                 375                 380
Tyr Gly Ile Leu His Leu Phe Val Leu Gln Pro Leu Lys Leu Tyr Ser
385                 390                 395                 400
Leu Xaa Thr Ile Lys Asn Thr Glu Trp Gly Thr Arg Lys Lys Val Thr
            405                 410                 415
Ile Phe Lys

<210> SEQ ID NO 79
<211> LENGTH: 419
<212> TYPE: PRT
<213> ORGANISM: Streptococcus pyogenes
<220> FEATURE:
<221> NAME/KEY: MISC_FEATURE
<222> LOCATION: (124)..(124)
<223> OTHER INFORMATION: Xaa = Ala, Ser or any other amino acid
<220> FEATURE:
<221> NAME/KEY: MISC_FEATURE
<222> LOCATION: (261)..(261)
<223> OTHER INFORMATION: Xaa = Ala, Ser or any other amino acid
<220> FEATURE:
<221> NAME/KEY: MISC_FEATURE
<222> LOCATION: (366)..(366)
<223> OTHER INFORMATION: Xaa = Ala, Ser or any other amino acid
<220> FEATURE:
```

```
<221> NAME/KEY: MISC_FEATURE
<222> LOCATION: (402)..(402)
<223> OTHER INFORMATION: Xaa = Ala, Ser or any other amino acid

<400> SEQUENCE: 79
```

Met Pro Ile Phe Lys Lys Thr Leu Ile Val Leu Ser Phe Ile Phe Leu
1               5                   10                  15

Ile Ser Ile Leu Ile Tyr Leu Asn Met Tyr Leu Phe Gly Thr Ser Thr
            20                  25                  30

Val Gly Ile Tyr Gly Val Ile Leu Ile Thr Tyr Leu Val Ile Lys Leu
            35                  40                  45

Gly Leu Ser Phe Leu Tyr Glu Pro Phe Lys Gly Asn Pro His Asp Tyr
    50                  55                  60

Lys Val Ala Ala Val Ile Pro Ser Tyr Asn Glu Asp Ala Glu Ser Leu
65                  70                  75                  80

Leu Glu Thr Leu Lys Ser Val Leu Ala Gln Thr Tyr Pro Leu Ser Glu
                85                  90                  95

Ile Tyr Ile Val Asp Asp Gly Ser Ser Asn Thr Asp Ala Ile Gln Leu
            100                 105                 110

Ile Glu Glu Tyr Val Asn Arg Glu Val Asp Ile Xaa Arg Asn Val Ile
            115                 120                 125

Val His Arg Ser Leu Val Asn Lys Gly Lys Arg His Ala Gln Ala Trp
130                 135                 140

Ala Phe Glu Arg Ser Asp Ala Asp Val Phe Leu Thr Val Asp Ser Asp
145                 150                 155                 160

Thr Tyr Ile Tyr Pro Asn Ala Leu Glu Glu Leu Leu Lys Ser Phe Asn
                165                 170                 175

Asp Glu Thr Val Tyr Ala Ala Thr Gly His Leu Asn Ala Arg Asn Arg
            180                 185                 190

Gln Thr Asn Leu Leu Thr Arg Leu Thr Asp Ile Arg Tyr Asp Asn Ala
            195                 200                 205

Phe Gly Val Glu Arg Ala Ala Gln Ser Leu Thr Gly Asn Ile Leu Val
210                 215                 220

Cys Ser Gly Pro Leu Ser Ile Tyr Arg Arg Glu Val Ile Ile Pro Asn
225                 230                 235                 240

Leu Glu Arg Tyr Lys Asn Gln Thr Phe Leu Gly Leu Pro Val Ser Ile
                245                 250                 255

Gly Asp Asp Arg Xaa Leu Thr Asn Tyr Ala Ile Asp Leu Gly Arg Thr
            260                 265                 270

Val Tyr Gln Ser Thr Ala Arg Cys Asp Thr Asp Val Pro Phe Gln Leu
            275                 280                 285

Lys Ser Tyr Leu Lys Gln Gln Asn Arg Trp Asn Lys Ser Phe Phe Arg
290                 295                 300

Glu Ser Ile Ile Ser Val Lys Lys Ile Leu Ser Asn Pro Ile Val Ala
305                 310                 315                 320

Leu Trp Thr Ile Phe Glu Val Val Met Phe Met Leu Ile Val Ala
                325                 330                 335

Ile Gly Asn Leu Leu Phe Asn Gln Ala Ile Gln Leu Asp Leu Ile Lys
            340                 345                 350

Leu Phe Ala Phe Leu Ser Ile Ile Phe Ile Val Ala Leu Xaa Arg Asn
            355                 360                 365

Val His Tyr Met Val Lys His Pro Ala Ser Phe Leu Leu Ser Pro Leu
370                 375                 380

Tyr Gly Ile Leu His Leu Phe Val Leu Gln Pro Leu Lys Leu Tyr Ser

-continued

```
                385                 390                 395                 400
Leu Xaa Thr Ile Lys Asn Thr Glu Trp Gly Thr Arg Lys Lys Val Thr
                    405                 410                 415

Ile Phe Lys

<210> SEQ ID NO 80
<211> LENGTH: 419
<212> TYPE: PRT
<213> ORGANISM: Streptococcus pyogenes
<220> FEATURE:
<221> NAME/KEY: MISC_FEATURE
<222> LOCATION: (124)..(124)
<223> OTHER INFORMATION: Xaa = Ala, Ser or any other amino acid
<220> FEATURE:
<221> NAME/KEY: MISC_FEATURE
<222> LOCATION: (280)..(280)
<223> OTHER INFORMATION: Xaa = Ala, Ser or any other amino acid
<220> FEATURE:
<221> NAME/KEY: MISC_FEATURE
<222> LOCATION: (366)..(366)
<223> OTHER INFORMATION: Xaa = Ala, Ser or any other amino acid
<220> FEATURE:
<221> NAME/KEY: MISC_FEATURE
<222> LOCATION: (402)..(402)
<223> OTHER INFORMATION: Xaa = Ala, Ser or any other amino acid

<400> SEQUENCE: 80

Met Pro Ile Phe Lys Lys Thr Leu Ile Val Leu Ser Phe Ile Phe Leu
1               5                   10                  15

Ile Ser Ile Leu Ile Tyr Leu Asn Met Tyr Leu Phe Gly Thr Ser Thr
            20                  25                  30

Val Gly Ile Tyr Gly Val Ile Leu Ile Thr Tyr Leu Val Ile Lys Leu
        35                  40                  45

Gly Leu Ser Phe Leu Tyr Glu Pro Phe Lys Gly Asn Pro His Asp Tyr
    50                  55                  60

Lys Val Ala Ala Val Ile Pro Ser Tyr Asn Glu Asp Ala Glu Ser Leu
65                  70                  75                  80

Leu Glu Thr Leu Lys Ser Val Leu Ala Gln Thr Tyr Pro Leu Ser Glu
                85                  90                  95

Ile Tyr Ile Val Asp Asp Gly Ser Ser Asn Thr Asp Ala Ile Gln Leu
            100                 105                 110

Ile Glu Glu Tyr Val Asn Arg Glu Val Asp Ile Xaa Arg Asn Val Ile
        115                 120                 125

Val His Arg Ser Leu Val Asn Lys Gly Lys Arg His Ala Gln Ala Trp
    130                 135                 140

Ala Phe Glu Arg Ser Asp Ala Asp Val Phe Leu Thr Val Asp Ser Asp
145                 150                 155                 160

Thr Tyr Ile Tyr Pro Asn Ala Leu Glu Glu Leu Leu Lys Ser Phe Asn
                165                 170                 175

Asp Glu Thr Val Tyr Ala Ala Thr Gly His Leu Asn Ala Arg Asn Arg
            180                 185                 190

Gln Thr Asn Leu Leu Thr Arg Leu Thr Asp Ile Arg Tyr Asp Asn Ala
        195                 200                 205

Phe Gly Val Glu Arg Ala Ala Gln Ser Leu Thr Gly Asn Ile Leu Val
    210                 215                 220

Cys Ser Gly Pro Leu Ser Ile Tyr Arg Arg Glu Val Ile Ile Pro Asn
225                 230                 235                 240

Leu Glu Arg Tyr Lys Asn Gln Thr Phe Leu Gly Leu Pro Val Ser Ile
                245                 250                 255
```

```
Gly Asp Asp Arg Cys Leu Thr Asn Tyr Ala Ile Asp Leu Gly Arg Thr
            260                 265                 270

Val Tyr Gln Ser Thr Ala Arg Xaa Asp Thr Asp Val Pro Phe Gln Leu
        275                 280                 285

Lys Ser Tyr Leu Lys Gln Gln Asn Arg Trp Asn Lys Ser Phe Phe Arg
    290                 295                 300

Glu Ser Ile Ile Ser Val Lys Lys Ile Leu Ser Asn Pro Ile Val Ala
305                 310                 315                 320

Leu Trp Thr Ile Phe Glu Val Val Met Phe Met Leu Ile Val Ala
                325                 330                 335

Ile Gly Asn Leu Leu Phe Asn Gln Ala Ile Gln Leu Asp Leu Ile Lys
            340                 345                 350

Leu Phe Ala Phe Leu Ser Ile Ile Phe Ile Val Ala Leu Xaa Arg Asn
        355                 360                 365

Val His Tyr Met Val Lys His Pro Ala Ser Phe Leu Leu Ser Pro Leu
    370                 375                 380

Tyr Gly Ile Leu His Leu Phe Val Leu Gln Pro Leu Lys Leu Tyr Ser
385                 390                 395                 400

Leu Xaa Thr Ile Lys Asn Thr Glu Trp Gly Thr Arg Lys Lys Val Thr
                405                 410                 415

Ile Phe Lys

<210> SEQ ID NO 81
<211> LENGTH: 419
<212> TYPE: PRT
<213> ORGANISM: Streptococcus pyogenes
<220> FEATURE:
<221> NAME/KEY: MISC_FEATURE
<222> LOCATION: (225)..(225)
<223> OTHER INFORMATION: Xaa = Ala, Ser or any other amino acid
<220> FEATURE:
<221> NAME/KEY: MISC_FEATURE
<222> LOCATION: (261)..(261)
<223> OTHER INFORMATION: Xaa = Ala, Ser or any other amino acid
<220> FEATURE:
<221> NAME/KEY: MISC_FEATURE
<222> LOCATION: (280)..(280)
<223> OTHER INFORMATION: Xaa = Ala, Ser or any other amino acid
<220> FEATURE:
<221> NAME/KEY: MISC_FEATURE
<222> LOCATION: (366)..(366)
<223> OTHER INFORMATION: Xaa = Ala, Ser or any other amino acid

<400> SEQUENCE: 81

Met Pro Ile Phe Lys Lys Thr Leu Ile Val Leu Ser Phe Ile Phe Leu
1               5                   10                  15

Ile Ser Ile Leu Ile Tyr Leu Asn Met Tyr Leu Phe Gly Thr Ser Thr
            20                  25                  30

Val Gly Ile Tyr Gly Val Ile Leu Ile Thr Tyr Leu Val Ile Lys Leu
        35                  40                  45

Gly Leu Ser Phe Leu Tyr Glu Pro Phe Lys Gly Asn Pro His Asp Tyr
    50                  55                  60

Lys Val Ala Ala Val Ile Pro Ser Tyr Asn Glu Asp Ala Glu Ser Leu
65                  70                  75                  80

Leu Glu Thr Leu Lys Ser Val Leu Ala Gln Thr Tyr Pro Leu Ser Glu
                85                  90                  95

Ile Tyr Ile Val Asp Asp Gly Ser Ser Asn Thr Asp Ala Ile Gln Leu
            100                 105                 110

Ile Glu Glu Tyr Val Asn Arg Glu Val Asp Ile Cys Arg Asn Val Ile
        115                 120                 125
```

```
Val His Arg Ser Leu Val Asn Lys Gly Lys Arg His Ala Gln Ala Trp
        130                 135                 140

Ala Phe Glu Arg Ser Asp Ala Asp Val Phe Leu Thr Val Asp Ser Asp
145                 150                 155                 160

Thr Tyr Ile Tyr Pro Asn Ala Leu Glu Glu Leu Leu Lys Ser Phe Asn
                165                 170                 175

Asp Glu Thr Val Tyr Ala Ala Thr Gly His Leu Asn Ala Arg Asn Arg
            180                 185                 190

Gln Thr Asn Leu Leu Thr Arg Leu Thr Asp Ile Arg Tyr Asp Asn Ala
        195                 200                 205

Phe Gly Val Glu Arg Ala Ala Gln Ser Leu Thr Gly Asn Ile Leu Val
    210                 215                 220

Xaa Ser Gly Pro Leu Ser Ile Tyr Arg Arg Glu Val Ile Ile Pro Asn
225                 230                 235                 240

Leu Glu Arg Tyr Lys Asn Gln Thr Phe Leu Gly Leu Pro Val Ser Ile
                245                 250                 255

Gly Asp Asp Arg Xaa Leu Thr Asn Tyr Ala Ile Asp Leu Gly Arg Thr
            260                 265                 270

Val Tyr Gln Ser Thr Ala Arg Xaa Asp Thr Asp Val Pro Phe Gln Leu
        275                 280                 285

Lys Ser Tyr Leu Lys Gln Gln Asn Arg Trp Asn Lys Ser Phe Phe Arg
    290                 295                 300

Glu Ser Ile Ile Ser Val Lys Lys Ile Leu Ser Asn Pro Ile Val Ala
305                 310                 315                 320

Leu Trp Thr Ile Phe Glu Val Val Met Phe Met Leu Ile Val Ala
                325                 330                 335

Ile Gly Asn Leu Leu Phe Asn Gln Ala Ile Gln Leu Asp Leu Ile Lys
            340                 345                 350

Leu Phe Ala Phe Leu Ser Ile Ile Phe Ile Val Ala Leu Xaa Arg Asn
        355                 360                 365

Val His Tyr Met Val Lys His Pro Ala Ser Phe Leu Leu Ser Pro Leu
    370                 375                 380

Tyr Gly Ile Leu His Leu Phe Val Leu Gln Pro Leu Lys Leu Tyr Ser
385                 390                 395                 400

Leu Cys Thr Ile Lys Asn Thr Glu Trp Gly Thr Arg Lys Lys Val Thr
                405                 410                 415

Ile Phe Lys

<210> SEQ ID NO 82
<211> LENGTH: 419
<212> TYPE: PRT
<213> ORGANISM: Streptococcus pyogenes
<220> FEATURE:
<221> NAME/KEY: MISC_FEATURE
<222> LOCATION: (225)..(225)
<223> OTHER INFORMATION: Xaa = Ala, Ser or any other amino acid
<220> FEATURE:
<221> NAME/KEY: MISC_FEATURE
<222> LOCATION: (261)..(261)
<223> OTHER INFORMATION: Xaa = Ala, Ser or any other amino acid
<220> FEATURE:
<221> NAME/KEY: MISC_FEATURE
<222> LOCATION: (280)..(280)
<223> OTHER INFORMATION: Xaa = Ala, Ser or any other amino acid
<220> FEATURE:
<221> NAME/KEY: MISC_FEATURE
<222> LOCATION: (402)..(402)
<223> OTHER INFORMATION: Xaa = Ala, Ser or any other amino acid
```

-continued

```
<400> SEQUENCE: 82

Met Pro Ile Phe Lys Lys Thr Leu Ile Val Leu Ser Phe Ile Phe Leu
1               5                   10                  15

Ile Ser Ile Leu Ile Tyr Leu Asn Met Tyr Leu Phe Gly Thr Ser Thr
            20                  25                  30

Val Gly Ile Tyr Gly Val Ile Leu Ile Thr Tyr Leu Val Ile Lys Leu
        35                  40                  45

Gly Leu Ser Phe Leu Tyr Glu Pro Phe Lys Gly Asn Pro His Asp Tyr
    50                  55                  60

Lys Val Ala Ala Val Ile Pro Ser Tyr Asn Glu Asp Ala Glu Ser Leu
65                  70                  75                  80

Leu Glu Thr Leu Lys Ser Val Leu Ala Gln Thr Tyr Pro Leu Ser Glu
                85                  90                  95

Ile Tyr Ile Val Asp Asp Gly Ser Ser Asn Thr Asp Ala Ile Gln Leu
            100                 105                 110

Ile Glu Glu Tyr Val Asn Arg Glu Val Asp Ile Cys Arg Asn Val Ile
        115                 120                 125

Val His Arg Ser Leu Val Asn Lys Gly Lys Arg His Ala Gln Ala Trp
130                 135                 140

Ala Phe Glu Arg Ser Asp Ala Asp Val Phe Leu Thr Val Asp Ser Asp
145                 150                 155                 160

Thr Tyr Ile Tyr Pro Asn Ala Leu Glu Glu Leu Leu Lys Ser Phe Asn
                165                 170                 175

Asp Glu Thr Val Tyr Ala Ala Thr Gly His Leu Asn Ala Arg Asn Arg
            180                 185                 190

Gln Thr Asn Leu Leu Thr Arg Leu Thr Asp Ile Arg Tyr Asp Asn Ala
        195                 200                 205

Phe Gly Val Glu Arg Ala Ala Gln Ser Leu Thr Gly Asn Ile Leu Val
    210                 215                 220

Xaa Ser Gly Pro Leu Ser Ile Tyr Arg Arg Glu Val Ile Ile Pro Asn
225                 230                 235                 240

Leu Glu Arg Tyr Lys Asn Gln Thr Phe Leu Gly Leu Pro Val Ser Ile
                245                 250                 255

Gly Asp Asp Arg Xaa Leu Thr Asn Tyr Ala Ile Asp Leu Gly Arg Thr
            260                 265                 270

Val Tyr Gln Ser Thr Ala Arg Xaa Asp Thr Asp Val Pro Phe Gln Leu
        275                 280                 285

Lys Ser Tyr Leu Lys Gln Gln Asn Arg Trp Asn Lys Ser Phe Phe Arg
    290                 295                 300

Glu Ser Ile Ile Ser Val Lys Lys Ile Leu Ser Asn Pro Ile Val Ala
305                 310                 315                 320

Leu Trp Thr Ile Phe Glu Val Val Met Phe Met Met Leu Ile Val Ala
                325                 330                 335

Ile Gly Asn Leu Leu Phe Asn Gln Ala Ile Gln Leu Asp Leu Ile Lys
            340                 345                 350

Leu Phe Ala Phe Leu Ser Ile Ile Phe Ile Val Ala Leu Cys Arg Asn
        355                 360                 365

Val His Tyr Met Val Lys His Pro Ala Ser Phe Leu Leu Ser Pro Leu
    370                 375                 380

Tyr Gly Ile Leu His Leu Phe Val Leu Gln Pro Leu Lys Leu Tyr Ser
385                 390                 395                 400

Leu Xaa Thr Ile Lys Asn Thr Glu Trp Gly Thr Arg Lys Lys Val Thr
                405                 410                 415
```

Ile Phe Lys

<210> SEQ ID NO 83
<211> LENGTH: 419
<212> TYPE: PRT
<213> ORGANISM: Streptococcus pyogenes
<220> FEATURE:
<221> NAME/KEY: MISC_FEATURE
<222> LOCATION: (225)..(225)
<223> OTHER INFORMATION: Xaa = Ala, Ser or any other amino acid
<220> FEATURE:
<221> NAME/KEY: MISC_FEATURE
<222> LOCATION: (261)..(261)
<223> OTHER INFORMATION: Xaa = Ala, Ser or any other amino acid
<220> FEATURE:
<221> NAME/KEY: MISC_FEATURE
<222> LOCATION: (366)..(366)
<223> OTHER INFORMATION: Xaa = Ala, Ser or any other amino acid
<220> FEATURE:
<221> NAME/KEY: MISC_FEATURE
<222> LOCATION: (402)..(402)
<223> OTHER INFORMATION: Xaa = Ala, Ser or any other amino acid

<400> SEQUENCE: 83

```
Met Pro Ile Phe Lys Lys Thr Leu Ile Val Leu Ser Phe Ile Phe Leu
1               5                   10                  15

Ile Ser Ile Leu Ile Tyr Leu Asn Met Tyr Leu Phe Gly Thr Ser Thr
            20                  25                  30

Val Gly Ile Tyr Gly Val Ile Leu Ile Thr Tyr Leu Val Ile Lys Leu
        35                  40                  45

Gly Leu Ser Phe Leu Tyr Glu Pro Phe Lys Gly Asn Pro His Asp Tyr
    50                  55                  60

Lys Val Ala Ala Val Ile Pro Ser Tyr Asn Glu Asp Ala Glu Ser Leu
65                  70                  75                  80

Leu Glu Thr Leu Lys Ser Val Leu Ala Gln Thr Tyr Pro Leu Ser Glu
                85                  90                  95

Ile Tyr Ile Val Asp Asp Gly Ser Ser Asn Thr Asp Ala Ile Gln Leu
            100                 105                 110

Ile Glu Glu Tyr Val Asn Arg Glu Val Asp Ile Cys Arg Asn Val Ile
        115                 120                 125

Val His Arg Ser Leu Val Asn Lys Gly Lys Arg His Ala Gln Ala Trp
    130                 135                 140

Ala Phe Glu Arg Ser Asp Ala Asp Val Phe Leu Thr Val Asp Ser Asp
145                 150                 155                 160

Thr Tyr Ile Tyr Pro Asn Ala Leu Glu Glu Leu Leu Lys Ser Phe Asn
                165                 170                 175

Asp Glu Thr Val Tyr Ala Ala Thr Gly His Leu Asn Ala Arg Asn Arg
            180                 185                 190

Gln Thr Asn Leu Leu Thr Arg Leu Thr Asp Ile Arg Tyr Asp Asn Ala
        195                 200                 205

Phe Gly Val Glu Arg Ala Ala Gln Ser Leu Thr Gly Asn Ile Leu Val
    210                 215                 220

Xaa Ser Gly Pro Leu Ser Ile Tyr Arg Arg Glu Val Ile Ile Pro Asn
225                 230                 235                 240

Leu Glu Arg Tyr Lys Asn Gln Thr Phe Leu Gly Leu Pro Val Ser Ile
                245                 250                 255

Gly Asp Asp Arg Xaa Leu Thr Asn Tyr Ala Ile Asp Leu Gly Arg Thr
            260                 265                 270

Val Tyr Gln Ser Thr Ala Arg Cys Asp Thr Asp Val Pro Phe Gln Leu
```

```
                    275                 280                 285
Lys Ser Tyr Leu Lys Gln Gln Asn Arg Trp Asn Lys Ser Phe Phe Arg
    290                 295                 300

Glu Ser Ile Ile Ser Val Lys Lys Ile Leu Ser Asn Pro Ile Val Ala
305                 310                 315                 320

Leu Trp Thr Ile Phe Glu Val Val Met Phe Met Leu Ile Val Ala
                    325                 330                 335

Ile Gly Asn Leu Leu Phe Asn Gln Ala Ile Gln Leu Asp Leu Ile Lys
                340                 345                 350

Leu Phe Ala Phe Leu Ser Ile Ile Phe Ile Val Ala Leu Xaa Arg Asn
            355                 360                 365

Val His Tyr Met Val Lys His Pro Ala Ser Phe Leu Leu Ser Pro Leu
    370                 375                 380

Tyr Gly Ile Leu His Leu Phe Val Leu Gln Pro Leu Lys Leu Tyr Ser
385                 390                 395                 400

Leu Xaa Thr Ile Lys Asn Thr Glu Trp Gly Thr Arg Lys Lys Val Thr
                405                 410                 415

Ile Phe Lys

<210> SEQ ID NO 84
<211> LENGTH: 419
<212> TYPE: PRT
<213> ORGANISM: Streptococcus pyogenes
<220> FEATURE:
<221> NAME/KEY: MISC_FEATURE
<222> LOCATION: (225)..(225)
<223> OTHER INFORMATION: Xaa = Ala, Ser or any other amino acid
<220> FEATURE:
<221> NAME/KEY: MISC_FEATURE
<222> LOCATION: (280)..(280)
<223> OTHER INFORMATION: Xaa = Ala, Ser or any other amino acid
<220> FEATURE:
<221> NAME/KEY: MISC_FEATURE
<222> LOCATION: (366)..(366)
<223> OTHER INFORMATION: Xaa = Ala, Ser or any other amino acid
<220> FEATURE:
<221> NAME/KEY: MISC_FEATURE
<222> LOCATION: (402)..(402)
<223> OTHER INFORMATION: Xaa = Ala, Ser or any other amino acid

<400> SEQUENCE: 84

Met Pro Ile Phe Lys Lys Thr Leu Ile Val Leu Ser Phe Ile Phe Leu
1               5                   10                  15

Ile Ser Ile Leu Ile Tyr Leu Asn Met Tyr Leu Phe Gly Thr Ser Thr
                20                  25                  30

Val Gly Ile Tyr Gly Val Ile Leu Ile Thr Tyr Leu Val Ile Lys Leu
            35                  40                  45

Gly Leu Ser Phe Leu Tyr Glu Pro Phe Lys Gly Asn Pro His Asp Tyr
    50                  55                  60

Lys Val Ala Ala Val Ile Pro Ser Tyr Asn Glu Asp Ala Glu Ser Leu
65                  70                  75                  80

Leu Glu Thr Leu Lys Ser Val Leu Ala Gln Thr Tyr Pro Leu Ser Glu
                85                  90                  95

Ile Tyr Ile Val Asp Asp Gly Ser Ser Asn Thr Asp Ala Ile Gln Leu
                100                 105                 110

Ile Glu Glu Tyr Val Asn Arg Glu Val Asp Ile Cys Arg Asn Val Ile
            115                 120                 125

Val His Arg Ser Leu Val Asn Lys Gly Lys Arg His Ala Gln Ala Trp
    130                 135                 140
```

-continued

```
Ala Phe Glu Arg Ser Asp Ala Asp Val Phe Leu Thr Val Asp Ser Asp
145                 150                 155                 160

Thr Tyr Ile Tyr Pro Asn Ala Leu Glu Glu Leu Leu Lys Ser Phe Asn
                165                 170                 175

Asp Glu Thr Val Tyr Ala Ala Thr Gly His Leu Asn Ala Arg Asn Arg
            180                 185                 190

Gln Thr Asn Leu Leu Thr Arg Leu Thr Asp Ile Arg Tyr Asp Asn Ala
        195                 200                 205

Phe Gly Val Glu Arg Ala Ala Gln Ser Leu Thr Gly Asn Ile Leu Val
    210                 215                 220

Xaa Ser Gly Pro Leu Ser Ile Tyr Arg Arg Glu Val Ile Ile Pro Asn
225                 230                 235                 240

Leu Glu Arg Tyr Lys Asn Gln Thr Phe Leu Gly Leu Pro Val Ser Ile
                245                 250                 255

Gly Asp Asp Arg Cys Leu Thr Asn Tyr Ala Ile Asp Leu Gly Arg Thr
            260                 265                 270

Val Tyr Gln Ser Thr Ala Arg Xaa Asp Thr Asp Val Pro Phe Gln Leu
        275                 280                 285

Lys Ser Tyr Leu Lys Gln Gln Asn Arg Trp Asn Lys Ser Phe Phe Arg
    290                 295                 300

Glu Ser Ile Ile Ser Val Lys Lys Ile Leu Ser Asn Pro Ile Val Ala
305                 310                 315                 320

Leu Trp Thr Ile Phe Glu Val Val Met Phe Met Leu Ile Val Ala
                325                 330                 335

Ile Gly Asn Leu Leu Phe Asn Gln Ala Ile Gln Leu Asp Leu Ile Lys
            340                 345                 350

Leu Phe Ala Phe Leu Ser Ile Ile Phe Ile Val Ala Leu Xaa Arg Asn
        355                 360                 365

Val His Tyr Met Val Lys His Pro Ala Ser Phe Leu Leu Ser Pro Leu
    370                 375                 380

Tyr Gly Ile Leu His Leu Phe Val Leu Gln Pro Leu Lys Leu Tyr Ser
385                 390                 395                 400

Leu Xaa Thr Ile Lys Asn Thr Glu Trp Gly Thr Arg Lys Lys Val Thr
                405                 410                 415

Ile Phe Lys
```

<210> SEQ ID NO 85
<211> LENGTH: 419
<212> TYPE: PRT
<213> ORGANISM: Streptococcus pyogenes
<220> FEATURE:
<221> NAME/KEY: MISC_FEATURE
<222> LOCATION: (261)..(261)
<223> OTHER INFORMATION: Xaa = Ala, Ser or any other amino acid
<220> FEATURE:
<221> NAME/KEY: MISC_FEATURE
<222> LOCATION: (280)..(280)
<223> OTHER INFORMATION: Xaa = Ala, Ser or any other amino acid
<220> FEATURE:
<221> NAME/KEY: MISC_FEATURE
<222> LOCATION: (366)..(366)
<223> OTHER INFORMATION: Xaa = Ala, Ser or any other amino acid
<220> FEATURE:
<221> NAME/KEY: MISC_FEATURE
<222> LOCATION: (402)..(402)
<223> OTHER INFORMATION: Xaa = Ala, Ser or any other amino acid

<400> SEQUENCE: 85

```
Met Pro Ile Phe Lys Lys Thr Leu Ile Val Leu Ser Phe Ile Phe Leu
1               5                   10                  15
```

```
Ile Ser Ile Leu Ile Tyr Leu Asn Met Tyr Leu Phe Gly Thr Ser Thr
             20                  25                  30

Val Gly Ile Tyr Gly Val Ile Leu Ile Thr Tyr Leu Val Ile Lys Leu
             35                  40                  45

Gly Leu Ser Phe Leu Tyr Glu Pro Phe Lys Gly Asn Pro His Asp Tyr
             50                  55                  60

Lys Val Ala Ala Val Ile Pro Ser Tyr Asn Glu Asp Ala Glu Ser Leu
 65                  70                  75                  80

Leu Glu Thr Leu Lys Ser Val Leu Ala Gln Thr Tyr Pro Leu Ser Glu
                 85                  90                  95

Ile Tyr Ile Val Asp Asp Gly Ser Ser Asn Thr Asp Ala Ile Gln Leu
            100                 105                 110

Ile Glu Glu Tyr Val Asn Arg Glu Val Asp Ile Cys Arg Asn Val Ile
            115                 120                 125

Val His Arg Ser Leu Val Asn Lys Gly Lys Arg His Ala Gln Ala Trp
            130                 135                 140

Ala Phe Glu Arg Ser Asp Ala Asp Val Phe Leu Thr Val Asp Ser Asp
145                 150                 155                 160

Thr Tyr Ile Tyr Pro Asn Ala Leu Glu Glu Leu Leu Lys Ser Phe Asn
                165                 170                 175

Asp Glu Thr Val Tyr Ala Ala Thr Gly His Leu Asn Ala Arg Asn Arg
            180                 185                 190

Gln Thr Asn Leu Leu Thr Arg Leu Thr Asp Ile Arg Tyr Asp Asn Ala
            195                 200                 205

Phe Gly Val Glu Arg Ala Ala Gln Ser Leu Thr Gly Asn Ile Leu Val
            210                 215                 220

Cys Ser Gly Pro Leu Ser Ile Tyr Arg Arg Glu Val Ile Ile Pro Asn
225                 230                 235                 240

Leu Glu Arg Tyr Lys Asn Gln Thr Phe Leu Gly Leu Pro Val Ser Ile
                245                 250                 255

Gly Asp Asp Arg Xaa Leu Thr Asn Tyr Ala Ile Asp Leu Gly Arg Thr
            260                 265                 270

Val Tyr Gln Ser Thr Ala Arg Xaa Asp Thr Asp Val Pro Phe Gln Leu
            275                 280                 285

Lys Ser Tyr Leu Lys Gln Gln Asn Arg Trp Asn Lys Ser Phe Phe Arg
            290                 295                 300

Glu Ser Ile Ile Ser Val Lys Lys Ile Leu Ser Asn Pro Ile Val Ala
305                 310                 315                 320

Leu Trp Thr Ile Phe Glu Val Val Met Phe Met Met Leu Ile Val Ala
                325                 330                 335

Ile Gly Asn Leu Leu Phe Asn Gln Ala Ile Gln Leu Asp Leu Ile Lys
            340                 345                 350

Leu Phe Ala Phe Leu Ser Ile Ile Phe Ile Val Ala Leu Xaa Arg Asn
            355                 360                 365

Val His Tyr Met Val Lys His Pro Ala Ser Phe Leu Leu Ser Pro Leu
            370                 375                 380

Tyr Gly Ile Leu His Leu Phe Val Leu Gln Pro Leu Lys Leu Tyr Ser
385                 390                 395                 400

Leu Xaa Thr Ile Lys Asn Thr Glu Trp Gly Thr Arg Lys Lys Val Thr
                405                 410                 415

Ile Phe Lys
```

```
<210> SEQ ID NO 86
<211> LENGTH: 419
<212> TYPE: PRT
<213> ORGANISM: Streptococcus pyogenes
<220> FEATURE:
<221> NAME/KEY: MISC_FEATURE
<222> LOCATION: (124)..(124)
<223> OTHER INFORMATION: Xaa = Ala, Ser or any other amino acid
<220> FEATURE:
<221> NAME/KEY: MISC_FEATURE
<222> LOCATION: (225)..(225)
<223> OTHER INFORMATION: Xaa = Ala, Ser or any other amino acid
<220> FEATURE:
<221> NAME/KEY: MISC_FEATURE
<222> LOCATION: (261)..(261)
<223> OTHER INFORMATION: Xaa = Ala, Ser or any other amino acid
<220> FEATURE:
<221> NAME/KEY: MISC_FEATURE
<222> LOCATION: (280)..(280)
<223> OTHER INFORMATION: Xaa = Ala, Ser or any other amino acid
<220> FEATURE:
<221> NAME/KEY: MISC_FEATURE
<222> LOCATION: (366)..(366)
<223> OTHER INFORMATION: Xaa = Ala, Ser or any other amino acid

<400> SEQUENCE: 86

Met Pro Ile Phe Lys Lys Thr Leu Ile Val Leu Ser Phe Ile Phe Leu
 1               5                  10                  15

Ile Ser Ile Leu Ile Tyr Leu Asn Met Tyr Leu Phe Gly Thr Ser Thr
             20                  25                  30

Val Gly Ile Tyr Gly Val Ile Leu Ile Thr Tyr Leu Val Ile Lys Leu
         35                  40                  45

Gly Leu Ser Phe Leu Tyr Glu Pro Phe Lys Gly Asn Pro His Asp Tyr
     50                  55                  60

Lys Val Ala Ala Val Ile Pro Ser Tyr Asn Glu Asp Ala Glu Ser Leu
 65                  70                  75                  80

Leu Glu Thr Leu Lys Ser Val Leu Ala Gln Thr Tyr Pro Leu Ser Glu
                 85                  90                  95

Ile Tyr Ile Val Asp Asp Gly Ser Ser Asn Thr Asp Ala Ile Gln Leu
            100                 105                 110

Ile Glu Glu Tyr Val Asn Arg Glu Val Asp Ile Xaa Arg Asn Val Ile
        115                 120                 125

Val His Arg Ser Leu Val Asn Lys Gly Lys Arg His Ala Gln Ala Trp
    130                 135                 140

Ala Phe Glu Arg Ser Asp Ala Asp Val Phe Leu Thr Val Asp Ser Asp
145                 150                 155                 160

Thr Tyr Ile Tyr Pro Asn Ala Leu Glu Glu Leu Leu Lys Ser Phe Asn
                165                 170                 175

Asp Glu Thr Val Tyr Ala Ala Thr Gly His Leu Asn Ala Arg Asn Arg
            180                 185                 190

Gln Thr Asn Leu Leu Thr Arg Leu Thr Asp Ile Arg Tyr Asp Asn Ala
        195                 200                 205

Phe Gly Val Glu Arg Ala Ala Gln Ser Leu Thr Gly Asn Ile Leu Val
    210                 215                 220

Xaa Ser Gly Pro Leu Ser Ile Tyr Arg Arg Glu Val Ile Ile Pro Asn
225                 230                 235                 240

Leu Glu Arg Tyr Lys Asn Gln Thr Phe Leu Gly Leu Pro Val Ser Ile
                245                 250                 255

Gly Asp Asp Arg Xaa Leu Thr Asn Tyr Ala Ile Asp Leu Gly Arg Thr
            260                 265                 270

Val Tyr Gln Ser Thr Ala Arg Xaa Asp Thr Asp Val Pro Phe Gln Leu
```

-continued

```
                275                 280                 285
Lys Ser Tyr Leu Lys Gln Gln Asn Arg Trp Asn Lys Ser Phe Phe Arg
    290                 295                 300

Glu Ser Ile Ile Ser Val Lys Lys Ile Leu Ser Asn Pro Ile Val Ala
305                 310                 315                 320

Leu Trp Thr Ile Phe Glu Val Val Met Phe Met Leu Ile Val Ala
                325                 330                 335

Ile Gly Asn Leu Leu Phe Asn Gln Ala Ile Gln Leu Asp Leu Ile Lys
                340                 345                 350

Leu Phe Ala Phe Leu Ser Ile Ile Phe Ile Val Ala Leu Xaa Arg Asn
            355                 360                 365

Val His Tyr Met Val Lys His Pro Ala Ser Phe Leu Leu Ser Pro Leu
    370                 375                 380

Tyr Gly Ile Leu His Leu Phe Val Leu Gln Pro Leu Lys Leu Tyr Ser
385                 390                 395                 400

Leu Cys Thr Ile Lys Asn Thr Glu Trp Gly Thr Arg Lys Lys Val Thr
                405                 410                 415

Ile Phe Lys

<210> SEQ ID NO 87
<211> LENGTH: 419
<212> TYPE: PRT
<213> ORGANISM: Streptococcus pyogenes
<220> FEATURE:
<221> NAME/KEY: MISC_FEATURE
<222> LOCATION: (124)..(124)
<223> OTHER INFORMATION: Xaa = Ala, Ser or any other amino acid
<220> FEATURE:
<221> NAME/KEY: MISC_FEATURE
<222> LOCATION: (225)..(225)
<223> OTHER INFORMATION: Xaa = Ala, Ser or any other amino acid
<220> FEATURE:
<221> NAME/KEY: MISC_FEATURE
<222> LOCATION: (261)..(261)
<223> OTHER INFORMATION: Xaa = Ala, Ser or any other amino acid
<220> FEATURE:
<221> NAME/KEY: MISC_FEATURE
<222> LOCATION: (280)..(280)
<223> OTHER INFORMATION: Xaa = Ala, Ser or any other amino acid
<220> FEATURE:
<221> NAME/KEY: MISC_FEATURE
<222> LOCATION: (402)..(402)
<223> OTHER INFORMATION: Xaa = Ala, Ser or any other amino acid

<400> SEQUENCE: 87

Met Pro Ile Phe Lys Lys Thr Leu Ile Val Leu Ser Phe Ile Phe Leu
1               5                   10                  15

Ile Ser Ile Leu Ile Tyr Leu Asn Met Tyr Leu Phe Gly Thr Ser Thr
                20                  25                  30

Val Gly Ile Tyr Gly Val Ile Leu Ile Thr Tyr Leu Val Ile Lys Leu
            35                  40                  45

Gly Leu Ser Phe Leu Tyr Glu Pro Phe Lys Gly Asn Pro His Asp Tyr
        50                  55                  60

Lys Val Ala Ala Val Ile Pro Ser Tyr Asn Glu Asp Ala Glu Ser Leu
65                  70                  75                  80

Leu Glu Thr Leu Lys Ser Val Leu Ala Gln Thr Tyr Pro Leu Ser Glu
                85                  90                  95

Ile Tyr Ile Val Asp Asp Gly Ser Ser Asn Thr Asp Ala Ile Gln Leu
                100                 105                 110

Ile Glu Glu Tyr Val Asn Arg Glu Val Asp Ile Xaa Arg Asn Val Ile
            115                 120                 125
```

```
Val His Arg Ser Leu Val Asn Lys Gly Lys Arg His Ala Gln Ala Trp
    130                 135                 140

Ala Phe Glu Arg Ser Asp Ala Asp Val Phe Leu Thr Val Asp Ser Asp
145                 150                 155                 160

Thr Tyr Ile Tyr Pro Asn Ala Leu Glu Glu Leu Leu Lys Ser Phe Asn
                165                 170                 175

Asp Glu Thr Val Tyr Ala Ala Thr Gly His Leu Asn Ala Arg Asn Arg
            180                 185                 190

Gln Thr Asn Leu Leu Thr Arg Leu Thr Asp Ile Arg Tyr Asp Asn Ala
        195                 200                 205

Phe Gly Val Glu Arg Ala Ala Gln Ser Leu Thr Gly Asn Ile Leu Val
    210                 215                 220

Xaa Ser Gly Pro Leu Ser Ile Tyr Arg Arg Glu Val Ile Ile Pro Asn
225                 230                 235                 240

Leu Glu Arg Tyr Lys Asn Gln Thr Phe Leu Gly Leu Pro Val Ser Ile
                245                 250                 255

Gly Asp Asp Arg Xaa Leu Thr Asn Tyr Ala Ile Asp Leu Gly Arg Thr
            260                 265                 270

Val Tyr Gln Ser Thr Ala Arg Xaa Asp Thr Asp Val Pro Phe Gln Leu
        275                 280                 285

Lys Ser Tyr Leu Lys Gln Gln Asn Arg Trp Asn Lys Ser Phe Phe Arg
    290                 295                 300

Glu Ser Ile Ile Ser Val Lys Lys Ile Leu Ser Asn Pro Ile Val Ala
305                 310                 315                 320

Leu Trp Thr Ile Phe Glu Val Val Met Phe Met Met Leu Ile Val Ala
                325                 330                 335

Ile Gly Asn Leu Leu Phe Asn Gln Ala Ile Gln Leu Asp Leu Ile Lys
            340                 345                 350

Leu Phe Ala Phe Leu Ser Ile Ile Phe Ile Val Ala Leu Cys Arg Asn
        355                 360                 365

Val His Tyr Met Val Lys His Pro Ala Ser Phe Leu Leu Ser Pro Leu
    370                 375                 380

Tyr Gly Ile Leu His Leu Phe Val Leu Gln Pro Leu Lys Leu Tyr Ser
385                 390                 395                 400

Leu Xaa Thr Ile Lys Asn Thr Glu Trp Gly Thr Arg Lys Lys Val Thr
                405                 410                 415

Ile Phe Lys

<210> SEQ ID NO 88
<211> LENGTH: 419
<212> TYPE: PRT
<213> ORGANISM: Streptococcus pyogenes
<220> FEATURE:
<221> NAME/KEY: MISC_FEATURE
<222> LOCATION: (124)..(124)
<223> OTHER INFORMATION: Xaa = Ala, Ser or any other amino acid
<220> FEATURE:
<221> NAME/KEY: MISC_FEATURE
<222> LOCATION: (225)..(225)
<223> OTHER INFORMATION: Xaa = Ala, Ser or any other amino acid
<220> FEATURE:
<221> NAME/KEY: MISC_FEATURE
<222> LOCATION: (261)..(261)
<223> OTHER INFORMATION: Xaa = Ala, Ser or any other amino acid
<220> FEATURE:
<221> NAME/KEY: MISC_FEATURE
<222> LOCATION: (366)..(366)
<223> OTHER INFORMATION: Xaa = Ala, Ser or any other amino acid
<220> FEATURE:
```

-continued

```
<221> NAME/KEY: MISC_FEATURE
<222> LOCATION: (402)..(402)
<223> OTHER INFORMATION: Xaa = Ala, Ser or any other amino acid

<400> SEQUENCE: 88
```

Met Pro Ile Phe Lys Lys Thr Leu Ile Val Leu Ser Phe Ile Phe Leu
1               5                   10                  15

Ile Ser Ile Leu Ile Tyr Leu Asn Met Tyr Leu Phe Gly Thr Ser Thr
            20                  25                  30

Val Gly Ile Tyr Gly Val Ile Leu Ile Thr Tyr Leu Val Ile Lys Leu
            35                  40                  45

Gly Leu Ser Phe Leu Tyr Glu Pro Phe Lys Gly Asn Pro His Asp Tyr
    50                  55                  60

Lys Val Ala Ala Val Ile Pro Ser Tyr Asn Glu Asp Ala Glu Ser Leu
65                  70                  75                  80

Leu Glu Thr Leu Lys Ser Val Leu Ala Gln Thr Tyr Pro Leu Ser Glu
                85                  90                  95

Ile Tyr Ile Val Asp Asp Gly Ser Ser Asn Thr Asp Ala Ile Gln Leu
            100                 105                 110

Ile Glu Glu Tyr Val Asn Arg Glu Val Asp Ile Xaa Arg Asn Val Ile
        115                 120                 125

Val His Arg Ser Leu Val Asn Lys Gly Lys Arg His Ala Gln Ala Trp
130                 135                 140

Ala Phe Glu Arg Ser Asp Ala Asp Val Phe Leu Thr Val Asp Ser Asp
145                 150                 155                 160

Thr Tyr Ile Tyr Pro Asn Ala Leu Glu Glu Leu Leu Lys Ser Phe Asn
                165                 170                 175

Asp Glu Thr Val Tyr Ala Ala Thr Gly His Leu Asn Ala Arg Asn Arg
            180                 185                 190

Gln Thr Asn Leu Leu Thr Arg Leu Thr Asp Ile Arg Tyr Asp Asn Ala
        195                 200                 205

Phe Gly Val Glu Arg Ala Ala Gln Ser Leu Thr Gly Asn Ile Leu Val
210                 215                 220

Xaa Ser Gly Pro Leu Ser Ile Tyr Arg Arg Glu Val Ile Ile Pro Asn
225                 230                 235                 240

Leu Glu Arg Tyr Lys Asn Gln Thr Phe Leu Gly Leu Pro Val Ser Ile
                245                 250                 255

Gly Asp Asp Arg Xaa Leu Thr Asn Tyr Ala Ile Asp Leu Gly Arg Thr
            260                 265                 270

Val Tyr Gln Ser Thr Ala Arg Cys Asp Thr Asp Val Pro Phe Gln Leu
        275                 280                 285

Lys Ser Tyr Leu Lys Gln Gln Asn Arg Trp Asn Lys Ser Phe Phe Arg
290                 295                 300

Glu Ser Ile Ile Ser Val Lys Lys Ile Leu Ser Asn Pro Ile Val Ala
305                 310                 315                 320

Leu Trp Thr Ile Phe Glu Val Val Met Phe Met Leu Ile Val Ala
                325                 330                 335

Ile Gly Asn Leu Leu Phe Asn Gln Ala Ile Gln Leu Asp Leu Ile Lys
            340                 345                 350

Leu Phe Ala Phe Leu Ser Ile Ile Phe Ile Val Ala Leu Xaa Arg Asn
        355                 360                 365

Val His Tyr Met Val Lys His Pro Ala Ser Phe Leu Leu Ser Pro Leu
370                 375                 380

Tyr Gly Ile Leu His Leu Phe Val Leu Gln Pro Leu Lys Leu Tyr Ser

```
                385                 390                 395                 400
Leu Xaa Thr Ile Lys Asn Thr Glu Trp Gly Thr Arg Lys Lys Val Thr
                    405                 410                 415
Ile Phe Lys

<210> SEQ ID NO 89
<211> LENGTH: 419
<212> TYPE: PRT
<213> ORGANISM: Streptococcus pyogenes
<220> FEATURE:
<221> NAME/KEY: MISC_FEATURE
<222> LOCATION: (124)..(124)
<223> OTHER INFORMATION: Xaa = Ala, Ser or any other amino acid
<220> FEATURE:
<221> NAME/KEY: MISC_FEATURE
<222> LOCATION: (225)..(225)
<223> OTHER INFORMATION: Xaa = Ala, Ser or any other amino acid
<220> FEATURE:
<221> NAME/KEY: MISC_FEATURE
<222> LOCATION: (280)..(280)
<223> OTHER INFORMATION: Xaa = Ala, Ser or any other amino acid
<220> FEATURE:
<221> NAME/KEY: MISC_FEATURE
<222> LOCATION: (366)..(366)
<223> OTHER INFORMATION: Xaa = Ala, Ser or any other amino acid
<220> FEATURE:
<221> NAME/KEY: MISC_FEATURE
<222> LOCATION: (402)..(402)
<223> OTHER INFORMATION: Xaa = Ala, Ser or any other amino acid

<400> SEQUENCE: 89

Met Pro Ile Phe Lys Lys Thr Leu Ile Val Leu Ser Phe Ile Phe Leu
1               5                   10                  15

Ile Ser Ile Leu Ile Tyr Leu Asn Met Tyr Leu Phe Gly Thr Ser Thr
            20                  25                  30

Val Gly Ile Tyr Gly Val Ile Leu Ile Thr Tyr Leu Val Ile Lys Leu
        35                  40                  45

Gly Leu Ser Phe Leu Tyr Glu Pro Phe Lys Gly Asn Pro His Asp Tyr
    50                  55                  60

Lys Val Ala Ala Val Ile Pro Ser Tyr Asn Glu Asp Ala Glu Ser Leu
65                  70                  75                  80

Leu Glu Thr Leu Lys Ser Val Leu Ala Gln Thr Tyr Pro Leu Ser Glu
                85                  90                  95

Ile Tyr Ile Val Asp Asp Gly Ser Ser Asn Thr Asp Ala Ile Gln Leu
            100                 105                 110

Ile Glu Glu Tyr Val Asn Arg Glu Val Asp Ile Xaa Arg Asn Val Ile
        115                 120                 125

Val His Arg Ser Leu Val Asn Lys Gly Lys Arg His Ala Gln Ala Trp
    130                 135                 140

Ala Phe Glu Arg Ser Asp Ala Asp Val Phe Leu Thr Val Asp Ser Asp
145                 150                 155                 160

Thr Tyr Ile Tyr Pro Asn Ala Leu Glu Glu Leu Leu Lys Ser Phe Asn
                165                 170                 175

Asp Glu Thr Val Tyr Ala Ala Thr Gly His Leu Asn Ala Arg Asn Arg
            180                 185                 190

Gln Thr Asn Leu Leu Thr Arg Leu Thr Asp Ile Arg Tyr Asp Asn Ala
        195                 200                 205

Phe Gly Val Glu Arg Ala Ala Gln Ser Leu Thr Gly Asn Ile Leu Val
    210                 215                 220

Xaa Ser Gly Pro Leu Ser Ile Tyr Arg Arg Glu Val Ile Ile Pro Asn
225                 230                 235                 240
```

-continued

```
Leu Glu Arg Tyr Lys Asn Gln Thr Phe Leu Gly Leu Pro Val Ser Ile
                245                 250                 255

Gly Asp Asp Arg Cys Leu Thr Asn Tyr Ala Ile Asp Leu Gly Arg Thr
            260                 265                 270

Val Tyr Gln Ser Thr Ala Arg Xaa Asp Thr Asp Val Pro Phe Gln Leu
        275                 280                 285

Lys Ser Tyr Leu Lys Gln Gln Asn Arg Trp Asn Lys Ser Phe Phe Arg
    290                 295                 300

Glu Ser Ile Ile Ser Val Lys Lys Ile Leu Ser Asn Pro Ile Val Ala
305                 310                 315                 320

Leu Trp Thr Ile Phe Glu Val Val Met Phe Met Met Leu Ile Val Ala
                325                 330                 335

Ile Gly Asn Leu Leu Phe Asn Gln Ala Ile Gln Leu Asp Leu Ile Lys
            340                 345                 350

Leu Phe Ala Phe Leu Ser Ile Ile Phe Ile Val Ala Leu Xaa Arg Asn
        355                 360                 365

Val His Tyr Met Val Lys His Pro Ala Ser Phe Leu Leu Ser Pro Leu
    370                 375                 380

Tyr Gly Ile Leu His Leu Phe Val Leu Gln Pro Leu Lys Leu Tyr Ser
385                 390                 395                 400

Leu Xaa Thr Ile Lys Asn Thr Glu Trp Gly Thr Arg Lys Lys Val Thr
                405                 410                 415

Ile Phe Lys

<210> SEQ ID NO 90
<211> LENGTH: 419
<212> TYPE: PRT
<213> ORGANISM: Streptococcus pyogenes
<220> FEATURE:
<221> NAME/KEY: MISC_FEATURE
<222> LOCATION: (124)..(124)
<223> OTHER INFORMATION: Xaa = Ala, Ser or any other amino acid
<220> FEATURE:
<221> NAME/KEY: MISC_FEATURE
<222> LOCATION: (261)..(261)
<223> OTHER INFORMATION: Xaa = Ala, Ser or any other amino acid
<220> FEATURE:
<221> NAME/KEY: MISC_FEATURE
<222> LOCATION: (280)..(280)
<223> OTHER INFORMATION: Xaa = Ala, Ser or any other amino acid
<220> FEATURE:
<221> NAME/KEY: MISC_FEATURE
<222> LOCATION: (366)..(366)
<223> OTHER INFORMATION: Xaa = Ala, Ser or any other amino acid
<220> FEATURE:
<221> NAME/KEY: MISC_FEATURE
<222> LOCATION: (402)..(402)
<223> OTHER INFORMATION: Xaa = Ala, Ser or any other amino acid

<400> SEQUENCE: 90

Met Pro Ile Phe Lys Lys Thr Leu Ile Val Leu Ser Phe Ile Phe Leu
1               5                   10                  15

Ile Ser Ile Leu Ile Tyr Leu Asn Met Tyr Leu Phe Gly Thr Ser Thr
            20                  25                  30

Val Gly Ile Tyr Gly Val Ile Leu Ile Thr Tyr Leu Val Ile Lys Leu
        35                  40                  45

Gly Leu Ser Phe Leu Tyr Glu Pro Phe Lys Gly Asn Pro His Asp Tyr
    50                  55                  60

Lys Val Ala Ala Val Ile Pro Ser Tyr Asn Glu Asp Ala Glu Ser Leu
65                  70                  75                  80
```

```
Leu Glu Thr Leu Lys Ser Val Leu Ala Gln Thr Tyr Pro Leu Ser Glu
            85                  90                  95
Ile Tyr Ile Val Asp Asp Gly Ser Ser Asn Thr Asp Ala Ile Gln Leu
            100                 105                 110
Ile Glu Glu Tyr Val Asn Arg Glu Val Asp Ile Xaa Arg Asn Val Ile
            115                 120                 125
Val His Arg Ser Leu Val Asn Lys Gly Lys Arg His Ala Gln Ala Trp
130                 135                 140
Ala Phe Glu Arg Ser Asp Ala Asp Val Phe Leu Thr Val Asp Ser Asp
145                 150                 155                 160
Thr Tyr Ile Tyr Pro Asn Ala Leu Glu Glu Leu Leu Lys Ser Phe Asn
                165                 170                 175
Asp Glu Thr Val Tyr Ala Ala Thr Gly His Leu Asn Ala Arg Asn Arg
            180                 185                 190
Gln Thr Asn Leu Leu Thr Arg Leu Thr Asp Ile Arg Tyr Asp Asn Ala
            195                 200                 205
Phe Gly Val Glu Arg Ala Ala Gln Ser Leu Thr Gly Asn Ile Leu Val
210                 215                 220
Cys Ser Gly Pro Leu Ser Ile Tyr Arg Arg Glu Val Ile Ile Pro Asn
225                 230                 235                 240
Leu Glu Arg Tyr Lys Asn Gln Thr Phe Leu Gly Leu Pro Val Ser Ile
            245                 250                 255
Gly Asp Asp Arg Xaa Leu Thr Asn Tyr Ala Ile Asp Leu Gly Arg Thr
            260                 265                 270
Val Tyr Gln Ser Thr Ala Arg Xaa Asp Thr Asp Val Pro Phe Gln Leu
            275                 280                 285
Lys Ser Tyr Leu Lys Gln Gln Asn Arg Trp Asn Lys Ser Phe Phe Arg
            290                 295                 300
Glu Ser Ile Ile Ser Val Lys Lys Ile Leu Ser Asn Pro Ile Val Ala
305                 310                 315                 320
Leu Trp Thr Ile Phe Glu Val Val Met Phe Met Leu Ile Val Ala
            325                 330                 335
Ile Gly Asn Leu Leu Phe Asn Gln Ala Ile Gln Leu Asp Leu Ile Lys
            340                 345                 350
Leu Phe Ala Phe Leu Ser Ile Ile Phe Ile Val Ala Leu Xaa Arg Asn
            355                 360                 365
Val His Tyr Met Val Lys His Pro Ala Ser Phe Leu Leu Ser Pro Leu
370                 375                 380
Tyr Gly Ile Leu His Leu Phe Val Leu Gln Pro Leu Lys Leu Tyr Ser
385                 390                 395                 400
Leu Xaa Thr Ile Lys Asn Thr Glu Trp Gly Thr Arg Lys Lys Val Thr
            405                 410                 415
Ile Phe Lys

<210> SEQ ID NO 91
<211> LENGTH: 419
<212> TYPE: PRT
<213> ORGANISM: Streptococcus pyogenes
<220> FEATURE:
<221> NAME/KEY: MISC_FEATURE
<222> LOCATION: (225)..(225)
<223> OTHER INFORMATION: Xaa = Ala, Ser or any other amino acid
<220> FEATURE:
<221> NAME/KEY: MISC_FEATURE
<222> LOCATION: (261)..(261)
<223> OTHER INFORMATION: Xaa = Ala, Ser or any other amino acid
<220> FEATURE:
```

-continued

```
<221> NAME/KEY: MISC_FEATURE
<222> LOCATION: (280)..(280)
<223> OTHER INFORMATION: Xaa = Ala, Ser or any other amino acid
<220> FEATURE:
<221> NAME/KEY: MISC_FEATURE
<222> LOCATION: (366)..(366)
<223> OTHER INFORMATION: Xaa = Ala, Ser or any other amino acid
<220> FEATURE:
<221> NAME/KEY: MISC_FEATURE
<222> LOCATION: (402)..(402)
<223> OTHER INFORMATION: Xaa = Ala, Ser or any other amino acid

<400> SEQUENCE: 91

Met Pro Ile Phe Lys Lys Thr Leu Ile Val Ser Phe Ile Phe Leu
1               5                   10                  15

Ile Ser Ile Leu Ile Tyr Leu Asn Met Tyr Leu Phe Gly Thr Ser Thr
            20                  25                  30

Val Gly Ile Tyr Gly Val Ile Leu Ile Thr Tyr Leu Val Ile Lys Leu
            35                  40                  45

Gly Leu Ser Phe Leu Tyr Glu Pro Phe Lys Gly Asn Pro His Asp Tyr
    50                  55                  60

Lys Val Ala Ala Val Ile Pro Ser Tyr Asn Glu Asp Ala Glu Ser Leu
65                  70                  75                  80

Leu Glu Thr Leu Lys Ser Val Leu Ala Gln Thr Tyr Pro Leu Ser Glu
                85                  90                  95

Ile Tyr Ile Val Asp Asp Gly Ser Ser Asn Thr Asp Ala Ile Gln Leu
                100                 105                 110

Ile Glu Glu Tyr Val Asn Arg Glu Val Asp Ile Cys Arg Asn Val Ile
                115                 120                 125

Val His Arg Ser Leu Val Asn Lys Gly Lys Arg His Ala Gln Ala Trp
130                 135                 140

Ala Phe Glu Arg Ser Asp Ala Asp Val Phe Leu Thr Val Asp Ser Asp
145                 150                 155                 160

Thr Tyr Ile Tyr Pro Asn Ala Leu Glu Glu Leu Leu Lys Ser Phe Asn
                165                 170                 175

Asp Glu Thr Val Tyr Ala Ala Thr Gly His Leu Asn Ala Arg Asn Arg
                180                 185                 190

Gln Thr Asn Leu Leu Thr Arg Leu Thr Asp Ile Arg Tyr Asp Asn Ala
                195                 200                 205

Phe Gly Val Glu Arg Ala Ala Gln Ser Leu Thr Gly Asn Ile Leu Val
210                 215                 220

Xaa Ser Gly Pro Leu Ser Ile Tyr Arg Arg Glu Val Ile Ile Pro Asn
225                 230                 235                 240

Leu Glu Arg Tyr Lys Asn Gln Thr Phe Leu Gly Leu Pro Val Ser Ile
                245                 250                 255

Gly Asp Asp Arg Xaa Leu Thr Asn Tyr Ala Ile Asp Leu Gly Arg Thr
                260                 265                 270

Val Tyr Gln Ser Thr Ala Arg Xaa Asp Thr Asp Val Pro Phe Gln Leu
                275                 280                 285

Lys Ser Tyr Leu Lys Gln Gln Asn Arg Trp Asn Lys Ser Phe Arg
290                 295                 300

Glu Ser Ile Ile Ser Val Lys Lys Ile Leu Ser Asn Pro Ile Val Ala
305                 310                 315                 320

Leu Trp Thr Ile Phe Glu Val Met Phe Met Leu Ile Val Ala
                325                 330                 335

Ile Gly Asn Leu Leu Phe Asn Gln Ala Ile Gln Leu Asp Leu Ile Lys
                340                 345                 350
```

-continued

```
Leu Phe Ala Phe Leu Ser Ile Ile Phe Ile Val Ala Leu Xaa Arg Asn
            355                 360                 365

Val His Tyr Met Val Lys His Pro Ala Ser Phe Leu Leu Ser Pro Leu
    370                 375                 380

Tyr Gly Ile Leu His Leu Phe Val Leu Gln Pro Leu Lys Leu Tyr Ser
385                 390                 395                 400

Leu Xaa Thr Ile Lys Asn Thr Glu Trp Gly Thr Arg Lys Lys Val Thr
                405                 410                 415

Ile Phe Lys

<210> SEQ ID NO 92
<211> LENGTH: 419
<212> TYPE: PRT
<213> ORGANISM: Streptococcus pyogenes
<220> FEATURE:
<221> NAME/KEY: MISC_FEATURE
<222> LOCATION: (124)..(124)
<223> OTHER INFORMATION: Xaa = Ala, Ser or any other amino acid
<220> FEATURE:
<221> NAME/KEY: MISC_FEATURE
<222> LOCATION: (225)..(225)
<223> OTHER INFORMATION: Xaa = Ala, Ser or any other amino acid
<220> FEATURE:
<221> NAME/KEY: MISC_FEATURE
<222> LOCATION: (261)..(261)
<223> OTHER INFORMATION: Xaa = Ala, Ser or any other amino acid
<220> FEATURE:
<221> NAME/KEY: MISC_FEATURE
<222> LOCATION: (280)..(280)
<223> OTHER INFORMATION: Xaa = Ala, Ser or any other amino acid
<220> FEATURE:
<221> NAME/KEY: MISC_FEATURE
<222> LOCATION: (366)..(366)
<223> OTHER INFORMATION: Xaa = Ala, Ser or any other amino acid
<220> FEATURE:
<221> NAME/KEY: MISC_FEATURE
<222> LOCATION: (402)..(402)
<223> OTHER INFORMATION: Xaa = Ala, Ser or any other amino acid

<400> SEQUENCE: 92

Met Pro Ile Phe Lys Lys Thr Leu Ile Val Leu Ser Phe Ile Phe Leu
1               5                   10                  15

Ile Ser Ile Leu Ile Tyr Leu Asn Met Tyr Leu Phe Gly Thr Ser Thr
            20                  25                  30

Val Gly Ile Tyr Gly Val Ile Leu Ile Thr Tyr Leu Val Ile Lys Leu
        35                  40                  45

Gly Leu Ser Phe Leu Tyr Glu Pro Phe Lys Gly Asn Pro His Asp Tyr
    50                  55                  60

Lys Val Ala Ala Val Ile Pro Ser Tyr Asn Glu Asp Ala Glu Ser Leu
65                  70                  75                  80

Leu Glu Thr Leu Lys Ser Val Leu Ala Gln Thr Tyr Pro Leu Ser Glu
                85                  90                  95

Ile Tyr Ile Val Asp Asp Gly Ser Ser Asn Thr Asp Ala Ile Gln Leu
            100                 105                 110

Ile Glu Glu Tyr Val Asn Arg Glu Val Asp Ile Xaa Arg Asn Val Ile
        115                 120                 125

Val His Arg Ser Leu Val Asn Lys Gly Lys Arg His Ala Gln Ala Trp
    130                 135                 140

Ala Phe Glu Arg Ser Asp Ala Asp Val Phe Leu Thr Val Asp Ser Asp
145                 150                 155                 160

Thr Tyr Ile Tyr Pro Asn Ala Leu Glu Glu Leu Leu Lys Ser Phe Asn
                165                 170                 175
```

-continued

```
Asp Glu Thr Val Tyr Ala Ala Thr Gly His Leu Asn Ala Arg Asn Arg
            180                 185                 190

Gln Thr Asn Leu Leu Thr Arg Leu Thr Asp Ile Arg Tyr Asp Asn Ala
            195                 200                 205

Phe Gly Val Glu Arg Ala Ala Gln Ser Leu Thr Gly Asn Ile Leu Val
            210                 215                 220

Xaa Ser Gly Pro Leu Ser Ile Tyr Arg Arg Glu Val Ile Ile Pro Asn
225                 230                 235                 240

Leu Glu Arg Tyr Lys Asn Gln Thr Phe Leu Gly Leu Pro Val Ser Ile
            245                 250                 255

Gly Asp Asp Arg Xaa Leu Thr Asn Tyr Ala Ile Asp Leu Gly Arg Thr
            260                 265                 270

Val Tyr Gln Ser Thr Ala Arg Xaa Asp Thr Asp Val Pro Phe Gln Leu
            275                 280                 285

Lys Ser Tyr Leu Lys Gln Gln Asn Arg Trp Asn Lys Ser Phe Phe Arg
            290                 295                 300

Glu Ser Ile Ile Ser Val Lys Lys Ile Leu Ser Asn Pro Ile Val Ala
305                 310                 315                 320

Leu Trp Thr Ile Phe Glu Val Val Met Phe Met Met Leu Ile Val Ala
            325                 330                 335

Ile Gly Asn Leu Leu Phe Asn Gln Ala Ile Gln Leu Asp Leu Ile Lys
            340                 345                 350

Leu Phe Ala Phe Leu Ser Ile Ile Phe Ile Val Ala Leu Xaa Arg Asn
            355                 360                 365

Val His Tyr Met Val Lys His Pro Ala Ser Phe Leu Leu Ser Pro Leu
            370                 375                 380

Tyr Gly Ile Leu His Leu Phe Val Leu Gln Pro Leu Lys Leu Tyr Ser
385                 390                 395                 400

Leu Xaa Thr Ile Lys Asn Thr Glu Trp Gly Thr Arg Lys Lys Val Thr
            405                 410                 415

Ile Phe Lys
```